US012753188B2

(12) United States Patent
Pennington et al.

(10) Patent No.: US 12,753,188 B2
(45) **Date of Patent: *Oct. 6, 2026**

(54) SUBSTITUTED MACROCYCLIC COMPOUNDS AND RELATED METHODS OF TREATMENT

(71) Applicant: Alkermes, Inc., Waltham, MA (US)

(72) Inventors: Lewis D. Pennington, Arlington, MA (US); Younggi Choi, Stow, MA (US); Hoan Huynh, Waltham, MA (US); Brian M. Aquila, Marlborough, MA (US); Ingo Andreas Mugge, Waltham, MA (US); Yuan Hu, Waltham, MA (US); James R. Woods, Waltham, MA (US); Brian Kenneth Raymer, Holliston, MA (US); Jörg Martin Bentzien, White Plains, NY (US); Jonathan Ward Lehmann, Burlington, MA (US); Michael R. Hale, Bedford, MA (US); Srinivasa Karra, Pembroke, MA (US); Roman A. Valiulin, Cambridge, MA (US); Daljit Matharu, Lexington, MA (US)

(73) Assignee: Alkermes, Inc., Waltham, MA (US)

( * ) Notice: Subject to any disclaimer, the term of this patent is extended or adjusted under 35 U.S.C. 154(b) by 248 days.

This patent is subject to a terminal disclaimer.

(21) Appl. No.: 18/628,635

(22) Filed: Apr. 5, 2024

(65) Prior Publication Data

US 2024/0368182 A1 Nov. 7, 2024

Related U.S. Application Data

(63) Continuation of application No. 17/556,250, filed on Dec. 20, 2021, now Pat. No. 12,006,330.

(60) Provisional application No. 63/190,937, filed on May 20, 2021, provisional application No. 63/128,404, filed on Dec. 21, 2020.

(51) Int. Cl.

| | |
|---|---|
| ***C07D 498/04*** | (2006.01) |
| ***A61K 31/4353*** | (2006.01) |
| ***A61P 25/00*** | (2006.01) |
| ***A61P 25/10*** | (2006.01) |
| ***C07D 498/14*** | (2006.01) |

(52) U.S. Cl.

CPC ......... *C07D 498/04* (2013.01); *C07D 498/14* (2013.01)

(58) Field of Classification Search

CPC ................ C07D 498/04; C07D 498/14; A61K 31/4353; A61P 25/00; A61P 25/10

See application file for complete search history.

(56) References Cited

U.S. PATENT DOCUMENTS

| | | | | |
|---|---|---|---|---|
| 5,635,599 | A | 6/1997 | Pastan et al. | |
| 6,428,985 | B1 | 8/2002 | Bromberg et al. | |
| 6,492,492 | B1 | 12/2002 | Stayton et al. | |
| 6,808,902 | B1 | 10/2004 | Treuheit et al. | |
| 7,211,253 | B1 | 5/2007 | Way | |
| 7,271,149 | B2 | 9/2007 | Glaesner et al. | |
| 7,696,322 | B2 | 4/2010 | Bleck et al. | |
| 7,829,679 | B2 | 11/2010 | Ushida et al. | |
| 7,928,074 | B2 | 4/2011 | Khare | |
| 8,063,182 | B1 | 11/2011 | Brockhaus et al. | |
| 8,163,522 | B1 | 4/2012 | Brockhaus et al. | |
| 8,258,163 | B2 | 9/2012 | Yanagisawa et al. | |
| 8,765,669 | B2 | 7/2014 | Kajihara et al. | |
| 8,933,197 | B2 | 1/2015 | Stemmer et al. | |
| 9,527,807 | B2 | 12/2016 | Fukumoto et al. | |
| 9,611,262 | B2 | 4/2017 | Shireman et al. | |
| 9,815,787 | B2 | 11/2017 | Nagase et al. | |
| 10,017,481 | B2 | 7/2018 | Obrecht et al. | |
| 10,287,305 | B2 | 5/2019 | Fujimoto et al. | |
| 10,351,522 | B2 | 7/2019 | Nagase et al. | |
| 10,377,770 | B2 | 8/2019 | Aversa et al. | |
| 10,428,023 | B2 | 10/2019 | Kajita et al. | |
| 10,508,083 | B2 | 12/2019 | Fujimoto et al. | |
| 10,584,097 | B2 | 3/2020 | Kajita et al. | |
| 10,898,737 | B2 | 1/2021 | Fujimoto et al. | |
| 11,472,805 | B2 | 10/2022 | Chappie et al. | |
| 11,479,552 | B2 | 10/2022 | Yoshida et al. | |
| 11,760,747 | B2 | 9/2023 | Pennington et al. | |
| 12,006,330 | B2 * | 6/2024 | Pennington .......... | C07D 498/14 |
| 2002/0127227 | A1 | 9/2002 | Holmes et al. | |
| 2002/0159969 | A1 | 10/2002 | Agrawal et al. | |
| 2003/0073822 | A1 | 4/2003 | Lofling et al. | |
| 2003/0229226 | A1 | 12/2003 | Okamoto et al. | |
| 2004/0137580 | A1 | 7/2004 | Holgersson et al. | |
| 2005/0069552 | A1 | 3/2005 | Bleck et al. | |
| 2005/0260222 | A1 | 11/2005 | Gupta et al. | |

(Continued)

FOREIGN PATENT DOCUMENTS

| | | | |
|---|---|---|---|
| CN | 101962413 | A | 2/2011 |
| CN | 107787322 | A | 3/2018 |

(Continued)

OTHER PUBLICATIONS

Publications Related to P18510-IL1RA Human, www.uniprot.org 1990.
Uniprot Protein Database, Protein Accession Q8N3074, Human Mucin 20, accessed on Oct. 16, 2016.
"3-(Cycohexylmethoxy)piperidine", PubChem, CID 43196817, create date Jul. 21, 2009.
"4-[Pyrrolidin-3-yloxy)methyl]piperidine", Pubchem CID 130141993, Create date: Oct. 7, 2017.

(Continued)

*Primary Examiner* — Brenda L Coleman
(74) *Attorney, Agent, or Firm* — Elmore Patent Law Group, P.C.; Joseph C. Zucchero; Carolyn S. Elmore

(57) ABSTRACT

The present invention provides compounds useful for the treatment of narcolepsy or cataplexy in a subject in need thereof. Related pharmaceutical compositions and methods are also provided herein.

22 Claims, No Drawings

(56) References Cited

U.S. PATENT DOCUMENTS

| | | | |
|---|---|---|---|
| 2005/0265995 | A1 | 12/2005 | Tomlinson et al. |
| 2006/0110429 | A1 | 5/2006 | Reiff et al. |
| 2007/0010445 | A1 | 1/2007 | Siegel et al. |
| 2007/0105767 | A1 | 5/2007 | Kharbanda et al. |
| 2008/0045493 | A1 | 2/2008 | Drescher et al. |
| 2008/0286211 | A1 | 11/2008 | Barker et al. |
| 2009/0054489 | A1 | 2/2009 | Hauske |
| 2010/0016547 | A1 | 1/2010 | Ito et al. |
| 2010/0035865 | A1 | 2/2010 | Estep et al. |
| 2010/0227394 | A1 | 9/2010 | Bleck et al. |
| 2010/0285014 | A1 | 11/2010 | Cox et al. |
| 2013/0217864 | A1 | 8/2013 | Cho et al. |
| 2013/0295084 | A1 | 11/2013 | Hunter et al. |
| 2013/0316404 | A1 | 11/2013 | Roers et al. |
| 2013/0336925 | A1 | 12/2013 | Alvarez et al. |
| 2014/0024650 | A1 | 1/2014 | Fukumoto et al. |
| 2014/0056895 | A1 | 2/2014 | Baurin et al. |
| 2014/0072581 | A1 | 3/2014 | Dixit et al. |
| 2014/0234962 | A1 | 8/2014 | Alvarez et al. |
| 2015/0071948 | A1 | 3/2015 | Lazar et al. |
| 2016/0068583 | A1 | 3/2016 | Mccauley et al. |
| 2016/0175458 | A1 | 6/2016 | Alvarez et al. |
| 2017/0114098 | A1 | 4/2017 | Aivado et al. |
| 2017/0226137 | A1 | 8/2017 | Fujimoto et al. |
| 2017/0233447 | A1 | 8/2017 | Qin |
| 2018/0179151 | A1 | 6/2018 | Nagase et al. |
| 2018/0289825 | A1 | 10/2018 | Alvarez et al. |
| 2019/0031611 | A1 | 1/2019 | Fujimoto et al. |
| 2019/0040010 | A1 | 2/2019 | Kajita et al. |
| 2019/0167590 | A1 | 6/2019 | Zamloot et al. |
| 2020/0017444 | A1 | 1/2020 | Kajita et al. |
| 2020/0115399 | A1 | 4/2020 | Fujimoto et al. |
| 2020/0207715 | A1 | 7/2020 | Kajita et al. |
| 2020/0207734 | A1 | 7/2020 | Kajita et al. |
| 2020/0247747 | A1 | 8/2020 | Hattori et al. |
| 2020/0255403 | A1 | 8/2020 | Bogen et al. |
| 2020/0385345 | A1 | 12/2020 | Daini et al. |
| 2020/0385346 | A1 | 12/2020 | Fujimoto et al. |
| 2020/0392149 | A1 | 12/2020 | Mikami et al. |
| 2021/0078955 | A1 | 3/2021 | Nagase et al. |
| 2021/0155636 | A1 | 5/2021 | Pennington et al. |
| 2021/0198240 | A1 | 7/2021 | Oda et al. |
| 2021/0269420 | A1 | 9/2021 | Fujimoto et al. |
| 2022/0017514 | A1 | 1/2022 | Kajita et al. |
| 2022/0017517 | A1 | 1/2022 | Yoshida et al. |
| 2022/0081441 | A1 | 3/2022 | Ideue et al. |
| 2022/0194926 | A1 | 6/2022 | Pennington et al. |
| 2023/0037557 | A1 | 2/2023 | Ito et al. |
| 2023/0042358 | A1 | 2/2023 | Miyanohana et al. |
| 2023/0192692 | A1 | 6/2023 | Li et al. |

FOREIGN PATENT DOCUMENTS

| | | | |
|---|---|---|---|
| CN | 108699065 | A | 10/2018 |
| EP | 2836485 | B1 | 1/2018 |
| EP | 3191468 | B1 | 12/2018 |
| EP | 3663281 | A1 | 6/2020 |
| EP | 3816154 | A1 | 5/2021 |
| EP | 3895707 | A1 | 10/2021 |
| EP | 3896060 | A1 | 10/2021 |
| JP | 2003508023 | A | 3/2003 |
| JP | 2003513656 | A | 4/2003 |
| JP | 2003514552 | A | 4/2003 |
| JP | 2004528014 | A | 9/2004 |
| JP | 2006517191 | A | 7/2006 |
| JP | 2008521489 | A | 6/2008 |
| JP | 2010523540 | A | 7/2010 |
| JP | 2010536341 | A | 12/2010 |
| JP | 2022064180 | A | 4/2022 |
| WO | 9946392 | A1 | 9/1999 |
| WO | 0103737 | A1 | 1/2001 |
| WO | 0158950 | A1 | 8/2001 |
| WO | 2002062375 | A1 | 8/2002 |
| WO | 2004033651 | A2 | 4/2004 |
| WO | 2004044006 | A1 | 5/2004 |
| WO | 2004101740 | A2 | 11/2004 |
| WO | 2005034863 | A2 | 4/2005 |
| WO | 2007020889 | A1 | 2/2007 |
| WO | 2007062844 | A1 | 6/2007 |
| WO | 2007063907 | A1 | 6/2007 |
| WO | 2008140595 | A2 | 11/2008 |
| WO | 2009153960 | A1 | 12/2009 |
| WO | 2010018233 | A1 | 2/2010 |
| WO | 2010127029 | A1 | 11/2010 |
| WO | 2010150192 | A1 | 12/2010 |
| WO | 2011076781 | A1 | 6/2011 |
| WO | 2011090762 | A1 | 7/2011 |
| WO | 2011122923 | A2 | 10/2011 |
| WO | 2012137982 | A2 | 10/2012 |
| WO | 2012146628 | A1 | 11/2012 |
| WO | 2012178137 | A1 | 12/2012 |
| WO | 2013026833 | A1 | 2/2013 |
| WO | 2013139697 | A1 | 9/2013 |
| WO | 2013184942 | A1 | 12/2013 |
| WO | 2014006402 | A1 | 1/2014 |
| WO | 2014018572 | A2 | 1/2014 |
| WO | 2014023673 | A1 | 2/2014 |
| WO | 2014151910 | A1 | 9/2014 |
| WO | 2014198880 | A1 | 12/2014 |
| WO | 2015017548 | A2 | 2/2015 |
| WO | 2015117930 | A1 | 8/2015 |
| WO | 2016082677 | A1 | 6/2016 |
| WO | 2016100788 | A1 | 6/2016 |
| WO | 2016101119 | A1 | 6/2016 |
| WO | 2016133160 | A1 | 8/2016 |
| WO | 2017035354 | A1 | 3/2017 |
| WO | 2017135306 | A1 | 8/2017 |
| WO | 2017165464 | A1 | 9/2017 |
| WO | 2018005226 | A2 | 1/2018 |
| WO | 2018005226 | A3 | 4/2018 |
| WO | 2019027058 | A1 | 2/2019 |
| WO | 2019063605 | A1 | 4/2019 |
| WO | 2019191327 | A1 | 10/2019 |
| WO | 2020004536 | A1 | 1/2020 |
| WO | 2020004537 | A1 | 1/2020 |
| WO | 2020122092 | A1 | 6/2020 |
| WO | 2020122093 | A1 | 6/2020 |
| WO | 2020158958 | A1 | 8/2020 |
| WO | 2020167701 | A1 | 8/2020 |
| WO | 2020167706 | A1 | 8/2020 |
| WO | 2021026047 | A1 | 2/2021 |
| WO | 2021048821 | A1 | 3/2021 |
| WO | 2021106975 | A1 | 6/2021 |
| WO | 2021108628 | A1 | 6/2021 |
| WO | 2021142083 | A1 | 7/2021 |
| WO | 2022009117 | A1 | 1/2022 |
| WO | 2022014680 | A1 | 1/2022 |
| WO | 2022040058 | A1 | 2/2022 |
| WO | 2022040070 | A1 | 2/2022 |
| WO | 2022051583 | A1 | 3/2022 |
| WO | 2022051596 | A1 | 3/2022 |
| WO | 2022094012 | A1 | 5/2022 |
| WO | 2022109117 | A1 | 5/2022 |
| WO | 2022119888 | A1 | 6/2022 |
| WO | 2022132696 | A1 | 6/2022 |
| WO | 2022140316 | A1 | 6/2022 |
| WO | 2022140317 | A1 | 6/2022 |
| WO | 2022187231 | A1 | 9/2022 |
| WO | 2022207935 | A1 | 10/2022 |
| WO | 2022233872 | A1 | 11/2022 |
| WO | 2022250108 | A1 | 12/2022 |
| WO | 2022269049 | A1 | 12/2022 |
| WO | 2023017180 | A1 | 2/2023 |

OTHER PUBLICATIONS

Arai, R. , "Design of the linkers which effectively separate domains of a bifunctional fusion protein", Protein Eng, 14(8), Sep. 21, 2001, 529-532.

Cao, W. , "Tim-4 inhibition of T-cell activation and T helper type 17 differentiation requires both the immunoglobuln V and mucin domains and occurs via the mitogen-activated protein kinase pathway", Immunology, 133, 2011, 179-189.

(56) References Cited

OTHER PUBLICATIONS

Chen, X. , "Fusion Protein Linkers: Property, Design and Functionality", Advanced Drug Delivery Reviews, 65, 2012, 1357-1369.
Cox, C. D., "Conformational analysis of N,N-disubstituted-1,4-diazepane orexin receptor antagonists and implications for receptor binding", Bioorganic & Medicinal Chemistry Letters, 19(11), , DOI:10. 1016/J.BMCL.2009. 04.026, 2009, 2997-3001.
Czajkowsky, D. M., "Fc-fusion proteins: new developments and future perspectives", EMBO Mol Med, 4(10), DOI 10.1002/emmm.201201379, Jul. 26, 2012, 1015-1028.
Ding, Y. , "A Single Amino Acid Determines the Immunostimulatory Activity of Interleukin 10", J. Exp. Med., 191(2), Jan. 17, 2000, 213-223.
Fontenot, D. , "Human Immunodeficiency Virus (HIV) antigens: Structure and Serology of Multivalent Human Mucin MUC1-HIV V3 Chimeric Proteins", PNAS, 92, Jan. 1995, 315-319.
Hasanain, S. , "Effect of Topical IL-1 RA on Signs and Symptoms of Dry Eye Disease in Patients With Ocular Graftversus-host Disease (GVHD)", ARVO Annual Meeting, 53, Abstract 579, Mar. 2012.
Irukayama-Tomobe, Y. , "Nonpeptide orexin type-2 receptor agonist ameliorates narcolepsy-cataplexy symptoms in mouse models", PNAS, 114(22), May 30, 2017, 5731-5736.
Linderholm, A. L, "Immunoglobulin Fc-Fusion Proteins Part 2: Therapeutic Uses and Clinical Development", Bioprocess Intl, 12(10), Nov. 1, 2014, 1-7.
McGaughey, G. , "Shaping suvorexant: application of experimental and theoretical methods for driving synthetic designs", J. Comput. Aided Mol. Des., 28, 2014, 5-12.
Nagahara, T. , "Design and Synthesis of Non-Peptide, Selective Orexin Receptor 2 Agonists", J. Med. Chem., 58, 2015, 7931-7937.
No Longer ND To Cite , "DNU—Now U.S. Appl. No. 15/949,596, filed Apr. 10, 2018", U.S. Appl. No. 15/949,596, filed Apr. 10, 2018 (pub as US 2018-0289825 A1).
Nomellini, J. F, "S-Layer-Mediated Display of the Immunoglobulin G-Binding Domain of Streptococcal Protein G on the Surface of Caulobacter crescenius: Development of an Immunoactive Reagent", Appl. Environ. Micro Biol., 73(10), 2007, 3245-3253.
Sabnis, R. W., "Novel 5-Alkyl Pyrrolidine Orexin Receptor Agonists for Treating Sleep Disorders", ACS Med. Chem. Lett., 11(11), , https://dx.doi.org/10.1021/acsmedchemlett.0c00501, Sep. 29, 2020, 2085-2086.
Shen, H. , "Deletion of the Linker Connecting the Catalytic and Cellulose-Binding Domains of Endoglucanase A (CenA) of Cellulomonas fimi Alters Its Conformation and Catalytic Activity", The Journal of Biological Chemistry, 266(17), 1991, 11335-11340.
Shimamoto, G. , "Peptibodies: A flexible alternative format to antibodies", MABS, 4(5), Sep. 1, 2012, 586-591.
Turku, A. , "Orexin receptor agonist Yan 7874 is a weak agonist of orexin/hypocretin receptors and shows orexin receptor-independent cytotoxicity", PLOS One, 12(6): e0178526, , doi:10.1371/journal.pone.0178526, Jun. 2, 2017, 1-15.
Vallee, S. , "Pulmonary Administration of Interferon Beta-1a-Fc Fusion Protein in Non-Human Primates Using an Immunoglobulin Transport Pathway", J linterferon & Cytokine Res, 32(4), Apr. 1, 2012, 178-184.
Wriggers, W. , "Control of Protein Functional Dynamics by Peptide Linkers", Biopolymers (Peptide Science), 80, May 6, 2005, 736-746.
Wu, B. , "Pharmacokinetics of Peptide-Fe Fusion Proteins", J Pharm Sci., 103(1), Jan. 27, 2014, 53-64.
Yoon, S. , "Conformational changes mediate interleukin-10 receptor 2 (IL-10R2) binding to IL-10 and assembly of the signaling complex", J Biol Chem., 281(46), 2006, 35088-96.
Yukitake, H. , "TAK-925, an orexin 2 receptor-selective agonist, shows robust wakepromoting effects in mice", Pharmacology, Biochemistry and Behavior, 187, 2019, 172794.
Zhang, J. , "Design and optimization of a linker for fusion protein construction", Progress in Natural Science, 19, Sep. 17, 2009, 1197-1200.
Zhao, L. , "Eradication of non-Hodgkin lymphoma through the induction of tumor-specific T-cell immunity by CD20-Flex BiFP", Blood, 122(26), 2013, 4230-6.
Zheng, X. X, "Administration of noncytolytic IL-10/Fc in murine models of lipopolysaccharide-induced septic shock and allogeneic islet transplantation", J. Immunol., 154(10), May 15, 1995, 5590-5600.
Zheng, X. X, "I L-2 receptor-targeted cytolytic IL-2/Fc fusion protein treatment blocks diabetogenic autoimmunity in nonobese diabetic mice", J. Immunol., 163(7), Oct. 1, 1999, 4041-4048.
Zheng, X. X, "Noncytolytic IL-10/Fc fusion protein prevents diabetes, blocks autoimmunity, and promotes suppressor phenomena in NOD mice", J. Immunol., 158(9), May 1, 1997, 4507-4513.
Collins, "Emac—a comparative index for the assessment of macrocyclization efficiency", Medicical Chemistry Communications, 3(12), Dec. 2012, 1489-1495.
Keinan, E., "Organic Synthesis: From Glorious Past to Brilliant Future", Israel J Chem, 58, Feb. 22, 2018, 7-10.

* cited by examiner

SUBSTITUTED MACROCYCLIC COMPOUNDS AND RELATED METHODS OF TREATMENT

RELATED APPLICATIONS

This application is a continuation of U.S. application Ser. No. 17/556,250, filed on Dec. 20, 2021, which claims the benefit of U.S. Provisional Application No. 63/128,404, filed on Dec. 21, 2020, and U.S. Provisional Application No. 63/190,937, filed on May 20, 2021. The entire contents of the above-identified applications are herein incorporated by reference.

TECHNICAL FIELD

The present invention relates to substituted macrocyclic compounds, particularly, substituted macrocyclic compounds having agonist activity.

BACKGROUND OF THE INVENTION

Orexin is a neuropeptide synthesized and released by a subpopulation of neurons within the lateral hypothalamus and its surrounding regions. It consists of two subtypes: orexin A and orexin B. Orexin A and orexin B bind to orexin receptors. Orexin receptors are G protein-coupled receptors expressed preferentially in the brain. There are two subtypes (type 1 and type 2) of orexin receptors (Cell, Vol. 92, 573-585, 1998). Activation of orexin receptors is known to be important for a variety of central nervous system functions, such as maintenance of wakefulness, energy homeostasis, reward processing and motivation (Saper et al., TRENDS in Neuroscience 2001; Yamanaka et al., Neuron 2003; Sakurai, Nature Reviews Neuroscience 2014).

Narcolepsy is a neurological disease that results in excessive daytime sleepiness, sudden bouts of muscular paralysis (cataplexy), and disrupted sleep patterns (Mahoney et al., Nature Reviews Neuroscience, 2019). It is known that narcolepsy is caused by the degeneration of orexin neurons. Narcoleptic symptoms can be modeled in transgenic mice engineered to degenerate orexin neurons, and their symptoms can be reversed by intraventricular administration of orexin peptides (Proc. Natl. Acad. Sci. USA, Vol. 101, 4649-4654, 2004). Studies of orexin-2 receptor knockout mice have suggested that the orexin-2 receptor plays a preferential role in maintaining wakefulness (Cell, Vol. 98, 437-451, 1999, Neuron, Vol. 38, 715-730, 2003). As such, orexin-2 receptor agonists can be therapeutic agents for narcolepsy or other disorders exhibiting excessive daytime sleepiness, such as Parkinson's disease (CNS Drugs, Vol. 27, 83-90, 2013; Brain, Vol. 130, 2007, 1586-1595).

A compound having agonist activity at the orexin-2 receptor is hypothesized to be useful as a novel therapeutic agent for narcolepsy, idiopathic hypersomnia, hypersomnia, sleep apnea syndrome, disturbance of consciousness such as coma and the like, narcolepsy syndrome, hypersomnolence syndrome characterized by hypersomnia (e.g., in Parkinson's disease, Guillain-Barre syndrome or Kleine Levin syndrome), Alzheimer's disease, obesity, insulin resistance syndrome, cardiac failure, diseases related to bone loss, or sepsis and the like. (Cell Metabolism, Vol. 9, 64-76, 2009; Neuroscience, Vol. 121, 855-863, 2003; Respiration, Vol. 71, 575-579, 2004; Peptides, Vol. 23, 1683-1688, 2002; WO 2015/073707; Journal of the American College of Cardiology, Vol. 66, 2015, pages 2522-2533; WO 2015/048091; WO 2015/147240).

Some compounds having orexin-2 receptor agonist activity have been reported (U.S. Pat. No. 8,258,163; WO 2015/088000; WO 2014/198880; Journal of Medicinal Chemistry, Vol. 58, pages 7931-7937; US 20190040010; US 20190031611; US 20170226137). However, it is considered that these compounds are not satisfactory, for example, in terms of activity, pharmacokinetics, permeability into the brain/central nervous system or safety, and the development of an improved compound having orexin-2 receptor agonist activity is desired.

SUMMARY OF THE INVENTION

The present invention aims to provide substituted macrocyclic compounds having orexin-2 receptor agonist activity.

Accordingly, in an initial aspect, the present invention provides a compound represented by Formula I-A or a pharmaceutically acceptable salt thereof:

(I-A)

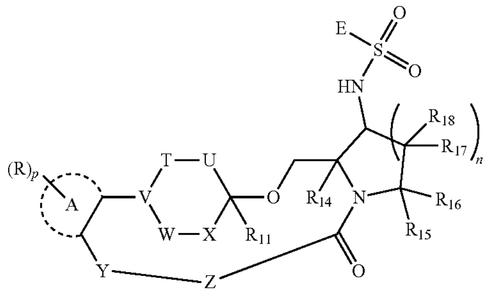

wherein:

ring A is selected from the group consisting of phenyl, pyridinyl, pyridazinyl, pyrimidinyl, pyrazinyl, and triazinyl;

n is 1, 2, or 3;

E is selected from the group consisting of $NR_aR_b$, $C_1$-$C_3$ alkylene-$NR_aR_b$, $C_1$-$C_3$ alkyl, $C_2$-$C_4$ alkenyl, $C_2$-$C_4$ alkynyl, $C_3$-$C_8$ cycloalkyl, $C_1$-$C_3$ alkylene-($C_3$-$C_8$ cycloalkyl), 4- to 10-membered heterocyclyl, $C_1$-$C_3$ alkylene-(4- to 10-membered heterocyclyl), $C_6$-$C_{10}$ aryl, $C_1$-$C_3$ alkylene-($C_6$-$C_{10}$ aryl), 5- to 10-membered heteroaryl, and $C_1$-$C_3$ alkylene-(5- to 10-membered heteroaryl), wherein the $C_1$-$C_3$ alkylene-$NR_aR_b$, $C_1$-$C_3$alkyl, $C_2$-$C_4$ alkenyl, $C_2$-$C_4$ alkynyl, $C_3$-$C_8$ cycloalkyl, $C_1$-$C_3$ alkylene-($C_3$-$C_8$ cycloalkyl), 4- to 10-membered heterocyclyl, $C_1$-$C_3$ alkylene-(4- to 10-membered heterocyclyl), $C_6$-$C_{10}$ aryl, $C_1$-$C_3$ alkylene-($C_6$-$C_{10}$ aryl), 5- to 10-membered heteroaryl, or $C_1$-$C_3$ alkylene-(5- to 10-membered heteroaryl) is unsubstituted or substituted with one or more halogen, hydroxyl, $C_1$-$C_3$ alkyl, or $C_1$-$C_3$ alkoxyl;

T is $CR_1R_2$ or O;

W is $CR_4R_5$ or O;

U is $CR_6R_7$;

X is $CR_8R_9$;

V is $CR_3$ or N;

Y is $NR_{10}$, O or absent;

Z is $(CR_{12}R_{13})_m$;

each R is, independently, selected from the group consisting of halogen, deuterium, hydroxyl, cyano, unsubstituted $C_1$-$C_3$ alkyl, and $C_1$-$C_3$ alkyl substituted with one or more halogen or deuterium;

p is 0, 1, 2, 3, or 4;

$R_a$ and $R_b$ are each, independently, H or unsubstituted $C_1$-$C_3$ alkyl;

m is 1, 2, 3, or 4;

and further wherein:

$R_1$, $R_2$, $R_4$, and $R_5$ are each, independently, selected from the group consisting of H, hydroxyl, halogen, and deuterium;

or, alternatively, $R_2$ and $R_5$ together with the carbon atoms to which they are attached, form a single bond;

$R_3$ is selected from the group consisting of H, deuterium, halogen, hydroxyl, and cyano;

or, alternatively, $R_3$ and $R_1$, together with the carbon atoms to which they are attached, form a $C_3$-$C_5$ cycloalkyl;

or, alternatively, $R_3$ and $R_4$, together with the carbon atoms to which they are attached, form a $C_3$-$C_5$ cycloalkyl;

$R_6$, $R_7$, $R_8$, $R_9$, and $R_{11}$ are each, independently, selected from the group consisting of H, hydroxyl, halogen, and deuterium;

$R_{10}$ is selected from the group consisting of H, unsubstituted $C_1$-$C_3$ alkyl, and $C_1$-$C_3$ alkyl substituted with one or more halogen;

each $R_{12}$ and $R_{13}$ is, independently, selected from the group consisting of H, halogen, deuterium, unsubstituted $C_1$-$C_3$ alkyl, and $C_1$-$C_3$ alkyl substituted with hydroxyl or one or more halogen; and $R_{14}$, $R_{15}$, and $R_{16}$ are each, independently, selected from the group consisting of H, unsubstituted $C_1$-$C_3$ alkyl or $C_1$-$C_3$ alkyl substituted with one or more halogen; and each $R_{17}$ and $R_{18}$ is, independently, selected from the group consisting of H, unsubstituted $C_1$-$C_3$ alkyl or $C_1$-$C_3$ alkyl substituted with one or more halogen;

with the proviso that one or more of (a)-(f) is present:

(a) at least one R is selected from the group consisting of hydroxyl, cyano, unsubstituted $C_1$-$C_3$ alkyl, and $C_1$-$C_3$ alkyl substituted with one or more halogen or deuterium;

(b) E is $NR_aR_b$, $C_1$-$C_3$ alkylene-$NR_aR_b$, $C_2$-$C_3$ alkyl, $C_2$-$C_4$ alkenyl, $C_2$-$C_4$ alkynyl, $C_3$-$C_8$ cycloalkyl, $C_1$-$C_3$ alkylene-($C_3$-$C_8$ cycloalkyl), 4- to 10-membered heterocyclyl, $C_1$-$C_3$ alkylene-(4- to 10-membered heterocyclyl), $C_6$-$C_{10}$ aryl, $C_1$-$C_3$ alkylene-($C_6$-$C_{10}$ aryl), 5- to 10-membered heteroaryl, or $C_1$-$C_3$ alkylene-(5- to 10-membered heteroaryl), wherein the $C_1$-$C_3$ alkylene-$NR_aR_b$, $C_2$-$C_3$ alkyl, $C_2$-$C_4$ alkenyl, $C_2$-$C_4$ alkynyl, $C_3$-$C_8$ cycloalkyl, $C_1$-$C_3$ alkylene-($C_3$-$C_8$ cycloalkyl), 4- to 10-membered heterocyclyl, $C_1$-$C_3$ alkylene-(4- to 10-membered heterocyclyl), $C_6$-$C_{10}$ aryl, $C_1$-$C_3$ alkylene-($C_6$-$C_{10}$ aryl), 5- to 10-membered heteroaryl, or $C_1$-$C_3$ alkylene-(5- to 10-membered heteroaryl) is unsubstituted or substituted with one or more halogen, hydroxyl, $C_1$-$C_3$ alkyl, or $C_1$-$C_3$ alkoxyl;

(c) E is $C_1$ alkyl substituted with one or more halogen, hydroxyl, $C_1$-$C_3$ alkyl, or $C_1$-$C_3$ alkoxyl;

(d) at least one of $R_{14}$, $R_{15}$, $R_{16}$, $R_{17}$, and $R_{18}$ is unsubstituted $C_1$-$C_3$ alkyl or $C_1$-$C_3$ alkyl substituted with one or more halogen;

(e) at least one of $R_1$, $R_2$, $R_4$, $R_5$, $R_6$, $R_7$, $R_8$, $R_9$, and $R_{11}$ is hydroxyl; or (f) at least one of $R_{12}$ and $R_{13}$ is $C_1$-$C_3$ alkyl substituted with hydroxyl.

In one embodiment, provided herein are compounds of Formula I-A having the structure of Formula I or a pharmaceutically acceptable salt thereof:

(I)

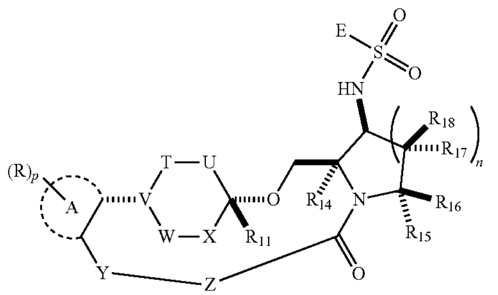

wherein:

ring A is selected from the group consisting of phenyl, pyridinyl, pyridazinyl, pyrimidinyl, pyrazinyl, and triazinyl;

n is 1, 2, or 3;

E is selected from the group consisting of $NR_aR_b$, $C_1$-$C_3$ alkylene-$NR_aR_b$, $C_1$-$C_3$ alkyl, $C_2$-$C_4$ alkenyl, $C_2$-$C_4$ alkynyl, $C_3$-$C_8$ cycloalkyl, $C_1$-$C_3$ alkylene-($C_3$-$C_8$ cycloalkyl), 4- to 10-membered heterocyclyl, $C_1$-$C_3$ alkylene-(4- to 10-membered heterocyclyl), $C_6$-$C_{10}$ aryl, $C_1$-$C_3$ alkylene-($C_6$-$C_{10}$ aryl), 5- to 10-membered heteroaryl, and $C_1$-$C_3$ alkylene-(5- to 10-membered heteroaryl), wherein the $C_1$-$C_3$ alkylene-$NR_aR_b$, $C_1$-$C_3$alkyl, $C_2$-$C_4$ alkenyl, $C_2$-$C_4$ alkynyl, $C_3$-$C_8$ cycloalkyl, $C_1$-$C_3$ alkylene-($C_3$-$C_8$ cycloalkyl), 4- to 10-membered heterocyclyl, $C_1$-$C_3$ alkylene-(4- to 10-membered heterocyclyl), $C_6$-$C_{10}$ aryl, $C_1$-$C_3$ alkylene-($C_6$-$C_{10}$ aryl), 5- to 10-membered heteroaryl, or $C_1$-$C_3$ alkylene-(5- to 10-membered heteroaryl) is unsubstituted or substituted with one or more halogen, hydroxyl, $C_1$-$C_3$ alkyl, or $C_1$-$C_3$ alkoxyl;

T is $CR_1R_2$ or O;

W is $CR_4R_5$ or O;

U is $CR_6R_7$;

X is $CR_8R_9$;

V is $CR_3$ or N;

Y is $NR_{10}$, O or absent;

Z is $(CR_{12}R_{13})_m$;

each R is, independently, selected from the group consisting of halogen, deuterium, hydroxyl, cyano, unsubstituted $C_1$-$C_3$ alkyl, and $C_1$-$C_3$ alkyl substituted with one or more halogen or deuterium;

p is 0, 1, 2, 3, or 4;

$R_a$ and $R_b$ are each, independently, H or unsubstituted $C_1$-$C_3$ alkyl;

m is 1, 2, 3, or 4;

and further wherein:

$R_1$, $R_2$, $R_4$, and $R_5$ are each, independently, selected from the group consisting of H, hydroxyl, halogen, and deuterium;

or, alternatively, $R_2$ and $R_5$ together with the carbon atoms to which they are attached, form a single bond;

$R_3$ is selected from the group consisting of H, deuterium, halogen, hydroxyl, and cyano;

or, alternatively, $R_3$ and $R_1$, together with the carbon atoms to which they are attached, form a $C_3$-$C_5$ cycloalkyl;

or, alternatively, $R_3$ and $R_4$, together with the carbon atoms to which they are attached, form a $C_3$-$C_5$ cycloalkyl;

$R_6$, $R_7$, $R_8$, $R_9$, and $R_{11}$ are each, independently, selected from the group consisting of H, hydroxyl, halogen, and deuterium;

$R_{10}$ is selected from the group consisting of H, unsubstituted $C_1$-$C_3$ alkyl, and $C_1$-$C_3$ alkyl substituted with one or more halogen;

each $R_{12}$ and $R_{13}$ is, independently, selected from the group consisting of H, halogen, deuterium, unsubstituted $C_1$-$C_3$ alkyl, and $C_1$-$C_3$ alkyl substituted with hydroxyl or one or more halogen; and $R_{14}$, $R_{15}$, and $R_{16}$ are each, independently, selected from the group consisting of H, unsubstituted $C_1$-$C_3$ alkyl or $C_1$-$C_3$ alkyl substituted with one or more halogen; and each $R_{17}$ and $R_{18}$ is, independently, selected from the group consisting of H, unsubstituted $C_1$-$C_3$ alkyl or $C_1$-$C_3$ alkyl substituted with one or more halogen;

with the proviso that one or more of (a)-(f) is present:

(a) at least one R is selected from the group consisting of hydroxyl, cyano, unsubstituted $C_1$-$C_3$ alkyl, and $C_1$-$C_3$ alkyl substituted with one or more halogen or deuterium;

(b) E is $NR_aR_b$, $C_1$-$C_3$ alkylene-$NR_aR_b$, $C_2$-$C_3$ alkyl, $C_2$-$C_4$ alkenyl, $C_2$-$C_4$ alkynyl, $C_3$-$C_8$ cycloalkyl, $C_1$-$C_3$ alkylene-($C_3$-$C_8$ cycloalkyl), 4- to 10-membered heterocyclyl, $C_1$-$C_3$ alkylene-(4- to 10-membered heterocyclyl), $C_6$-$C_{10}$ aryl, $C_1$-$C_3$ alkylene-($C_6$-$C_{10}$ aryl), 5- to 10-membered heteroaryl, or $C_1$-$C_3$ alkylene-(5- to 10-membered heteroaryl), wherein the $C_1$-$C_3$ alkylene-$NR_aR_b$, $C_2$-$C_3$ alkyl, $C_2$-$C_4$ alkenyl, $C_2$-$C_4$ alkynyl, $C_3$-$C_8$ cycloalkyl, $C_1$-$C_3$ alkylene-($C_3$-$C_8$ cycloalkyl), 4- to 10-membered heterocyclyl, $C_1$-$C_3$ alkylene-(4- to 10-membered heterocyclyl), $C_6$-$C_{10}$ aryl, $C_1$-$C_3$ alkylene-($C_6$-$C_{10}$ aryl), 5- to 10-membered heteroaryl, or $C_1$-$C_3$ alkylene-(5- to 10-membered heteroaryl) is unsubstituted or substituted with one or more halogen, hydroxyl, $C_1$-$C_3$ alkyl, or $C_1$-$C_3$ alkoxyl;

(c) E is $C_1$ alkyl substituted with one or more halogen, hydroxyl, $C_1$-$C_3$ alkyl, or $C_1$-$C_3$ alkoxyl;

(d) at least one of $R_{14}$, $R_{15}$, $R_{16}$, $R_{17}$, and $R_{18}$ is unsubstituted $C_1$-$C_3$ alkyl or $C_1$-$C_3$ alkyl substituted with one or more halogen;

(e) at least one of $R_1$, $R_2$, $R_4$, $R_5$, $R_6$, $R_7$, $R_8$, $R_9$, and $R_{11}$ is hydroxyl; or (f) at least one of $R_{12}$ and $R_{13}$ is $C_1$-$C_3$ alkyl substituted with hydroxyl.

Also provided herein is a compound having the structure of Formula II-A or a pharmaceutically acceptable salt thereof:

(II-A)

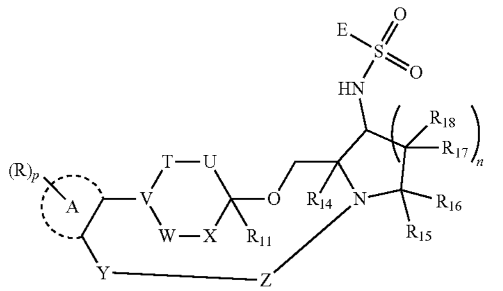

wherein:

ring A is selected from the group consisting of phenyl, pyridinyl, pyridazinyl, pyrimidinyl, pyrazinyl, and triazinyl;

n is 1, 2, or 3;

E is selected from the group consisting of $NR_aR_b$, $C_1$-$C_3$ alkylene-$NR_aR_b$, $C_1$-$C_3$ alkyl, $C_2$-$C_4$ alkenyl, $C_2$-$C_4$ alkynyl, $C_3$-$C_8$ cycloalkyl, $C_1$-$C_3$ alkylene-($C_3$-$C_8$ cycloalkyl), 4- to 10-membered heterocyclyl, $C_1$-$C_3$ alkylene-(4- to 10-membered heterocyclyl), $C_6$-$C_{10}$ aryl, $C_1$-$C_3$ alkylene-($C_6$-$C_{10}$ aryl), 5- to 10-membered heteroaryl, and $C_1$-$C_3$ alkylene-(5- to 10-membered heteroaryl), wherein the $C_1$-$C_3$ alkylene-$NR_aR_b$, $C_1$-$C_3$alkyl, $C_2$-$C_4$ alkenyl, $C_2$-$C_4$ alkynyl, $C_3$-$C_8$ cycloalkyl, $C_1$-$C_3$ alkylene-($C_3$-$C_8$ cycloalkyl), 4- to 10-membered heterocyclyl, $C_1$-$C_3$ alkylene-(4- to 10-membered heterocyclyl), $C_6$-$C_{10}$ aryl, $C_1$-$C_3$ alkylene-($C_6$-$C_{10}$ aryl), 5- to 10-membered heteroaryl, or $C_1$-$C_3$ alkylene-(5- to 10-membered heteroaryl) is unsubstituted or substituted with one or more halogen, hydroxyl, $C_1$-$C_3$ alkyl, or $C_1$-$C_3$ alkoxyl;

T is $CR_1R_2$ or O;

W is $CR_4R_5$ or O;

U is $CR_6R_7$;

X is $CR_8R_9$;

V is $CR_3$ or N;

Y is $NR_{10}$, O or absent;

Z is $(CR_{12}R_{13})_m$;

each R is, independently, selected from the group consisting of halogen, deuterium, hydroxyl, cyano, unsubstituted $C_1$-$C_3$ alkyl, and $C_1$-$C_3$ alkyl substituted with one or more halogen or deuterium;

p is 0, 1, 2, 3, or 4;

$R_a$ and $R_b$ are each, independently, H or unsubstituted $C_1$-$C_3$ alkyl;

m is 2, 3, 4, or 5 when Y is absent; or m is 1, 2, 3, or 4 when Y is $NR_{10}$ or 0;

and further wherein:

$R_1$, $R_2$, $R_4$, and $R_5$ are each, independently, selected from the group consisting of H, hydroxyl, halogen, and deuterium;

or, alternatively, $R_2$ and $R_5$ together with the carbon atoms to which they are attached, form a single bond;

$R_3$ is selected from the group consisting of H, deuterium, halogen, hydroxyl, and cyano;

or, alternatively, $R_3$ and $R_1$, together with the carbon atoms to which they are attached, form a $C_3$-$C_5$ cycloalkyl;

or, alternatively, $R_3$ and $R_4$, together with the carbon atoms to which they are attached, form a $C_3$-$C_5$ cycloalkyl;

$R_6$, $R_7$, $R_8$, $R_9$, and $R_{11}$ are each, independently, selected from the group consisting of H, hydroxyl, halogen, and deuterium;

$R_{10}$ is selected from the group consisting of H, unsubstituted $C_1$-$C_3$ alkyl, and $C_1$-$C_3$ alkyl substituted with one or more halogen;

each $R_{12}$ and $R_{13}$ is, independently, selected from the group consisting of H, halogen, deuterium, unsubstituted $C_1$-$C_3$ alkyl, and $C_1$-$C_3$ alkyl substituted with hydroxyl or one or more halogen; and $R_{14}$, $R_{15}$, and $R_{16}$ are each, independently, selected from the group consisting of H, unsubstituted $C_1$-$C_3$ alkyl or $C_1$-$C_3$ alkyl substituted with one or more halogen; and each $R_{17}$ and $R_{18}$ is, independently, selected from the group consisting of H, unsubstituted $C_1$-$C_3$ alkyl or $C_1$-$C_3$ alkyl substituted with one or more halogen;

with the proviso that one or more of (a)-(f) is present:

(a) at least one R is selected from the group consisting of hydroxyl, cyano, unsubstituted $C_1$-$C_3$ alkyl, and $C_1$-$C_3$ alkyl substituted with one or more halogen or deuterium;

(b) E is $NR_aR_b$, $C_1$-$C_3$ alkylene-$NR_aR_b$, $C_2$-$C_3$ alkyl, $C_2$-$C_4$ alkenyl, $C_2$-$C_4$ alkynyl, $C_3$-$C_8$ cycloalkyl, $C_1$-$C_3$ alkylene-($C_3$-$C_8$ cycloalkyl), 4- to 10-membered heterocyclyl, $C_1$-$C_3$ alkylene-(4- to 10-membered heterocyclyl), $C_6$-$C_{10}$ aryl, $C_1$-$C_3$ alkylene-($C_6$-$C_{10}$ aryl), 5- to 10-membered heteroaryl, or $C_1$-$C_3$ alkylene-(5- to 10-membered heteroaryl), wherein the $C_1$-$C_3$ alkylene-$NR_aR_b$, $C_2$-$C_3$ alkyl, $C_2$-$C_4$ alkenyl, $C_2$-$C_4$ alkynyl, $C_3$-$C_8$ cycloalkyl, $C_1$-$C_3$ alkylene-($C_3$-$C_8$ cycloalkyl), 4- to 10-membered heterocyclyl, $C_1$-$C_3$ alkylene-(4- to 10-membered heterocyclyl), $C_6$-$C_{10}$ aryl, $C_1$-$C_3$ alkylene-($C_6$-$C_{10}$ aryl), 5- to 10-membered heteroaryl, or $C_1$-$C_3$ alkylene-(5- to 10-membered heteroaryl) is unsubstituted or substituted with one or more halogen, hydroxyl, $C_1$-$C_3$ alkyl, or $C_1$-$C_3$ alkoxyl;

(c) E is $C_1$ alkyl substituted with one or more halogen, hydroxyl, $C_1$-$C_3$ alkyl, or $C_1$-$C_3$ alkoxyl;

(d) at least one of $R_{14}$, $R_{15}$, $R_{16}$, $R_{17}$, and $R_{18}$ is unsubstituted $C_1$-$C_3$ alkyl or $C_1$-$C_3$ alkyl substituted with one or more halogen;

(e) at least one of $R_1$, $R_2$, $R_4$, $R_5$, $R_6$, $R_7$, $R_8$, $R_9$, and $R_{11}$ is hydroxyl; or (f) at least one of $R_{12}$ and $R_{13}$ is $C_1$-$C_3$ alkyl substituted with hydroxyl.

In one embodiment, provided herein are compounds of Formula II-A having the structure of Formula II or a pharmaceutically acceptable salt thereof:

(II)

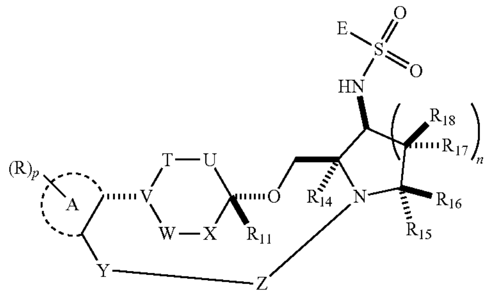

wherein:

ring A is selected from the group consisting of phenyl, pyridinyl, pyridazinyl, pyrimidinyl, pyrazinyl, and triazinyl;

n is 1, 2, or 3;

E is selected from the group consisting of $NR_aR_b$, $C_1$-$C_3$ alkylene-$NR_aR_b$, $C_1$-$C_3$ alkyl, $C_2$-$C_4$ alkenyl, $C_2$-$C_4$ alkynyl, $C_3$-$C_8$ cycloalkyl, $C_1$-$C_3$ alkylene-($C_3$-$C_8$ cycloalkyl), 4- to 10-membered heterocyclyl, $C_1$-$C_3$ alkylene-(4- to 10-membered heterocyclyl), $C_6$-$C_{10}$ aryl, $C_1$-$C_3$ alkylene-($C_6$-$C_{10}$ aryl), 5- to 10-membered heteroaryl, and $C_1$-$C_3$ alkylene-(5- to 10-membered heteroaryl), wherein the $C_1$-$C_3$ alkylene-$NR_aR_b$, $C_1$-$C_3$alkyl, $C_2$-$C_4$ alkenyl, $C_2$-$C_4$ alkynyl, $C_3$-$C_8$ cycloalkyl, $C_1$-$C_3$ alkylene-($C_3$-$C_8$ cycloalkyl), 4- to 10-membered heterocyclyl, $C_1$-$C_3$ alkylene-(4- to 10-membered heterocyclyl), $C_6$-$C_{10}$ aryl, $C_1$-$C_3$ alkylene-($C_6$-$C_{10}$ aryl), 5- to 10-membered heteroaryl, or $C_1$-$C_3$ alkylene-(5- to 10-membered heteroaryl) is unsubstituted or substituted with one or more halogen, hydroxyl, $C_1$-$C_3$ alkyl, or $C_1$-$C_3$ alkoxyl;

T is $CR_1R_2$ or O;

W is $CR_4R_5$ or O;

U is $CR_6R_7$;

X is $CR_8R_9$;

V is $CR_3$ or N;

Y is $NR_{10}$, O or absent;

Z is $(CR_{12}R_{13})_m$;

each R is, independently, selected from the group consisting of halogen, deuterium, hydroxyl, cyano, unsubstituted $C_1$-$C_3$ alkyl, and $C_1$-$C_3$ alkyl substituted with one or more halogen or deuterium;

p is 0, 1, 2, 3, or 4;

$R_a$ and $R_b$ are each, independently, H or unsubstituted $C_1$-$C_3$ alkyl;

m is 2, 3, 4, or 5 when Y is absent; or m is 1, 2, 3, or 4 when Y is $NR_{10}$ or 0;

and further wherein:

$R_1$, $R_2$, $R_4$, and $R_5$ are each, independently, selected from the group consisting of H, hydroxyl, halogen, and deuterium;

or, alternatively, $R_2$ and $R_5$ together with the carbon atoms to which they are attached, form a single bond;

$R_3$ is selected from the group consisting of H, deuterium, halogen, hydroxyl, and cyano;

or, alternatively, $R_3$ and $R_1$, together with the carbon atoms to which they are attached, form a $C_3$-$C_5$ cycloalkyl;

or, alternatively, $R_3$ and $R_4$, together with the carbon atoms to which they are attached, form a $C_3$-$C_5$ cycloalkyl;

$R_6$, $R_7$, $R_8$, $R_9$, and $R_{11}$ are each, independently, selected from the group consisting of H, hydroxyl, halogen, and deuterium;

$R_{10}$ is selected from the group consisting of H, unsubstituted $C_1$-$C_3$ alkyl, and $C_1$-$C_3$ alkyl substituted with one or more halogen;

each $R_{12}$ and $R_{13}$ is, independently, selected from the group consisting of H, halogen, deuterium, unsubstituted $C_1$-$C_3$ alkyl, and $C_1$-$C_3$ alkyl substituted with hydroxyl or one or more halogen; and $R_{14}$, $R_{15}$, and $R_{16}$ are each, independently, selected from the group consisting of H, unsubstituted $C_1$-$C_3$ alkyl or $C_1$-$C_3$ alkyl substituted with one or more halogen; and each $R_{17}$ and $R_{18}$ is, independently, selected from the group consisting of H, unsubstituted $C_1$-$C_3$ alkyl or $C_1$-$C_3$ alkyl substituted with one or more halogen;

with the proviso that one or more of (a)-(f) is present:

(a) at least one R is selected from the group consisting of hydroxyl, cyano, unsubstituted $C_1$-$C_3$ alkyl, and $C_1$-$C_3$ alkyl substituted with one or more halogen or deuterium;

(b) E is $NR_aR_b$, $C_1$-$C_3$ alkylene-$NR_aR_b$, $C_2$-$C_3$ alkyl, $C_2$-$C_4$ alkenyl, $C_2$-$C_4$ alkynyl, $C_3$-$C_8$ cycloalkyl, $C_1$-$C_3$ alkylene-($C_3$-$C_8$ cycloalkyl), 4- to 10-membered heterocyclyl, $C_1$-$C_3$ alkylene-(4- to 10-membered heterocyclyl), $C_6$-$C_{10}$ aryl, $C_1$-$C_3$ alkylene-($C_6$-$C_{10}$ aryl), 5- to 10-membered heteroaryl, or $C_1$-$C_3$ alkylene-(5- to 10-membered heteroaryl), wherein the $C_1$-$C_3$ alkylene-$NR_aR_b$, $C_2$-$C_3$ alkyl, $C_2$-$C_4$ alkenyl, $C_2$-$C_4$ alkynyl, $C_3$-$C_8$ cycloalkyl, $C_1$-$C_3$ alkylene-($C_3$-$C_8$ cycloalkyl), 4- to 10-membered heterocyclyl, $C_1$-$C_3$ alkylene-(4- to 10-membered heterocyclyl), $C_6$-$C_{10}$ aryl, $C_1$-$C_3$ alkylene-($C_6$-$C_{10}$ aryl), 5- to 10-membered heteroaryl, or $C_1$-$C_3$ alkylene-(5- to 10-membered heteroaryl) is unsubstituted or substituted with one or more halogen, hydroxyl, $C_1$-$C_3$ alkyl, or $C_1$-$C_3$ alkoxyl;

(c) E is $C_1$ alkyl substituted with one or more halogen, hydroxyl, $C_1$-$C_3$ alkyl, or $C_1$-$C_3$ alkoxyl;

(d) at least one of $R_{14}$, $R_{15}$, $R_{16}$, $R_{17}$, and $R_{18}$ is unsubstituted $C_1$-$C_3$ alkyl or $C_1$-$C_3$ alkyl substituted with one or more halogen;

(e) at least one of $R_1$, $R_2$, $R_4$, $R_5$, $R_6$, $R_7$, $R_8$, $R_9$, and $R_{11}$ is hydroxyl; or (f) at least one of $R_{12}$ and $R_{13}$ is $C_1$-$C_3$ alkyl substituted with hydroxyl.

Also provided herein is a pharmaceutical composition comprising a compound of any of Formula I-A, I, II-A, or II, or a pharmaceutically acceptable salt thereof, and a pharmaceutically acceptable carrier.

In another aspect, provided herein is a method of treating narcolepsy in a subject in need thereof comprising administering to the subject a compound of Formula I-A, I, II-A, or II, or a pharmaceutically acceptable salt thereof.

In another aspect, provided herein is a method of treating cataplexy in a subject in need thereof comprising administering to the subject a compound of Formula I-A, I, II-A, or II, or a pharmaceutically acceptable salt thereof.

DETAILED DESCRIPTION OF THE INVENTION

Provided herein are compounds, e.g., the compounds of Formula I-A, I, II-A, or II, or pharmaceutically acceptable salts thereof, that are useful in the treatment of narcolepsy or cataplexy in a subject.

In a non-limiting aspect, these compounds may modulate the orexin-2 receptor. In a particular embodiment, the compounds provided herein are considered orexin-2 agonists. As such, in one aspect, the compounds provided herein are useful in treatment of narcolepsy in a subject by acting as an agonist of the orexin-2 receptor.

Definitions

Listed below are definitions of various terms used to describe this invention. These definitions apply to the terms as they are used throughout this specification and claims, unless otherwise limited in specific instances, either individually or as part of a larger group.

Unless defined otherwise, all technical and scientific terms used herein generally have the same meaning as commonly understood by one of ordinary skill in the art to which this invention belongs. Generally, the nomenclature used herein and the laboratory procedures in cell culture, molecular genetics, organic chemistry, and peptide chemistry are those well-known and commonly employed in the art.

As used herein, the articles "a" and "an" refer to one or to more than one (i.e., to at least one) of the grammatical object of the article. By way of example, "an element" means one element or more than one element. Furthermore, use of the term "including" as well as other forms, such as "include," "includes," and "included," is not limiting.

As used herein, the term "about" will be understood by persons of ordinary skill in the art and will vary to some extent on the context in which it is used. As used herein when referring to a measurable value such as an amount, a temporal duration, and the like, the term "about" is meant to encompass variations of ±20% or ±10%, including ±5%, ±1%, and ±0.1% from the specified value, as such variations are appropriate to perform the disclosed methods.

As used to herein, the term "$EC_{50}$" refers to the concentration of a compound required to achieve an effect that is 50% of the maximal observed effect of a compound.

The term "agonist," as used herein, refers to a compound that, when contacted with a target of interest (e.g., the orexin-2 receptor), causes an increase in the magnitude of a certain activity or function of the target compared to the magnitude of the activity or function observed in the absence of the agonist.

The term "treat," "treated," "treating," or "treatment" includes the diminishment or alleviation of at least one symptom associated or caused by the state, disorder or disease being treated. In certain embodiments, the treatment comprises bringing into contact with the orexin-2 receptor an effective amount of a compound of the invention for conditions related to narcolepsy or cataplexy.

As used herein, the term "prevent" or "prevention" means no disorder or disease development if none had occurred, or no further disorder or disease development if there had already been development of the disorder or disease. Also considered is the ability of one to prevent some or all of the symptoms associated with the disorder or disease.

As used herein, the term "patient," "individual" or "subject" refers to a human or a non-human mammal. Non-human mammals include, for example, livestock and pets, such as ovine, bovine, porcine, canine, feline and murine mammals. Preferably, the patient, subject, or individual is human.

As used herein, the terms "effective amount," "pharmaceutically effective amount," and "therapeutically effective amount" refer to a nontoxic but sufficient amount of an agent to provide the desired biological result. That result may be reduction or alleviation of the signs, symptoms, or causes of a disease, or any other desired alteration of a biological system. An appropriate therapeutic amount in any individual case may be determined by one of ordinary skill in the art using routine experimentation.

As used herein, the term "pharmaceutically acceptable" refers to a material, such as a carrier or diluent, which does not abrogate the biological activity or properties of the compound, and is relatively non-toxic, i.e., the material may be administered to an individual without causing undesirable biological effects or interacting in a deleterious manner with any of the components of the composition in which it is contained.

As used herein, the term "pharmaceutically acceptable salt" refers to derivatives of the disclosed compounds wherein the parent compound is modified by converting an existing acid or base moiety to its salt form. Examples of pharmaceutically acceptable salts include, but are not limited to, mineral or organic acid salts of basic residues such as amines; alkali or organic salts of acidic residues such as carboxylic acids; and the like. The pharmaceutically acceptable salts of the present invention include the conventional non-toxic salts of the parent compound formed, for example, from non-toxic inorganic or organic acids. The pharmaceutically acceptable salts of the present invention can be synthesized from the parent compound which contains a basic or acidic moiety by conventional chemical methods. Generally, such salts can be prepared by reacting the free acid or base forms of these compounds with a stoichiometric amount of the appropriate base or acid in water or in an organic solvent, or in a mixture of the two; generally, nonaqueous media like ether, ethyl acetate, ethanol, isopropanol, or acetonitrile are preferred. The phrase "pharmaceutically acceptable salt" is not limited to a mono, or 1:1, salt. For example, "pharmaceutically acceptable salt" also includes bis-salts, such as a bis-hydrochloride salt. Lists of suitable salts are found in Remington's Pharmaceutical Sciences, 17th ed., Mack Publishing Company, Easton, Pa., 1985, p. 1418 and Journal of Pharmaceutical Science, 66, 2 (1977), each of which is incorporated herein by reference in its entirety.

As used herein, the term "composition" or "pharmaceutical composition" refers to a mixture of at least one compound useful within the invention with a pharmaceutically acceptable carrier. The pharmaceutical composition facilitates administration of the compound to a patient or subject. Multiple techniques of administering a compound exist in the art including, but not limited to, intravenous, oral, aerosol, parenteral, ophthalmic, pulmonary, and topical administration.

As used herein, the term "pharmaceutically acceptable carrier" means a pharmaceutically acceptable material, composition or carrier, such as a liquid or solid filler, stabilizer, dispersing agent, suspending agent, diluent, excipient, thickening agent, solvent or encapsulating material, involved in carrying or transporting a compound useful within the invention within or to the patient such that it may perform its intended function. Typically, such constructs are carried or transported from one organ, or portion of the body, to another organ, or portion of the body. Each carrier must be "acceptable" in the sense of being compatible with the other ingredients of the formulation, including the compound useful within the invention, and not injurious to the patient. Some examples of materials that may serve as pharmaceutically acceptable carriers include: sugars, such as lactose, glucose and sucrose; starches, such as corn starch and potato starch; cellulose, and its derivatives, such as sodium carboxymethyl cellulose, ethyl cellulose and cellulose acetate; powdered tragacanth; malt; gelatin; talc; excipients, such as cocoa butter and suppository waxes; oils, such as peanut oil, cottonseed oil, safflower oil, sesame oil, olive oil, corn oil and soybean oil; glycols, such as propylene glycol; polyols, such as glycerin, sorbitol, mannitol and polyethylene glycol; esters, such as ethyl oleate and ethyl laurate; agar; buffering agents, such as magnesium hydroxide and aluminum hydroxide; surface active agents; alginic acid; pyrogen-free water; isotonic saline; Ringer's solution; ethyl alcohol; phosphate buffer solutions; and other non-toxic compatible substances employed in pharmaceutical formulations.

As used herein, "pharmaceutically acceptable carrier" also includes any and all coatings, antibacterial and antifungal agents, and absorption delaying agents, and the like that are compatible with the activity of the compound useful within the invention and are physiologically acceptable to the patient. Supplementary active compounds may also be incorporated into the compositions. The "pharmaceutically acceptable carrier" may further include a pharmaceutically acceptable salt of the compound useful within the invention. Other additional ingredients that may be included in the pharmaceutical compositions used in the practice of the invention are known in the art and described, for example in Remington's Pharmaceutical Sciences (Genaro, Ed., Mack Publishing Co., 1985, Easton, PA), which is incorporated herein by reference.

As used herein, the term "alkyl," by itself or as part of another substituent means, unless otherwise stated, a straight or branched chain hydrocarbon having the number of carbon atoms designated (i.e., $C_{1-6}$ alkyl means an alkyl having one to six carbon atoms) and includes straight and branched chains. Examples include methyl, ethyl, propyl, isopropyl, butyl, isobutyl, tert-butyl, pentyl, neopentyl, and hexyl. Other examples of $C_1$-$C_6$-alkyl include ethyl, methyl, isopropyl, isobutyl, n-pentyl, and n-hexyl.

As used herein, the term "halo" or "halogen" alone or as part of another substituent means, unless otherwise stated, a fluorine, chlorine, bromine, or iodine atom, preferably, fluorine, chlorine, or bromine, more preferably, fluorine or chlorine.

As used herein, the term "alkylene" refers to divalent aliphatic hydrocarbyl groups, for example, having from 1 to 4 carbon atoms that are either straight-chained or branched. This term includes, by way of example, methylene ($—CH_2—$), ethylene ($—CH_2CH_2—$), n-propylene ($—CH_2CH_2CH_2—$), iso-propylene ($—CH_2CH(CH_3)—$), and the like.

As used herein, the term "alkenyl" denotes a monovalent group derived from a hydrocarbon moiety containing at least two carbon atoms and at least one carbon-carbon double bond. The double bond may or may not be the point of attachment to another group. Alkenyl groups (e.g., $C_2$-$C_8$-alkenyl) include, but are not limited to, for example, ethenyl, propenyl, prop-1-en-2-yl, butenyl, 1-methyl-2-buten-1-yl, heptenyl, octenyl and the like.

As used herein, the term "alkynyl" denotes a monovalent group derived from a hydrocarbon moiety containing at least two carbon atoms and at least one carbon-carbon triple bond. The triple bond may or may not be the point of attachment to another group. Alkynyl groups (e.g., $C_2$-$C_8$-alkynyl) include, but are not limited to, for example, ethynyl, propynyl, prop-1-yn-2-yl, butynyl, 1-methyl-2-butyn-1-yl, heptynyl, octynyl and the like.

As used herein, the term "alkoxy," refers to the group —O-alkyl, wherein alkyl is as defined herein. Alkoxy includes, by way of example, methoxy, ethoxy, n-propoxy, isopropoxy, n-butoxy, sec-butoxy, t-butoxy and the like.

As used herein, the term "cycloalkyl" means a non-aromatic carbocyclic system that is partially or fully saturated having 1, 2 or 3 rings wherein such rings may be fused. The term "fused" means that a second ring is present (i.e., attached or formed) by having two adjacent atoms in common (i.e., shared) with the first ring. Cycloalkyl also includes bicyclic structures that may be bridged or spirocyclic in nature with each individual ring within the bicycle varying from 3-8 atoms. The term "cycloalkyl" includes, but is not limited to, cyclopropyl, cyclobutyl, cyclopentyl, cyclohexyl, bicyclo[3.1.0]hexyl, spiro[3.3]heptanyl, and bicyclo[1.1.1]pentyl.

As used herein, the term "heterocyclyl" means a non-aromatic carbocyclic system containing 1, 2, 3 or 4 heteroatoms selected independently from N, O, and S and having 1, 2 or 3 rings wherein such rings may be fused, wherein fused is defined above. Heterocyclyl also includes bicyclic structures that may be bridged or spirocyclic in nature with each individual ring within the bicycle varying from 3-8 atoms, and containing 0, 1, or 2 N, O, or S atoms. The term "heterocyclyl" includes cyclic esters (i.e., lactones) and cyclic amides (i.e., lactams) and also specifically includes, but is not limited to, epoxidyl, oxetanyl, tetrahydrofuranyl, tetrahydropyranyl (i.e., oxanyl), pyranyl, dioxanyl, aziridinyl, azetidinyl, pyrrolidinyl, 2,5-dihydro-1H-pyrrolyl, oxazolidinyl, thiazolidinyl, piperidinyl, morpholinyl, piperazinyl, thiomorpholinyl, 1,3-oxazinanyl, 1,3-thiazinanyl, and the like. For example, the term "heterocyclyl" can include 4- to 10-membered heterocyclyl, 4- to 7-membered heterocyclyl, 5- to 10-membered heterocyclyl, 6- to 10-membered heterocyclyl, 4- to 6-membered heterocyclyl, 4-membered heterocyclyl, 5-membered heterocyclyl, 6-membered heterocyclyl, 7-membered heterocyclyl, 8-membered heterocyclyl, 9-membered heterocyclyl, or 10-membered heterocyclyl.

As used herein, the term "aromatic" refers to a carbocycle or heterocycle with one or more polyunsaturated rings and having aromatic character, i.e., having (4n+2) delocalized π (pi) electrons, where n is an integer.

As used herein, the term "aryl" means an aromatic carbocyclic system containing 1, 2 or 3 rings, wherein such rings may be fused, wherein fused is defined above. If the rings are fused, one of the rings must be fully unsaturated and the fused ring(s) may be fully saturated, partially unsaturated or fully unsaturated. The term "aryl" includes, but is not limited to, phenyl, naphthyl, indanyl, and 1,2,3,4-tetrahydronaphthalenyl. For example, the term "aryl" can include $C_6$-$C_{10}$ aryl, $C_6$-$C_8$ aryl, or $C_6$ aryl (i.e., phenyl).

As used herein, the term "heteroaryl" means an aromatic carbocyclic system containing 1, 2, 3, or 4 heteroatoms selected independently from N, O, and S and having 1, 2, or 3 rings wherein such rings may be fused, wherein fused is defined above. The term "heteroaryl" includes, but is not limited to, furanyl, thiophenyl, oxazolyl, thiazolyl, imidazolyl, pyrazolyl, triazolyl, tetrazolyl, isoxazolyl, isothiazolyl, oxadiazolyl, thiadiazolyl, pyridinyl, pyridazinyl, pyrimidinyl, pyrazinyl and the like. For example, the term "heteroaryl" can include 5- to 10-membered heteroaryl, 5- to 8-membered heteroaryl, 5- to 6-membered heteroaryl, 6- to 10-membered heteroaryl, 6- to 8-membered heteroaryl, 5-membered heteroaryl, 6-membered heteroaryl, 7-membered heteroaryl, 8-membered heteroaryl, 9-membered heteroaryl, or 10-membered heteroaryl.

It is to be understood that if an aryl, heteroaryl, cycloalkyl, or heterocyclyl moiety may be bonded or otherwise attached to a designated moiety through differing ring atoms (i.e., shown or described without denotation of a specific point of attachment), then all possible points are intended, whether through a carbon atom or, for example, a trivalent nitrogen atom. For example, the term "pyridinyl" means 2-, 3- or 4-pyridinyl, the term "thiophenyl" means 2- or 3-thiophenyl, and so forth.

As used herein, the term "substituted" means that an atom or group of atoms has replaced hydrogen as the substituent attached to another group.

Compounds of the Invention

Accordingly, in an initial aspect, the present invention provides a compound represented by Formula I-A or a pharmaceutically acceptable salt thereof:

(I-A)

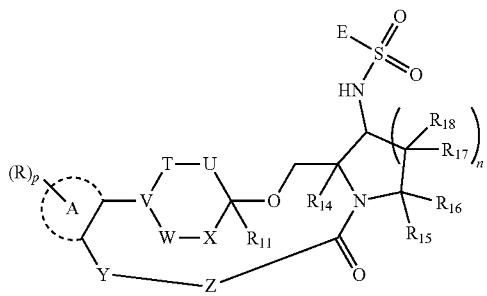

wherein:

ring A is selected from the group consisting of phenyl, pyridinyl, pyridazinyl, pyrimidinyl, pyrazinyl, and triazinyl;

n is 1, 2, or 3;

E is selected from the group consisting of $NR_aR_b$, $C_1$-$C_3$ alkylene-$NR_aR_b$, $C_1$-$C_3$ alkyl, $C_2$-$C_4$ alkenyl, $C_2$-$C_4$ alkynyl, $C_3$-$C_8$ cycloalkyl, $C_1$-$C_3$ alkylene-($C_3$-$C_8$ cycloalkyl), 4- to 10-membered heterocyclyl, $C_1$-$C_3$ alkylene-(4- to 10-membered heterocyclyl), $C_6$-$C_{10}$ aryl, $C_1$-$C_3$ alkylene-($C_6$-$C_{10}$ aryl), 5- to 10-membered heteroaryl, and $C_1$-$C_3$ alkylene-(5- to 10-membered heteroaryl), wherein the $C_1$-$C_3$ alkylene-$NR_aR_b$, $C_1$-$C_3$alkyl, $C_2$-$C_4$ alkenyl, $C_2$-$C_4$ alkynyl, $C_3$-$C_8$ cycloalkyl, $C_1$-$C_3$ alkylene-($C_3$-$C_8$ cycloalkyl), 4- to 10-membered heterocyclyl, $C_1$-$C_3$ alkylene-(4- to 10-membered heterocyclyl), $C_6$-$C_{10}$ aryl, $C_1$-$C_3$ alkylene-($C_6$-$C_{10}$ aryl), 5- to 10-membered heteroaryl, or $C_1$-$C_3$ alkylene-(5- to 10-membered heteroaryl) is unsubstituted or substituted with one or more halogen, hydroxyl, $C_1$-$C_3$ alkyl, or $C_1$-$C_3$ alkoxyl;

T is $CR_1R_2$ or O;

W is $CR_4R_5$ or O;

U is $CR_6R_7$;

X is $CR_8R_9$;

V is $CR_3$ or N;

Y is $NR_{10}$, O or absent;

Z is $(CR_{12}R_{13})_m$;

each R is, independently, selected from the group consisting of halogen, deuterium, hydroxyl, cyano, unsubstituted $C_1$-$C_3$ alkyl, and $C_1$-$C_3$ alkyl substituted with one or more halogen or deuterium;

p is 0, 1, 2, 3, or 4;

$R_a$ and $R_b$ are each, independently, H or unsubstituted $C_1$-$C_3$ alkyl;

m is 1, 2, 3, or 4;

and further wherein:

$R_1$, $R_2$, $R_4$, and $R_5$ are each, independently, selected from the group consisting of H, hydroxyl, halogen, and deuterium;

or, alternatively, $R_2$ and $R_5$ together with the carbon atoms to which they are attached, form a single bond;

$R_3$ is selected from the group consisting of H, deuterium, halogen, hydroxyl, and cyano;

or, alternatively, $R_3$ and $R_1$, together with the carbon atoms to which they are attached, form a $C_3$-$C_5$ cycloalkyl;

or, alternatively, $R_3$ and $R_4$, together with the carbon atoms to which they are attached, form a $C_3$-$C_5$ cycloalkyl;

$R_6$, $R_7$, $R_8$, $R_9$, and $R_{11}$ are each, independently, selected from the group consisting of H, hydroxyl, halogen, and deuterium;

$R_{10}$ is selected from the group consisting of H, unsubstituted $C_1$-$C_3$ alkyl, and $C_1$-$C_3$ alkyl substituted with one or more halogen;

each $R_{12}$ and $R_{13}$ is, independently, selected from the group consisting of H, halogen, deuterium, unsubstituted $C_1$-$C_3$ alkyl, and $C_1$-$C_3$ alkyl substituted with hydroxyl or one or more halogen; and $R_{14}$, $R_{15}$, and $R_{16}$ are each, independently, selected from the group consisting of H, unsubstituted $C_1$-$C_3$ alkyl or $C_1$-$C_3$ alkyl substituted with one or more halogen; and each $R_{17}$ and $R_{18}$ is, independently, selected from the group consisting of H, unsubstituted $C_1$-$C_3$ alkyl or $C_1$-$C_3$ alkyl substituted with one or more halogen;

with the proviso that one or more of (a)-(f) is present:

(a) at least one R is selected from the group consisting of hydroxyl, cyano, unsubstituted $C_1$-$C_3$ alkyl, and $C_1$-$C_3$ alkyl substituted with one or more halogen or deuterium;

(b) E is $NR_aR_b$, $C_1$-$C_3$ alkylene-$NR_aR_b$, $C_2$-$C_3$ alkyl, $C_2$-$C_4$ alkenyl, $C_2$-$C_4$ alkynyl, $C_3$-$C_8$ cycloalkyl, $C_1$-$C_3$ alkylene-($C_3$-$C_8$ cycloalkyl), 4- to 10-membered heterocyclyl, $C_1$-$C_3$ alkylene-(4- to 10-membered heterocyclyl), $C_6$-$C_{10}$ aryl, $C_1$-$C_3$ alkylene-($C_6$-$C_{10}$ aryl), 5- to 10-membered heteroaryl, or $C_1$-$C_3$ alkylene-(5- to 10-membered heteroaryl), wherein the $C_1$-$C_3$ alkylene-$NR_aR_b$, $C_2$-$C_3$ alkyl, $C_2$-$C_4$ alkenyl, $C_2$-$C_4$ alkynyl, $C_3$-$C_8$ cycloalkyl, $C_1$-$C_3$ alkylene-($C_3$-$C_8$ cycloalkyl), 4- to 10-membered heterocyclyl, $C_1$-$C_3$ alkylene-(4- to 10-membered heterocyclyl), $C_6$-$C_{10}$ aryl, $C_1$-$C_3$ alkylene-($C_6$-$C_{10}$ aryl), 5- to 10-membered heteroaryl, or $C_1$-$C_3$ alkylene-(5- to 10-membered heteroaryl) is unsubstituted or substituted with one or more halogen, hydroxyl, $C_1$-$C_3$ alkyl, or $C_1$-$C_3$ alkoxyl;

(c) E is $C_1$ alkyl substituted with one or more halogen, hydroxyl, $C_1$-$C_3$ alkyl, or $C_1$-$C_3$ alkoxyl;

(d) at least one of $R_{14}$, $R_{15}$, $R_{16}$, $R_{17}$, and $R_{18}$ is unsubstituted $C_1$-$C_3$ alkyl or $C_1$-$C_3$ alkyl substituted with one or more halogen;

(e) at least one of $R_1$, $R_2$, $R_4$, $R_5$, $R_6$, $R_7$, $R_8$, $R_9$, and $R_{11}$ is hydroxyl; or (f) at least one of $R_{12}$ and $R_{13}$ is $C_1$-$C_3$ alkyl substituted with hydroxyl.

In one embodiment, provided herein is a compound of Formula I-A having the structure of Formula I or a pharmaceutically acceptable salt thereof:

(I)

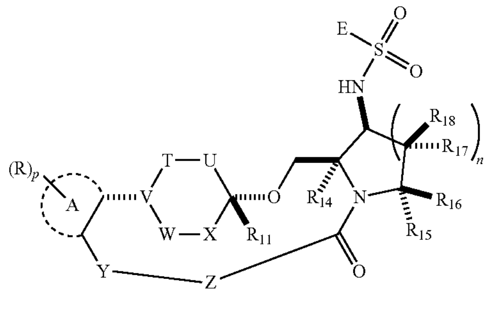

wherein:

ring A is selected from the group consisting of phenyl, pyridinyl, pyridazinyl, pyrimidinyl, pyrazinyl, and triazinyl;

n is 1, 2, or 3;

E is selected from the group consisting of $NR_aR_b$, $C_1$-$C_3$ alkylene-$NR_aR_b$, $C_1$-$C_3$ alkyl, $C_2$-$C_4$ alkenyl, $C_2$-$C_4$ alkynyl, $C_3$-$C_8$ cycloalkyl, $C_1$-$C_3$ alkylene-($C_3$-$C_8$ cycloalkyl), 4- to 10-membered heterocyclyl, $C_1$-$C_3$ alkylene-(4- to 10-membered heterocyclyl), $C_6$-$C_{10}$ aryl, $C_1$-$C_3$ alkylene-($C_6$-$C_{10}$ aryl), 5- to 10-membered heteroaryl, and $C_1$-$C_3$ alkylene-(5- to 10-membered heteroaryl), wherein the $C_1$-$C_3$ alkylene-$NR_aR_b$, $C_1$-$C_3$alkyl, $C_2$-$C_4$ alkenyl, $C_2$-$C_4$ alkynyl, $C_3$-$C_8$ cycloalkyl, $C_1$-$C_3$ alkylene-($C_3$-$C_8$ cycloalkyl), 4- to 10-membered heterocyclyl, $C_1$-$C_3$ alkylene-(4- to 10-membered heterocyclyl), $C_6$-$C_{10}$ aryl, $C_1$-$C_3$ alkylene-($C_6$-$C_{10}$ aryl), 5- to 10-membered heteroaryl, or $C_1$-$C_3$ alkylene-(5- to 10-membered heteroaryl) is unsubstituted or substituted with one or more halogen, hydroxyl, $C_1$-$C_3$ alkyl, or $C_1$-$C_3$ alkoxyl;

T is $CR_1R_2$ or O;

W is $CR_4R_5$ or O;

U is $CR_6R_7$;

X is $CR_8R_9$;

V is $CR_3$ or N;

Y is $NR_{10}$, O or absent;

Z is $(CR_{12}R_{13})_m$;

each R is, independently, selected from the group consisting of halogen, deuterium, hydroxyl, cyano, unsubstituted $C_1$-$C_3$ alkyl, and $C_1$-$C_3$ alkyl substituted with one or more halogen or deuterium;

p is 0, 1, 2, 3, or 4;

$R_a$ and $R_b$ are each, independently, H or unsubstituted $C_1$-$C_3$ alkyl;

m is 1, 2, 3, or 4;

and further wherein:

$R_1$, $R_2$, $R_4$, and $R_5$ are each, independently, selected from the group consisting of H, hydroxyl, halogen, and deuterium;

or, alternatively, $R_2$ and $R_5$ together with the carbon atoms to which they are attached, form a single bond;

$R_3$ is selected from the group consisting of H, deuterium, halogen, hydroxyl, and cyano;

or, alternatively, $R_3$ and $R_1$, together with the carbon atoms to which they are attached, form a $C_3$-$C_5$ cycloalkyl;

or, alternatively, $R_3$ and $R_4$, together with the carbon atoms to which they are attached, form a $C_3$-$C_5$ cycloalkyl;

$R_6$, $R_7$, $R_8$, $R_9$, and $R_{11}$ are each, independently, selected from the group consisting of H, hydroxyl, halogen, and deuterium;

$R_{10}$ is selected from the group consisting of H, unsubstituted $C_1$-$C_3$ alkyl, and $C_1$-$C_3$ alkyl substituted with one or more halogen;

each $R_{12}$ and $R_{13}$ is, independently, selected from the group consisting of H, halogen, deuterium, unsubstituted $C_1$-$C_3$ alkyl, and $C_1$-$C_3$ alkyl substituted with hydroxyl or one or more halogen; and $R_{14}$, $R_{15}$, and $R_{16}$ are each, independently, selected from the group consisting of H, unsubstituted $C_1$-$C_3$ alkyl or $C_1$-$C_3$ alkyl substituted with one or more halogen; and each $R_{17}$ and $R_{18}$ is, independently, selected from the group consisting of H, unsubstituted $C_1$-$C_3$ alkyl or $C_1$-$C_3$ alkyl substituted with one or more halogen;

with the proviso that one or more of (a)-(f) is present:

(a) at least one R is selected from the group consisting of hydroxyl, cyano, unsubstituted $C_1$-$C_3$ alkyl, and $C_1$-$C_3$ alkyl substituted with one or more halogen or deuterium;

(b) E is $NR_aR_b$, $C_1$-$C_3$ alkylene-$NR_aR_b$, $C_2$-$C_3$ alkyl, $C_2$-$C_4$ alkenyl, $C_2$-$C_4$ alkynyl, $C_3$-$C_8$ cycloalkyl, $C_1$-$C_3$ alkylene-($C_3$-$C_8$ cycloalkyl), 4- to 10-membered heterocyclyl, $C_1$-$C_3$ alkylene-(4- to 10-membered heterocyclyl), $C_6$-$C_{10}$ aryl, $C_1$-$C_3$ alkylene-($C_6$-$C_{10}$ aryl), 5- to 10-membered heteroaryl, or $C_1$-$C_3$ alkylene-(5- to 10-membered heteroaryl), wherein the $C_1$-$C_3$ alkylene-$NR_aR_b$, $C_2$-$C_3$ alkyl, $C_2$-$C_4$ alkenyl, $C_2$-$C_4$ alkynyl, $C_3$-$C_8$ cycloalkyl, $C_1$-$C_3$ alkylene-($C_3$-$C_8$ cycloalkyl), 4- to 10-membered heterocyclyl, $C_1$-$C_3$ alkylene-(4- to 10-membered heterocyclyl), $C_6$-$C_{10}$ aryl, $C_1$-$C_3$ alkylene-($C_6$-$C_{10}$ aryl), 5- to 10-membered heteroaryl, or $C_1$-$C_3$ alkylene-(5- to 10-membered heteroaryl) is unsubstituted or substituted with one or more halogen, hydroxyl, $C_1$-$C_3$ alkyl, or $C_1$-$C_3$ alkoxyl;

(c) E is $C_1$ alkyl substituted with one or more halogen, hydroxyl, $C_1$-$C_3$ alkyl, or $C_1$-$C_3$ alkoxyl;

(d) at least one of $R_{14}$, $R_{15}$, $R_{16}$, $R_{17}$, and $R_{18}$ is unsubstituted $C_1$-$C_3$ alkyl or $C_1$-$C_3$ alkyl substituted with one or more halogen;

(e) at least one of $R_1$, $R_2$, $R_4$, $R_5$, $R_6$, $R_7$, $R_8$, $R_9$, and $R_{11}$ is hydroxyl; or (f) at least one of $R_{12}$ and $R_{13}$ is $C_1$-$C_3$ alkyl substituted with hydroxyl.

In one embodiment of Formula (I), one or more of (a)-(d) is present:

(a) at least one R is selected from the group consisting of cyano, unsubstituted $C_1$-$C_3$ alkyl, and $C_1$-$C_3$ alkyl substituted with one or more halogen or deuterium;

(b) E is $NR_aR_b$, $C_1$-$C_3$ alkylene-$NR_aR_b$, $C_2$-$C_3$ alkyl, $C_2$-$C_4$ alkenyl, $C_2$-$C_4$ alkynyl, $C_3$-$C_8$ cycloalkyl, $C_1$-$C_3$ alkylene-($C_3$-$C_8$ cycloalkyl), 4- to 10-membered heterocyclyl, $C_1$-$C_3$ alkylene-(4- to 10-membered heterocyclyl), $C_6$-$C_{10}$ aryl, $C_1$-$C_3$ alkylene-($C_6$-$C_{10}$ aryl), 5- to 10-membered heteroaryl, or $C_1$-$C_3$ alkylene-(5- to 10-membered heteroaryl), wherein the $C_1$-$C_3$ alkylene-$NR_aR_b$, $C_2$-$C_3$ alkyl, $C_2$-$C_4$ alkenyl, $C_2$-$C_4$ alkynyl, $C_3$-$C_8$ cycloalkyl, $C_1$-$C_3$ alkylene-($C_3$-$C_8$ cycloalkyl), 4- to 10-membered heterocyclyl, $C_1$-$C_3$ alkylene-(4- to 10-membered heterocyclyl), $C_6$-$C_{10}$ aryl, $C_1$-$C_3$ alkylene-($C_6$-$C_{10}$ aryl), 5- to 10-membered heteroaryl, or $C_1$-$C_3$ alkylene-(5- to 10-membered heteroaryl) is unsubstituted or substituted with one or more halogen, $C_1$-$C_3$ alkyl, or $C_1$-$C_3$ alkoxyl;

(c) E is $C_1$ alkyl substituted with one or more halogen, $C_1$-$C_3$ alkyl, or $C_1$-$C_3$ alkoxyl; or (d) at least one of $R_{14}$, $R_{15}$, $R_{16}$, $R_{17}$, and $R_{18}$ is unsubstituted $C_1$-$C_3$ alkyl or $C_1$-$C_3$ alkyl substituted with one or more halogen.

In another embodiment of Formula (I), at least one R is selected from the group consisting of hydroxyl, cyano, unsubstituted $C_1$-$C_3$ alkyl, and $C_1$-$C_3$ alkyl substituted with one or more halogen or deuterium.

In another embodiment of Formula (I), E is $NR_aR_b$, $C_1$-$C_3$ alkylene-$NR_aR_b$, $C_2$-$C_3$ alkyl, $C_2$-$C_4$ alkenyl, $C_2$-$C_4$ alkynyl, $C_3$-$C_8$ cycloalkyl, $C_1$-$C_3$ alkylene-($C_3$-$C_8$ cycloalkyl), 4- to 10-membered heterocyclyl, $C_1$-$C_3$ alkylene-(4- to 10-membered heterocyclyl), $C_6$-$C_{10}$ aryl, $C_1$-$C_3$ alkylene-($C_6$-$C_{10}$ aryl), 5- to 10-membered heteroaryl, or $C_1$-$C_3$ alkylene-(5- to 10-membered heteroaryl), wherein the $C_1$-$C_3$ alkylene-$NR_aR_b$, $C_2$-$C_3$ alkyl, $C_2$-$C_4$ alkenyl, $C_2$-$C_4$ alkynyl, $C_3$-$C_8$ cycloalkyl, $C_1$-$C_3$ alkylene-($C_3$-$C_8$ cycloalkyl), 4- to 10-membered heterocyclyl, $C_1$-$C_3$ alkylene-(4- to 10-membered heterocyclyl), $C_6$-$C_{10}$ aryl, $C_1$-$C_3$ alkylene-($C_6$-$C_{10}$ aryl), 5- to 10-membered heteroaryl, or $C_1$-$C_3$ alkylene-(5- to 10-membered heteroaryl) is unsubstituted or substituted with one or more halogen, hydroxyl, $C_1$-$C_3$ alkyl, or $C_1$-$C_3$ alkoxyl.

In another embodiment of Formula (I), E is $C_1$ alkyl substituted with one or more halogen, hydroxyl, $C_1$-$C_3$ alkyl, or $C_1$-$C_3$ alkoxyl. In another embodiment of Formula (I), E is trifluoromethyl. In another embodiment of Formula (I), E is methyl. In another embodiment of Formula (I), E is ethyl. In another embodiment of Formula (I), E is propyl. In another embodiment of Formula (I), E is isopropyl. In another embodiment of Formula (I), E is cyclopropyl. In another embodiment of Formula (I), E is tetrahydrofuranyl.

In another embodiment of Formula (I), at least one of $R_{14}$, $R_{15}$, $R_{16}$, $R_{17}$, and $R_{18}$ is unsubstituted $C_1$-$C_3$ alkyl or $C_1$-$C_3$ alkyl substituted with one or more halogen.

In another embodiment of Formula (I), at least one of $R_1$, $R_2$, $R_4$, $R_5$, $R_6$, $R_7$, $R_8$, $R_9$, and $R_{11}$ is hydroxyl.

In another embodiment of Formula (I), at least one of $R_{12}$ and $R_{13}$ is $C_1$-$C_3$ alkyl substituted with hydroxyl.

In another embodiment of Formula (I), n is 1. In another embodiment of Formula (I), n is 2. In another embodiment of Formula (I), n is 3.

In another embodiment of Formula (I), ring A is phenyl. In another embodiment of Formula (I), ring A is pyridinyl. In another embodiment of Formula (I), ring A is pyridazinyl.

In another embodiment of Formula (I), ring A is pyrimidinyl. In another embodiment of Formula (I), ring A is pyrazinyl. In another embodiment of Formula (I), ring A is triazinyl.

In another embodiment of Formula (I), Y is $NR_{10}$. In another embodiment of Formula (I), Y is O. In another embodiment of Formula (I), Y is absent. In another embodiment of Formula (I), ring A is phenyl and Y is $NR_{10}$. In another embodiment of Formula (I), ring A is phenyl and Y is O. In another embodiment of Formula (I), ring A is phenyl and Y is absent. In another embodiment of Formula (I), ring A is pyridinyl and Y is $NR_{10}$. In another embodiment of Formula (I), ring A is pyridinyl and Y is O. In another embodiment of Formula (I), ring A is pyridinyl and Y is absent. In another embodiment of Formula (I), ring A is pyridazinyl and Y is $NR_{10}$. In another embodiment of Formula (I), ring A is pyridazinyl and Y is O. In another embodiment of Formula (I), ring A is pyridazinyl and Y is absent. In another embodiment of Formula (I), ring A is pyrimidinyl and Y is $NR_{10}$. In another embodiment of Formula (I), ring A is pyrimidinyl and Y is O. In another embodiment of Formula (I), ring A is pyrimidinyl and Y is absent. In another embodiment of Formula (I), ring A is pyrazinyl and Y is $NR_{10}$. In another embodiment of Formula (I), ring A is pyrazinyl and Y is O. In another embodiment of Formula (I), ring A is pyrazinyl and Y is absent. In another embodiment of Formula (I), ring A is triazinyl and Y is $NR_{10}$. In another embodiment of Formula (I), ring A is triazinyl and Y is O. In another embodiment of Formula (I), ring A is triazinyl and Y is absent.

In another embodiment of Formula (I), T is $CR_1R_2$. In another embodiment of Formula (I), T is O. In another embodiment of Formula (I), W is $CR_4R_5$. In another embodiment of Formula (I), W is O. In another embodiment of Formula (I), T is $CR_1R_2$ and W is $CR_4R_5$. In another embodiment of Formula (I), T is O and W is $CR_4R_5$. In another embodiment of Formula (I), T is $CR_1R_2$ and W is O.

In another embodiment of Formula (I), V is $CR_3$. In another embodiment of Formula (I), V is N.

In another embodiment of Formula (I), T is $CR_1R_2$ and V is $CR_3$. In another embodiment of Formula (I), T is O and V is $CR_3$. In another embodiment of Formula (I), T is $CR_1R_2$ and V is N. In another embodiment of Formula (I), T is O and V is N.

In another embodiment of Formula (I), W is $CR_4R_5$ and V is $CR_3$. In another embodiment of Formula (I), W is O and V is $CR_3$. In another embodiment of Formula (I), W is $CR_4R_5$ and V is N. In another embodiment of Formula (I), W is O and V is N.

In another embodiment of Formula (I), T is $CR_1R_2$, W is $CR_4R_5$, and V is $CR_3$. In another embodiment of Formula (I), T is $CR_1R_2$, W is O, and V is $CR_3$. In another embodiment of Formula (I), T is $CR_1R_2$, W is $CR_4R_5$, and V is N. In another embodiment of Formula (I), T is $CR_1R_2$, W is O, and V is N. In another embodiment of Formula (I), T is O, W is $CR_4R_5$, and V is $CR_3$.

In another embodiment of Formula (I), E is $NR_aR_b$. In another embodiment of Formula (I), E is $C_1$-$C_3$ alkylene-$NR_aR_b$. In another embodiment of Formula (I), E is unsubstituted $C_2$-$C_3$ alkyl, unsubstituted $C_2$-$C_4$ alkenyl or unsubstituted $C_2$-$C_4$ alkynyl. In another embodiment of Formula (I), E is $C_2$-$C_3$ alkyl, $C_2$-$C_4$ alkenyl or $C_2$-$C_4$ alkynyl substituted with one or more halogen, hydroxyl, $C_1$-$C_3$ alkyl, or $C_1$-$C_3$ alkoxyl. In another embodiment of Formula (I), E is unsubstituted $C_2$-$C_3$ alkyl. In another embodiment of Formula (I), E is $C_2$-$C_3$ alkyl substituted with one or more halogen, hydroxyl, $C_1$-$C_3$ alkyl, or $C_1$-$C_3$ alkoxyl. In another embodiment of Formula (I), E is unsubstituted $C_3$-$C_8$ cycloalkyl. In another embodiment of Formula (I), E is $C_3$-$C_8$ cycloalkyl substituted with one or more halogen, hydroxyl, $C_1$-$C_3$ alkyl, or $C_1$-$C_3$ alkoxyl. In another embodiment of Formula (I), E is unsubstituted $C_1$-$C_3$ alkylene-($C_3$-$C_8$ cycloalkyl). In another embodiment of Formula (I), E is $C_1$-$C_3$ alkylene-($C_3$-$C_8$ cycloalkyl) substituted with one or more halogen, hydroxyl, $C_1$-$C_3$ alkyl, or $C_1$-$C_3$ alkoxyl. In another embodiment of Formula (I), E is unsubstituted 4- to 10-membered heterocyclyl. In another embodiment of Formula (I), E is 4- to 10-membered heterocyclyl substituted with one or more halogen, hydroxyl, $C_1$-$C_3$ alkyl, or $C_1$-$C_3$ alkoxyl. In another embodiment of Formula (I), E is unsubstituted $C_1$-$C_3$ alkylene-(4- to 10-membered heterocyclyl). In another embodiment of Formula (I), E is $C_1$-$C_3$ alkylene-(4- to 10-membered heterocyclyl) substituted with one or more halogen, hydroxyl, $C_1$-$C_3$ alkyl, or $C_1$-$C_3$ alkoxyl. In another embodiment of Formula (I), E is unsubstituted $C_6$-$C_{10}$ aryl. In another embodiment of Formula (I), E is $C_6$-$C_{10}$ aryl substituted with one or more halogen, hydroxyl, $C_1$-$C_3$ alkyl, or $C_1$-$C_3$ alkoxyl. In another embodiment of Formula (I), E is unsubstituted $C_1$-$C_3$ alkylene-($C_6$-$C_{10}$ aryl). In another embodiment of Formula (I), E is $C_1$-$C_3$ alkylene-($C_6$-$C_{10}$ aryl) substituted with one or more halogen, hydroxyl, $C_1$-$C_3$ alkyl, or $C_1$-$C_3$ alkoxyl. In another embodiment of Formula (I), E is unsubstituted 5- to 10-membered heteroaryl. In another embodiment of Formula (I), E is 5- to 10-membered heteroaryl substituted with one or more halogen, hydroxyl, $C_1$-$C_3$ alkyl, or $C_1$-$C_3$ alkoxyl.

In another embodiment of Formula (I), E is unsubstituted 4- to 10-membered heterocyclyl. In another embodiment of Formula (I), E is 4- to 10-membered heterocyclyl substituted with one or more halogen, hydroxyl, $C_1$-$C_3$ alkyl, or $C_1$-$C_3$ alkoxyl. In another embodiment of Formula (I), E is unsubstituted 8- to 10-membered heterocyclyl. In another embodiment of Formula (I), E is 8- to 10-membered heterocyclyl substituted with one or more halogen, hydroxyl, $C_1$-$C_3$ alkyl, or $C_1$-$C_3$ alkoxyl. In another embodiment of Formula (I), E is unsubstituted 4- to 7-membered heterocyclyl. In another embodiment of Formula (I), E is 4- to 7-membered heterocyclyl substituted with one or more halogen, hydroxyl, $C_1$-$C_3$ alkyl, or $C_1$-$C_3$ alkoxyl. In another embodiment of Formula (I), E is unsubstituted 4- to 6-membered heterocyclyl. In another embodiment of Formula (I), E is 4- to 6-membered heterocyclyl substituted with one or more halogen, hydroxyl, $C_1$-$C_3$ alkyl, or $C_1$-$C_3$ alkoxyl. In another embodiment of Formula (I), E is unsubstituted 4-membered heterocyclyl. In another embodiment of Formula (I), E is 4-membered heterocyclyl substituted with one or more halogen, hydroxyl, $C_1$-$C_3$ alkyl, or $C_1$-$C_3$ alkoxyl. In another embodiment of Formula (I), E is unsubstituted 5-membered heterocyclyl. In another embodiment of Formula (I), E is 5-membered heterocyclyl substituted with one or more halogen, hydroxyl, $C_1$-$C_3$ alkyl, or $C_1$-$C_3$ alkoxyl. In another embodiment of Formula (I), E is unsubstituted 6-membered heterocyclyl. In another embodiment of Formula (I), E is 6-membered heterocyclyl substituted with one or more halogen, hydroxyl, $C_1$-$C_3$ alkyl, or $C_1$-$C_3$ alkoxyl.

In another embodiment of Formula (I), E is unsubstituted 5- to 10-membered heteroaryl. In another embodiment of Formula (I), E is 5- to 10-membered heteroaryl substituted with one or more halogen, hydroxyl, $C_1$-$C_3$ alkyl, or $C_1$-$C_3$ alkoxyl. In another embodiment of Formula (I), E is unsubstituted 5- to 6-membered heteroaryl. In another embodiment of Formula (I), E is 5- to 6-membered heteroaryl substituted with one or more halogen, hydroxyl, $C_1$-$C_3$ alkyl, or $C_1$-$C_3$ alkoxyl. In another embodiment of Formula (I), E is unsubstituted 5-membered heteroaryl. In another embodiment of Formula (I), E is 5-membered heteroaryl substituted with one or more halogen, hydroxyl, $C_1$-$C_3$ alkyl, or $C_1$-$C_3$ alkoxyl. In another embodiment of Formula (I), E is unsubstituted 6-membered heteroaryl. In another embodiment of Formula (I), E is 6-membered heteroaryl substituted with one or more halogen, hydroxyl, $C_1$-$C_3$ alkyl, or $C_1$-$C_3$ alkoxyl. In another embodiment of Formula (I), E is unsubstituted 8-membered heteroaryl. In another embodiment of Formula (I), E is 8-membered heteroaryl substituted with one or more halogen, hydroxyl, $C_1$-$C_3$ alkyl, or $C_1$-$C_3$ alkoxyl. In another embodiment of Formula (I), E is unsubstituted 10-membered heteroaryl. In another embodiment of Formula (I), E is 10-membered heteroaryl substituted with one or more halogen, hydroxyl, $C_1$-$C_3$ alkyl, or $C_1$-$C_3$ alkoxyl.

In another embodiment of Formula (I), E is $NR_aR_b$, $C_1$-$C_3$ alkylene-$NR_aR_b$, $C_1$-$C_3$ alkyl, $C_2$-$C_4$ alkenyl, $C_2$-$C_4$ alkynyl, $C_3$-$C_8$ cycloalkyl, $C_1$-$C_3$ alkylene-($C_3$-$C_8$ cycloalkyl), 4- to 10-membered heterocyclyl, $C_1$-$C_3$ alkylene-(4- to 10-membered heterocyclyl), $C_6$-$C_{10}$ aryl, or $C_1$-$C_3$ alkylene-($C_6$-$C_{10}$ aryl), wherein the $C_1$-$C_3$ alkylene-$NR_aR_b$, $C_1$-$C_3$alkyl, $C_2$-$C_4$ alkenyl, $C_2$-$C_4$ alkynyl, $C_3$-$C_8$ cycloalkyl, $C_1$-$C_3$ alkylene-($C_3$-$C_8$ cycloalkyl), 4- to 10-membered heterocyclyl, $C_1$-$C_3$ alkylene-(4- to 10-membered heterocyclyl), $C_6$-$C_{10}$ aryl, or $C_1$-$C_3$ alkylene-($C_6$-$C_{10}$ aryl) is unsubstituted or substituted with one or more halogen, hydroxyl, $C_1$-$C_3$ alkyl, or $C_1$-$C_3$ alkoxyl.

In another embodiment of Formula (I), E is $C_1$-$C_3$ alkyl, $C_2$-$C_4$ alkenyl, $C_2$-$C_4$ alkynyl, $C_3$-$C_8$ cycloalkyl, $C_1$-$C_3$ alkylene-($C_3$-$C_8$ cycloalkyl), 4- to 10-membered heterocyclyl, $C_1$-$C_3$ alkylene-(4- to 10-membered heterocyclyl), $C_6$-$C_{10}$ aryl, or $C_1$-$C_3$ alkylene-($C_6$-$C_{10}$ aryl), wherein the $C_1$-$C_3$alkyl, $C_2$-$C_4$ alkenyl, $C_2$-$C_4$ alkynyl, $C_3$-$C_8$ cycloalkyl, $C_1$-$C_3$ alkylene-($C_3$-$C_8$ cycloalkyl), 4- to 10-membered heterocyclyl, $C_1$-$C_3$ alkylene-(4- to 10-membered heterocyclyl), $C_6$-$C_{10}$ aryl, or $C_1$-$C_3$ alkylene-($C_6$-$C_{10}$ aryl) is unsubstituted or substituted with one or more halogen, hydroxyl, $C_1$-$C_3$ alkyl, or $C_1$-$C_3$ alkoxyl.

In another embodiment of Formula (I), E is $C_1$-$C_3$ alkyl, $C_3$-$C_8$ cycloalkyl, $C_1$-$C_3$ alkylene-($C_3$-$C_8$ cycloalkyl), 4- to 10-membered heterocyclyl, $C_1$-$C_3$ alkylene-(4- to 10-membered heterocyclyl), $C_6$-$C_{10}$ aryl, or $C_1$-$C_3$ alkylene-($C_6$-$C_{10}$ aryl), wherein the $C_1$-$C_3$alkyl, $C_3$-$C_8$ cycloalkyl, $C_1$-$C_3$ alkylene-($C_3$-$C_8$ cycloalkyl), 4- to 10-membered heterocyclyl, $C_1$-$C_3$ alkylene-(4- to 10-membered heterocyclyl), $C_6$-$C_{10}$ aryl, or $C_1$-$C_3$ alkylene-($C_6$-$C_{10}$ aryl) is unsubstituted or substituted with one or more halogen, hydroxyl, $C_1$-$C_3$ alkyl, or $C_1$-$C_3$ alkoxyl.

In another embodiment of Formula (I), E is $C_1$-$C_3$ alkyl, $C_3$-$C_8$ cycloalkyl, $C_1$-$C_3$ alkylene-($C_3$-$C_8$ cycloalkyl), 4- to 10-membered heterocyclyl, or $C_1$-$C_3$ alkylene-(4- to 10-membered heterocyclyl), wherein the $C_1$-$C_3$alkyl, $C_3$-$C_8$ cycloalkyl, $C_1$-$C_3$ alkylene-($C_3$-$C_8$ cycloalkyl), 4- to 10-membered heterocyclyl, or $C_1$-$C_3$ alkylene-(4- to 10-membered heterocyclyl) is unsubstituted or substituted with one or more halogen, hydroxyl, $C_1$-$C_3$ alkyl, or $C_1$-$C_3$ alkoxyl.

In another embodiment of Formula (I), E is $C_1$-$C_3$ alkyl, $C_3$-$C_8$ cycloalkyl, or $C_1$-$C_3$ alkylene-($C_3$-$C_8$ cycloalkyl), wherein the $C_1$-$C_3$alkyl, $C_3$-$C_8$ cycloalkyl, or $C_1$-$C_3$ alkylene-($C_3$-$C_8$ cycloalkyl) is unsubstituted or substituted with one or more halogen, hydroxyl, $C_1$-$C_3$ alkyl, or $C_1$-$C_3$ alkoxyl.

In another embodiment of Formula (I), E is methyl, wherein the methyl is unsubstituted or substituted with one or more halogen, hydroxyl, $C_1$-$C_3$ alkyl, or $C_1$-$C_3$ alkoxyl. In another embodiment of Formula (I), E is methyl. In another embodiment of Formula (I), E is trifluoromethyl. In another embodiment of Formula (I), E is dioxanyl, wherein the dioxanyl is unsubstituted or substituted with one or more halogen, hydroxyl, $C_1$-$C_3$ alkyl, or $C_1$-$C_3$ alkoxyl. In another embodiment of Formula (I), E is tetrahydropyranyl, wherein the tetrahydropyranyl is unsubstituted or substituted with one or more halogen, hydroxyl, $C_1$-$C_3$ alkyl, or $C_1$-$C_3$ alkoxyl. In another embodiment of Formula (I), E is tetrahydrofuranyl, wherein the tetrahydrofuranyl is unsubstituted or substituted with one or more halogen, hydroxyl, $C_1$-$C_3$ alkyl, or $C_1$-$C_3$ alkoxyl. In another embodiment of Formula (I), E is azetidinyl, wherein the azetidinyl is unsubstituted or substituted with one or more halogen, hydroxyl, $C_1$-$C_3$ alkyl, or $C_1$-$C_3$ alkoxyl. In another embodiment of Formula (I), E is oxetanyl, wherein the oxetanyl is unsubstituted or substituted with one or more halogen, hydroxyl, $C_1$-$C_3$ alkyl, or $C_1$-$C_3$ alkoxyl. In another embodiment of Formula (I), E is morpholinyl, wherein the morpholinyl is unsubstituted or substituted with one or more halogen, hydroxyl, $C_1$-$C_3$ alkyl, or $C_1$-$C_3$ alkoxyl.

In another embodiment of Formula (I), $R_{14}$ is H. In another embodiment of Formula (I), $R_{14}$ is unsubstituted $C_1$-$C_3$ alkyl. In another embodiment of Formula (I), $R_{15}$ and $R_{16}$ are each H. In another embodiment of Formula (I), $R_{15}$ is unsubstituted $C_1$-$C_3$ alkyl and $R_{16}$ is H. In another embodiment of Formula (I), $R_{16}$ is unsubstituted $C_1$-$C_3$ alkyl and $R_{18}$ is H. In another embodiment of Formula (I), each $R_{17}$ and $R_{18}$ is H. In another embodiment of Formula (I), $R_{17}$ is unsubstituted $C_1$-$C_3$ alkyl and $R_{18}$ is H. In another embodiment of Formula (I), $R_{18}$ is unsubstituted $C_1$-$C_3$ alkyl and $R_{17}$ is H. In another embodiment of Formula (I), one of $R_{14}$, $R_{15}$, $R_{16}$, $R_{17}$ and $R_{18}$ is unsubstituted $C_1$-$C_3$ alkyl and the others are each H.

In another embodiment of Formula (I), m is 1. In another embodiment of Formula (I), m is 2. In another embodiment of Formula (I), m is 3. In another embodiment of Formula (I), m is 4. In another embodiment of Formula (I), m is 1, 2 or 3. In another embodiment of Formula (I), m is 2, 3, or 4. In another embodiment of Formula (I), m is 1 or 2. In another embodiment of Formula (I), m is 3 or 4.

In another embodiment of Formula (I), Y is O and m is 1. In another embodiment of Formula (I), Y is O and m is 2. In another embodiment of Formula (I), Y is O and m is 3. In another embodiment of Formula (I), Y is O and m is 4. In another embodiment of Formula (I), Y is O and m is 1, 2, or 3. In another embodiment of Formula (I), Y is O and m is 2, 3, or 4. In another embodiment of Formula (I), Y is O and m is 1 or 2. In another embodiment of Formula (I), Y is O and m is 3 or 4.

In another embodiment of Formula (I), Y is absent and m is 1. In another embodiment of Formula (I), Y is absent and m is 2. In another embodiment of Formula (I), Y is absent and m is 3. In another embodiment of Formula (I), Y is absent and m is 4. In another embodiment of Formula (I), Y is absent and m is 1, 2, or 3. In another embodiment of Formula (I), Y is absent and m is 2, 3, or 4. In another embodiment of Formula (I), Y is absent and m is 1 or 2. In another embodiment of Formula (I), Y is absent and m is 3 or 4.

In another embodiment of Formula (I), Y is $NR_{10}$ and m is 1. In another embodiment of Formula (I), Y is $NR_{10}$ and m is 2. In another embodiment of Formula (I), Y is $NR_{10}$ and m is 3. In another embodiment of Formula (I), Y is $NR_{10}$ and m is 4. In another embodiment of Formula (I), Y is $NR_{10}$ and m is 1, 2, or 3. In another embodiment of Formula (I), Y is $NR_{10}$ and m is 2, 3, or 4. In another embodiment of Formula (I), Y is $NR_{10}$ and m is 1 or 2. In another embodiment of Formula (I), Y is $NR_{10}$ and m is 3 or 4.

In another embodiment of Formula (I), ring A is phenyl and n is 1. In another embodiment of Formula (I), ring A is phenyl and n is 2. In another embodiment of Formula (I), ring A is phenyl and n is 3. In another embodiment of Formula (I), ring A is pyridinyl and n is 1. In another embodiment of Formula (I), ring A is pyridinyl and n is 2. In another embodiment of Formula (I), ring A is pyridinyl and n is 3. In another embodiment of Formula (I), ring A is pyridazinyl and n is 1. In another embodiment of Formula (I), ring A is pyridazinyl and n is 2. In another embodiment of Formula (I), ring A is pyridazinyl and n is 3. In another embodiment of Formula (I), ring A is pyrimidinyl and n is 1. In another embodiment of Formula (I), ring A is pyrimidinyl and n is 2. In another embodiment of Formula (I), ring A is pyrimidinyl and n is 3. In another embodiment of Formula (I), ring A is pyrazinyl and n is 1. In another embodiment of Formula (I), ring A is pyrazinyl and n is 2. In another embodiment of Formula (I), ring A is pyrazinyl and n is 3. In another embodiment of Formula (I), ring A is triazinyl and n is 1. In another embodiment of Formula (I), ring A is triazinyl and n is 2. In another embodiment of Formula (I), ring A is triazinyl and n is 3.

In another embodiment of Formula (I), ring A is phenyl, n is 1, and Y is $NR_{10}$. In another embodiment of Formula (I), ring A is phenyl, n is 2, and Y is $NR_{10}$. In another embodiment of Formula (I), ring A is phenyl, n is 3, and Y is $NR_{10}$. In another embodiment of Formula (I), ring A is phenyl, n is 1, and Y is O. In another embodiment of Formula (I), ring A is phenyl, n is 2, and Y is O. In another embodiment of Formula (I), ring A is phenyl, n is 3, and Y is O. In another embodiment of Formula (I), ring A is phenyl, n is 1, and Y is absent. In another embodiment of Formula (I), ring A is phenyl, n is 2, and Y is absent. In another embodiment of Formula (I), ring A is phenyl, n is 3, and Y is absent.

In another embodiment of Formula (I), ring A is phenyl, n is 1, Y is $NR_{10}$, and m is 1 or 2. In another embodiment of Formula (I), ring A is phenyl, n is 2, Y is $NR_{10}$, and m is 1 or 2. In another embodiment of Formula (I), ring A is phenyl, n is 3, Y is $NR_{10}$, and m is 1 or 2. In another embodiment of Formula (I), ring A is phenyl, n is 1, Y is O, and m is 1 or 2. In another embodiment of Formula (I), ring A is phenyl, n is 2, Y is O, and m is 1 or 2. In another embodiment of Formula (I), ring A is phenyl, n is 3, Y is O, and m is 1 or 2. In another embodiment of Formula (I), ring A is phenyl, n is 1, Y is absent, and m is 1 or 2. In another embodiment of Formula (I), ring A is phenyl, n is 2, Y is absent, and m is 1 or 2. In another embodiment of Formula (I), ring A is phenyl, n is 3, Y is absent, and m is 1 or 2. In another embodiment of Formula (I), ring A is phenyl, n is 1, Y is $NR_{10}$, and m is 3 or 4. In another embodiment of Formula (I), ring A is phenyl, n is 2, Y is $NR_{10}$, and m is 3 or 4. In another embodiment of Formula (I), ring A is phenyl, n is 3, Y is $NR_{10}$, and m is 3 or 4. In another embodiment of Formula (I), ring A is phenyl, n is 1, Y is O, and m is 3 or 4. In another embodiment of Formula (I), ring A is phenyl, n is 2, Y is O, and m is 3 or 4. In another embodiment of Formula (I), ring A is phenyl, n is 3, Y is O, and m is 3 or 4. In another embodiment of Formula (I), ring A is phenyl, n is 1, Y is absent, and m is 3 or 4. In another embodiment of Formula (I), ring A is phenyl, n is 2, Y is absent, and m is 3 or 4. In another embodiment of Formula (I), ring A is phenyl, n is 3, Y is absent, and m is 3 or 4.

In another embodiment of Formula (I), ring A is pyridinyl, n is 1, and Y is $NR_{10}$. In another embodiment of Formula (I), ring A is pyridinyl, n is 2, and Y is $NR_{10}$. In another embodiment of Formula (I), ring A is pyridinyl, n is 3, and Y is $NR_{10}$. In another embodiment of Formula (I), ring A is pyridinyl, n is 1, and Y is O. In another embodiment of Formula (I), ring A is pyridinyl, n is 2, and Y is O. In another embodiment of Formula (I), ring A is pyridinyl, n is 3, and Y is O. In another embodiment of Formula (I), ring A is pyridinyl, n is 1, and Y is absent.

In another embodiment of Formula (I), ring A is pyridinyl, n is 2, and Y is absent. In another embodiment of Formula (I), ring A is pyridinyl, n is 3, and Y is absent. In another embodiment of Formula (I), ring A is pyridinyl, n is 1, Y is $NR_{10}$, and m is 1 or 2. In another embodiment of Formula (I), ring A is pyridinyl, n is 2, Y is $NR_{10}$, and m is 1 or 2. In another embodiment of Formula (I), ring A is pyridinyl, n is 3, Y is $NR_{10}$, and m is 1 or 2.

In another embodiment of Formula (I), ring A is pyridinyl, n is 1, Y is O, and m is 1 or 2. In another embodiment of Formula (I), ring A is pyridinyl, n is 2, Y is O, and m is 1 or 2. In another embodiment of Formula (I), ring A is pyridinyl, n is 3, Y is O, and m is 1 or 2. In another embodiment of Formula (I), ring A is pyridinyl, n is 1, Y is absent, and m is 1 or 2. In another embodiment of Formula (I), ring A is pyridinyl, n is 2, Y is absent, and m is 1 or 2. In another embodiment of Formula (I), ring A is pyridinyl, n is 3, Y is absent, and m is 1 or 2. In another embodiment of Formula (I), ring A is pyridinyl, n is 1, Y is $NR_{10}$, and m is 3 or 4. In another embodiment of Formula (I), ring A is pyridinyl, n is 2, Y is $NR_{10}$, and m is 3 or 4. In another embodiment of Formula (I), ring A is pyridinyl, n is 3, Y is $NR_{10}$, and m is 3 or 4. In another embodiment of Formula (I), ring A is pyridinyl, n is 1, Y is O, and m is 3 or 4. In another embodiment of Formula (I), ring A is pyridinyl, n is 2, Y is O, and m is 3 or 4. In another embodiment of Formula (I), ring A is pyridinyl, n is 3, Y is O, and m is 3 or 4. In another embodiment of Formula (I), ring A is pyridinyl, n is 1, Y is absent, and m is 3 or 4. In another embodiment of Formula (I), ring A is pyridinyl, n is 2, Y is absent, and m is 3 or 4. In another embodiment of Formula (I), ring A is pyridinyl, n is 3, Y is absent, and m is 3 or 4.

In another embodiment of Formula (I), ring A is pyridazinyl, n is 1, and Y is $NR_{10}$. In another embodiment of Formula (I), ring A is pyridazinyl, n is 2, and Y is $NR_{10}$. In another embodiment of Formula (I), ring A is pyridazinyl, n is 3, and Y is $NR_{10}$. In another embodiment of Formula (I), ring A is pyridazinyl, n is 1, and Y is O. In another embodiment of Formula (I), ring A is pyridazinyl, n is 2, and Y is O. In another embodiment of Formula (I), ring A is pyridazinyl, n is 3, and Y is O. In another embodiment of Formula (I), ring A is pyridazinyl, n is 1, and Y is absent. In another embodiment of Formula (I), ring A is pyridazinyl, n is 2, and Y is absent. In another embodiment of Formula (I), ring A is pyridazinyl, n is 3, and Y is absent.

In another embodiment of Formula (I), ring A is pyridazinyl, n is 1, Y is $NR_{10}$, and m is 1 or 2. In another embodiment of Formula (I), ring A is pyridazinyl, n is 2, Y is $NR_{10}$, and m is 1 or 2. In another embodiment of Formula (I), ring A is pyridazinyl, n is 3, Y is $NR_{10}$, and m is 1 or 2. In another embodiment of Formula (I), ring A is pyridazinyl, n is 1, Y is O, and m is 1 or 2. In another embodiment of Formula (I), ring A is pyridazinyl, n is 2, Y is O, and m is 1 or 2. In another embodiment of Formula (I), ring A is pyridazinyl, n is 3, Y is O, and m is 1 or 2. In another embodiment of Formula (I), ring A is pyridazinyl, n is 1, Y is absent, and m is 1 or 2. In another embodiment of Formula (I), ring A is pyridazinyl, n is 2, Y is absent, and m is 1 or 2. In another embodiment of Formula (I), ring A is pyridazinyl, n is 3, Y is absent, and m is 1 or 2. In another embodiment of Formula (I), ring A is pyridazinyl, n is 1, Y is $NR_{10}$, and m is 3 or 4. In another embodiment of Formula (I), ring A is pyridazinyl, n is 2, Y is $NR_{10}$, and m is 3 or 4. In another embodiment of Formula (I), ring A is pyridazinyl, n is 3, Y is $NR_{10}$, and m is 3 or 4. In another embodiment of Formula (I), ring A is pyridazinyl, n is 1, Y is O, and m is 3 or 4. In another embodiment of Formula (I), ring A is pyridazinyl, n is 2, Y is O, and m is 3 or 4. In another embodiment of Formula (I), ring A is pyridazinyl, n is 3, Y is O, and m is 3 or 4. In another embodiment of Formula (I), ring A is pyridazinyl, n is 1, Y is absent, and m is 3 or 4. In another embodiment of Formula (I), ring A is pyridazinyl, n is 2, Y is absent, and m is 3 or 4. In another embodiment of Formula (I), ring A is pyridazinyl, n is 3, Y is absent, and m is 3 or 4.

In another embodiment of Formula (I), ring A is pyrimidinyl, n is 1, and Y is $NR_{10}$. In another embodiment of Formula (I), ring A is pyrimidinyl, n is 2, and Y is $NR_{10}$. In another embodiment of Formula (I), ring A is pyrimidinyl, n is 3, and Y is $NR_{10}$. In another embodiment of Formula (I), ring A is pyrimidinyl, n is 1, and Y is O. In another embodiment of Formula (I), ring A is pyrimidinyl, n is 2, and Y is O. In another embodiment of Formula (I), ring A is pyrimidinyl, n is 3, and Y is O. In another embodiment of Formula (I), ring A is pyrimidinyl, n is 1, and Y is absent. In another embodiment of Formula (I), ring A is pyrimidinyl, n is 2, and Y is absent. In another embodiment of Formula (I), ring A is pyrimidinyl, n is 3, and Y is absent.

In another embodiment of Formula (I), ring A is pyrimidinyl, n is 1, Y is $NR_{10}$, and m is 1 or 2. In another embodiment of Formula (I), ring A is pyrimidinyl, n is 2, Y is $NR_{10}$, and m is 1 or 2. In another embodiment of Formula (I), ring A is pyrimidinyl, n is 3, Y is $NR_{10}$, and m is 1 or 2. In another embodiment of Formula (I), ring A is pyrimidinyl, n is 1, Y is O, and m is 1 or 2. In another embodiment of Formula (I), ring A is pyrimidinyl, n is 2, Y is O, and m is 1 or 2. In another embodiment of Formula (I), ring A is pyrimidinyl, n is 3, Y is O, and m is 1 or 2. In another embodiment of Formula (I), ring A is pyrimidinyl, n is 1, Y is absent, and m is 1 or 2. In another embodiment of Formula (I), ring A is pyrimidinyl, n is 2, Y is absent, and m is 1 or 2. In another embodiment of Formula (I), ring A is pyrimidinyl, n is 3, Y is absent, and m is 1 or 2. In another embodiment of Formula (I), ring A is pyrimidinyl, n is 1, Y is $NR_{10}$, and m is 3 or 4. In another embodiment of Formula (I), ring A is pyrimidinyl, n is 2, Y is $NR_{10}$, and m is 3 or 4. In another embodiment of Formula (I), ring A is pyrimidinyl, n is 3, Y is $NR_{10}$, and m is 3 or 4. In another embodiment of Formula (I), ring A is pyrimidinyl, n is 1, Y is O, and m is 3 or 4. In another embodiment of Formula (I), ring A is pyrimidinyl, n is 2, Y is O, and m is 3 or 4. In another embodiment of Formula (I), ring A is pyrimidinyl, n is 3, Y is O, and m is 3 or 4. In another embodiment of Formula (I), ring A is pyrimidinyl, n is 1, Y is absent, and m is 3 or 4. In another embodiment of Formula (I), ring A is pyrimidinyl, n is 2, Y is absent, and m is 3 or 4. In another embodiment of Formula (I), ring A is pyrimidinyl, n is 3, Y is absent, and m is 3 or 4.

In another embodiment of Formula (I), ring A is pyrazinyl, n is 1, and Y is $NR_{10}$. In another embodiment of Formula (I), ring A is pyrazinyl, n is 2, and Y is $NR_{10}$. In another embodiment of Formula (I), ring A is pyrazinyl, n is 3, and Y is $NR_{10}$. In another embodiment of Formula (I), ring A is pyrazinyl, n is 1, and Y is O. In another embodiment of Formula (I), ring A is pyrazinyl, n is 2, and Y is O. In another embodiment of Formula (I), ring A is pyrazinyl, n is 3, and Y is O. In another embodiment of Formula (I), ring A is pyrazinyl, n is 1, and Y is absent. In another embodiment of Formula (I), ring A is pyrazinyl, n is 2, and Y is absent. In another embodiment of Formula (I), ring A is pyrazinyl, n is 3, and Y is absent.

In another embodiment of Formula (I), ring A is pyrazinyl, n is 1, Y is $NR_{10}$, and m is 1 or 2. In another embodiment of Formula (I), ring A is pyrazinyl, n is 2, Y is $NR_{10}$, and m is 1 or 2. In another embodiment of Formula (I), ring A is pyrazinyl, n is 3, Y is $NR_{10}$, and m is 1 or 2. In another embodiment of Formula (I), ring A is pyrazinyl, n is 1, Y is O, and m is 1 or 2. In another embodiment of Formula (I), ring A is pyrazinyl, n is 2, Y is O, and m is 1 or 2. In another embodiment of Formula (I), ring A is pyrazinyl, n is 3, Y is O, and m is 1 or 2. In another embodiment of Formula (I), ring A is pyrazinyl, n is 1, Y is absent, and m is 1 or 2. In another embodiment of Formula (I), ring A is pyrazinyl, n is 2, Y is absent, and m is 1 or 2. In another embodiment of Formula (I), ring A is pyrazinyl, n is 3, Y is absent, and m is 1 or 2. In another embodiment of Formula (I), ring A is pyrazinyl, n is 1, Y is $NR_{10}$, and m is 3 or 4. In another embodiment of Formula (I), ring A is pyrazinyl, n is 2, Y is $NR_{10}$, and m is 3 or 4. In another embodiment of Formula (I), ring A is pyrazinyl, n is 3, Y is $NR_{10}$, and m is 3 or 4. In another embodiment of Formula (I), ring A is pyrazinyl, n is 1, Y is O, and m is 3 or 4. In another embodiment of Formula (I), ring A is pyrazinyl, n is 2, Y is O, and m is 3 or 4. In another embodiment of Formula (I), ring A is pyrazinyl, n is 3, Y is O, and m is 3 or 4. In another embodiment of Formula (I), ring A is pyrazinyl, n is 1, Y is absent, and m is 3 or 4. In another embodiment of Formula (I), ring A is pyrazinyl, n is 2, Y is absent, and m is 3 or 4. In another embodiment of Formula (I), ring A is pyrazinyl, n is 3, Y is absent, and m is 3 or 4.

In another embodiment of Formula (I), ring A is triazinyl, n is 1, and Y is $NR_{10}$. In another embodiment of Formula (I), ring A is triazinyl, n is 2, and Y is $NR_{10}$. In another embodiment of Formula (I), ring A is triazinyl, n is 3, and Y is $NR_{10}$. In another embodiment of Formula (I), ring A is triazinyl, n is 1, and Y is O. In another embodiment of Formula (I), ring A is triazinyl, n is 2, and Y is O. In another embodiment of Formula (I), ring A is triazinyl, n is 3, and Y is O. In another embodiment of Formula (I), ring A is triazinyl, n is 1, and Y is absent. In another embodiment of Formula (I), ring A is triazinyl, n is 2, and Y is absent. In another embodiment of Formula (I), ring A is triazinyl, n is 3, and Y is absent.

In another embodiment of Formula (I), ring A is triazinyl, n is 1, Y is $NR_{10}$, and m is 1 or 2. In another embodiment of Formula (I), ring A is triazinyl, n is 2, Y is $NR_{10}$, and m is 1 or 2. In another embodiment of Formula (I), ring A is triazinyl, n is 3, Y is $NR_{10}$, and m is 1 or 2. In another embodiment of Formula (I), ring A is triazinyl, n is 1, Y is O, and m is 1 or 2. In another embodiment of Formula (I), ring A is triazinyl, n is 2, Y is O, and m is 1 or 2. In another embodiment of Formula (I), ring A is triazinyl, n is 3, Y is O, and m is 1 or 2. In another embodiment of Formula (I), ring A is triazinyl, n is 1, Y is absent, and m is 1 or 2. In another embodiment of Formula (I), ring A is triazinyl, n is 2, Y is absent, and m is 1 or 2. In another embodiment of Formula (I), ring A is triazinyl, n is 3, Y is absent, and m is 1 or 2. In another embodiment of Formula (I), ring A is triazinyl, n is 1, Y is $NR_{10}$, and m is 3 or 4. In another embodiment of Formula (I), ring A is triazinyl, n is 2, Y is $NR_{10}$, and m is 3 or 4. In another embodiment of Formula (I), ring A is triazinyl, n is 3, Y is $NR_{10}$, and m is 3 or 4. In another embodiment of Formula (I), ring A is triazinyl, n is 1, Y is O, and m is 3 or 4. In another embodiment of Formula (I), ring A is triazinyl, n is 2, Y is O, and m is 3 or 4. In another embodiment of Formula (I), ring A is triazinyl, n is 3, Y is O, and m is 3 or 4. In another embodiment of Formula (I), ring A is triazinyl, n is 1, Y is absent, and m is 3 or 4. In another embodiment of Formula (I), ring A is triazinyl, n is 2, Y is absent, and m is 3 or 4. In another embodiment of Formula (I), ring A is triazinyl, n is 3, Y is absent, and m is 3 or 4.

In another embodiment of Formula (I), ring A is phenyl, T is $CR_1R_2$, W is $CR_4R_5$, and V is $CR_3$. In another embodiment of Formula (I), ring A is phenyl, p is 0, T is $CR_1R_2$, W is $CR_4R_5$, and V is $CR_3$. In another embodiment of Formula (I), ring A is phenyl, T is $CR_1R_2$, W is $CR_4R_5$, V is $CR_3$, and n is 1. In another embodiment of Formula (I), ring A is phenyl, T is $CR_1R_2$, W is $CR_4R_5$, V is $CR_3$, and n is 2. In another embodiment of Formula (I), ring A is phenyl, T is $CR_1R_2$, W is $CR_4R_5$, V is $CR_3$, and n is 3. In another embodiment of Formula (I), ring A is phenyl, p is 0, T is $CR_1R_2$, W is $CR_4R_5$, V is $CR_3$, and n is 1. In another embodiment of Formula (I), ring A is phenyl, p is 0, T is $CR_1R_2$, W is $CR_4R_5$, V is $CR_3$, and n is 2. In another embodiment of Formula (I), ring A is phenyl, p is 0, T is $CR_1R_2$, W is $CR_4R_5$, V is $CR_3$, and n is 3.

In another embodiment of Formula (I), ring A is phenyl, T is $CR_1R_2$, W is $CR_4R_5$, V is $CR_3$, and Y is O. In another embodiment of Formula (I), ring A is phenyl, p is 0, T is $CR_1R_2$, W is $CR_4R_5$, V is $CR_3$, and Y is O. In another embodiment of Formula (I), ring A is phenyl, T is $CR_1R_2$, W is $CR_4R_5$, V is $CR_3$, Y is O, and n is 1. In another embodiment of Formula (I), ring A is phenyl, T is $CR_1R_2$, W is $CR_4R_5$, V is $CR_3$, Y is O, and n is 2. In another embodiment of Formula (I), ring A is phenyl, T is $CR_1R_2$, W is $CR_4R_5$, V is $CR_3$, Y is O, and n is 3. In another embodiment of Formula (I), ring A is phenyl, p is 0, T is $CR_1R_2$, W is $CR_4R_5$, V is $CR_3$, Y is O, and n is 1. In another embodiment of Formula (I), ring A is phenyl, p is 0, T is $CR_1R_2$, W is $CR_4R_5$, V is $CR_3$, Y is O, and n is 2. In another embodiment of Formula (I), ring A is phenyl, p is 0, T is $CR_1R_2$, W is $CR_4R_5$, V is $CR_3$, Y is O, and n is 3.

In another embodiment of Formula (I), ring A is phenyl, T is $CR_1R_2$, W is $CR_4R_5$, V is $CR_3$, Y is O, and m is 1 or 2. In another embodiment of Formula (I), ring A is phenyl, p is 0, T is $CR_1R_2$, W is $CR_4R_5$, V is $CR_3$, Y is O, and m is 1 or 2. In another embodiment of Formula (I), ring A is phenyl, T is $CR_1R_2$, W is $CR_4R_5$, V is $CR_3$, Y is O, n is 1, and m is 1 or 2. In another embodiment of Formula (I), ring A is phenyl, T is $CR_1R_2$, W is $CR_4R_5$, V is $CR_3$, Y is O, n is 2, and m is 1 or 2. In another embodiment of Formula (I), ring A is phenyl, T is $CR_1R_2$, W is $CR_4R_5$, V is $CR_3$, Y is O, n is 3, and m is 1 or 2. In another embodiment of Formula (I), ring A is phenyl, p is 0, T is $CR_1R_2$, W is $CR_4R_5$, V is $CR_3$, Y is O, n is 1, and m is 1 or 2. In another embodiment of Formula (I), ring A is phenyl, p is 0, T is $CR_1R_2$, W is $CR_4R_5$, V is $CR_3$, Y is O, n is 2, and m is 1 or 2. In another embodiment of Formula (I), ring A is phenyl, p is 0, T is $CR_1R_2$, W is $CR_4R_5$, V is $CR_3$, Y is O, n is 3, and m is 1 or 2. In another embodiment of Formula (I), ring A is phenyl, T is $CR_1R_2$, W is $CR_4R_5$, V is $CR_3$, Y is O, and m is 3 or 4. In another embodiment of Formula (I), ring A is phenyl, p is 0, T is $CR_1R_2$, W is $CR_4R_5$, V is $CR_3$, Y is O, and m is 3 or 4. In another embodiment of Formula (I), ring A is phenyl, T is $CR_1R_2$, W is $CR_4R_5$, V is $CR_3$, Y is O, n is 1, and m is 3 or 4. In another embodiment of Formula (I), ring A is phenyl, T is $CR_1R_2$, W is $CR_4R_5$, V is $CR_3$, Y is O, n is 2, and m is 3 or 4. In another embodiment of Formula (I), ring A is phenyl, T is $CR_1R_2$, W is $CR_4R_5$, V is $CR_3$, Y is O, n is 3, and m is 3 or 4. In another embodiment of Formula (I), ring A is phenyl, p is 0, T is $CR_1R_2$, W is $CR_4R_5$, V is $CR_3$, Y is O, n is 1, and m is 3 or 4. In another embodiment of Formula (I), ring A is phenyl, p is 0, T is $CR_1R_2$, W is $CR_4R_5$, V is $CR_3$, Y is O, n is 2, and m is 3 or 4. In another embodiment of Formula (I), ring A is phenyl, p is 0, T is $CR_1R_2$, W is $CR_4R_5$, V is $CR_3$, Y is O, n is 3, and m is 3 or 4.

In another embodiment of Formula (I), p is 0 and $R_1$, $R_2$, $R_4$, and $R_5$ are each H. In another embodiment of Formula (I), p is 0; $R_1$, $R_2$, $R_4$, and $R_5$ are each H; and $R_3$ is H. In another embodiment of Formula (I), p is 0; $R_1$, $R_2$, $R_4$, and $R_5$ are each H; $R_3$ is H; and $R_6$, $R_7$, $R_8$, $R_9$, and $R_{11}$ are each H. In another embodiment of Formula (I), p is 0; $R_1$, $R_2$, $R_4$, and $R_5$ are each H; $R_3$ is H; $R_6$, $R_7$, $R_8$, $R_9$, and $R_{11}$ are each H; and $R_{12}$ and $R_{13}$ are each H.

In another embodiment of Formula (I), p is 1 and $R_1$, $R_2$, $R_4$, and $R_5$ are each H. In another embodiment of Formula (I), p is 1; $R_1$, $R_2$, $R_4$, and $R_5$ are each H; and $R_3$ is H. In another embodiment of Formula (I), p is 1; $R_1$, $R_2$, $R_4$, and $R_5$ are each H; $R_3$ is H; and $R_6$, $R_7$, $R_8$, $R_9$, and $R_{11}$ are each H. In another embodiment of Formula (I), p is 1; $R_1$, $R_2$, $R_4$, and $R_5$ are each H; $R_3$ is H; $R_6$, $R_7$, $R_8$, $R_9$, and $R_{11}$ are each H; and $R_{12}$ and $R_{13}$ are each H.

In another embodiment of Formula (I), p is 2 and $R_1$, $R_2$, $R_4$, and $R_5$ are each H. In another embodiment of Formula (I), p is 2; $R_1$, $R_2$, $R_4$, and $R_5$ are each H; and $R_3$ is H. In another embodiment of Formula (I), p is 2; $R_1$, $R_2$, $R_4$, and $R_5$ are each H; $R_3$ is H; and $R_6$, $R_7$, $R_8$, $R_9$, and $R_{11}$ are each H. In another embodiment of Formula (I), p is 2; $R_1$, $R_2$, $R_4$, and $R_5$ are each H; $R_3$ is H; $R_6$, $R_7$, $R_8$, $R_9$, and $R_{11}$ are each H; and $R_{12}$ and $R_{13}$ are each H.

In another embodiment of Formula (I), p is 1, 2, 3, or 4 and R is fluorine. In another embodiment of Formula (I), p is 1, 2, 3, or 4 and R is deuterium. In another embodiment of Formula (I), p is 1, 2, 3, or 4 and each R is, independently, selected from the group consisting of hydroxyl, cyano, unsubstituted $C_1$-$C_3$ alkyl, and $C_1$-$C_3$ alkyl substituted with one or more halogen or deuterium. In another embodiment of Formula (I), p is 1, 2, 3, or 4 and each R is, independently, selected from the group consisting of cyano, unsubstituted $C_1$-$C_3$ alkyl, and $C_1$-$C_3$ alkyl substituted with one or more halogen or deuterium. In another embodiment of Formula (I), p is 1 and R is unsubstituted $C_1$-$C_3$ alkyl. In another embodiment of Formula (I), p is 1 and R is methyl. In another embodiment of Formula (I), p is 1 or 2 and each R is methyl. In another embodiment of Formula (I), p is 1 and R is $C_1$-$C_3$ alkyl substituted with one or more halogen. In another embodiment of Formula (I), p is 1 and R is $CF_3$. In another embodiment of Formula (I), p is 1 or 2 and each R is $CF_3$.

In another embodiment of Formula (I), one or more of $R_1$, $R_2$, $R_4$, and $R_5$ is fluorine. In another embodiment of Formula (I), one or more of $R_1$, $R_2$, $R_4$, and $R_5$ is deuterium. In another embodiment of Formula (I), one or more of $R_6$, $R_7$, $R_8$, $R_9$, and $R_{11}$ is fluorine. In another embodiment of Formula (I), one or more of $R_6$, $R_7$, $R_8$, $R_9$, and $R_{11}$ is deuterium. In another embodiment of Formula (I), one or more of each $R_{12}$ and $R_{13}$ is fluorine. In another embodiment of Formula (I), one or more of each $R_{12}$ and $R_{13}$ is deuterium.

In another embodiment of Formula (I), Y is O, T is $CR_1R_2$, V is $CR_3$, W is $CR_4R_5$, and $R_{11}$ is H. In another embodiment of Formula (I), Y is O, T is $CR_1R_2$, V is $CR_3$, W is $CR_4R_5$, $R_{11}$ is H, and m is 1. In another embodiment of Formula (I), Y is O, T is $CR_1R_2$, V is $CR_3$, W is $CR_4R_5$, and each of $R_{11}$, $R_{14}$, $R_{15}$, $R_{16}$, $R_{17}$, and $R_{18}$ is H. In another embodiment of Formula (I), Y is O, T is $CR_1R_2$, V is $CR_3$, W is $CR_4R_5$, each of $R_1$, $R_{14}$, $R_{15}$, $R_{16}$, $R_{17}$, and $R_{18}$ is H, and m is 1. In another embodiment of Formula (I), Y is O, T is $CR_1R_2$, V is $CR_3$, W is $CR_4R_5$, and each of $R_1$, $R_{12}$, $R_{13}$, $R_{14}$, $R_{15}$, $R_{16}$, $R_{17}$, and $R_{18}$ is H. In another embodiment of Formula (I), Y is O, T is $CR_1R_2$, V is $CR_3$, W is $CR_4R_5$, each of $R_1$, $R_{12}$, $R_{13}$, $R_{14}$, $R_{15}$, $R_{16}$, $R_{17}$, and $R_{18}$ is H, and m is 1.

Each of the embodiments described herein with respect to compounds of Formula I also applies to compounds of Formula I-A.

Also provided herein is a compound having the structure of Formula II-A or a pharmaceutically acceptable salt thereof:

(II-A)

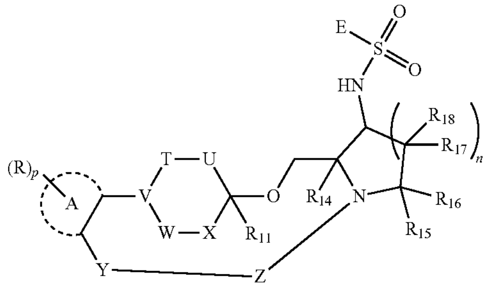

wherein:

ring A is selected from the group consisting of phenyl, pyridinyl, pyridazinyl, pyrimidinyl, pyrazinyl, and triazinyl;

n is 1, 2, or 3;

E is selected from the group consisting of $NR_aR_b$, $C_1$-$C_3$ alkylene-$NR_aR_b$, $C_1$-$C_3$ alkyl, $C_2$-$C_4$ alkenyl, $C_2$-$C_4$ alkynyl, $C_3$-$C_8$ cycloalkyl, $C_1$-$C_3$ alkylene-($C_3$-$C_8$ cycloalkyl), 4- to 10-membered heterocyclyl, $C_1$-$C_3$ alkylene-(4- to 10-membered heterocyclyl), $C_6$-$C_{10}$ aryl, $C_1$-$C_3$ alkylene-($C_6$-$C_{10}$ aryl), 5- to 10-membered heteroaryl, and $C_1$-$C_3$ alkylene-(5- to 10-membered heteroaryl), wherein the $C_1$-$C_3$ alkylene-$NR_aR_b$, $C_1$-$C_3$alkyl, $C_2$-$C_4$ alkenyl, $C_2$-$C_4$ alkynyl, $C_3$-$C_8$ cycloalkyl, $C_1$-$C_3$ alkylene-($C_3$-$C_8$ cycloalkyl), 4- to 10-membered heterocyclyl, $C_1$-$C_3$ alkylene-(4- to 10-membered heterocyclyl), $C_6$-$C_{10}$ aryl, $C_1$-$C_3$ alkylene-($C_6$-$C_{10}$ aryl), 5- to 10-membered heteroaryl, or $C_1$-$C_3$ alkylene-(5- to 10-membered heteroaryl) is unsubstituted or substituted with one or more halogen, hydroxyl, $C_1$-$C_3$ alkyl, or $C_1$-$C_3$ alkoxyl;

T is $CR_1R_2$ or O;

W is $CR_4R_5$ or O;

U is $CR_6R_7$;

X is $CR_8R_9$;

V is $CR_3$ or N;

Y is $NR_{10}$, O or absent;

Z is $(CR_{12}R_{13})_m$;

each R is, independently, selected from the group consisting of halogen, deuterium, hydroxyl, cyano, unsubstituted $C_1$-$C_3$ alkyl, and $C_1$-$C_3$ alkyl substituted with one or more halogen or deuterium;

p is 0, 1, 2, 3, or 4;

$R_a$ and $R_b$ are each, independently, H or unsubstituted $C_1$-$C_3$ alkyl;

m is 2, 3, 4, or 5 when Y is absent; or m is 1, 2, 3, or 4 when Y is $NR_{10}$ or O;

and further wherein:

$R_1$, $R_2$, $R_4$, and $R_5$ are each, independently, selected from the group consisting of H, hydroxyl, halogen, and deuterium;

or, alternatively, $R_2$ and $R_5$ together with the carbon atoms to which they are attached, form a single bond;

$R_3$ is selected from the group consisting of H, deuterium, halogen, hydroxyl, and cyano;

or, alternatively, $R_3$ and $R_1$, together with the carbon atoms to which they are attached, form a $C_3$-$C_5$ cycloalkyl;

or, alternatively, $R_3$ and $R_4$, together with the carbon atoms to which they are attached, form a $C_3$-$C_5$ cycloalkyl;

$R_6$, $R_7$, $R_8$, $R_9$, and $R_{11}$ are each, independently, selected from the group consisting of H, hydroxyl, halogen, and deuterium;

$R_{10}$ is selected from the group consisting of H, unsubstituted $C_1$-$C_3$ alkyl, and $C_1$-$C_3$ alkyl substituted with one or more halogen;

each $R_{12}$ and $R_{13}$ is, independently, selected from the group consisting of H, halogen, deuterium, unsubstituted $C_1$-$C_3$ alkyl, and $C_1$-$C_3$ alkyl substituted with hydroxyl or one or more halogen; and $R_{14}$, $R_{15}$, and $R_{16}$ are each, independently, selected from the group consisting of H, unsubstituted $C_1$-$C_3$ alkyl or $C_1$-$C_3$ alkyl substituted with one or more halogen; and each $R_{17}$ and $R_{18}$ is, independently, selected from the group consisting of H, unsubstituted $C_1$-$C_3$ alkyl or $C_1$-$C_3$ alkyl substituted with one or more halogen;

with the proviso that one or more of (a)-(f) is present:

(a) at least one R is selected from the group consisting of hydroxyl, cyano, unsubstituted $C_1$-$C_3$ alkyl, and $C_1$-$C_3$ alkyl substituted with one or more halogen or deuterium;

(b) E is $NR_aR_b$, $C_1$-$C_3$ alkylene-$NR_aR_b$, $C_2$-$C_3$ alkyl, $C_2$-$C_4$ alkenyl, $C_2$-$C_4$ alkynyl, $C_3$-$C_8$ cycloalkyl, $C_1$-$C_3$ alkylene-($C_3$-$C_8$ cycloalkyl), 4- to 10-membered heterocyclyl, $C_1$-$C_3$ alkylene-(4- to 10-membered heterocyclyl), $C_6$-$C_{10}$ aryl, $C_1$-$C_3$ alkylene-($C_6$-$C_{10}$ aryl), 5- to 10-membered heteroaryl, or $C_1$-$C_3$ alkylene-(5- to 10-membered heteroaryl), wherein the $C_1$-$C_3$ alkylene-$NR_aR_b$, $C_2$-$C_3$ alkyl, $C_2$-$C_4$ alkenyl, $C_2$-$C_4$ alkynyl, $C_3$-$C_8$ cycloalkyl, $C_1$-$C_3$ alkylene-($C_3$-$C_8$ cycloalkyl), 4- to 10-membered heterocyclyl, $C_1$-$C_3$ alkylene-(4- to 10-membered heterocyclyl), $C_6$-$C_{10}$ aryl, $C_1$-$C_3$ alkylene-($C_6$-$C_{10}$ aryl), 5- to 10-membered heteroaryl, or $C_1$-$C_3$ alkylene-(5- to 10-membered heteroaryl) is unsubstituted or substituted with one or more halogen, hydroxyl, $C_1$-$C_3$ alkyl, or $C_1$-$C_3$ alkoxyl;

(c) E is $C_1$ alkyl substituted with one or more halogen, hydroxyl, $C_1$-$C_3$ alkyl, or $C_1$-$C_3$ alkoxyl;

(d) at least one of $R_{14}$, $R_{15}$, $R_{16}$, $R_{17}$, and $R_{18}$ is unsubstituted $C_1$-$C_3$ alkyl or $C_1$-$C_3$ alkyl substituted with one or more halogen;

(e) at least one of $R_1$, $R_2$, $R_4$, $R_5$, $R_6$, $R_7$, $R_8$, $R_9$, and $R_{11}$ is hydroxyl; or (f) at least one of $R_{12}$ and $R_{13}$ is $C_1$-$C_3$ alkyl substituted with hydroxyl.

In one embodiment, provided herein are compounds of Formula II-A having the structure of Formula II or a pharmaceutically acceptable salt thereof:

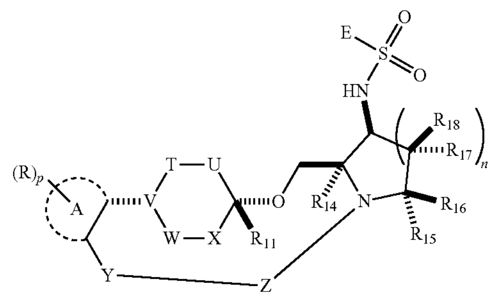

(II)

wherein:

ring A is selected from the group consisting of phenyl, pyridinyl, pyridazinyl, pyrimidinyl, pyrazinyl, and triazinyl;

n is 1, 2, or 3;

E is selected from the group consisting of $NR_aR_b$, $C_1$-$C_3$ alkylene-$NR_aR_b$, $C_1$-$C_3$ alkyl, $C_2$-$C_4$ alkenyl, $C_2$-$C_4$ alkynyl, $C_3$-$C_8$ cycloalkyl, $C_1$-$C_3$ alkylene-($C_3$-$C_8$ cycloalkyl), 4- to 10-membered heterocyclyl, $C_1$-$C_3$ alkylene-(4- to 10-membered heterocyclyl), $C_6$-$C_{10}$ aryl, $C_1$-$C_3$ alkylene-($C_6$-$C_{10}$ aryl), 5- to 10-membered heteroaryl, and $C_1$-$C_3$ alkylene-(5- to 10-membered heteroaryl), wherein the $C_1$-$C_3$ alkylene-$NR_aR_b$, $C_1$-$C_3$alkyl, $C_2$-$C_4$ alkenyl, $C_2$-$C_4$ alkynyl, $C_3$-$C_8$ cycloalkyl, $C_1$-$C_3$ alkylene-($C_3$-$C_8$ cycloalkyl), 4- to 10-membered heterocyclyl, $C_1$-$C_3$ alkylene-(4- to 10-membered heterocyclyl), $C_6$-$C_{10}$ aryl, $C_1$-$C_3$ alkylene-($C_6$-$C_{10}$ aryl), 5- to 10-membered heteroaryl, or $C_1$-$C_3$ alkylene-(5- to 10-membered heteroaryl) is unsubstituted or substituted with one or more halogen, hydroxyl, $C_1$-$C_3$ alkyl, or $C_1$-$C_3$ alkoxyl;

T is $CR_1R_2$ or O;

W is $CR_4R_5$ or O;

U is $CR_6R_7$;

X is $CR_8R_9$;

V is $CR_3$ or N;

Y is $NR_{10}$, O or absent;

Z is $(CR_{12}R_{13})_m$;

each R is, independently, selected from the group consisting of halogen, deuterium, hydroxyl, cyano, unsubstituted $C_1$-$C_3$ alkyl, and $C_1$-$C_3$ alkyl substituted with one or more halogen or deuterium;

p is 0, 1, 2, 3, or 4;

$R_a$ and $R_b$ are each, independently, H or unsubstituted $C_1$-$C_3$ alkyl;

m is 2, 3, 4, or 5 when Y is absent; or m is 1, 2, 3, or 4 when Y is $NR_{10}$ or 0;

and further wherein:

$R_1$, $R_2$, $R_4$, and $R_5$ are each, independently, selected from the group consisting of H, hydroxyl, halogen, and deuterium;

or, alternatively, $R_2$ and $R_5$ together with the carbon atoms to which they are attached, form a single bond;

$R_3$ is selected from the group consisting of H, deuterium, halogen, hydroxyl, and cyano;

or, alternatively, $R_3$ and $R_1$, together with the carbon atoms to which they are attached, form a $C_3$-$C_5$ cycloalkyl;

or, alternatively, $R_3$ and $R_4$, together with the carbon atoms to which they are attached, form a $C_3$-$C_5$ cycloalkyl;

$R_6$, $R_7$, $R_8$, $R_9$, and $R_{11}$ are each, independently, selected from the group consisting of H, hydroxyl, halogen, and deuterium;

$R_{10}$ is selected from the group consisting of H, unsubstituted $C_1$-$C_3$ alkyl, and $C_1$-$C_3$ alkyl substituted with one or more halogen;

each $R_{12}$ and $R_{13}$ is, independently, selected from the group consisting of H, halogen, deuterium, unsubstituted $C_1$-$C_3$ alkyl, and $C_1$-$C_3$ alkyl substituted with hydroxyl or one or more halogen; and $R_{14}$, $R_{15}$, and $R_{16}$ are each, independently, selected from the group consisting of H, unsubstituted $C_1$-$C_3$ alkyl or $C_1$-$C_3$ alkyl substituted with one or more halogen; and each $R_{17}$ and $R_{18}$ is, independently, selected from the group consisting of H, unsubstituted $C_1$-$C_3$ alkyl or $C_1$-$C_3$ alkyl substituted with one or more halogen;

with the proviso that one or more of (a)-(f) is present:

(a) at least one R is selected from the group consisting of hydroxyl, cyano, unsubstituted $C_1$-$C_3$ alkyl, and $C_1$-$C_3$ alkyl substituted with one or more halogen or deuterium;

(b) E is $NR_aR_b$, $C_1$-$C_3$ alkylene-$NR_aR_b$, $C_2$-$C_3$ alkyl, $C_2$-$C_4$ alkenyl, $C_2$-$C_4$ alkynyl, $C_3$-$C_8$ cycloalkyl, $C_1$-$C_3$ alkylene-($C_3$-$C_8$ cycloalkyl), 4- to 10-membered heterocyclyl, $C_1$-$C_3$ alkylene-(4- to 10-membered heterocyclyl), $C_6$-$C_{10}$ aryl, $C_1$-$C_3$ alkylene-($C_6$-$C_{10}$ aryl), 5- to 10-membered heteroaryl, or $C_1$-$C_3$ alkylene-(5- to 10-membered heteroaryl), wherein the $C_1$-$C_3$ alkylene-$NR_aR_b$, $C_2$-$C_3$ alkyl, $C_2$-$C_4$ alkenyl, $C_2$-$C_4$ alkynyl, $C_3$-$C_8$ cycloalkyl, $C_1$-$C_3$ alkylene-($C_3$-$C_8$ cycloalkyl), 4- to 10-membered heterocyclyl, $C_1$-$C_3$ alkylene-(4- to 10-membered heterocyclyl), $C_6$-$C_{10}$ aryl, $C_1$-$C_3$ alkylene-($C_6$-$C_{10}$ aryl), 5- to 10-membered heteroaryl, or $C_1$-$C_3$ alkylene-(5- to 10-membered heteroaryl) is unsubstituted or substituted with one or more halogen, hydroxyl, $C_1$-$C_3$ alkyl, or $C_1$-$C_3$ alkoxyl;

(c) E is $C_1$ alkyl substituted with one or more halogen, hydroxyl, $C_1$-$C_3$ alkyl, or $C_1$-$C_3$ alkoxyl;

(d) at least one of $R_{14}$, $R_{15}$, $R_{16}$, $R_{17}$, and $R_{18}$ is unsubstituted $C_1$-$C_3$ alkyl or $C_1$-$C_3$ alkyl substituted with one or more halogen;

(e) at least one of $R_1$, $R_2$, $R_4$, $R_5$, $R_6$, $R_7$, $R_8$, $R_9$, and $R_{11}$ is hydroxyl; or (f) at least one of $R_{12}$ and $R_{13}$ is $C_1$-$C_3$ alkyl substituted with hydroxyl.

In one embodiment of Formula (II), one or more of (a)-(d) is present:

(a) at least one R is selected from the group consisting of cyano, unsubstituted $C_1$-$C_3$ alkyl, and $C_1$-$C_3$ alkyl substituted with one or more halogen or deuterium;

(b) E is $NR_aR_b$, $C_1$-$C_3$ alkylene-$NR_aR_b$, $C_2$-$C_3$ alkyl, $C_2$-$C_4$ alkenyl, $C_2$-$C_4$ alkynyl, $C_3$-$C_8$ cycloalkyl, $C_1$-$C_3$ alkylene-($C_3$-$C_8$ cycloalkyl), 4- to 10-membered heterocyclyl, $C_1$-$C_3$ alkylene-(4- to 10-membered heterocyclyl), $C_6$-$C_{10}$ aryl, $C_1$-$C_3$ alkylene-($C_6$-$C_{10}$ aryl), 5- to 10-membered heteroaryl, or $C_1$-$C_3$ alkylene-(5- to 10-membered heteroaryl), wherein the $C_1$-$C_3$ alkylene-$NR_aR_b$, $C_2$-$C_3$ alkyl, $C_2$-$C_4$ alkenyl, $C_2$-$C_4$ alkynyl, $C_3$-$C_8$ cycloalkyl, $C_1$-$C_3$ alkylene-($C_3$-$C_8$ cycloalkyl), 4- to 10-membered heterocyclyl, $C_1$-$C_3$ alkylene-(4- to 10-membered heterocyclyl), $C_6$-$C_{10}$ aryl, $C_1$-$C_3$ alkylene-($C_6$-$C_{10}$ aryl), 5- to 10-membered heteroaryl, or $C_1$-$C_3$ alkylene-(5- to 10-membered heteroaryl) is unsubstituted or substituted with one or more halogen, $C_1$-$C_3$ alkyl, or $C_1$-$C_3$ alkoxyl;

(c) E is $C_1$ alkyl substituted with one or more halogen, $C_1$-$C_3$ alkyl, or $C_1$-$C_3$ alkoxyl; or (d) at least one of $R_{14}$, $R_{15}$, $R_{16}$, $R_{17}$, and $R_{18}$ is unsubstituted $C_1$-$C_3$ alkyl or $C_1$-$C_3$ alkyl substituted with one or more halogen.

In another embodiment of Formula (II), at least one R is selected from the group consisting of hydroxyl, cyano, unsubstituted $C_1$-$C_3$ alkyl, and $C_1$-$C_3$ alkyl substituted with one or more halogen or deuterium.

In another embodiment of Formula (II), E is $NR_aR_b$, $C_1$-$C_3$ alkylene-$NR_aR_b$, $C_2$-$C_3$ alkyl, $C_2$-$C_4$ alkenyl, $C_2$-$C_4$ alkynyl, $C_3$-$C_8$ cycloalkyl, $C_1$-$C_3$ alkylene-($C_3$-$C_8$ cycloalkyl), 4- to 10-membered heterocyclyl, $C_1$-$C_3$ alkylene-(4- to 10-membered heterocyclyl), $C_6$-$C_{10}$ aryl, $C_1$-$C_3$ alkylene-($C_6$-$C_{10}$ aryl), 5- to 10-membered heteroaryl, or $C_1$-$C_3$ alkylene-(5- to 10-membered heteroaryl), wherein the $C_1$-$C_3$ alkylene-$NR_aR_b$, $C_2$-$C_3$ alkyl, $C_2$-$C_4$ alkenyl, $C_2$-$C_4$ alkynyl, $C_3$-$C_8$ cycloalkyl, $C_1$-$C_3$ alkylene-($C_3$-$C_8$ cycloalkyl), 4- to 10-membered heterocyclyl, $C_1$-$C_3$ alkylene-(4- to 10-membered heterocyclyl), $C_6$-$C_{10}$ aryl, $C_1$-$C_3$ alkylene-($C_6$-$C_{10}$ aryl), 5- to 10-membered heteroaryl, or $C_1$-$C_3$ alkylene-(5- to 10-membered heteroaryl) is unsubstituted or substituted with one or more halogen, hydroxyl, $C_1$-$C_3$ alkyl, or $C_1$-$C_3$ alkoxyl.

In another embodiment of Formula (II), E is $C_1$ alkyl substituted with one or more halogen, hydroxyl, $C_1$-$C_3$ alkyl, or $C_1$-$C_3$ alkoxyl. In another embodiment of Formula (II), E is trifluoromethyl. In another embodiment of Formula (II), E is methyl. In another embodiment of Formula (II), E is ethyl. In another embodiment of Formula (II), E is propyl. In another embodiment of Formula (II), E is isopropyl. In another embodiment of Formula (II), E is cyclopropyl. In another embodiment of Formula (II), E is tetrahydrofuranyl.

In another embodiment of Formula (II), at least one of $R_{14}$, $R_{15}$, $R_{16}$, $R_{17}$, and $R_{18}$ is unsubstituted $C_1$-$C_3$ alkyl or $C_1$-$C_3$ alkyl substituted with one or more halogen.

In another embodiment of Formula (II), at least one of $R_1$, $R_2$, $R_4$, $R_5$, $R_6$, $R_7$, $R_8$, $R_9$, and $R_{11}$ is hydroxyl.

In another embodiment of Formula (II), at least one of $R_{12}$ and $R_{13}$ is $C_1$-$C_3$ alkyl substituted with hydroxyl.

In another embodiment of Formula (II), n is 1. In another embodiment of Formula (II), n is 2. In another embodiment of Formula (II), n is 3.

In another embodiment of Formula (II), ring A is phenyl. In another embodiment of Formula (II), ring A is pyridinyl. In another embodiment of Formula (II), ring A is pyridazinyl. In another embodiment of Formula (II), ring A is pyrimidinyl. In another embodiment of Formula (II), ring A is pyrazinyl. In another embodiment of Formula (II), ring A is triazinyl.

In another embodiment of Formula (II), Y is $NR_{10}$. In another embodiment of Formula (II), Y is O. In another embodiment of Formula (II), Y is absent. In another embodiment of Formula (II), ring A is phenyl and Y is $NR_{10}$. In another embodiment of Formula (II), ring A is phenyl and Y is O. In another embodiment of Formula (II), ring A is phenyl and Y is absent. In another embodiment of Formula (II), ring A is pyridinyl and Y is $NR_{10}$. In another embodiment of Formula (II), ring A is pyridinyl and Y is O. In another embodiment of Formula (II), ring A is pyridinyl and Y is absent. In another embodiment of Formula (II), ring A is pyridazinyl and Y is $NR_{10}$. In another embodiment of Formula (II), ring A is pyridazinyl and Y is O. In another embodiment of Formula (II), ring A is pyridazinyl and Y is absent. In another embodiment of Formula (II), ring A is pyrimidinyl and Y is $NR_{10}$. In another embodiment of Formula (II), ring A is pyrimidinyl and Y is O. In another embodiment of Formula (II), ring A is pyrimidinyl and Y is absent. In another embodiment of Formula (II), ring A is pyrazinyl and Y is $NR_{10}$. In another embodiment of Formula (II), ring A is pyrazinyl and Y is O. In another embodiment of Formula (II), ring A is pyrazinyl and Y is absent. In another embodiment of Formula (II), ring A is triazinyl and Y is $NR_{10}$. In another embodiment of Formula (II), ring A is triazinyl and Y is O. In another embodiment of Formula (II), ring A is triazinyl and Y is absent.

In another embodiment of Formula (II), T is $CR_1R_2$. In another embodiment of Formula (II), T is O. In another embodiment of Formula (II), W is $CR_4R_5$. In another embodiment of Formula (II), W is O. In another embodiment of Formula (II), T is $CR_1R_2$ and W is $CR_4R_5$. In another embodiment of Formula (II), T is O and W is $CR_4R_5$. In another embodiment of Formula (II), T is $CR_1R_2$ and W is O.

In another embodiment of Formula (II), V is $CR_3$. In another embodiment of Formula (II), V is N.

In another embodiment of Formula (II), T is $CR_1R_2$ and V is $CR_3$. In another embodiment of Formula (II), T is O and V is $CR_3$. In another embodiment of Formula (II), T is $CR_1R_2$ and V is N. In another embodiment of Formula (II), T is O and V is N.

In another embodiment of Formula (II), W is $CR_4R_5$ and V is $CR_3$. In another embodiment of Formula (II), W is O and V is $CR_3$. In another embodiment of Formula (II), W is $CR_4R_5$ and V is N. In another embodiment of Formula (II), W is O and V is N.

In another embodiment of Formula (II), T is $CR_1R_2$, W is $CR_4R_5$, and V is $CR_3$. In another embodiment of Formula (II), T is $CR_1R_2$, W is O, and V is $CR_3$. In another embodiment of Formula (II), T is $CR_1R_2$, W is $CR_4R_5$, and V is N. In another embodiment of Formula (II), T is $CR_1R_2$, W is O, and V is N. In another embodiment of Formula (II), T is O, W is $CR_4R_5$, and V is $CR_3$.

In another embodiment of Formula (II), E is $NR_aR_b$. In another embodiment of Formula (II), E is $C_1$-$C_3$ alkylene-$NR_aR_b$. In another embodiment of Formula (II), E is unsubstituted $C_2$-$C_3$ alkyl, unsubstituted $C_2$-$C_4$ alkenyl or unsubstituted $C_2$-$C_4$ alkynyl. In another embodiment of Formula (II), E is $C_2$-$C_3$ alkyl, $C_2$-$C_4$ alkenyl or $C_2$-$C_4$ alkynyl substituted with one or more halogen, hydroxyl, $C_1$-$C_3$ alkyl, or $C_1$-$C_3$ alkoxyl. In another embodiment of Formula (II), E is unsubstituted $C_2$-$C_3$ alkyl. In another embodiment of Formula (II), E is $C_2$-$C_3$ alkyl substituted with one or more halogen, hydroxyl, $C_1$-$C_3$ alkyl, or $C_1$-$C_3$ alkoxyl. In another embodiment of Formula (II), E is unsubstituted $C_3$-$C_8$ cycloalkyl. In another embodiment of Formula (II), E is $C_3$-$C_8$ cycloalkyl substituted with one or more halogen, hydroxyl, $C_1$-$C_3$ alkyl, or $C_1$-$C_3$ alkoxyl. In another embodiment of Formula (II), E is unsubstituted $C_1$-$C_3$ alkylene-($C_3$-$C_8$ cycloalkyl). In another embodiment of Formula (II), E is $C_1$-$C_3$ alkylene-($C_3$-$C_8$ cycloalkyl) substituted with one or more halogen, hydroxyl, $C_1$-$C_3$ alkyl, or $C_1$-$C_3$ alkoxyl. In another embodiment of Formula (II), E is unsubstituted 4- to 10-membered heterocyclyl. In another embodiment of Formula (II), E is 4- to 10-membered heterocyclyl substituted with one or more halogen, hydroxyl, $C_1$-$C_3$ alkyl, or $C_1$-$C_3$ alkoxyl. In another embodiment of Formula (II), E is unsubstituted $C_1$-$C_3$ alkylene-(4- to 10-membered heterocyclyl). In another embodiment of Formula (II), E is $C_1$-$C_3$ alkylene-(4- to 10-membered heterocyclyl) substituted with one or more halogen, hydroxyl, $C_1$-$C_3$ alkyl, or $C_1$-$C_3$ alkoxyl. In another embodiment of Formula (II), E is unsubstituted $C_6$-$C_{10}$ aryl. In another embodiment of Formula (II), E is $C_6$-$C_{10}$ aryl substituted with one or more halogen, hydroxyl, $C_1$-$C_3$ alkyl, or $C_1$-$C_3$ alkoxyl. In another embodiment of Formula (II), E is unsubstituted $C_1$-$C_3$ alkylene-($C_6$-$C_{10}$ aryl). In another embodiment of Formula (II), E is $C_1$-$C_3$ alkylene-($C_6$-$C_{10}$ aryl) substituted with one or more halogen, hydroxyl, $C_1$-$C_3$ alkyl, or $C_1$-$C_3$ alkoxyl. In another embodiment of Formula (II), E is unsubstituted 5- to 10-membered heteroaryl. In another embodiment of Formula (II), E is 5- to 10-membered heteroaryl substituted with one or more halogen, hydroxyl, $C_1$-$C_3$ alkyl, or $C_1$-$C_3$ alkoxyl.

In another embodiment of Formula (II), E is unsubstituted 4- to 10-membered heterocyclyl. In another embodiment of Formula (II), E is 4- to 10-membered heterocyclyl substituted with one or more halogen, hydroxyl, $C_1$-$C_3$ alkyl, or $C_1$-$C_3$ alkoxyl. In another embodiment of Formula (II), E is unsubstituted 8- to 10-membered heterocyclyl. In another embodiment of Formula (II), E is 8- to 10-membered heterocyclyl substituted with one or more halogen, hydroxyl, $C_1$-$C_3$ alkyl, or $C_1$-$C_3$ alkoxyl. In another embodiment of Formula (II), E is unsubstituted 4- to 7-membered heterocyclyl. In another embodiment of Formula (II), E is 4- to 7-membered heterocyclyl substituted with one or more halogen, hydroxyl, $C_1$-$C_3$ alkyl, or $C_1$-$C_3$ alkoxyl. In another embodiment of Formula (II), E is unsubstituted 4- to 6-membered heterocyclyl. In another embodiment of Formula (II), E is 4- to 6-membered heterocyclyl substituted with one or more halogen, hydroxyl, $C_1$-$C_3$ alkyl, or $C_1$-$C_3$ alkoxyl. In another embodiment of Formula (II), E is unsubstituted 4-membered heterocyclyl. In another embodiment of Formula (II), E is 4-membered heterocyclyl substituted with one or more halogen, hydroxyl, $C_1$-$C_3$ alkyl, or $C_1$-$C_3$ alkoxyl. In another embodiment of Formula (II), E is unsubstituted 5-membered heterocyclyl. In another embodiment of Formula (II), E is 5-membered heterocyclyl substituted with one or more halogen, hydroxyl, $C_1$-$C_3$ alkyl, or $C_1$-$C_3$ alkoxyl. In another embodiment of Formula (II), E is unsubstituted 6-membered heterocyclyl. In another embodiment of Formula (II), E is 6-membered heterocyclyl substituted with one or more halogen, hydroxyl, $C_1$-$C_3$ alkyl, or $C_1$-$C_3$ alkoxyl.

In another embodiment of Formula (II), E is unsubstituted 5- to 10-membered heteroaryl. In another embodiment of Formula (II), E is 5- to 10-membered heteroaryl substituted with one or more halogen, hydroxyl, $C_1$-$C_3$ alkyl, or $C_1$-$C_3$ alkoxyl. In another embodiment of Formula (II), E is unsubstituted 5- to 6-membered heteroaryl. In another embodiment of Formula (II), E is 5- to 6-membered heteroaryl substituted with one or more halogen, hydroxyl, $C_1$-$C_3$ alkyl, or $C_1$-$C_3$ alkoxyl. In another embodiment of Formula (II), E is unsubstituted 5-membered heteroaryl. In another embodiment of Formula (II), E is 5-membered heteroaryl substituted with one or more halogen, hydroxyl, $C_1$-$C_3$ alkyl, or $C_1$-$C_3$ alkoxyl. In another embodiment of Formula (II), E is unsubstituted 6-membered heteroaryl. In another embodiment of Formula (II), E is 6-membered heteroaryl substituted with one or more halogen, hydroxyl, $C_1$-$C_3$ alkyl, or $C_1$-$C_3$ alkoxyl. In another embodiment of Formula (II), E is unsubstituted 8-membered heteroaryl. In another embodiment of Formula (II), E is 8-membered heteroaryl substituted with one or more halogen, hydroxyl, $C_1$-$C_3$ alkyl, or $C_1$-$C_3$ alkoxyl. In another embodiment of Formula (II), E is unsubstituted 10-membered heteroaryl. In another embodiment of Formula (II), E is 10-membered heteroaryl substituted with one or more halogen, hydroxyl, $C_1$-$C_3$ alkyl, or $C_1$-$C_3$ alkoxyl.

In another embodiment of Formula (II), E is $NR_aR_b$, $C_1$-$C_3$ alkylene-$NR_aR_b$, $C_1$-$C_3$ alkyl, $C_2$-$C_4$ alkenyl, $C_2$-$C_4$ alkynyl, $C_3$-$C_8$ cycloalkyl, $C_1$-$C_3$ alkylene-($C_3$-$C_8$ cycloalkyl), 4- to 10-membered heterocyclyl, $C_1$-$C_3$ alkylene-(4- to 10-membered heterocyclyl), $C_6$-$C_{10}$ aryl, or $C_1$-$C_3$ alkylene- ($C_6$-$C_{10}$ aryl), wherein the $C_1$-$C_3$ alkylene-$NR_aR_b$, $C_1$-$C_3$alkyl, $C_2$-$C_4$ alkenyl, $C_2$-$C_4$ alkynyl, $C_3$-$C_8$ cycloalkyl, $C_1$-$C_3$ alkylene-($C_3$-$C_8$ cycloalkyl), 4- to 10-membered heterocyclyl, $C_1$-$C_3$ alkylene-(4- to 10-membered heterocyclyl), $C_6$-$C_{10}$ aryl, or $C_1$-$C_3$ alkylene-($C_6$-$C_{10}$ aryl) is unsubstituted or substituted with one or more halogen, hydroxyl, $C_1$-$C_3$ alkyl, or $C_1$-$C_3$ alkoxyl.

In another embodiment of Formula (II), E is $C_1$-$C_3$ alkyl, $C_2$-$C_4$ alkenyl, $C_2$-$C_4$ alkynyl, $C_3$-$C_8$ cycloalkyl, $C_1$-$C_3$ alkylene-($C_3$-$C_8$ cycloalkyl), 4- to 10-membered heterocyclyl, $C_1$-$C_3$ alkylene-(4- to 10-membered heterocyclyl), $C_6$-$C_{10}$ aryl, or $C_1$-$C_3$ alkylene-($C_6$-$C_{10}$ aryl), wherein the $C_1$-$C_3$alkyl, $C_2$-$C_4$ alkenyl, $C_2$-$C_4$ alkynyl, $C_3$-$C_8$ cycloalkyl, $C_1$-$C_3$ alkylene-($C_3$-$C_8$ cycloalkyl), 4- to 10-membered heterocyclyl, $C_1$-$C_3$ alkylene-(4- to 10-membered heterocyclyl), $C_6$-$C_{10}$ aryl, or $C_1$-$C_3$ alkylene-($C_6$-$C_{10}$ aryl) is unsubstituted or substituted with one or more halogen, hydroxyl, $C_1$-$C_3$ alkyl, or $C_1$-$C_3$ alkoxyl.

In another embodiment of Formula (II), E is $C_1$-$C_3$ alkyl, $C_3$-$C_8$ cycloalkyl, $C_1$-$C_3$ alkylene-($C_3$-$C_8$ cycloalkyl), 4- to 10-membered heterocyclyl, $C_1$-$C_3$ alkylene-(4- to 10-membered heterocyclyl), $C_6$-$C_{10}$ aryl, or $C_1$-$C_3$ alkylene-($C_6$-$C_{10}$ aryl), wherein the $C_1$-$C_3$alkyl, $C_3$-$C_8$ cycloalkyl, $C_1$-$C_3$ alkylene-($C_3$-$C_8$ cycloalkyl), 4- to 10-membered heterocyclyl, $C_1$-$C_3$ alkylene-(4- to 10-membered heterocyclyl), $C_6$-$C_{10}$ aryl, or $C_1$-$C_3$ alkylene-($C_6$-$C_{10}$ aryl) is unsubstituted or substituted with one or more halogen, hydroxyl, $C_1$-$C_3$ alkyl, or $C_1$-$C_3$ alkoxyl.

In another embodiment of Formula (II), E is $C_1$-$C_3$ alkyl, $C_3$-$C_8$ cycloalkyl, $C_1$-$C_3$ alkylene-($C_3$-$C_8$ cycloalkyl), 4- to 10-membered heterocyclyl, or $C_1$-$C_3$ alkylene-(4- to 10-membered heterocyclyl), wherein the $C_1$-$C_3$alkyl, $C_3$-$C_8$ cycloalkyl, $C_1$-$C_3$ alkylene-($C_3$-$C_8$ cycloalkyl), 4- to 10-membered heterocyclyl, or $C_1$-$C_3$ alkylene-(4- to 10-membered heterocyclyl) is unsubstituted or substituted with one or more halogen, hydroxyl, $C_1$-$C_3$ alkyl, or $C_1$-$C_3$ alkoxyl.

In another embodiment of Formula (II), E is $C_1$-$C_3$ alkyl, $C_3$-$C_8$ cycloalkyl, or $C_1$-$C_3$ alkylene-($C_3$-$C_8$ cycloalkyl), wherein the $C_1$-$C_3$alkyl, $C_3$-$C_8$ cycloalkyl, or $C_1$-$C_3$ alkylene-($C_3$-$C_8$ cycloalkyl) is unsubstituted or substituted with one or more halogen, hydroxyl, $C_1$-$C_3$ alkyl, or $C_1$-$C_3$ alkoxyl.

In another embodiment of Formula (II), E is methyl, wherein the methyl is unsubstituted or substituted with one or more halogen, hydroxyl, $C_1$-$C_3$ alkyl, or $C_1$-$C_3$ alkoxyl. In another embodiment of Formula (II), E is methyl. In another embodiment of Formula (II), E is trifluoromethyl. In another embodiment of Formula (II), E is dioxanyl, wherein the dioxanyl is unsubstituted or substituted with one or more halogen, hydroxyl, $C_1$-$C_3$ alkyl, or $C_1$-$C_3$ alkoxyl. In another embodiment of Formula (II), E is tetrahydropyranyl, wherein the tetrahydropyranyl is unsubstituted or substituted with one or more halogen, hydroxyl, $C_1$-$C_3$ alkyl, or $C_1$-$C_3$ alkoxyl. In another embodiment of Formula (II), E is tetrahydrofuranyl, wherein the tetrahydrofuranyl is unsubstituted or substituted with one or more halogen, hydroxyl, $C_1$-$C_3$ alkyl, or $C_1$-$C_3$ alkoxyl. In another embodiment of Formula (II), E is azetidinyl, wherein the azetidinyl is unsubstituted or substituted with one or more halogen, hydroxyl, $C_1$-$C_3$ alkyl, or $C_1$-$C_3$ alkoxyl. In another embodiment of Formula (II), E is oxetanyl, wherein the oxetanyl is unsubstituted or substituted with one or more halogen, hydroxyl, $C_1$-$C_3$ alkyl, or $C_1$-$C_3$ alkoxyl. In another embodiment of Formula (II), E is morpholinyl, wherein the morpholinyl is unsubstituted or substituted with one or more halogen, hydroxyl, $C_1$-$C_3$ alkyl, or $C_1$-$C_3$ alkoxyl.

In another embodiment of Formula (II), $R_{14}$ is H. In another embodiment of Formula (II), $R_{14}$ is unsubstituted $C_1$-$C_3$ alkyl. In another embodiment of Formula (II), $R_{18}$ and $R_{16}$ are each H. In another embodiment of Formula (II), $R_{18}$ is unsubstituted $C_1$-$C_3$ alkyl and $R_{16}$ is H. In another embodiment of Formula (II), $R_{16}$ is unsubstituted $C_1$-$C_3$ alkyl and $R_{18}$ is H. In another embodiment of Formula (II), each $R_{17}$ and $R_{18}$ is H. In another embodiment of Formula (II), $R_{17}$ is unsubstituted $C_1$-$C_3$ alkyl and $R_{18}$ is H. In another embodiment of Formula (II), $R_{18}$ is unsubstituted $C_1$-$C_3$ alkyl and $R_{17}$ is H. In another embodiment of Formula (II), one of $R_{14}$, $R_{15}$, $R_{16}$, $R_{17}$ and $R_{18}$ is unsubstituted $C_1$-$C_3$ alkyl and the others are each H.

In another embodiment of Formula (II), m is 1. In another embodiment of Formula (II), m is 2. In another embodiment of Formula (II), m is 3. In another embodiment of Formula (II), m is 4. In another embodiment of Formula (II), m is 5. In another embodiment of Formula (II), m is 1, 2 or 3. In another embodiment of Formula (II), m is 2, 3, or 4. In another embodiment of Formula (II), m is 1 or 2. In another embodiment of Formula (II), m is 3 or 4.

In another embodiment of Formula (II), Y is O and m is 1. In another embodiment of Formula (II), Y is O and m is 2. In another embodiment of Formula (II), Y is O and m is 3. In another embodiment of Formula (II), Y is O and m is 4. In another embodiment of Formula (II), Y is O and m is 1, 2, or 3. In another embodiment of Formula (II), Y is O and m is 2, 3, or 4. In another embodiment of Formula (II), Y is O and m is 1 or 2. In another embodiment of Formula (II), Y is O and m is 3 or 4.

In another embodiment of Formula (II), Y is absent and m is 2. In another embodiment of Formula (II), Y is absent and m is 3. In another embodiment of Formula (II), Y is absent and m is 4. In another embodiment of Formula (II), Y is absent and m is 2, 3, or 4. In another embodiment of Formula (II), Y is absent and m is 3 or 4.

In another embodiment of Formula (II), Y is $NR_{10}$ and m is 1. In another embodiment of Formula (II), Y is $NR_{10}$ and m is 2. In another embodiment of Formula (II), Y is $NR_{10}$ and m is 3. In another embodiment of Formula (II), Y is $NR_{10}$ and m is 4. In another embodiment of Formula (II), Y is $NR_{10}$ and m is 1, 2, or 3. In another embodiment of Formula (II), Y is $NR_{10}$ and m is 2, 3, or 4. In another embodiment of Formula (II), Y is $NR_{10}$ and m is 1 or 2. In another embodiment of Formula (II), Y is $NR_{10}$ and m is 3 or 4.

In another embodiment of Formula (II), ring A is phenyl and n is 1. In another embodiment of Formula (II), ring A is phenyl and n is 2. In another embodiment of Formula (II), ring A is phenyl and n is 3. In another embodiment of Formula (II), ring A is pyridinyl and n is 1. In another embodiment of Formula (II), ring A is pyridinyl and n is 2. In another embodiment of Formula (II), ring A is pyridinyl and n is 3. In another embodiment of Formula (II), ring A is pyridazinyl and n is 1. In another embodiment of Formula (II), ring A is pyridazinyl and n is 2. In another embodiment of Formula (II), ring A is pyridazinyl and n is 3. In another embodiment of Formula (II), ring A is pyrimidinyl and n is 1. In another embodiment of Formula (II), ring A is pyrimidinyl and n is 2. In another embodiment of Formula (II), ring A is pyrimidinyl and n is 3. In another embodiment of Formula (II), ring A is pyrazinyl and n is 1. In another embodiment of Formula (II), ring A is pyrazinyl and n is 2. In another embodiment of Formula (II), ring A is pyrazinyl and n is 3. In another embodiment of Formula (II), ring A is triazinyl and n is 1. In another embodiment of Formula (II), ring A is triazinyl and n is 2. In another embodiment of Formula (II), ring A is triazinyl and n is 3.

In another embodiment of Formula (II), ring A is phenyl, n is 1, and Y is $NR_{10}$. In another embodiment of Formula (II), ring A is phenyl, n is 2, and Y is $NR_{10}$. In another embodiment of Formula (II), ring A is phenyl, n is 3, and Y is $NR_{10}$. In another embodiment of Formula (II), ring A is phenyl, n is 1, and Y is O. In another embodiment of Formula (II), ring A is phenyl, n is 2, and Y is O. In another embodiment of Formula (II), ring A is phenyl, n is 3, and Y is O. In another embodiment of Formula (II), ring A is phenyl, n is 1, and Y is absent. In another embodiment of Formula (II), ring A is phenyl, n is 2, and Y is absent. In another embodiment of Formula (II), ring A is phenyl, n is 3, and Y is absent.

In another embodiment of Formula (II), ring A is phenyl, n is 1, Y is $NR_{10}$, and m is 1 or 2. In another embodiment of Formula (II), ring A is phenyl, n is 2, Y is $NR_{10}$, and m is 1 or 2. In another embodiment of Formula (II), ring A is phenyl, n is 3, Y is $NR_{10}$, and m is 1 or 2. In another embodiment of Formula (II), ring A is phenyl, n is 1, Y is O, and m is 1 or 2. In another embodiment of Formula (II), ring A is phenyl, n is 2, Y is O, and m is 1 or 2. In another embodiment of Formula (II), ring A is phenyl, n is 3, Y is O, and m is 1 or 2. In another embodiment of Formula (II), ring A is phenyl, n is 1, Y is absent, and m is 2. In another embodiment of Formula (II), ring A is phenyl, n is 2, Y is absent, and m is 2. In another embodiment of Formula (II), ring A is phenyl, n is 3, Y is absent, and m is 2. In another embodiment of Formula (II), ring A is phenyl, n is 1, Y is $NR_{10}$, and m is 3 or 4. In another embodiment of Formula (II), ring A is phenyl, n is 2, Y is $NR_{10}$, and m is 3 or 4. In another embodiment of Formula (II), ring A is phenyl, n is 3, Y is $NR_{10}$, and m is 3 or 4. In another embodiment of Formula (II), ring A is phenyl, n is 1, Y is O, and m is 3 or 4. In another embodiment of Formula (II), ring A is phenyl, n is 2, Y is O, and m is 3 or 4. In another embodiment of Formula (II), ring A is phenyl, n is 3, Y is O, and m is 3 or 4. In another embodiment of Formula (II), ring A is phenyl, n is 1, Y is absent, and m is 3 or 4. In another embodiment of Formula (II), ring A is phenyl, n is 2, Y is absent, and m is 3 or 4. In another embodiment of Formula (II), ring A is phenyl, n is 3, Y is absent, and m is 3 or 4.

In another embodiment of Formula (II), ring A is pyridinyl, n is 1, and Y is $NR_{10}$. In another embodiment of Formula (II), ring A is pyridinyl, n is 2, and Y is $NR_{10}$. In another embodiment of Formula (II), ring A is pyridinyl, n is 3, and Y is $NR_{10}$. In another embodiment of Formula (II), ring A is pyridinyl, n is 1, and Y is O. In another embodiment of Formula (II), ring A is pyridinyl, n is 2, and Y is O. In another embodiment of Formula (II), ring A is pyridinyl, n is 3, and Y is O. In another embodiment of Formula (II), ring A is pyridinyl, n is 1, and Y is absent. In another embodiment of Formula (II), ring A is pyridinyl, n is 2, and Y is absent. In another embodiment of Formula (II), ring A is pyridinyl, n is 3, and Y is absent.

In another embodiment of Formula (II), ring A is pyridinyl, n is 1, Y is $NR_{10}$, and m is 1 or 2. In another embodiment of Formula (II), ring A is pyridinyl, n is 2, Y is $NR_{10}$, and m is 1 or 2. In another embodiment of Formula (II), ring A is pyridinyl, n is 3, Y is $NR_{10}$, and m is 1 or 2. In another embodiment of Formula (II), ring A is pyridinyl, n is 1, Y is O, and m is 1 or 2. In another embodiment of Formula (II), ring A is pyridinyl, n is 2, Y is O, and m is 1 or 2. In another embodiment of Formula (II), ring A is pyridinyl, n is 3, Y is O, and m is 1 or 2. In another embodiment of Formula (II), ring A is pyridinyl, n is 1, Y is absent, and m is 2. In another embodiment of Formula (II), ring A is pyridinyl, n is 2, Y is absent, and m is 2. In another embodiment of Formula (II), ring A is pyridinyl, n is 3, Y is absent, and m is 2. In another embodiment of Formula (II), ring A is pyridinyl, n is 1, Y is $NR_{10}$, and m is 3 or 4. In another embodiment of Formula (II), ring A is pyridinyl, n is 2, Y is $NR_{10}$, and m is 3 or 4. In another embodiment of Formula (II), ring A is pyridinyl, n is 3, Y is $NR_{10}$, and m is 3 or 4. In another embodiment of Formula (II), ring A is pyridinyl, n is 1, Y is O, and m is 3 or 4. In another embodiment of Formula (II), ring A is pyridinyl, n is 2, Y is O, and m is 3 or 4. In another embodiment of Formula (II), ring A is pyridinyl, n is 3, Y is O, and m is 3 or 4. In another embodiment of Formula (II), ring A is pyridinyl, n is 1, Y is absent, and m is 3 or 4. In another embodiment of Formula (II), ring A is pyridinyl, n is 2, Y is absent, and m is 3 or 4. In another embodiment of Formula (II), ring A is pyridinyl, n is 3, Y is absent, and m is 3 or 4.

In another embodiment of Formula (II), ring A is pyridazinyl, n is 1, and Y is $NR_{10}$. In another embodiment of Formula (II), ring A is pyridazinyl, n is 2, and Y is $NR_{10}$. In another embodiment of Formula (II), ring A is pyridazinyl, n is 3, and Y is $NR_{10}$. In another embodiment of Formula (II), ring A is pyridazinyl, n is 1, and Y is O. In another embodiment of Formula (II), ring A is pyridazinyl, n is 2, and Y is O. In another embodiment of Formula (II), ring A is pyridazinyl, n is 3, and Y is O. In another embodiment of Formula (II), ring A is pyridazinyl, n is 1, and Y is absent. In another embodiment of Formula (II), ring A is pyridazinyl, n is 2, and Y is absent. In another embodiment of Formula (II), ring A is pyridazinyl, n is 3, and Y is absent.

In another embodiment of Formula (II), ring A is pyridazinyl, n is 1, Y is $NR_{10}$, and m is 1 or 2. In another embodiment of Formula (II), ring A is pyridazinyl, n is 2, Y is $NR_{10}$, and m is 1 or 2. In another embodiment of Formula (II), ring A is pyridazinyl, n is 3, Y is $NR_{10}$, and m is 1 or 2. In another embodiment of Formula (II), ring A is pyridazinyl, n is 1, Y is O, and m is 1 or 2. In another embodiment of Formula (II), ring A is pyridazinyl, n is 2, Y is O, and m is 1 or 2. In another embodiment of Formula (II), ring A is pyridazinyl, n is 3, Y is O, and m is 1 or 2. In another embodiment of Formula (II), ring A is pyridazinyl, n is 1, Y is absent, and m is 2. In another embodiment of Formula (II), ring A is pyridazinyl, n is 2, Y is absent, and m is 2. In another embodiment of Formula (II), ring A is pyridazinyl, n is 3, Y is absent, and m is 2. In another embodiment of Formula (II), ring A is pyridazinyl, n is 1, Y is $NR_{10}$, and m is 3 or 4. In another embodiment of Formula (II), ring A is pyridazinyl, n is 2, Y is $NR_{10}$, and m is 3 or 4. In another embodiment of Formula (II), ring A is pyridazinyl, n is 3, Y is $NR_{10}$, and m is 3 or 4. In another embodiment of Formula (II), ring A is pyridazinyl, n is 1, Y is O, and m is 3 or 4. In another embodiment of Formula (II), ring A is pyridazinyl, n is 2, Y is O, and m is 3 or 4. In another embodiment of Formula (II), ring A is pyridazinyl, n is 3, Y is O, and m is 3 or 4. In another embodiment of Formula (II), ring A is pyridazinyl, n is 1, Y is absent, and m is 3 or 4. In another embodiment of Formula (II), ring A is pyridazinyl, n is 2, Y is absent, and m is 3 or 4. In another embodiment of Formula (II), ring A is pyridazinyl, n is 3, Y is absent, and m is 3 or 4.

In another embodiment of Formula (II), ring A is pyrimidinyl, n is 1, and Y is $NR_{10}$. In another embodiment of Formula (II), ring A is pyrimidinyl, n is 2, and Y is $NR_{10}$. In another embodiment of Formula (II), ring A is pyrimidinyl, n is 3, and Y is $NR_{10}$. In another embodiment of Formula (II), ring A is pyrimidinyl, n is 1, and Y is O. In another embodiment of Formula (II), ring A is pyrimidinyl, n is 2, and Y is O. In another embodiment of Formula (II), ring A is pyrimidinyl, n is 3, and Y is O. In another embodiment of Formula (II), ring A is pyrimidinyl, n is 1, and Y is absent. In another embodiment of Formula (II), ring A is pyrimidinyl, n is 2, and Y is absent. In another embodiment of Formula (II), ring A is pyrimidinyl, n is 3, and Y is absent.

In another embodiment of Formula (II), ring A is pyrimidinyl, n is 1, Y is $NR_{10}$, and m is 1 or 2. In another embodiment of Formula (II), ring A is pyrimidinyl, n is 2, Y is $NR_{10}$, and m is 1 or 2. In another embodiment of Formula (II), ring A is pyrimidinyl, n is 3, Y is $NR_{10}$, and m is 1 or 2. In another embodiment of Formula (II), ring A is pyrimidinyl, n is 1, Y is O, and m is 1 or 2. In another embodiment of Formula (II), ring A is pyrimidinyl, n is 2, Y is O, and m is 1 or 2. In another embodiment of Formula (II), ring A is pyrimidinyl, n is 3, Y is O, and m is 1 or 2. In another embodiment of Formula (II), ring A is pyrimidinyl, n is 1, Y is absent, and m is 2. In another embodiment of Formula (II), ring A is pyrimidinyl, n is 2, Y is absent, and m is 2. In another embodiment of Formula (II), ring A is pyrimidinyl, n is 3, Y is absent, and m is 2. In another embodiment of Formula (II), ring A is pyrimidinyl, n is 1, Y is $NR_{10}$, and m is 3 or 4. In another embodiment of Formula (II), ring A is pyrimidinyl, n is 2, Y is $NR_{10}$, and m is 3 or 4. In another embodiment of Formula (II), ring A is pyrimidinyl, n is 3, Y is $NR_{10}$, and m is 3 or 4. In another embodiment of Formula (II), ring A is pyrimidinyl, n is 1, Y is O, and m is 3 or 4. In another embodiment of Formula (II), ring A is pyrimidinyl, n is 2, Y is O, and m is 3 or 4. In another embodiment of Formula (II), ring A is pyrimidinyl, n is 3, Y is O, and m is 3 or 4. In another embodiment of Formula (II), ring A is pyrimidinyl, n is 1, Y is absent, and m is 3 or 4. In another embodiment of Formula (II), ring A is pyrimidinyl, n is 2, Y is absent, and m is 3 or 4. In another embodiment of Formula (II), ring A is pyrimidinyl, n is 3, Y is absent, and m is 3 or 4.

In another embodiment of Formula (II), ring A is pyrazinyl, n is 1, and Y is $NR_{10}$. In another embodiment of Formula (II), ring A is pyrazinyl, n is 2, and Y is $NR_{10}$. In another embodiment of Formula (II), ring A is pyrazinyl, n is 3, and Y is $NR_{10}$. In another embodiment of Formula (II), ring A is pyrazinyl, n is 1, and Y is O. In another embodiment of Formula (II), ring A is pyrazinyl, n is 2, and Y is O. In another embodiment of Formula (II), ring A is pyrazinyl, n is 3, and Y is O. In another embodiment of Formula (II), ring A is pyrazinyl, n is 1, and Y is absent. In another embodiment of Formula (II), ring A is pyrazinyl, n is 2, and Y is absent. In another embodiment of Formula (II), ring A is pyrazinyl, n is 3, and Y is absent.

In another embodiment of Formula (II), ring A is pyrazinyl, n is 1, Y is $NR_{10}$, and m is 1 or 2. In another embodiment of Formula (II), ring A is pyrazinyl, n is 2, Y is $NR_{10}$, and m is 1 or 2. In another embodiment of Formula (II), ring A is pyrazinyl, n is 3, Y is $NR_{10}$, and m is 1 or 2. In another embodiment of Formula (II), ring A is pyrazinyl, n is 1, Y is O, and m is 1 or 2. In another embodiment of Formula (II), ring A is pyrazinyl, n is 2, Y is O, and m is 1 or 2. In another embodiment of Formula (II), ring A is pyrazinyl, n is 3, Y is O, and m is 1 or 2. In another embodiment of Formula (II), ring A is pyrazinyl, n is 1, Y is absent, and m is 2. In another embodiment of Formula (II), ring A is pyrazinyl, n is 2, Y is absent, and m is 2. In another embodiment of Formula (II), ring A is pyrazinyl, n is 3, Y is absent, and m is 2. In another embodiment of Formula (II), ring A is pyrazinyl, n is 1, Y is $NR_{10}$, and m is 3 or 4. In another embodiment of Formula (II), ring A is pyrazinyl, n is 2, Y is $NR_{10}$, and m is 3 or 4. In another embodiment of Formula (II), ring A is pyrazinyl, n is 3, Y is $NR_{10}$, and m is 3 or 4. In another embodiment of Formula (II), ring A is pyrazinyl, n is 1, Y is O, and m is 3 or 4. In another embodiment of Formula (II), ring A is pyrazinyl, n is 2, Y is O, and m is 3 or 4. In another embodiment of Formula (II), ring A is pyrazinyl, n is 3, Y is O, and m is 3 or 4. In another embodiment of Formula (II), ring A is pyrazinyl, n is 1, Y is absent, and m is 3 or 4. In another embodiment of Formula (II), ring A is pyrazinyl, n is 2, Y is absent, and m is 3 or 4. In another embodiment of Formula (II), ring A is pyrazinyl, n is 3, Y is absent, and m is 3 or 4.

In another embodiment of Formula (II), ring A is triazinyl, n is 1, and Y is $NR_{10}$. In another embodiment of Formula (II), ring A is triazinyl, n is 2, and Y is $NR_{10}$. In another embodiment of Formula (II), ring A is triazinyl, n is 3, and Y is $NR_{10}$. In another embodiment of Formula (II), ring A is triazinyl, n is 1, and Y is O. In another embodiment of Formula (II), ring A is triazinyl, n is 2, and Y is O. In another embodiment of Formula (II), ring A is triazinyl, n is 3, and Y is O. In another embodiment of Formula (II), ring A is triazinyl, n is 1, and Y is absent. In another embodiment of Formula (II), ring A is triazinyl, n is 2, and Y is absent. In another embodiment of Formula (II), ring A is triazinyl, n is 3, and Y is absent.

In another embodiment of Formula (II), ring A is triazinyl, n is 1, Y is $NR_{10}$, and m is 1 or 2. In another embodiment of Formula (II), ring A is triazinyl, n is 2, Y is $NR_{10}$, and m is 1 or 2. In another embodiment of Formula (II), ring A is triazinyl, n is 3, Y is $NR_{10}$, and m is 1 or 2. In another embodiment of Formula (II), ring A is triazinyl, n is 1, Y is O, and m is 1 or 2. In another embodiment of Formula (II), ring A is triazinyl, n is 2, Y is O, and m is 1 or 2. In another embodiment of Formula (II), ring A is triazinyl, n is 3, Y is O, and m is 1 or 2. In another embodiment of Formula (II), ring A is triazinyl, n is 1, Y is absent, and m is 2. In another embodiment of Formula (II), ring A is triazinyl, n is 2, Y is absent, and m is 2. In another embodiment of Formula (II), ring A is triazinyl, n is 3, Y is absent, and m is 2. In another embodiment of Formula (II), ring A is triazinyl, n is 1, Y is $NR_{10}$, and m is 3 or 4. In another embodiment of Formula (II), ring A is triazinyl, n is 2, Y is $NR_{10}$, and m is 3 or 4. In another embodiment of Formula (II), ring A is triazinyl, n is 3, Y is $NR_{10}$, and m is 3 or 4. In another embodiment of Formula (II), ring A is triazinyl, n is 1, Y is O, and m is 3 or 4. In another embodiment of Formula (II), ring A is triazinyl, n is 2, Y is O, and m is 3 or 4. In another embodiment of Formula (II), ring A is triazinyl, n is 3, Y is O, and m is 3 or 4. In another embodiment of Formula (II), ring A is triazinyl, n is 1, Y is absent, and m is 3 or 4. In another embodiment of Formula (II), ring A is triazinyl, n is 2, Y is absent, and m is 3 or 4. In another embodiment of Formula (II), ring A is triazinyl, n is 3, Y is absent, and m is 3 or 4.

In another embodiment of Formula (II), ring A is phenyl, T is $CR_1R_2$, W is $CR_4R_5$, and V is $CR_3$. In another embodiment of Formula (II), ring A is phenyl, p is 0, T is $CR_1R_2$, W is $CR_4R_5$, and V is $CR_3$. In another embodiment of Formula (II), ring A is phenyl, T is $CR_1R_2$, W is $CR_4R_5$, V is $CR_3$, and n is 1. In another embodiment of Formula (II), ring A is phenyl, T is $CR_1R_2$, W is $CR_4R_5$, V is $CR_3$, and n is 2. In another embodiment of Formula (II), ring A is phenyl, T is $CR_1R_2$, W is $CR_4R_5$, V is $CR_3$, and n is 3. In another embodiment of Formula (II), ring A is phenyl, p is 0, T is $CR_1R_2$, W is $CR_4R_5$, V is $CR_3$, and n is 1. In another embodiment of Formula (II), ring A is phenyl, p is 0, T is $CR_1R_2$, W is $CR_4R_5$, V is $CR_3$, and n is 2. In another embodiment of Formula (II), ring A is phenyl, p is 0, T is $CR_1R_2$, W is $CR_4R_5$, V is $CR_3$, and n is 3.

In another embodiment of Formula (II), ring A is phenyl, T is $CR_1R_2$, W is $CR_4R_5$, V is $CR_3$, and Y is O. In another embodiment of Formula (II), ring A is phenyl, p is 0, T is $CR_1R_2$, W is $CR_4R_5$, V is $CR_3$, and Y is O. In another embodiment of Formula (II), ring A is phenyl, T is $CR_1R_2$, W is $CR_4R_5$, V is $CR_3$, Y is O, and n is 1. In another embodiment of Formula (II), ring A is phenyl, T is $CR_1R_2$, W is $CR_4R_5$, V is $CR_3$, Y is O, and n is 2. In another embodiment of Formula (II), ring A is phenyl, T is $CR_1R_2$, W is $CR_4R_5$, V is $CR_3$, Y is O, and n is 3. In another embodiment of Formula (II), ring A is phenyl, p is 0, T is $CR_1R_2$, W is $CR_4R_5$, V is $CR_3$, Y is O, and n is 1. In another embodiment of Formula (II), ring A is phenyl, p is 0, T is $CR_1R_2$, W is $CR_4R_5$, V is $CR_3$, Y is O, and n is 2. In another embodiment of Formula (II), ring A is phenyl, p is 0, T is $CR_1R_2$, W is $CR_4R_5$, V is $CR_3$, Y is O, and n is 3.

In another embodiment of Formula (II), ring A is phenyl, T is $CR_1R_2$, W is $CR_4R_5$, V is $CR_3$, Y is O, and m is 1 or 2. In another embodiment of Formula (II), ring A is phenyl, p is 0, T is $CR_1R_2$, W is $CR_4R_5$, V is $CR_3$, Y is O, and m is 1 or 2. In another embodiment of Formula (II), ring A is phenyl, T is $CR_1R_2$, W is $CR_4R_5$, V is $CR_3$, Y is O, n is 1, and m is 1 or 2. In another embodiment of Formula (II), ring A is phenyl, T is $CR_1R_2$, W is $CR_4R_5$, V is $CR_3$, Y is O, n is 2, and m is 1 or 2. In another embodiment of Formula (II), ring A is phenyl, T is $CR_1R_2$, W is $CR_4R_5$, V is $CR_3$, Y is O, n is 3, and m is 1 or 2. In another embodiment of Formula (II), ring A is phenyl, p is 0, T is $CR_1R_2$, W is $CR_4R_5$, V is $CR_3$, Y is O, n is 1, and m is 1 or 2. In another embodiment of Formula (II), ring A is phenyl, p is 0, T is $CR_1R_2$, W is $CR_4R_5$, V is $CR_3$, Y is O, n is 2, and m is 1 or 2. In another embodiment of Formula (II), ring A is phenyl, p is 0, T is $CR_1R_2$, W is $CR_4R_5$, V is $CR_3$, Y is O, n is 3, and m is 1 or 2. In another embodiment of Formula (II), ring A is phenyl, T is $CR_1R_2$, W is $CR_4R_5$, V is $CR_3$, Y is O, and m is 3 or 4. In another embodiment of Formula (II), ring A is phenyl, p is 0, T is $CR_1R_2$, W is $CR_4R_5$, V is $CR_3$, Y is O, and m is 3 or 4. In another embodiment of Formula (II), ring A is phenyl, T is $CR_1R_2$, W is $CR_4R_5$, V is $CR_3$, Y is O, n is 1, and m is 3 or 4. In another embodiment of Formula (II), ring A is phenyl, T is $CR_1R_2$, W is $CR_4R_5$, V is $CR_3$, Y is O, n is 2, and m is 3 or 4. In another embodiment of Formula (II), ring A is phenyl, T is $CR_1R_2$, W is $CR_4R_5$, V is $CR_3$, Y is O, n is 3, and m is 3 or 4. In another embodiment of Formula (II), ring A is phenyl, p is 0, T is $CR_1R_2$, W is $CR_4R_5$, V is $CR_3$, Y is O, n is 1, and m is 3 or 4. In another embodiment of Formula (II), ring A is phenyl, p is 0, T is $CR_1R_2$, W is $CR_4R_5$, V is $CR_3$, Y is O, n is 2, and m is 3 or 4. In another embodiment of Formula (II), ring A is phenyl, p is 0, T is $CR_1R_2$, W is $CR_4R_5$, V is $CR_3$, Y is O, n is 3, and m is 3 or 4.

In another embodiment of Formula (II), p is 0 and $R_1$, $R_2$, $R_4$, and $R_5$ are each H. In another embodiment of Formula (II), p is 0; $R_1$, $R_2$, $R_4$, and $R_5$ are each H; and $R_3$ is H. In another embodiment of Formula (II), p is 0; $R_1$, $R_2$, $R_4$, and $R_5$ are each H; $R_3$ is H; and $R_6$, $R_7$, $R_8$, $R_9$, and $R_{11}$ are each H. In another embodiment of Formula (II), p is 0; $R_1$, $R_2$, $R_4$, and $R_5$ are each H; $R_3$ is H; $R_6$, $R_7$, $R_8$, $R_9$, and $R_{11}$ are each H; and $R_{12}$ and $R_{13}$ are each H.

In another embodiment of Formula (II), p is 1 and $R_1$, $R_2$, $R_4$, and $R_5$ are each H. In another embodiment of Formula (II), p is 1; $R_1$, $R_2$, $R_4$, and $R_5$ are each H; and $R_3$ is H. In another embodiment of Formula (II), p is 1; $R_1$, $R_2$, $R_4$, and $R_5$ are each H; $R_3$ is H; and $R_6$, $R_7$, $R_8$, $R_9$, and $R_{11}$ are each H. In another embodiment of Formula (II), p is 1; $R_1$, $R_2$, $R_4$, and $R_5$ are each H; $R_3$ is H; $R_6$, $R_7$, $R_8$, $R_9$, and $R_{11}$ are each H; and $R_{12}$ and $R_{13}$ are each H.

In another embodiment of Formula (II), p is 2 and $R_1$, $R_2$, $R_4$, and $R_5$ are each H. In another embodiment of Formula (II), p is 2; $R_1$, $R_2$, $R_4$, and $R_5$ are each H; and $R_3$ is H. In another embodiment of Formula (II), p is 2; $R_1$, $R_2$, $R_4$, and $R_5$ are each H; $R_3$ is H; and $R_6$, $R_7$, $R_8$, $R_9$, and $R_{11}$ are each H. In another embodiment of Formula (II), p is 2; $R_1$, $R_2$, $R_4$, and $R_5$ are each H; $R_3$ is H; $R_6$, $R_7$, $R_8$, $R_9$, and $R_{11}$ are each H; and $R_{12}$ and $R_{13}$ are each H.

In another embodiment of Formula (II), p is 1, 2, 3, or 4 and R is fluorine. In another embodiment of Formula (II), p is 1, 2, 3, or 4 and R is deuterium. In another embodiment of Formula (II), p is 1, 2, 3, or 4 and each R is, independently, selected from the group consisting of hydroxyl, cyano, unsubstituted $C_1$-$C_3$ alkyl, and $C_1$-$C_3$ alkyl substituted with one or more halogen or deuterium. In another embodiment of Formula (II), p is 1, 2, 3, or 4 and each R is, independently, selected from the group consisting of cyano, unsubstituted $C_1$-$C_3$ alkyl, and $C_1$-$C_3$ alkyl substituted with one or more halogen or deuterium. In another embodiment of Formula (II), p is 1 and R is unsubstituted $C_1$-$C_3$ alkyl. In another embodiment of Formula (II), p is 1 and R is methyl. In another embodiment of Formula (II), p is 1 or 2 and each R is methyl. In another embodiment of Formula (II), p is 1 and R is $C_1$-$C_3$ alkyl substituted with one or more halogen. In another embodiment of Formula (II), p is 1 and R is $CF_3$. In another embodiment of Formula (II), p is 1 or 2 and each R is $CF_3$.

In another embodiment of Formula (II), one or more of $R_1$, $R_2$, $R_4$, and $R_5$ is fluorine. In another embodiment of Formula (II), one or more of $R_1$, $R_2$, $R_4$, and $R_5$ is deuterium. In another embodiment of Formula (II), one or more of $R_6$, $R_7$, $R_8$, $R_9$, and $R_{11}$ is fluorine. In another embodiment of Formula (II), one or more of $R_6$, $R_7$, $R_8$, $R_9$, and $R_{11}$ is deuterium. In another embodiment of Formula (II), one or more of each $R_{12}$ and $R_{13}$ is fluorine. In another embodiment of Formula (II), one or more of each $R_{12}$ and $R_{13}$ is deuterium.

In another embodiment of Formula (II), Y is O, T is $CR_1R_2$, V is $CR_3$, W is $CR_4R_5$, and $R_{11}$ is H. In another embodiment of Formula (II), Y is O, T is $CR_1R_2$, V is $CR_3$, W is $CR_4R_5$, Rn is H, and m is 2. In another embodiment of Formula (II), Y is O, T is $CR_1R_2$, V is $CR_3$, W is $CR_4R_5$, and each of $R_{11}$, $R_{14}$, $R_{15}$, $R_{16}$, $R_{17}$, and $R_{18}$ is H. In another embodiment of Formula (II), Y is O, T is $CR_1R_2$, V is $CR_3$, W is $CR_4R_5$, each of $R_{11}$, $R_{14}$, $R_{15}$, $R_{16}$, $R_{17}$, and $R_{18}$ is H, and m is 2. In another embodiment of Formula (II), Y is O, T is $CR_1R_2$, V is $CR_3$, W is $CR_4R_5$, and each of $R_1$, $R_{12}$, $R_{13}$, $R_{14}$, $R_{15}$, $R_{16}$, $R_{17}$, and $R_{18}$ is H. In another embodiment of Formula (II), Y is O, T is $CR_1R_2$, V is $CR_3$, W is $CR_4R_5$, each of $R_{11}$, $R_{12}$, $R_{13}$, $R_{14}$, $R_{15}$, $R_{16}$, $R_{17}$, and $R_{18}$ is H, and m is 2.

Each of the embodiments described herein with respect to compounds of Formula II also applies to compounds of Formula II-A.

According to Formula I-A, I, II-A, or II herein, when ring A is pyridinyl, the position of the pyridinyl N atom is specified as shown below:

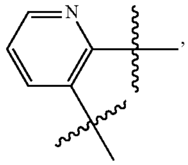,
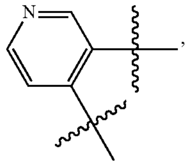,

-continued

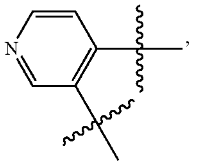

or

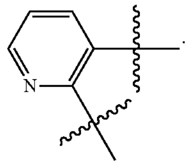

Further, according to Formula I-A, I, II-A, or II herein, when ring A is pyridazinyl, the positions of the pyridazinyl N atoms are specified as shown below:

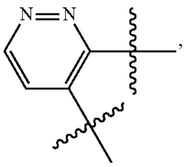

,

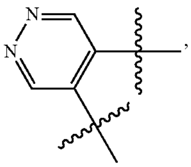

, or

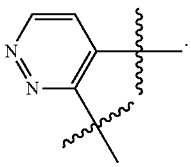

Further, according to Formula I-A, I, II-A, or II herein, when ring A is pyrimidinyl, the positions of the pyrimidinyl N atoms are specified as shown below:

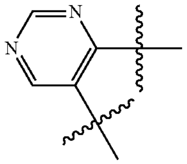

or

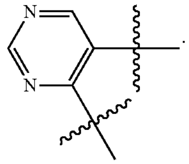

Further, according to Formula I-A, I, II-A, or II herein, when ring A is pyrazinyl, the positions of the pyrazinyl N atoms are specified as shown below:

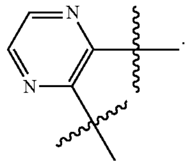 [SMILES: *c1nccnc1*]

Further, according to Formula I-A, I, II-A, or II herein, when ring A is triazinyl, the positions of the triazinyl N atoms are specified as shown below:

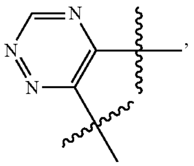

,

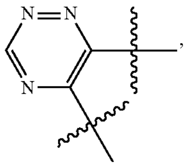

-continued

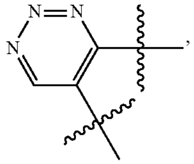

or

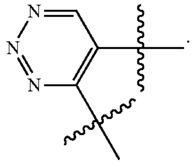

All other variables described in Formula I-A, I, II-A, or II are as defined above.

Certain embodiments of compounds of Formula I-A, I, II-A, II or pharmaceutically acceptable salts thereof, are shown below in Table 1. Compounds of Formula I-A, I, II-A, II or pharmaceutically acceptable salts thereof, and compounds of Table 1, or pharmaceutically acceptable salts thereof, collectively or individually are sometimes referred to herein as "compounds of the invention" or "compounds provided herein".

TABLE 1

| Structure | Compound No. |
| --- | --- |
| 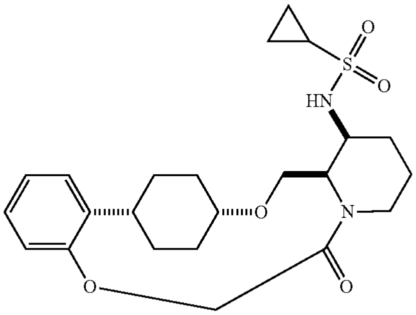 | 1 |
| 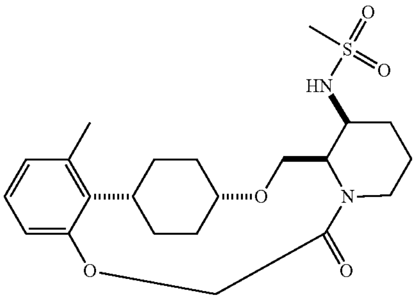 | 2 |
| 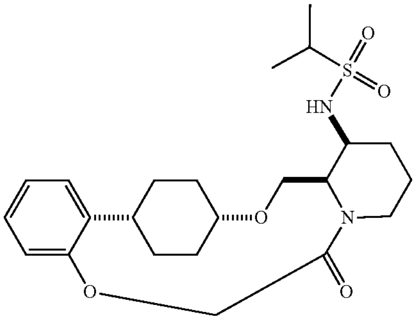 | 3 |

TABLE 1-continued
| Structure | Compound No. |
|---|---|
| 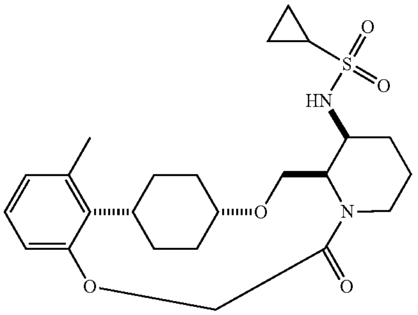 | 4 |
| 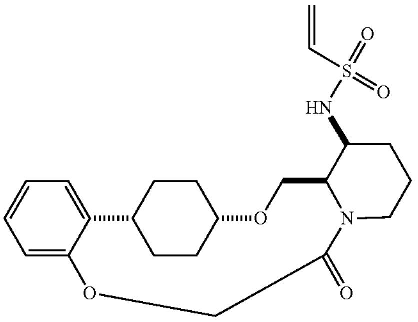 | 5 |
| 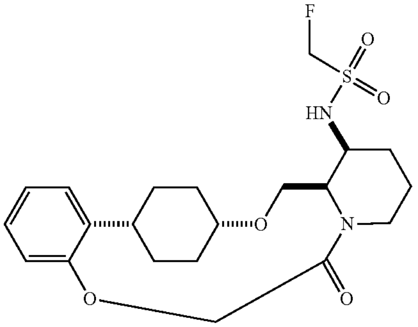 | 6 |
| 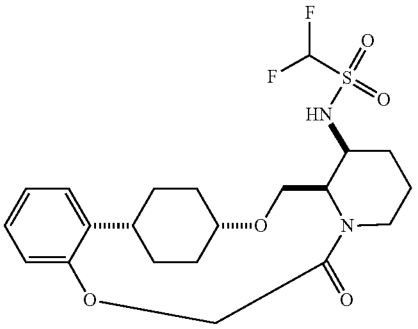 | 7 |
TABLE 1-continued
| Structure | Compound No. |
|---|---|
| 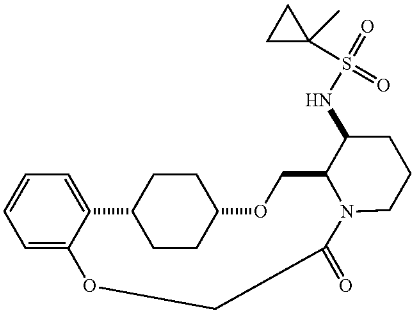 | 8 |
| 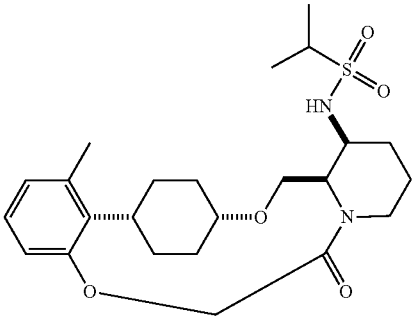 | 9 |
| 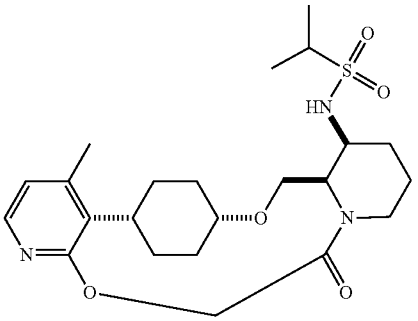 | 10 |
| 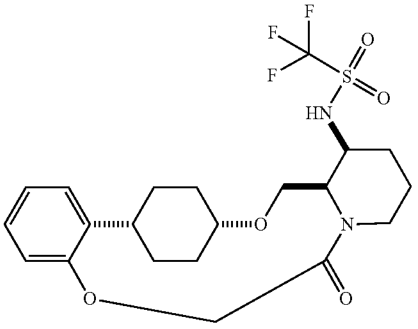 | 11 |

TABLE 1-continued
| Structure | Compound No. |
|---|---|
| 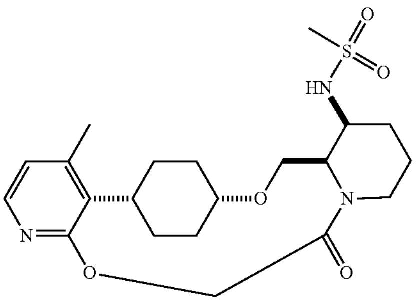 | 12 |
| 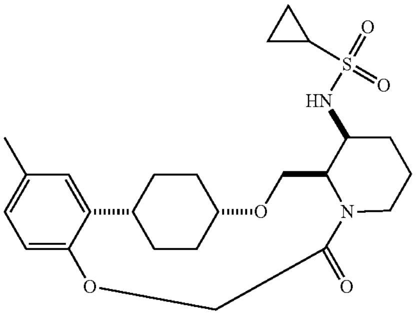 | 13 |
| 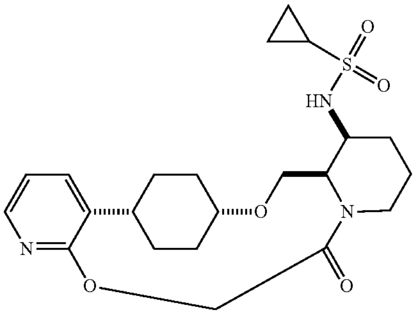 | 14 |
| 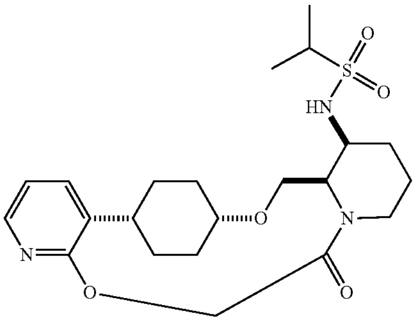 | 15 |
TABLE 1-continued
| Structure | Compound No. |
|---|---|
| 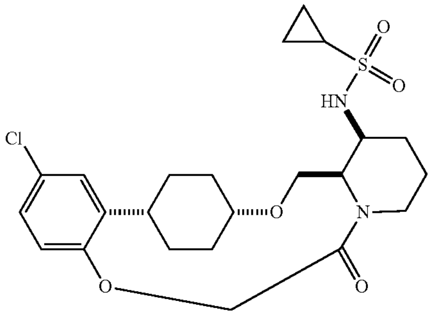 | 16 |
| 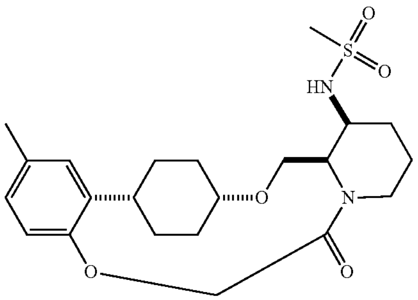 | 17 |
| 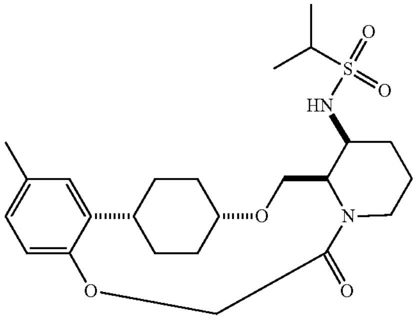 | 18 |
| 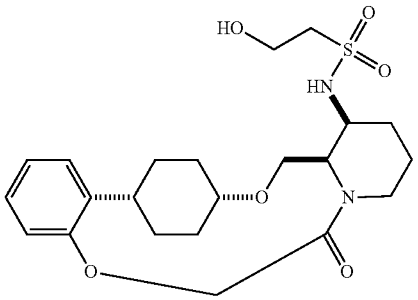 | 19 |
| 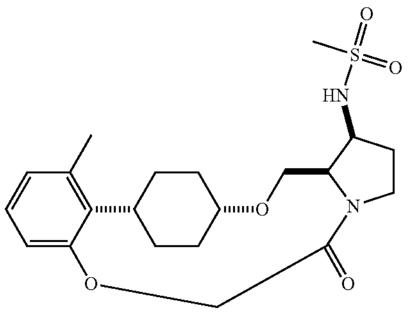 | 20 |

TABLE 1-continued
| Structure | Compound No. |
| --- | --- |
| 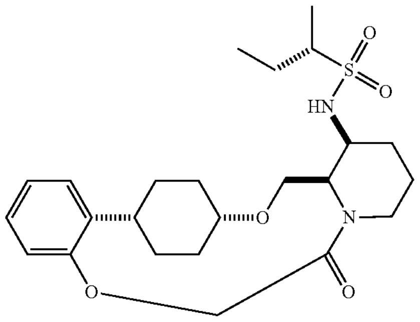 | 21 |
| 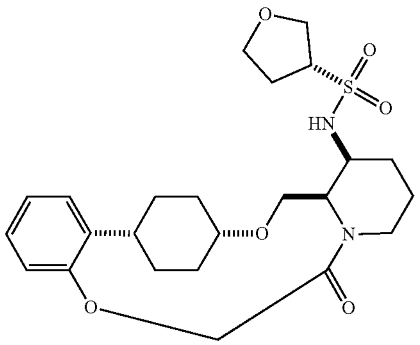 | 22 |
| 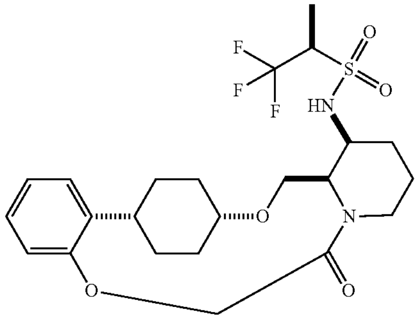 | 23 |
| 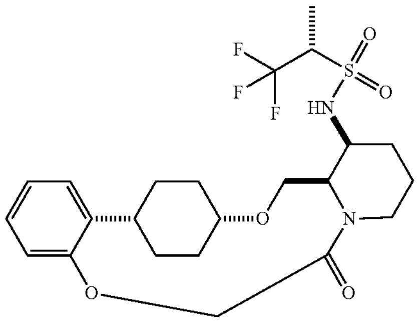 | 24 |
TABLE 1-continued
| Structure | Compound No. |
| --- | --- |
| 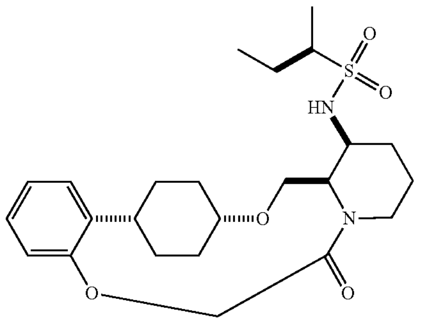 | 25 |
| 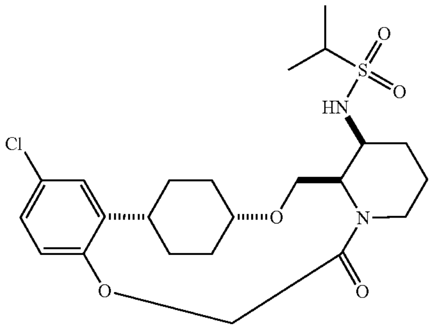 | 26 |
| 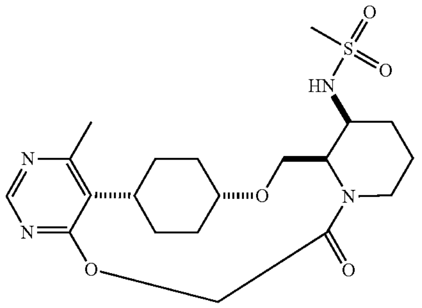 | 27 |
| 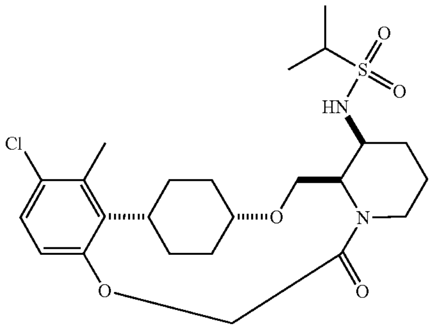 | 28 |

TABLE 1-continued
| Structure | Compound No. |
|---|---|
| 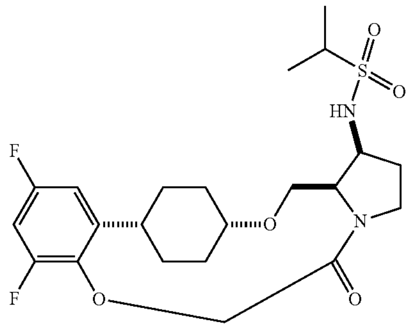 | 29 |
| 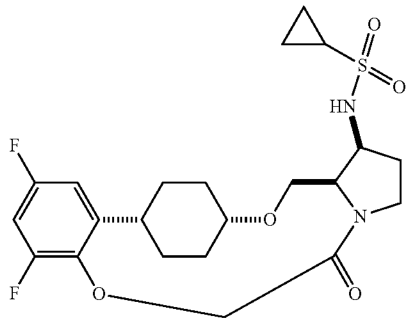 | 30 |
| 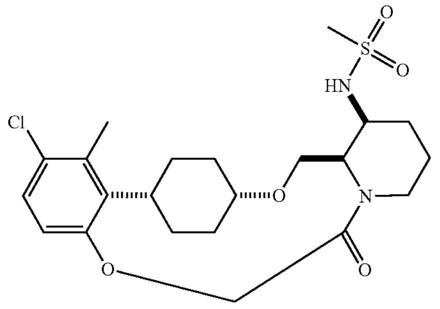 | 31 |
| 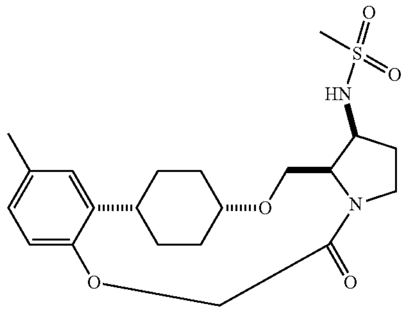 | 32 |
TABLE 1-continued
| Structure | Compound No. |
|---|---|
| 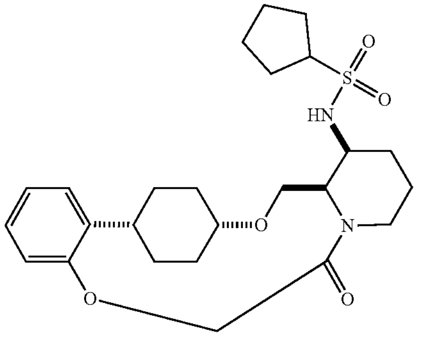 | 33 |
| 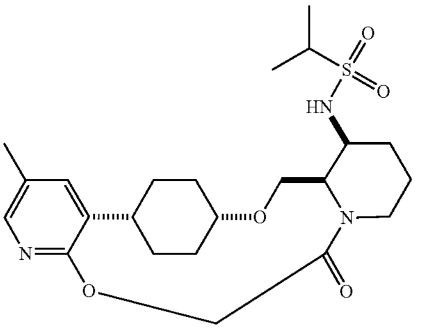 | 34 |
| 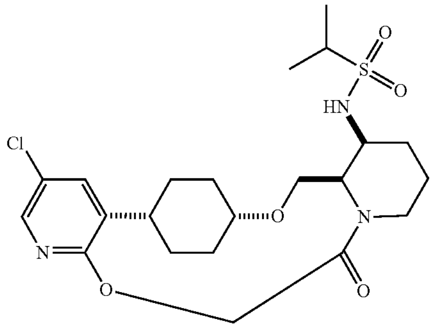 | 35 |
| 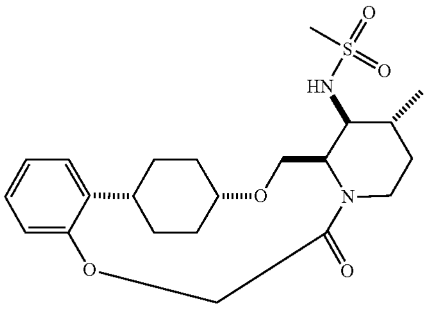 | 36 |

TABLE 1-continued
| Structure | Compound No. |
|---|---|
| 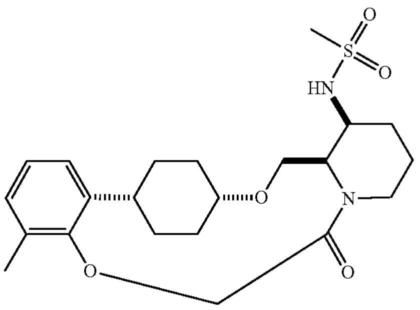 | 37 |
| 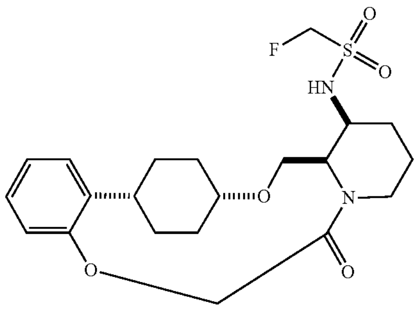 | 38 |
| 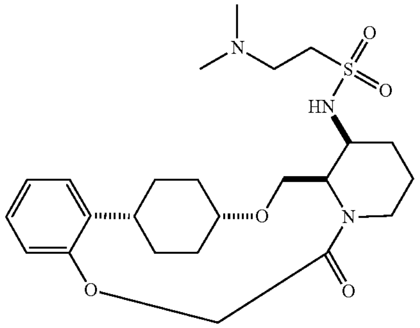 | 39 |
| 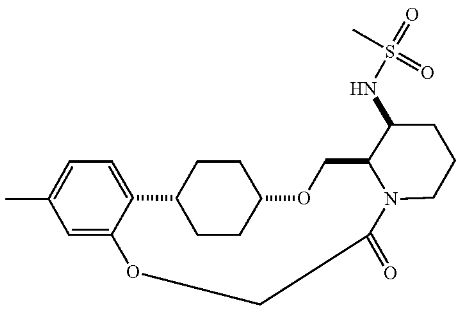 | 40 |
TABLE 1-continued
| Structure | Compound No. |
|---|---|
| 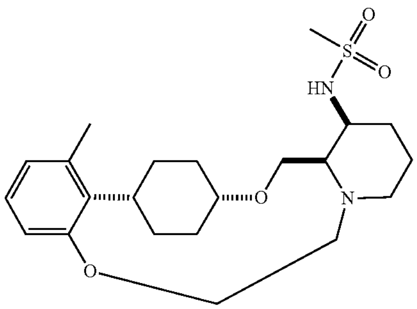 | 41 |
| 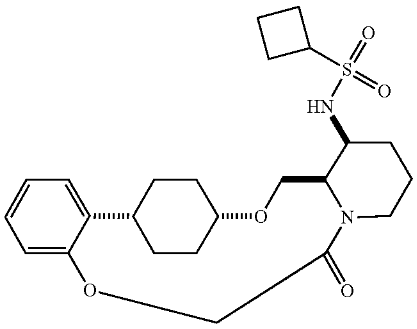 | 42 |
| 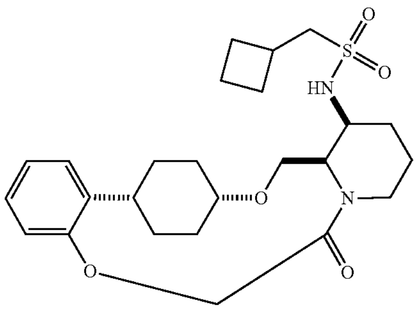 | 43 |
| 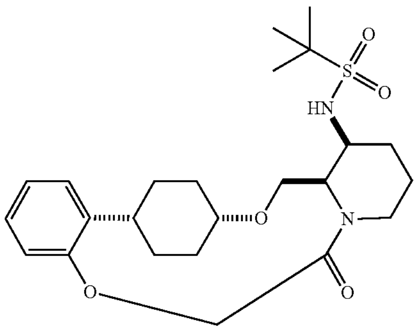 | 44 |

TABLE 1-continued
| Structure | Compound No. |
| --- | --- |
| 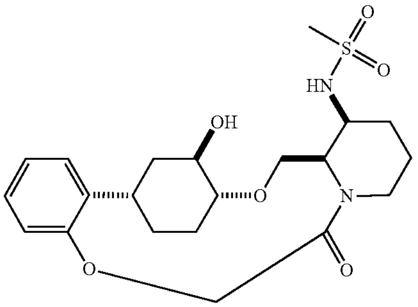 | 45 |
| 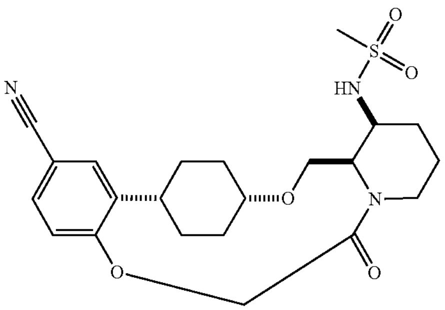 | 46 |
| 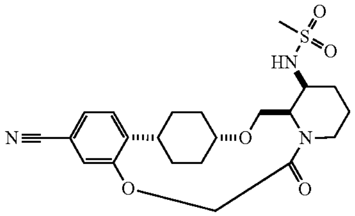 | 47 |
| 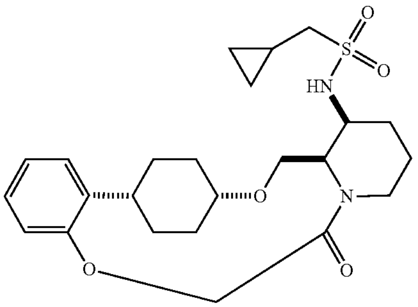 | 48 |
| 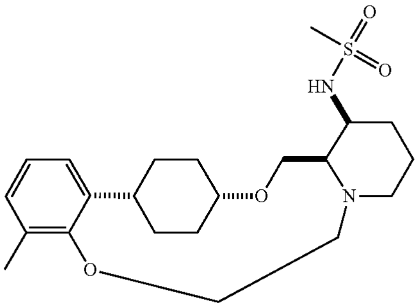 | 49 |
TABLE 1-continued
| Structure | Compound No. |
| --- | --- |
| 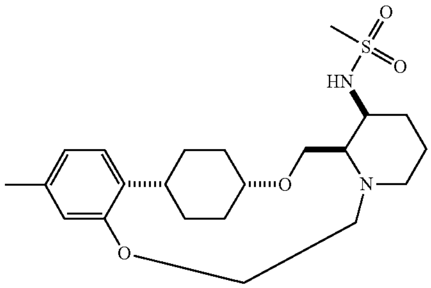 | 50 |
| 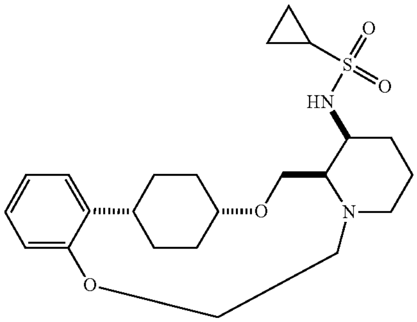 | 51 |
| 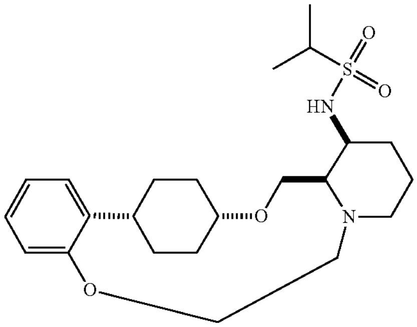 | 52 |
| 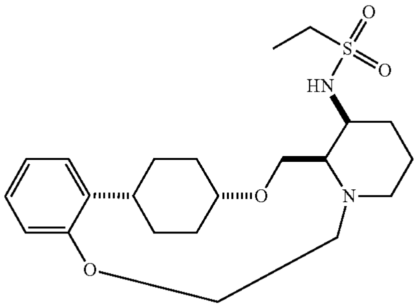 | 53 |
| 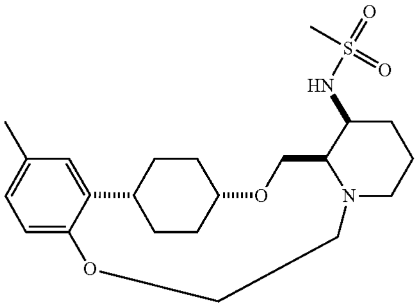 | 54 |

TABLE 1-continued
| Structure | Compound No. |
|---|---|
| 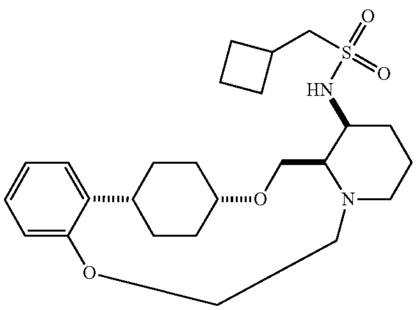 | 55 |
| 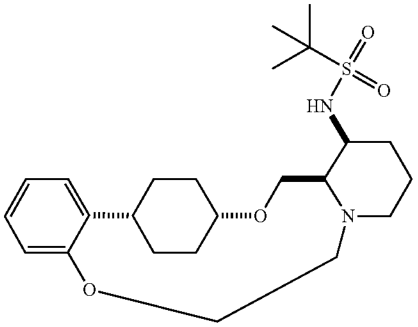 | 56 |
| 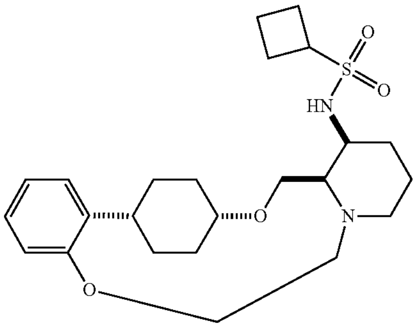 | 57 |
| 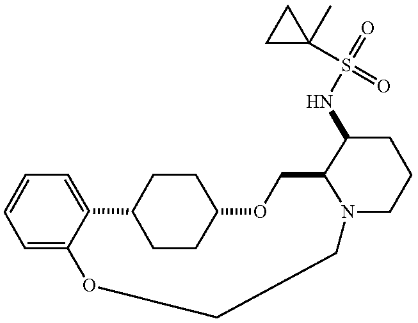 | 58 |
TABLE 1-continued
| Structure | Compound No. |
|---|---|
| 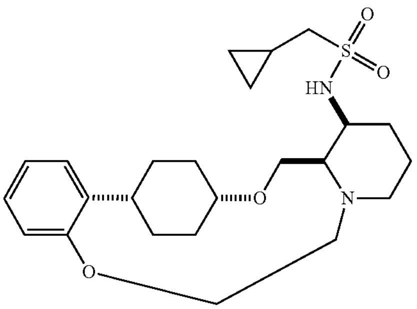 | 59 |
| 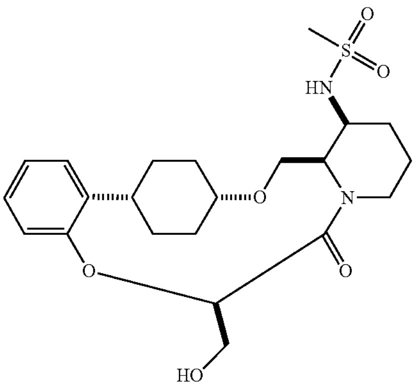 | 60 |
| 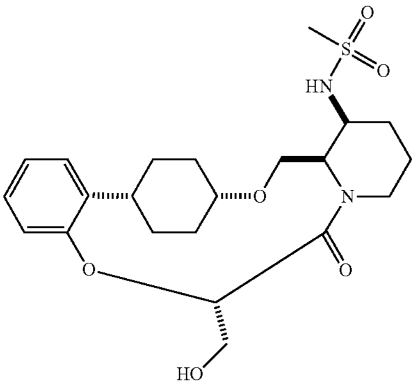 | 61 |
| 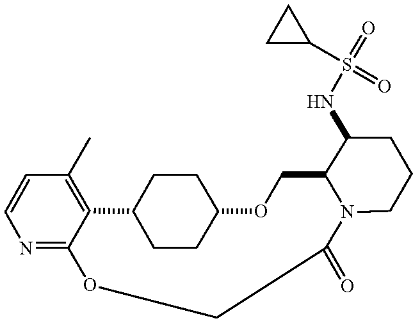 | 62 |

TABLE 1-continued
| Structure | Compound No. |
| --- | --- |
| 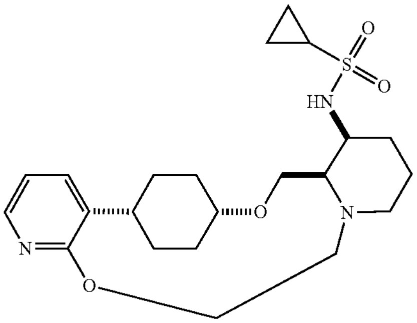 | 63 |
| 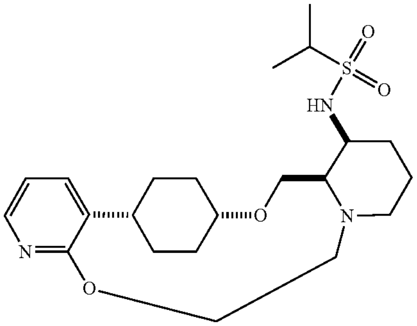 | 64 |
| 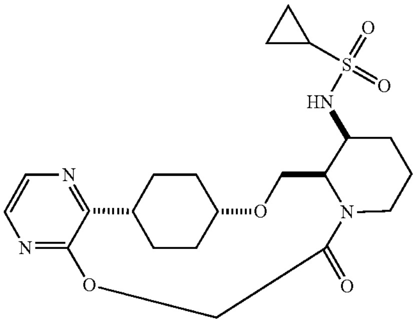 | 65 |
| 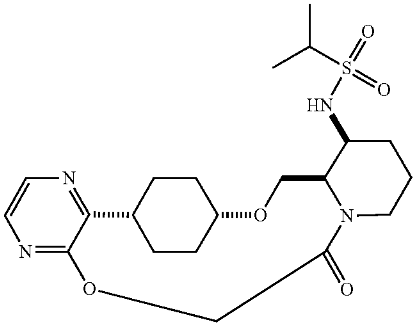 | 66 |
TABLE 1-continued
| Structure | Compound No. |
| --- | --- |
| 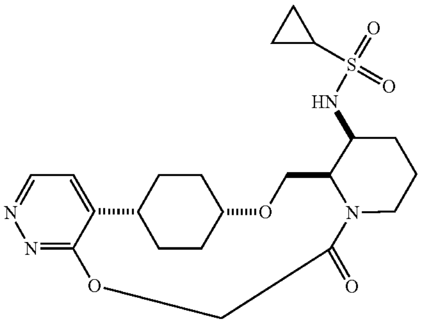 | 67 |
| 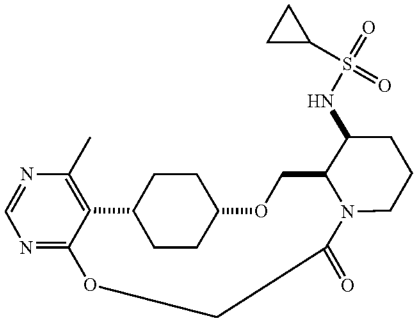 | 68 |
| 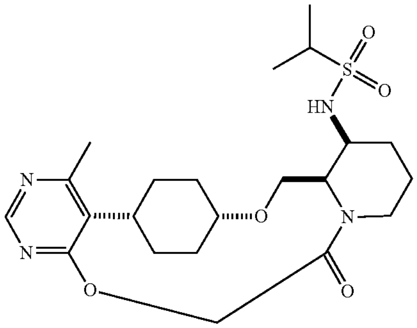 | 69 |
| 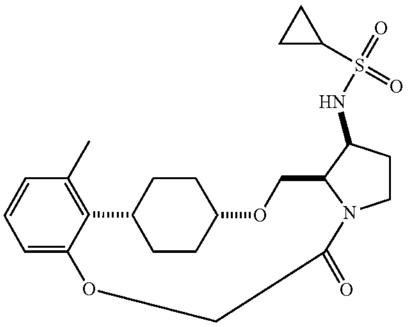 | 70 |

TABLE 1-continued
| Structure | Compound No. |
|---|---|
| 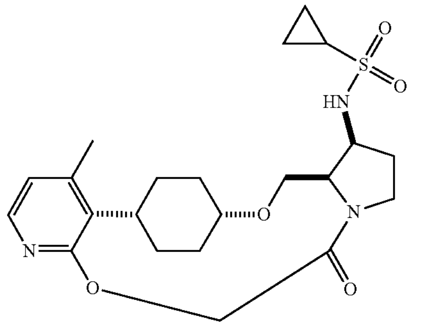 | 71 |
| 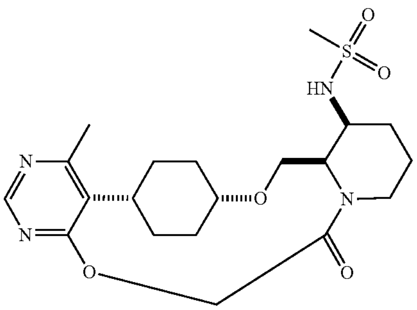 | 72 |
| 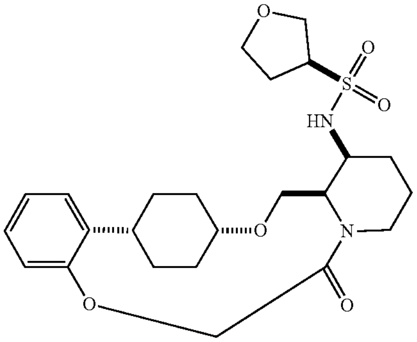 | 73 |
| 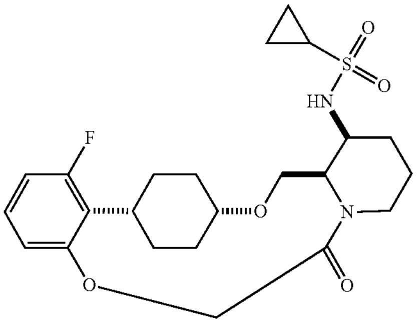 | 74 |
TABLE 1-continued
| Structure | Compound No. |
|---|---|
| 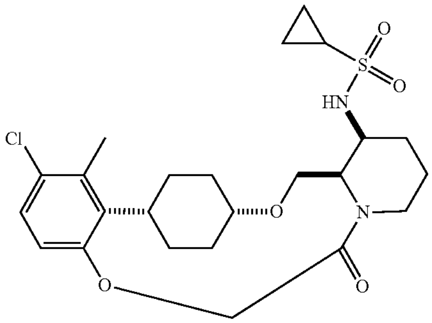 | 75 |
| 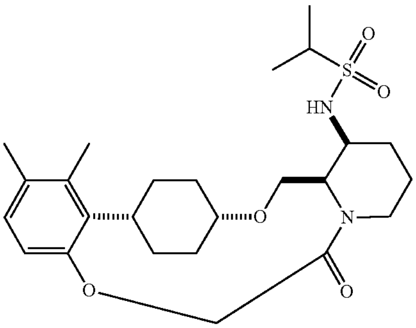 | 76 |
| 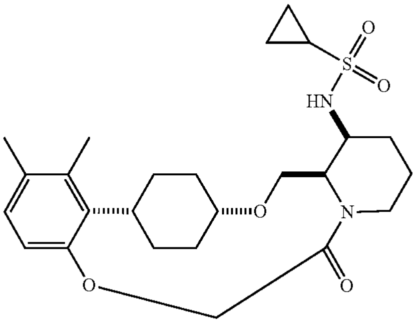 | 77 |
| 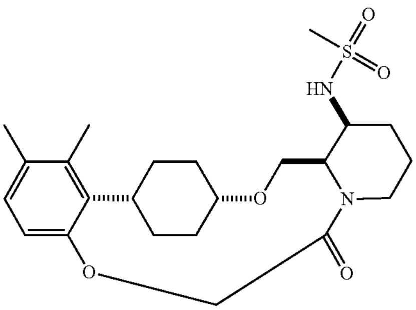 | 78 |

TABLE 1-continued
| Structure | Compound No. |
|---|---|
| 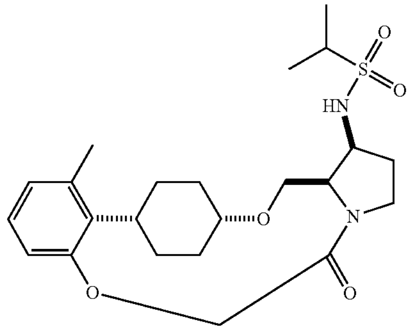 | 79 |
| 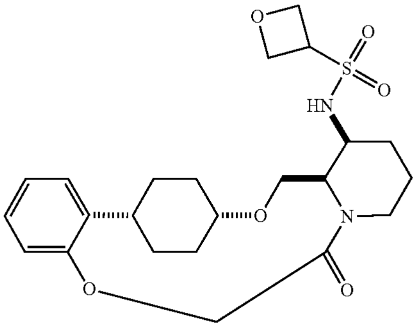 | 80 |
| 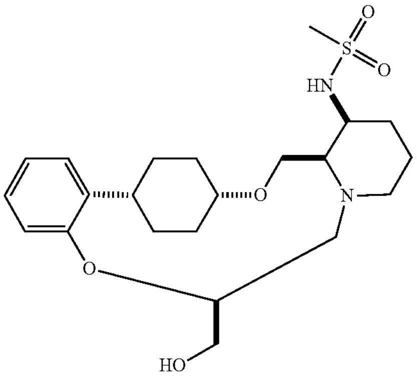 | 81 |
| 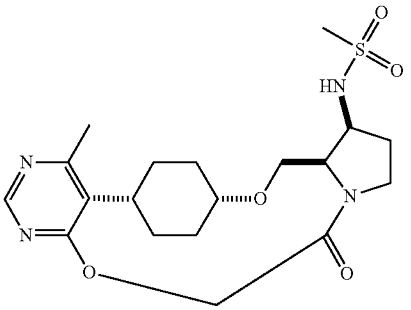 | 82 |
TABLE 1-continued
| Structure | Compound No. |
|---|---|
| 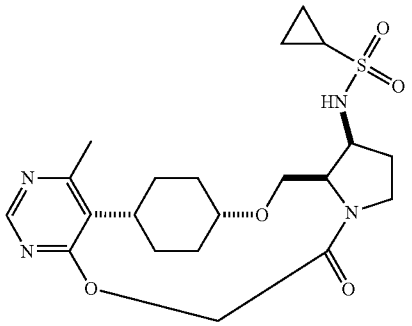 | 83 |
| 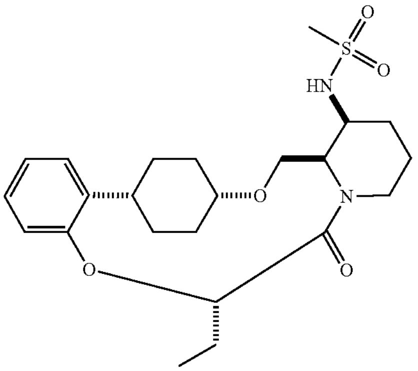 | 84 |
| 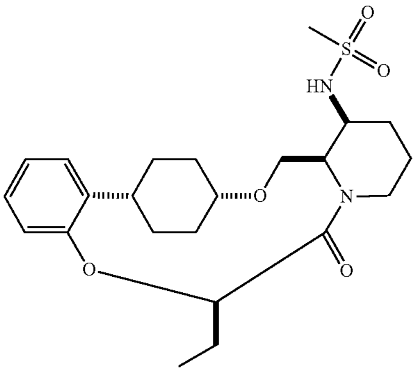 | 85 |
| 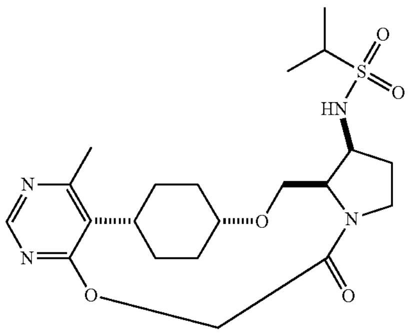 | 86 |

TABLE 1-continued
| Structure | Compound No. |
| --- | --- |
| 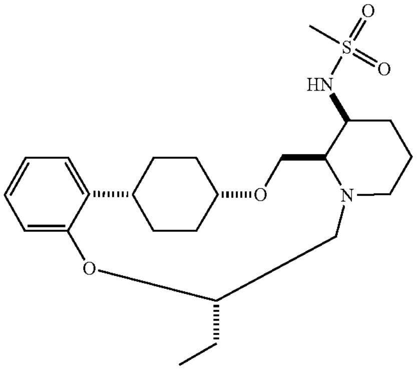 | 87 |
| 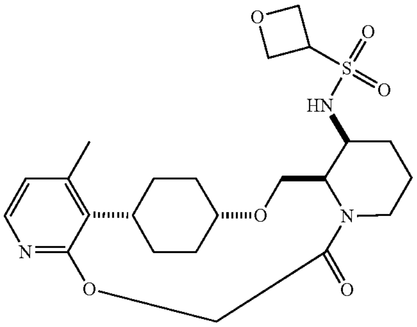 | 88 |
| 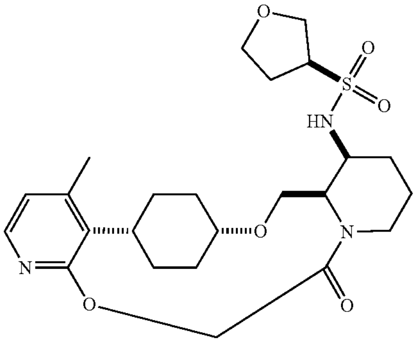 | 89 |
| 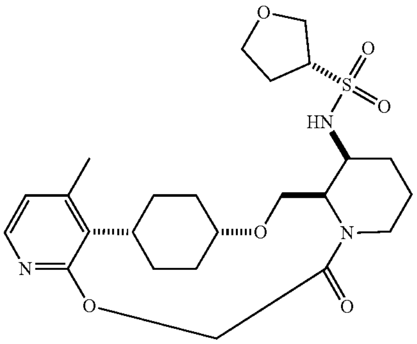 | 90 |
TABLE 1-continued
| Structure | Compound No. |
| --- | --- |
| 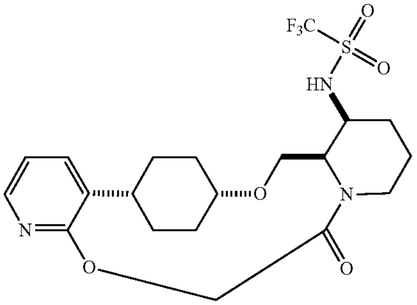 | 91 |
| 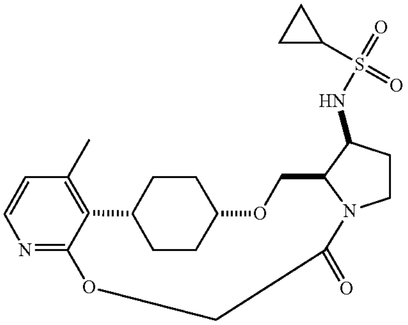 | 92 |
| 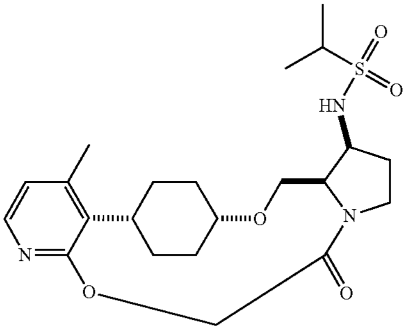 | 93 |
| 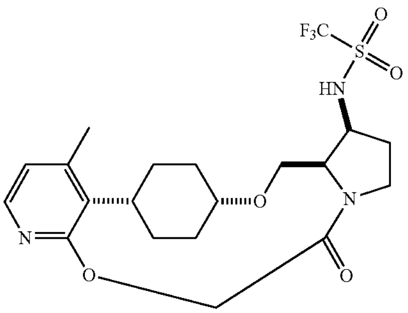 | 94 |

TABLE 1-continued
| Structure | Compound No. |
|---|---|
| 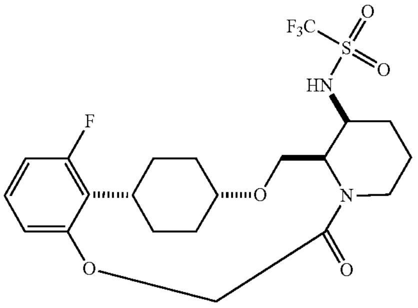 | 95 |
| 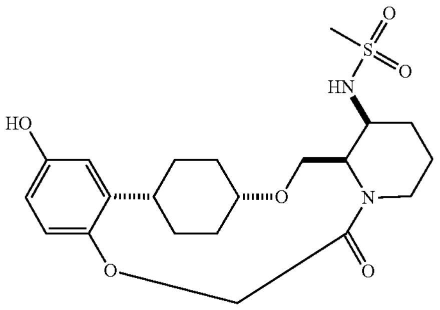 | 96 |
| 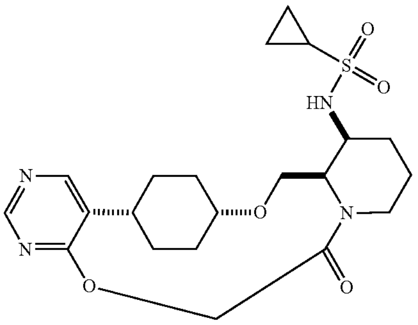 | 97 |
| 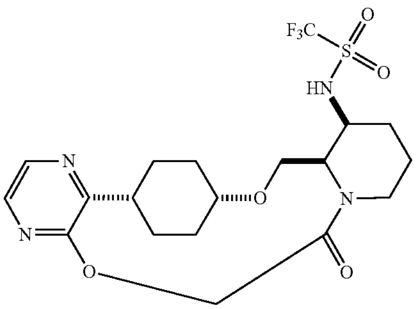 | 98 |
TABLE 1-continued
| Structure | Compound No. |
|---|---|
| 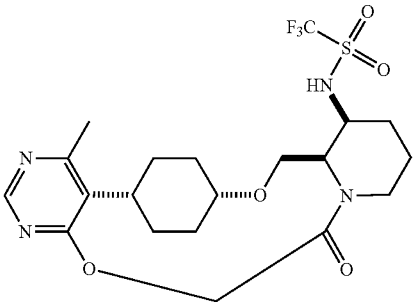 | 99 |
| 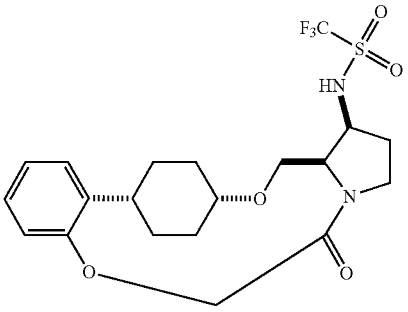 | 100 |
| 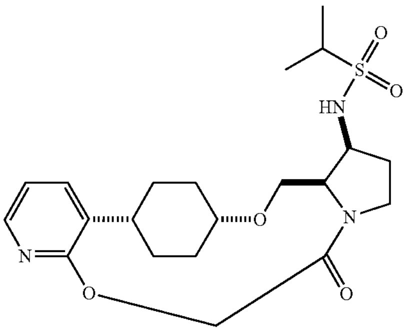 | 101 |
| 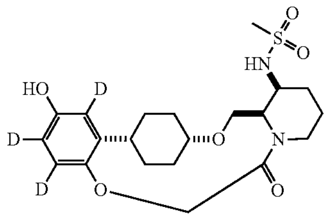 | 102 |
| 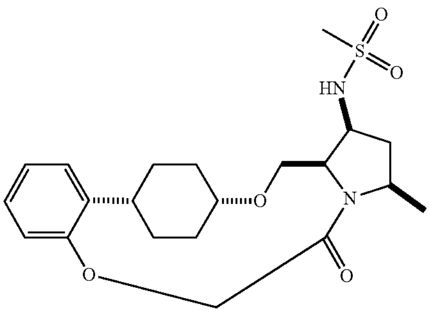 | 103 |

TABLE 1-continued

| Structure | Compound No. |
| --- | --- |
| 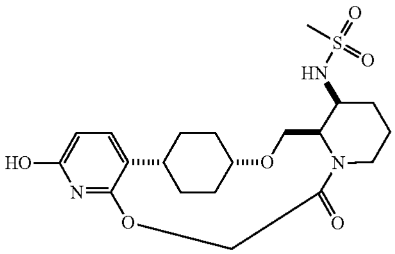 | 104 |
| 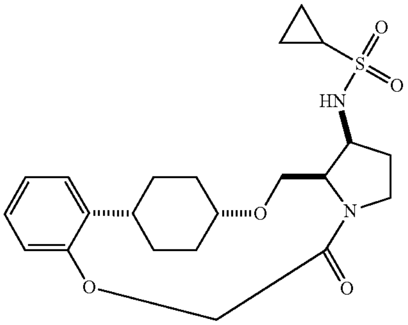 | 105 |
| 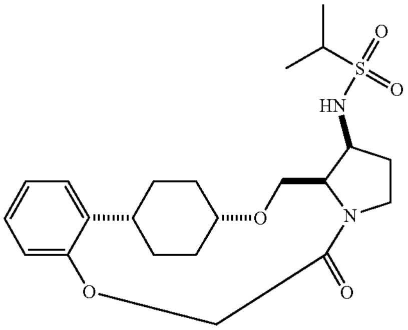 | 106 |
| 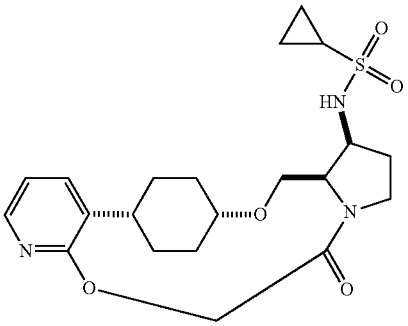 | 107 |
| 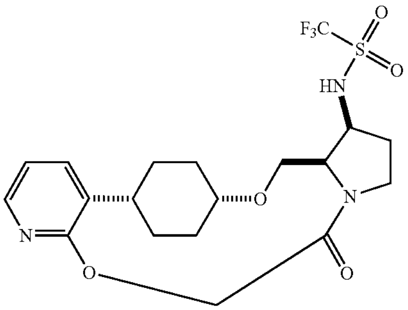 | 108 |

TABLE 1-continued

| Structure | Compound No. |
| --- | --- |
| 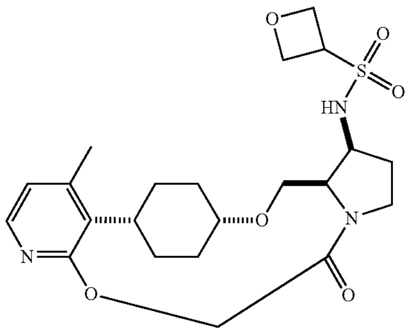 | 109 |
| 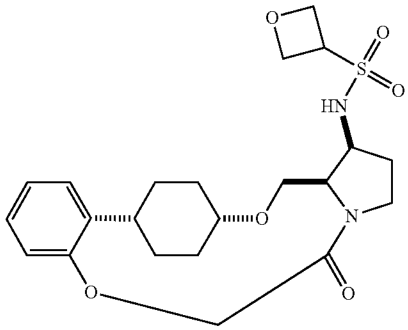 | 110 |
| 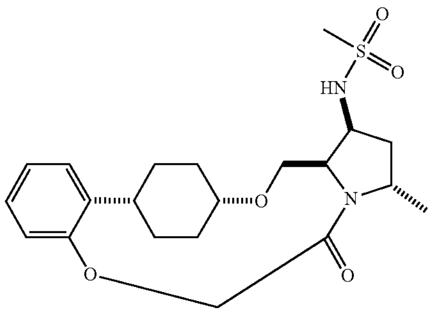 | 111 |

The disclosed compounds possess one or more stereocenters, and each stereocenter may exist independently in either the R or S configuration. In one embodiment, compounds described herein are present in optically active or racemic forms. It is to be understood that the compounds described herein encompass racemic, optically-active, regioisomeric and stereoisomeric forms, or combinations thereof that possess the therapeutically useful properties described herein.

Preparation of optically active forms is achieved in any suitable manner, including by way of non-limiting example, by resolution of the racemic form with recrystallization techniques, synthesis from optically-active starting materials, chiral synthesis, or chromatographic separation using a chiral stationary phase. In one embodiment, a mixture of two or more isomers is utilized as the disclosed compound described herein. In another embodiment, a pure isomer is utilized as the disclosed compound described herein. In another embodiment, compounds described herein contain one or more chiral centers. These compounds are prepared by any means, including stereoselective synthesis, enantioselective synthesis or separation of a mixture of enantiomers or diastereomers. Resolution of compounds and isomers thereof is achieved by any means including, by way of non-limiting example, chemical processes, enzymatic processes, fractional crystallization, distillation, and chromatography.

In one embodiment, the disclosed compounds may exist as tautomers. All tautomers are included within the scope of the compounds presented herein.

Compounds described herein also include isotopically-labeled compounds wherein one or more atoms is replaced by an atom having the same atomic number, but an atomic mass or mass number different from the atomic mass or mass number usually found in nature. Examples of isotopes suitable for inclusion in the compounds described herein include and are not limited to $^{2}H$, $^{3}H$, $^{11}C$, $^{13}C$, $^{14}C$, $^{36}Cl$, $^{18}F$, $^{123}I$, $^{125}I$, $^{13}N$, $^{15}N$, $^{15}O$, $^{17}O$, $^{18}O$, $^{32}P$, and $^{35}S$. In one embodiment, isotopically-labeled compounds are useful in drug or substrate tissue distribution studies. In another embodiment, substitution with heavier isotopes such as deuterium affords greater metabolic stability (for example, increased in vivo half-life or reduced dosage requirements). In another embodiment, the compounds described herein include a $^{2}H$ (i.e., deuterium) isotope.

In yet another embodiment, substitution with positron emitting isotopes, such as $^{11}C$, $^{18}F$, $^{15}O$ and $^{13}N$, is useful in Positron Emission Topography (PET) studies for examining substrate receptor occupancy. Isotopically-labeled compounds are prepared by any suitable method or by processes using an appropriate isotopically-labeled reagent in place of the non-labeled reagent otherwise employed.

The specific compounds described herein, and other compounds encompassed by one or more of the Formulas described herein having different substituents are synthesized using techniques and materials described herein and as described, for example, in Fieser and Fieser's Reagents for Organic Synthesis, Volumes 1-17 (John Wiley and Sons, 1991); Rodd's Chemistry of Carbon Compounds, Volumes 1-5 and Supplementals (Elsevier Science Publishers, 1989); Organic Reactions, Volumes 1-40 (John Wiley and Sons, 1991), Larock's Comprehensive Organic Transformations (VCH Publishers Inc., 1989), March, Advanced Organic Chemistry 4$^{th}$ Ed., (Wiley 1992); Carey and Sundberg, Advanced Organic Chemistry 4th Ed., Vols. A and B (Plenum 2000, 2001), and Green and Wuts, Protective Groups in Organic Synthesis 3rd Ed., (Wiley 1999) (all of which are incorporated by reference for such disclosure). General methods for the preparation of compounds as described herein are modified by the use of appropriate reagents and conditions, for the introduction of the various moieties found in the Formulas as provided herein.

Compounds described herein are synthesized using any suitable procedures starting from compounds that are available from commercial sources or are prepared using procedures described herein.

Methods of Treatment

The compounds of the invention can be used in a method of treating a disease or condition in a subject, said method comprising administering to the subject a compound of the invention, or a pharmaceutical composition comprising a compound of the invention. In one embodiment of the methods described herein, the subject is human. In one aspect, the compounds provided herein are useful in treatment of a disease or condition by acting as an agonist of the orexin-2 receptor.

The compounds of the invention can be used to treat a disease or condition selected from the group consisting of narcolepsy, cataplexy, or hypersomnia in a subject in need thereof.

In one embodiment, the compounds of the invention can be used to treat narcolepsy in a subject. In one embodiment, the compounds of the invention can be used to treat cataplexy in a subject. In one embodiment, the compounds of the invention can be used to treat hypersomnia in a subject.

Orexin-2 receptors are important in a wide range of biological functions. This suggests that orexin-2 receptors play a role in diverse disease processes in humans or other species. The compound of the present invention is useful for treating, preventing, or ameliorating the risk of one or more of the following symptoms or diseases of various neurological and psychiatric diseases associated with alterations in sleep/wake function. That is, narcolepsy, narcolepsy with cataplexy, idiopathic hypersomnia, hypersomnia, sleep apnea syndrome, narcolepsy syndrome, hypersomnolence syndrome characterized by hypersomnia (e.g., in subjects with Kleine Levin syndrome, major depression with hypersomnia, Lewy body dementia, Parkinson's disease, progressive supranuclear paralysis, Prader-Willi syndrome, Mobius syndrome, hypoventilation syndrome, Niemann-Pick disease type C, brain contusion, cerebral infarction, brain tumor, muscular dystrophy, multiple sclerosis, multiple systems atrophy, acute disseminated encephalomyelitis, Guillain-Barre syndrome, Rasmussen's encephalitis, Wernicke's encephalitis, limbic encephalitis, or Hashimoto's encephalopathy), coma, loss of consciousness, obesity (e.g., malignant mastocytosis, exogenous obesity, hyperinsulinar obesity, hyperplasmic obesity, hypop hyseal adiposity, hypoplasmic obesity, hypothyroid obesity, hypothalamic obesity, symptomatic obesity, infantile obesity, upper body obesity, alimentary obesity, hypogonadal obesity, systemic mastocytosis, simple obesity, or central obesity), insulin resistance syndrome, Alzheimer's disease, disturbance of consciousness such as coma and the like, side effects and complications due to anesthesia, sleep disturbance, excessive daytime sleepiness, sleep problem, insomnia, intermittent sleep, nocturnal myoclonus, REM sleep interruption, jet lag, jet lag syndrome, sleep disorder of alternating worker, sleep disorder, night terror, depression, major depression, sleepwalking disease, enuresis, sleep disorder, Alzheimer's dusk, sundowning, diseases associated with circadian rhythm, fibromyalgia, condition arising from decline in the quality of sleep, overeating, obsessive compulsive eating disorder, obesity-related disease, hypertension, diabetes, elevated plasma insulin concentration and insulin resistance, hyperlipidemia, hyperlipemia, endometrial cancer, breast cancer, prostate cancer, colorectal cancer, cancer, osteoarthritis, obstructive sleep apnea, cholelithiasis, gallstones, cardiac disease, abnormal heartbeat, arrhythmia, myocardial infarction, congestive cardiac failure, cardiac failure, coronary heart disease, cardiovascular disorder, polycysticovarian disease, craniopharingioma, Prader-Willi syndrome, Froelich's syndrome, growth hormone deficient, normal mutant short stature, Turner's syndrome, children suffering from acute lymphoblastic leukemia, syndrome X, reproductive hormone abnormality, declining fertility, infertility, male gonadal function decline, sexual and reproductive dysfunction such as female male hirsutism, fetal defects associated with pregnant women obesity, gastrointestinal motility disorders such as obesity-related gastroesophageal reflux, obesity hypoventilation syndrome (Pickwick syndrome), respiratory diseases such as dyspnea, inflammation such as systemic inflammation of the vascular system, arteriosclerosis, hypercholesterolemia, hyperuricemia, lower back pain, gall bladder disease, gout, kidney cancer, risk of secondary outcomes of obesity, such as lowering the risk of left ventricular hypertrophy, migraine pain, headache, neuropathic pain, Parkinson's disease, psychosis, autoimmune encephalitis, cancer related fatigue (such as excessive daytime sleepiness or fatigue associated with cancer and/or chemotherapy), cancer related nausea and vomiting, corticobasal degeneration, Huntington's disease, neuromyelitis optica, nociception, progressive supranuclear palsy, schizophrenia, systemic lupus erythematosus, traumatic brain injury, facial flushing, night sweats, diseases of the genital/urinary system, diseases related to sexual function or fertility, dysthymic disorder, bipolar disorder, bipolar I disorder, bipolar II disorder, cyclothymic disorder, acute stress disorder, agoraphobia, generalized anxiety disorder, obsessive disorder, panic attack, panic disorder, post-traumatic stress disorder (PTSD), separation anxiety disorder, social phobia, anxiety disorder, acute neurological and psychiatric disorders such as cardiac bypass surgery and post-transplant cerebral deficit, stroke, ischemic stroke, cerebral ischemia, spinal cord trauma, head trauma, perinatal hypoxia, cardiac arrest, hypoglycemic nerve injury, Huntington's chorea, amyotrophic lateral sclerosis, eye damage, retinopathy, cognitive impairment, muscle spasm, tremor, epilepsy, disorders associated with muscle spasticity, delirium, amnestic disorder, age-related cognitive decline, schizoaffective disorder, delusional disorder, drug addiction, dyskinesia, chronic fatigue syndrome, fatigue, medication-induced Parkinsonism syndrome, Jill-do La Tourette's syndrome, chorea, myoclonus, tic, restless legs syndrome, dystonia, dyskinesia, attention deficit hyperactivity disorder (ADHD), behavior disorder, urinary incontinence, withdrawal symptoms, trigeminal neuralgia, hearing loss, tinnitus, nerve damage, retinopathy, macular degeneration, vomiting, cerebral edema, pain, bone pain, arthralgia, toothache, cataplexy, and traumatic brain injury (TBI).

Particularly, the compound of the present invention is useful as a therapeutic or prophylactic drug for narcolepsy, idiopathic hypersomnia, hypersomnia, sleep apnea syndrome, narcolepsy syndrome, hypersomnolence syndrome characterized by hypersomnia (e.g., in Parkinson's disease, Guillain-Barre syndrome or Kleine Levin syndrome), Alzheimer's disease, obesity, insulin resistance syndrome, cardiac failure, diseases related to bone loss, sepsis, disturbance of consciousness such as coma and the like, side effects and complications due to anesthesia, and the like, or anesthetic antagonist.

In one embodiment, the compound of the present invention has orexin-2 receptor agonist activity and is useful as a prophylactic or therapeutic agent for narcolepsy.

In another embodiment, the compound of the present invention is useful as a prophylactic or therapeutic agent for narcolepsy type-1. In another embodiment, the compound of the present invention is useful as a prophylactic or therapeutic agent for narcolepsy type-2. In another embodiment, the compound of the present invention is useful as a prophylactic or therapeutic agent for narcolepsy and excessive daytime sleepiness. In another embodiment, the compound of the present invention is useful as a prophylactic or therapeutic agent for narcolepsy, cataplexy, and excessive daytime sleepiness. In another embodiment, the compound of the present invention is useful as a prophylactic or therapeutic agent for narcolepsy and cataplexy. In another embodiment, the compound of the present invention is useful as a prophylactic or therapeutic agent for excessive daytime sleepiness. In another embodiment, the compound of the present invention is useful as a prophylactic or therapeutic agent for idiopathic hypersomnia. In another embodiment, the compound of the present invention is useful as a prophylactic or therapeutic agent for obstructive sleep apnea.

In another embodiment, the compound of the present invention has orexin-2 receptor agonist activity and is useful as a prophylactic or therapeutic agent for hypersomnia in Parkinson's disease.

In another embodiment, the compound of the present invention has orexin-2 receptor agonist activity and is useful as a prophylactic or therapeutic agent for hypersomnia. In another embodiment, the compound of the present invention has orexin-2 receptor agonist activity and is useful as a prophylactic or therapeutic agent for excessive daytime sleepiness associated with Parkinson's disease.

In another embodiment, the compound of the present invention has orexin-2 receptor agonist activity and is useful as a prophylactic or therapeutic agent for excessive daytime sleepiness or fatigue associated with cancer and/or chemotherapy.

In another embodiment, the present invention provides a method of treating narcolepsy in a subject in need thereof comprising administering to the subject a compound of Formula I-A, I, II-A, or II, or a pharmaceutically acceptable salt thereof.

In another embodiment, the present invention provides a method of treating narcolepsy type-1 in a subject in need thereof comprising administering to the subject a compound of Formula I-A, I, II-A, or II, or a pharmaceutically acceptable salt thereof.

In another embodiment, the present invention provides a method of treating narcolepsy type-2 in a subject in need thereof comprising administering to the subject a compound of Formula I-A, I, II-A, or II, or a pharmaceutically acceptable salt thereof.

In another embodiment, the present invention provides a method of treating narcolepsy and excessive daytime sleepiness in a subject in need thereof comprising administering to the subject a compound of Formula I-A, I, II-A, or II, or a pharmaceutically acceptable salt thereof.

In another embodiment, the present invention provides a method of treating narcolepsy, cataplexy, and excessive daytime sleepiness in a subject in need thereof comprising administering to the subject a compound of Formula I-A, I, II-A, or II, or a pharmaceutically acceptable salt thereof.

In another embodiment, the present invention provides a method of treating narcolepsy and cataplexy in a subject in need thereof comprising administering to the subject a compound of Formula I-A, I, II-A, or II, or a pharmaceutically acceptable salt thereof.

In another embodiment, the present invention provides a method of treating excessive daytime sleepiness in a subject in need thereof comprising administering to the subject a compound of Formula I-A, I, II-A, or II, or a pharmaceutically acceptable salt thereof.

In another embodiment, the present invention provides a method of treating idiopathic hypersomnia in a subject in need thereof comprising administering to the subject a compound of Formula I-A, I, II-A, or II, or a pharmaceutically acceptable salt thereof.

In another embodiment, the present invention provides a method of treating excessive daytime sleepiness and idiopathic hypersomnia in a subject in need thereof comprising administering to the subject a compound of Formula I-A, I, II-A, or II, or a pharmaceutically acceptable salt thereof.

In another embodiment, the present invention provides a method of treating obstructive sleep apnea in a subject in need thereof comprising administering to the subject a compound of Formula I-A, I, II-A, or II, or a pharmaceutically acceptable salt thereof.

In another embodiment, the present invention provides a method of treating excessive daytime sleepiness and obstructive sleep apnea in a subject in need thereof comprising administering to the subject a compound of Formula I-A, I, II-A, or II, or a pharmaceutically acceptable salt thereof.

In any of the methods as described herein, the subject is administered a compound of Formula I. In any of the methods as described herein, the subject is administered a compound of Formula II.

Each of the embodiments described herein with respect to the use of compounds of Formula I also applies to compounds of Formula I-A. Each of the embodiments described herein with respect to the use of compounds of Formula II also applies to compounds of Formula II-A.

In any of the compositions or methods as described herein, the compound of Formula I-A, I, II-A, II, or a pharmaceutically acceptable salt thereof, is present and/or administered in a therapeutically effective amount.

Administration/Dosage/Formulations

In another aspect, provided herein is a pharmaceutical composition comprising at least one compound of the invention, together with a pharmaceutically acceptable carrier.

Actual dosage levels of the active ingredients in the pharmaceutical compositions of this invention may be varied so as to obtain an amount of the active ingredient that is effective to achieve the desired therapeutic response for a particular patient, composition, and mode of administration, without being toxic to the patient.

In particular, the selected dosage level will depend upon a variety of factors including the activity of the particular compound employed, the time of administration, the rate of excretion of the compound, the duration of the treatment, other drugs, compounds or materials used in combination with the compound, the age, sex, weight, condition, general health and prior medical history of the patient being treated, and like factors well, known in the medical arts.

A medical doctor, e.g., physician or veterinarian, having ordinary skill in the art may readily determine and prescribe the effective amount of the pharmaceutical composition required. For example, the physician or veterinarian could begin administration of the pharmaceutical composition to dose the disclosed compound at levels lower than that required in order to achieve the desired therapeutic effect and gradually increase the dosage until the desired effect is achieved.

In particular embodiments, it is especially advantageous to formulate the compound in dosage unit form for ease of administration and uniformity of dosage. Dosage unit form as used herein refers to physically discrete units suited as unitary dosages for the patients to be treated; each unit containing a predetermined quantity of the disclosed compound calculated to produce the desired therapeutic effect in association with the required pharmaceutical vehicle. The dosage unit forms of the invention are dictated by and directly dependent on (a) the unique characteristics of the disclosed compound and the particular therapeutic effect to be achieved, and (b) the limitations inherent in the art of compounding/formulating such a disclosed compound for the treatment of narcolepsy or cataplexy in a patient.

In one embodiment, the compounds of the invention are formulated using one or more pharmaceutically acceptable excipients or carriers. In one embodiment, the pharmaceutical compositions of the invention comprise a therapeutically effective amount of a disclosed compound and a pharmaceutically acceptable carrier.

In some embodiments, the dose of a disclosed compound is from about 1 mg to about 1,000 mg. In some embodiments, a dose of a disclosed compound used in compositions described herein is less than about 1,000 mg, or less than about 800 mg, or less than about 600 mg, or less than about 500 mg, or less than about 300 mg, or less than about 200 mg, or less than about 100 mg, or less than about 50 mg, or less than about 20 mg, or less than about 10 mg. For example, a dose is about 10 mg, 20 mg, 25 mg, 30 mg, 40 mg, 50 mg, 60 mg, 70 mg, 80 mg, 90 mg, 100 mg, 120 mg, 140 mg, 160 mg, 180 mg, 200 mg, 220 mg, 240, 260 mg, 280 mg, 300 mg, 350 mg, 400 mg, 450 mg, 500 mg, 550 mg, or about 600 mg.

Routes of administration of any of the compositions of the invention include oral, nasal, rectal, intravaginal, parenteral, buccal, sublingual or topical. The compounds for use in the invention may be formulated for administration by any suitable route, such as for oral or parenteral, for example, transdermal, transmucosal (e.g., sublingual, lingual, (trans) buccal, (trans)urethral, vaginal (e.g., trans- and perivaginally), (intra)nasal and (trans)rectal), intravesical, intrapulmonary, intraduodenal, intragastrical, intrathecal, subcutaneous, intramuscular, intradermal, intra-arterial, intravenous, intrabronchial, inhalation, and topical administration. In one embodiment, the preferred route of administration is oral.

Suitable compositions and dosage forms include, for example, tablets, capsules, caplets, pills, gel caps, troches, dispersions, suspensions, solutions, syrups, granules, beads, transdermal patches, gels, powders, pellets, magmas, lozenges, creams, pastes, plasters, lotions, discs, suppositories, liquid sprays for nasal or oral administration, dry powder or aerosolized formulations for inhalation, compositions and formulations for intravesical administration and the like. It should be understood that the formulations and compositions that would be useful in the present invention are not limited to the particular formulations and compositions that are described herein.

For oral application, particularly suitable are tablets, dragees, liquids, drops, suppositories, or capsules, caplets and gelcaps. The compositions intended for oral use may be prepared according to any method known in the art and such compositions may contain one or more agents selected from the group consisting of inert, non-toxic pharmaceutically excipients that are suitable for the manufacture of tablets. Such excipients include, for example an inert diluent such as lactose; granulating and disintegrating agents such as cornstarch; binding agents such as starch; and lubricating agents such as magnesium stearate. The tablets may be uncoated or they may be coated by known techniques for elegance or to delay the release of the active ingredients. Formulations for oral use may also be presented as hard gelatin capsules wherein the active ingredient is mixed with an inert diluent.

For parenteral administration, the disclosed compounds may be formulated for injection or infusion, for example, intravenous, intramuscular or subcutaneous injection or infusion, or for administration in a bolus dose or continuous infusion. Suspensions, solutions or emulsions in an oily or aqueous vehicle, optionally containing other formulatory agents such as suspending, stabilizing or dispersing agents may be used.

Those skilled in the art will recognize or be able to ascertain using no more than routine experimentation, numerous equivalents to the specific procedures, embodiments, claims, and examples described herein. Such equivalents are considered to be within the scope of this invention and covered by the claims appended hereto. For example, it should be understood, that modifications in reaction conditions, including but not limited to reaction times, reaction size/volume, and experimental reagents, such as solvents, catalysts, pressures, atmospheric conditions, e.g., nitrogen atmosphere, and reducing/oxidizing agents, with art-recognized alternatives and using no more than routine experimentation, are within the scope of the present application.

It is to be understood that wherever values and ranges are provided herein, all values and ranges encompassed by these values and ranges, are meant to be encompassed within the scope of the present invention. Moreover, all values that fall within these ranges, as well as the upper or lower limits of a range of values, are also contemplated by the present application.

The following examples further illustrate aspects of the present invention. However, they are in no way a limitation of the teachings or disclosure of the present invention as set forth herein.

EXAMPLES

The invention is further illustrated by the following examples, which should not be construed as further limiting. The practice of the present invention will employ, unless otherwise indicated, conventional techniques of organic synthesis, cell biology, cell culture, molecular biology, transgenic biology, microbiology and immunology, which are within the skill of the art.

General Procedures

Liquid chromatography mass spectroscopy (LCMS) data were acquired on a Shimadzu LCMS-2020 with LabSolutions software. Mass spectrometry data are reported from LCMS analyses. Mass spectrometry (MS) was performed via atmospheric pressure chemical ionization (APCI), electrospray Ionization (ESI), electron impact ionization (EI) or electron scatter (ES) ionization sources.

Nuclear magnetic resonance (NMR) data were acquired on a Bruker AVANCE III HD or on a Bruker AVANCE NEO instrument with Topspin 3.5pl7 or Topspin 4.1.1 software. Proton nuclear magnetic spectroscopy ($^1$H NMR) chemical shifts are reported in parts per million downfield from tetramethylsilane and were recorded on 300 or 400 MHz spectrometers, unless indicated otherwise. Chemical shifts are expressed in parts per million (ppm, δ) referenced to the deuterated solvent residual peaks.

Example 1: Synthesis Procedures

Synthesis procedures for preparation of the compounds of the invention are readily available to the ordinary skilled artisan. Unless otherwise indicated, starting materials were generally obtained from commercial sources. Synthetic procedures for related compounds can be found, for example, in U.S. application Ser. No. 17/104,993 and in PCT Application No.: PCT/US20/62320, both filed Nov. 25, 2020, and both of which are expressly incorporated by reference herein.

The following abbreviations are used in the synthetic examples below:

AcOH=acetic acid
DCM=dichloromethane
MsCl=methanesulfonyl chloride
MeOH=methanol
THF=tetrahydrofuran
EtOH=ethanol
$PtO_2$=platinum dioxide
HATU=1-[bis(dimethylamino)methylene]-1H-1,2,3-triazolo[4,5-b]pyridinium 3-oxide hexafluorophosphate
DIPEA or DIEA=N,N-diisopropylethylamine
$^t$Bu=tert-butyl
ACN or MeCN=acetonitrile
PE=petroleum ether
EtOAc=ethyl acetate
DMF=dimethyl formamide
TFA=trifluoroacetic acid
LiOH=lithium hydroxide
min=minutes
hr=hours
NaH=sodium hydride
$Pd_2(dba)_3$=tris(dibenzylideneacetone)dipalladium(0)
DMSO=dimethyl sulfoxide
i-PrOH=isopropanol
Pd/C=palladium on carbon
XantPhos=4,5-bis(diphenylphosphino)-9,9-dimethylxanthene
Boc=tert-butyloxycarbonyl
Ms=methanesulfonyl
Bn=benzyl
Et=ethyl
Cbz=carboxybenzyl
PMB=para-methoxybenzyl
DBU=1,8-diazabicyclo[5.4.0]undec-7-ene
NBS=N-bromosuccinimide
$Pd(dppf)Cl_2$=[1,1'-bis(diphenylphosphino)ferrocene]dichloropalladium(II)
DMAP=4-(dimethylamino)pyridine
NCS=N-chlorosuccinimide
DMPU=1,3-dimethyl-3,4,5,6-tetrahydro-2(1H)-pyrimidinone
LDA=lithium diisopropylamide
TfO=trifluoromethanesulfonate
KHMDS=Potassium bis(trimethylsilyl)amide solution
KOAc=potassium acetate
XPhos=2-dicyclohexylphosphino-2',4',6'-triisopropylbiphenyl
$Et_3N$ or TEA=triethylamine
TMSOTf=trimethylsilyl trifluoromethanesulfonate.

Scheme 1

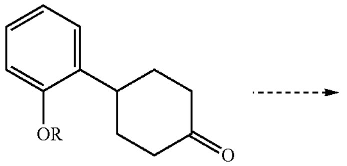

A

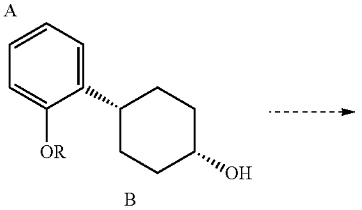

B

-continued

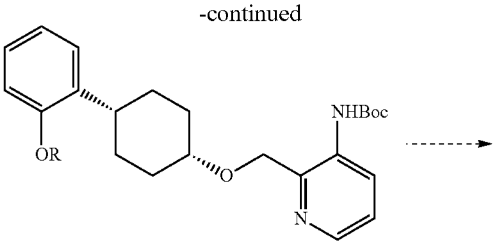

C

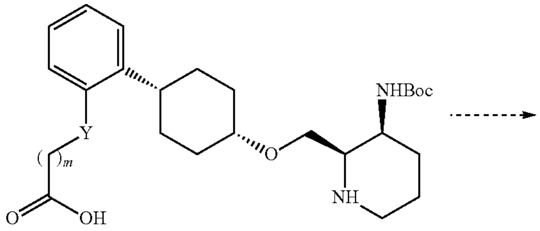

D

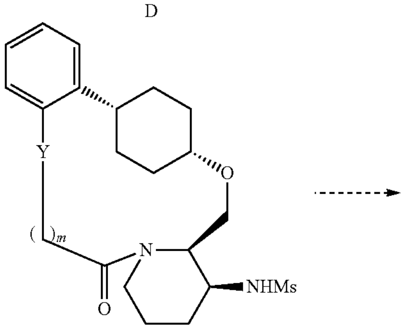

E

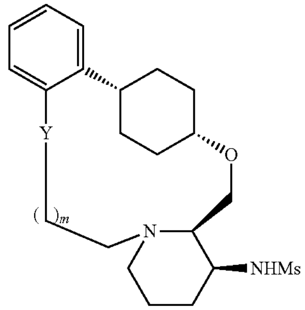

F

Example 1.1

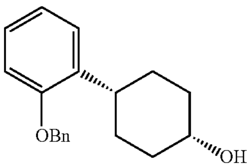 [SMILES: O[C@H]1CC[C@@H](c2ccccc2OCc2ccccc2)CC1]

Into a 5-L 4-necked round-bottom flask purged and maintained with an inert atmosphere of nitrogen, was placed 4-[2-(benzyloxy)phenyl]cyclohexan-1-one (210 g, 749 mmol, 1.00 equiv.) in tetrahydrofuran (2.1 L). This was followed by the addition of L-selectride (1 mol/L in THF) (1123 mL, 5257 mmol, 1.50 equiv.) dropwise with stirring at 0 degrees C. The resulting solution was stirred for 4 hr at room temperature. The reaction was then quenched by the addition of water/ice. The resulting solution was extracted with ethyl acetate, and the organic phase was washed with brine. The mixture was dried over anhydrous sodium sulfate, filtered, concentrated under vacuum. The residue was purified by silica gel column chromatography with ethyl acetate/petroleum ether (1:100-1:5) to give 137 g (64%) of (1s,4s)-4-[2-(benzyloxy)phenyl] cyclohexan-1-ol as a solid. $^1$H NMR (400 MHz, $CDCl_3$): δ 7.45-7.26 (6H, m), 7.16 (1H, dd), 6.98-6.90 (2H, m), 5.09 (2H, s), 4.13 (1H, s), 3.12-3.02 (1H, m), 1.93-1.82 (4H, m), 1.73-1.41 (4H, m).

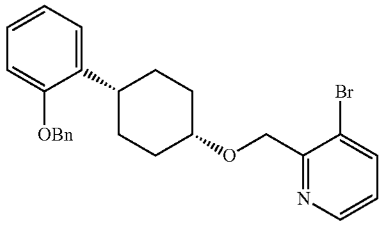 [SMILES: Brc1cccnc1CO[C@H]1CC[C@@H](c2ccccc2OCc2ccccc2)CC1]

Into a 2-L 4-necked round-bottom flask purged and maintained with an inert atmosphere of nitrogen, was placed NaH (60% wt, 26.9 g, 2.00 equiv.) in tetrahydrofuran (200 mL). This was followed by the addition of a solution of (1s, 4s)-4-[2-(benzyloxy)phenyl]cyclohexan-1-ol (95 g, 336 mmol, 1.00 equiv.) in THF (200 mL) dropwise with stirring at 50-55 degrees C. After stirring for 2 hr, to this was added a solution of 3-bromo-2-(bromomethyl)pyridine (143.5 g, 571 mmol, 1.70 equiv.) in THF (550 mL) dropwise with stirring at 50-55 degrees C. The resulting solution was stirred for 14 hr at 50-55 degrees C. The reaction mixture was cooled. The reaction was then quenched by the addition of water. The resulting solution was extracted with ethyl acetate and the organic layers combined and dried over anhydrous sodium sulfate. The solids were filtered out. The resulting mixture was concentrated under vacuum. The residue was purified by silica gel column chromatography with ethyl acetate/petroleum ether (1:100-1:2) to give 94 g (62%) of 3-bromo-2-([[(1s,4s)-4-[2-(benzyloxy) phenyl]cyclohexyl]oxy]methyl)pyridine as a solid. $^1$H NMR (400 MHz, $CDCl_3$): δ 8.57 (1H, d), 7.90 (1H, dd), 7.48-7.26 (6H, m), 7.18-7.14 (2H, m), 6.98-6.91 (2H, m), 5.12 (2H, s), 4.77 (2H, s), 3.86 (1H, s), 3.17-3.10 (1H, m), 2.20-2.15 (2H, m), 1.98-1.88 (2H, m), 1.69-1.57 (4H, m).

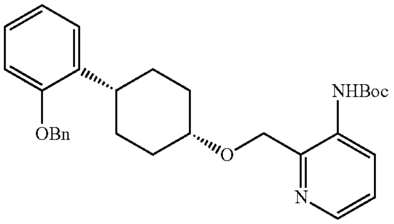

Into a 2-L 4-necked round-bottom flask purged and maintained with an inert atmosphere of nitrogen, was placed Xantphos (10.7 g, 18 mmol, 0.10 equiv.), $Cs_2CO_3$ (84 g, 258 mmol, 1.39 equiv.), 3-bromo-2-([[(1s,4s)-4-[2-(benzyloxy) phenyl]cyclohexyl]oxy]methyl)pyridine (84 g, 185 mmol, 1.00 equiv.), $Pd_2(dba)_3$ (8.5 g, 9 mmol, 0.05 equiv.) and tert-butyl carbamate (26 g, 222 mmol, 1.20 equiv.) in dioxane (840 mL). The resulting solution was stirred for 5 hr at 100 degrees C. The solids were filtered out. The filtrate was concentrated under vacuum. The residue was purified by silica gel column chromatography with ethyl acetate/petroleum ether (1:100-1:4) to provide 74 g (82%) of tert-butyl N-[2-([[(1s,4s)-4-[2-(benzyloxy)phenyl]cyclohexyl]oxy]methyl)pyridin-3-yl]carbamate as a solid.

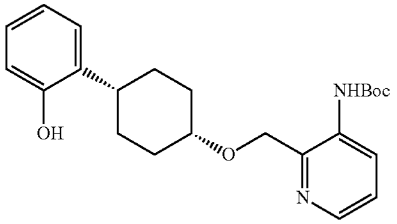 [SMILES: CC(C)(C)OC(=O)Nc1cccnc1CO[C@H]1CC[C@@H](c2ccccc2O)CC1]

Into a 2-L 3-necked round-bottom flask, was placed tert-butyl N-[2-([[(1s,4s)-4-[2-(benzyloxy)phenyl]cyclohexyl]oxy]methyl)pyridin-3-yl]carbamate (74 g, 151 mmol, 1.00 equiv.) and Pd/C (7.4 g, 10% wt) in ethyl alcohol (740 mL), then, hydrogen gas was through in. The resulting solution was stirred for 14 hr at room temperature. The solids were filtered out. The filtrate was concentrated under vacuum. The residue was purified by silica gel column chromatography with ethyl acetate/petroleum ether (1:100-1:2) to provide 51.36 g (85%) of tert-butyl N-[2-([[(1s,4s)-4-(2-hydroxyphenyl)cyclohexyl]oxy]methyl)pyridin-3-yl]carbamate as a solid. LCMS (ESI): m/z $[M+H]^+$=399.1; $^1$H NMR (300 MHz, $CDCl_3$): δ 8.65 (1H, s), 8.47 (1H, d), 8.19 (1H, q), 7.26-7.21 (1H, m), 7.09-7.03 (1H, m), 6.92-6.86 (1H, m), 6.75 (1H, q), 5.77 (1H, s), 4.84 (1H, s), 3.80 (1H, s), 2.94-2.93 (1H, m), 2.15-2.06 (2H, m), 1.88-1.47 (7H, m), 1.45 (9H, s), 1.26 (1H, d).

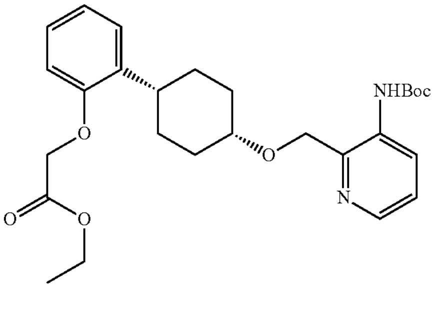 [SMILES: CCOC(=O)COc1ccccc1[C@H]1CC[C@@H](OCc2ncccc2NC(=O)OC(C)(C)C)CC1]

Into a 250-mL round-bottom flask purged and maintained with an inert atmosphere of nitrogen, was placed tert-butyl N-[2-([[(1s,4s)-4-(2-hydroxyphenyl)cyclohexyl]oxy]methyl)pyridin-3-yl]carbamate (8 g, 20.075 mmol, 1 equiv.), $K_2CO_3$ (13.97 g, 100.35 mmol, 5 equiv.), acetone (120 mL) and ethyl bromoacetate (5.03 g, 30.119 mmol, 1.5 equiv.). The resulting solution was stirred for 24 hr at 50 degrees C. The solids were filtered out. The filtrate was concentrated under vacuum. The residue was purified by silica gel column chromatography with ethyl acetate/petroleum ether (1:2) to provide ethyl 2-[2-[((1s,4s)-4-([33-[(tert-butoxycarbonyl)amino]pyridin-2-yl]methoxy)cyclohexyl]phenoxy]acetate (8.7 g, 89.43%) as a yellow oil. LCMS (ESI): m/z $[M+H]^+$=485.

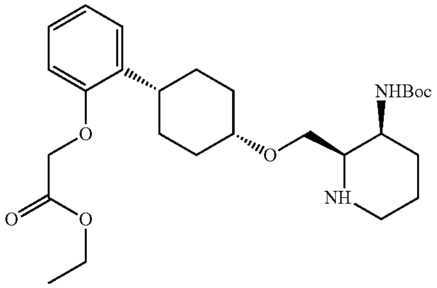 [SMILES: CCOC(=O)COc1ccccc1[C@H]1CC[C@@H](OC[C@@H]2NCCC[C@@H]2NC(=O)OC(C)(C)C)CC1]

To a stirred mixture of ethyl 2-[2-[(1s,4s)-4-([3-[(tert-butoxycarbonyl)amino]pyridin-2-yl]methoxy)cyclohexyl]phenoxy]acetate (7.89 g, 16.268 mmol, 1 equiv.) in MeOH (142 mL) and AcOH (15.8 mL) were added $PtO_2$ (1.85 g, 8.142 mmol, 0.50 equiv.) at room temperature under hydrogen atmosphere. The resulting mixture was stirred for 2 hr at room temperature under hydrogen atmosphere. The resulting mixture was filtered, the filter cake was concentrated under reduced pressure. The reaction was quenched with sat. $NaHCO_3$ (aq.) at 0 degrees C. The resulting mixture was extracted with $CH_2Cl_2$ (3×500 mL). The combined organic layers were washed with brine (3×200 mL), dried over anhydrous $Na_2SO_4$. After filtration, the filtrate was concentrated under reduced pressure to afford diastereomeric cis and trans mixture (7 g, 88.7%) as a solid. The crude product was purified by Prep-TLC (DCM/MeOH=20:1) to afford cis-racemic mixture of ethyl 2-(2-((1S,4s)-4-((3-((tert-butoxycarbonyl)amino)piperidin-2-yl)methoxy)cyclohexyl)phenoxy)acetate (4.1 g) and trans-racemic mixture (1.7 g). LCMS (ESI): m/z $[M+H]^+$=491.

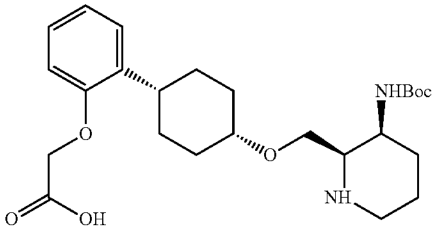 [SMILES: CC(C)(C)OC(=O)N[C@H]1CCCN[C@H]1CO[C@H]1CC[C@@H](c2ccccc2OCC(=O)O)CC1]

Into a 500 mL round-bottom flask purged and maintained with an atmosphere of nitrogen, was placed cis-racemic mixture of ethyl 2-(2-((1S,4s)-4-((3-((tert-butoxycarbonyl)amino)piperidin-2-yl)methoxy)cyclohexyl)phenoxy)acetate (4.1 g, 8.356 mmol, 1 equiv.), MeOH (30 mL), THF (60 mL), $H_2O$ (30 mL) and lithium hydroxide (83 mg, 3.465 mmol, 5 equiv.). The reaction was stirred for 2 hr at room temperature. The reaction was concentrated and the residue was purified by reverse phase flash with the following conditions, then freezing-drying to afford 2-(2-((1s,4s)-4-((3-((tert-butoxycarbonyl)amino)piperidin-2-yl)methoxy)cyclohexyl)phenoxy)acetic acid (2.35 g, 60.8%) as a solid. LCMS (ESI): m/z $[M+H]^+$=463.

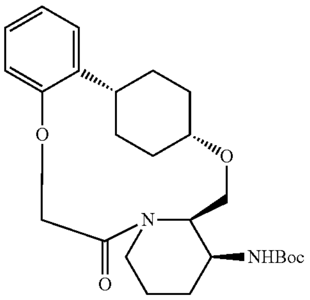 [SMILES: CC(C)(C)OC(=O)N[C@H]1CCCN2C(=O)COc3ccccc3[C@H]3CC[C@H](CC3)OC[C@@H]12]

Into a 2000-mL round-bottom flask was added 2-(2-((1s, 4s)-4-((3-((tert-butoxycarbonyl)amino)piperidin-2-yl) methoxy)cyclohexyl)phenoxy)acetic acid (100 mg, 0.216 mmol, 1 equiv.), MeCN (36 mL), DMF (9 mL), HATU (124 mg, 0.326 mmol, 1.51 equiv.) and DIPEA (56 mg, 0.436 mmol, 2.02 equiv.) under nitrogen atmosphere. The resulting solution was stirred for 3 hr at room temperature. LCMS showed full conversation. The resulting mixture was concentrated. The crude product tert-butyl (($2^1$S,$2^4$S,$5^2$R, $5^3$S)-6-oxo-3,8-dioxa-5(2,1)-piperidina-1(1,2)-benzena-2(1,4)-cyclohexanacyclooctaphane-$5^3$-yl)carbamate was used directly for the next step without purification. LCMS (ESI): m/z $[M+H]^+$=445.

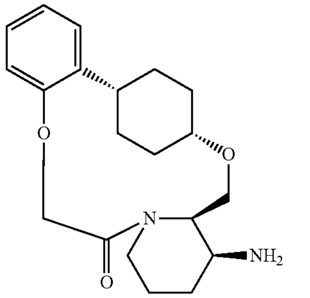 [SMILES: N[C@H]1CCCN2C(=O)COc3ccccc3[C@H]3CC[C@H](CC3)OC[C@@H]12]

Into a 500-mL round-bottom flask purged and maintained with an inert atmosphere of nitrogen, was placed crude mixture tert-butyl (($2^1$S,$2^4$S,$5^2$R,$5^3$S)-6-oxo-3,8-dioxa-5(2, 1)-piperidina-1(1,2)-benzena-2(1,4)-cyclohexanacyclooctaphane-$5^3$-yl)carbamate (2 g, 4.499 mmol, 1 equiv.), DCM (120 mL), TFA (40 mL). The resulting solution was stirred for 1 hr at 25 degrees C. LCMS showed full conversation. The resulting mixture was concentrated under vacuum. The crude product was purified by Prep-HPLC to afford ($2^1$S, $2^4$S,$5^2$R,$5^3$S)-$5^3$-amino-3,8-dioxa-5(2,1)-piperidina-1(1,2)-benzena-2(1,4)-cyclohexanacyclooctaphan-6-one 32.1 g (800 mg, 51.6%) as a solid. LCMS (ESI): m/z $[M+H]^+$=345.

(Compound 1)

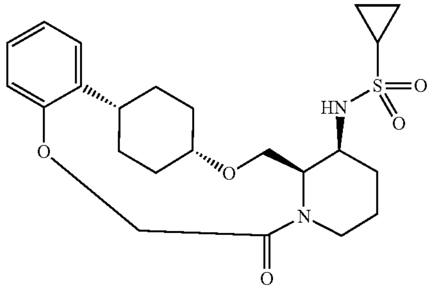

To a stirred mixture of ($2^1$S,$2^4$S,$5^2$R,$5^3$S)-$5^3$-amino-3,8-dioxa-5(2,1)-piperidina-1(1,2)-benzena-2(1,4)-cyclohexanacyclooctaphan-6-one (100 mg, 1.0 equiv., 0.3 mmol) and DIEA (112 mg, 0.3.0 equiv., 0.9 mmol) in dichloromethane (5 mL) was added cyclopropanesulfonyl chloride (81 mg, 2.0 equiv., 0.6 mmol) at room temperature under nitrogen atmosphere. The resulting mixture was stirred for 5 hr at room temperature. The resulting mixture was concentrated under reduced pressure. The residue was purified by Prep-TLC and chiral HPLC to afford N-(($2^1$S,$2^4$S,$5^2$R,$5^3$S)-6-oxo-3,8-dioxa-5(2,1)-piperidina-1(1,2)-benzena-2(1,4) cyclohexanacyclooctaphane-$5^3$-yl)cyclopropanesulfonamide (55 mg, 41%) as a solid. LCMS (ESI): m/z $[M+H]^+$=449; $^1$H NMR (400 MHz, Chloroform-d) δ 7.16-7.22 (m, 1H), 7.11 (dd, J=7.5, 1.7 Hz, 1H), 6.89-6.95 (m, 1H), 6.77 (dd, J=8.0, 1.2 Hz, 1H), 5.23-5.35 (m, 1H), 5.13 (d, J=10.5 Hz, 1H), 4.32 (dd, J=9.3, 6.3 Hz, 2H), 3.82-3.87 (m, 1H), 3.67-3.75 (m, 3H), 3.46-3.63 (m, 2H), 2.49-2.73 (m, 3H), 2.17-2.30 (m, 1H), 2.03 (s, 2H), 1.84-1.99 (m, 3H), 1.58-1.63 (m, 1H), 1.48-1.58 (m, 1H), 1.34-1.47 (m, 3H), 1.13-1.32 (m, 5H), 1.01-1.11 (m, 1H), 0.84-0.94 (m, 1H).

Example 1.2

(Compound 3)

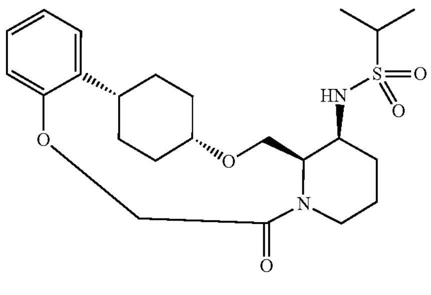

To a stirred mixture of ($2^1$S,$2^4$S,$5^2$R,$5^3$S)-$5^3$-amino-3,8-dioxa-5(2,1)-piperidina-1(1,2)-benzena-2(1,4)-cyclohexanacyclooctaphan-6-one (100 mg, 1.0 equiv., 0.3 mmol) and DBU (132 mg, 3.0 equiv., 0.9 mmol) in dichloromethane (20 mL) was added propane-2-sulfonyl chloride (82 mg, 2.0 equiv., 0.6 mmol) at room temperature under nitrogen atmosphere. The resulting mixture was stirred for 2 hr at room temperature under nitrogen atmosphere. The residue was purified by reverse flash chromatography and chiral HPLC to afford N-(($2^1$S,$2^4$S,$5^2$R,$5^3$S)-6-oxo-3,8-dioxa-5(2, 1)-piperidina-1(1,2)-benzena-2(1,4)-cyclohexanacyclooctaphane-$5^3$-yl)propane-2-sulfonamide (50 mg, 37%) as a solid. LCMS (ESI): m/z $[M+H]^+$=451; $^1$H NMR (400 MHz, Chloroform-d) δ 7.15-7.22 (m, 1H), 7.11 (dd, J=7.4, 1.8 Hz, 1H), 6.85-6.95 (m, 1H), 6.77 (dd, J=8.1, 1.2 Hz, 1H), 5.16-5.23 (m, 1H), 5.11-5.15 (m, 1H), 4.27-4.35 (m, 1H), 4.23-4.27 (m, 1H), 3.83-3.87 (m, 1H), 3.65-3.77 (m, 3H), 3.51-3.54 (m, 2H), 3.05-3.28 (m, 1H), 2.50-2.73 (m, 2H), 2.18-2.31 (m, 1H), 2.09-2.11 (m, 3H), 1.92-1.97 (m, 1H), 1.85-1.87 (m, 1H), 1.65-1.68 (m, 2H), 1.46-1.51 (m, 1H), 1.41-1.46 (m, 7H), 1.33-1.40 (m, 2H).

Example 1.3

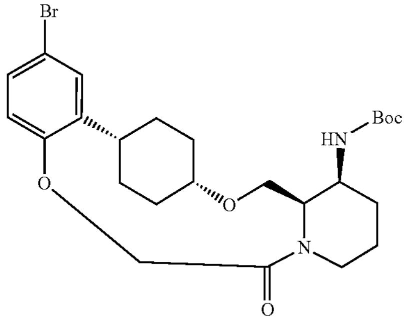 [SMILES: CC(C)(C)OC(=O)N[C@H]1CCCN2C(=O)COc3ccc(Br)cc3[C@H]3CC[C@H](CC3)OC[C@@H]12]

To a stirred mixture of tert-butyl tert-butyl ((2$^1$S,2$^4$S,5$^2$R,5$^3$S)-6-oxo-3,8-dioxa-5(2,1)-piperidina-1(1,2)-benzena-2(1,4)-cyclohexanacyclooctaphane-5$^3$-yl)carbamate (1.5 g, 1.0 equiv., 3.3 mmol) in MeCN (50 mL) and THF (50 mL) was added NBS (1.2 g, 2.0 equiv., 6.7 mmol) at room temperature under nitrogen atmosphere. The resulting mixture was concentrated under reduced pressure. The crude product was re-crystallized from PE/EtOAc (10:1 30 mL) to afford tert-butyl (2$^1$S,2$^4$S,5$^2$R,5$^3$S)-1$^5$-bromo-6-oxo-3,8-dioxa-5(2,1)-piperidina-1(1,2)-benzena-2(1,4)-cyclohexanacyclooctaphane-5$^3$-yl)carbamate (2.0 g, 90.5%) as a solid. LCMS (ESI): m/z $[M+H]^+$=523.

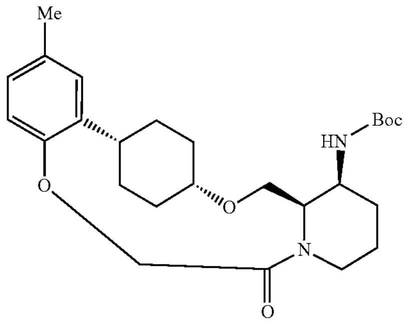 [SMILES: Cc1ccc2c(c1)[C@H]1CC[C@H](CC1)OC[C@H]1[C@@H](NC(=O)OC(C)(C)C)CCCN1C(=O)CO2]

To a stirred mixture of tert-butyl (2'S,2$^4$S,5$^2$R,5$^3$S)-1$^5$-bromo-6-oxo-3,8-dioxa-5(2,1)-piperidina-1(1,2)-benzena-2(1,4)-cyclohexanacyclooctaphane-5$^3$-yl)carbamate (1.0 g, 1.0 equiv., 1.9 mmol), $MeB(OH)_2$ (0.23 g, 2.0 equiv., 3.8 mmol) and $Pd(dppf)Cl_2$ (0.14 g, 0.1 equiv., 0.2 mmol) in 1,4-dioxane (100 mL) and $H_2O$ (10 mL) was added $K_2CO_3$ (0.79 g, 3.0 equiv., 5.7 mmol) at room temperature under nitrogen atmosphere. The resulting mixture was stirred for 4 hr at 100 degrees C. under nitrogen atmosphere. After filtration, the filtrate was concentrated under reduced pressure. The residue was purified by Prep-TLC to afford tert-butyl ((2$^1$S,2$^4$S,5$^2$R,5$^3$S)-1$^5$-methyl-6-oxo-3,8-dioxa-5(2,1)-piperidina-1(1,2)-benzena-2(1,4)-cyclohexanacyclooctaphane-5$^3$-yl)carbamate (525 mg, 41.9%) as a solid. LCMS (ESI): m/z $[M+H]^+$=459.

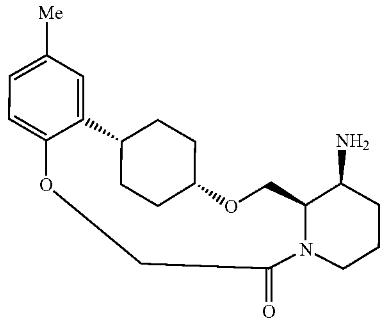 [SMILES: Cc1ccc2c(c1)[C@H]1CC[C@H](CC1)OC[C@H]1[C@@H](N)CCCN1C(=O)CO2]

To a solution of tert-butyl ((2$^1$S,2$^4$S,5$^2$R,5$^3$S)-1$^5$-methyl-6-oxo-3,8-dioxa-5(2,1)-piperidina-1(1,2)-benzena-2(1,4)-cyclohexanacyclooctaphane-5$^3$-yl)carbamate (1.0 g, 1.0 equiv., 2.2 mmol) in dichloromethane (50 mL) was added trifluoroacetic acid (1.24 g, 5.0 equiv., 10.9 mmol). The resulting mixture was stirred at room temperature for 2 hr. The mixture was concentrated under reduced pressure. The resulting mixture was diluted with dichloromethane (50 mL). The combined organic layers were washed with $NaHCO_3$ (3×500 mL), dried over anhydrous $Na_2SO_4$. After filtration, the filtrate was concentrated under reduced pressure. The crude product was purified by prep-HPLC to afford (2$^1$S,2$^4$S,5$^2$R,5$^3$S)-5$^3$-amino-1$^5$-methyl-3,8-dioxa-5(2,1)-piperidina-1(1,2)-benzena-2(1,4)-cyclohexanacyclooctaphan-6-one (440 mg, 51.0%) as a solid. LCMS (ESI): m/z $[M+H]^+$=359; $^1$H NMR (400 MHz, DMSO-d6) δ 6.94 (dd, J=8.4, 2.2 Hz, 1H), 6.88 (d, J=2.3 Hz, 1H), 6.71 (d, J=8.1 Hz, 1H), 5.76 (s, 1H), 5.24 (d, J=10.5 Hz, 1H), 4.77-4.88 (m, 1H), 3.88 (d, J=10.5 Hz, 1H), 3.72-3.81 (m, 1H), 3.59-3.65 (m, 2H), 3.45 (dd, J=9.0, 3.8 Hz, 1H), 2.87-2.91 (m, 1H), 2.59-2.70 (m, 1H), 2.16-2.19 (m, 4H), 2.07-2.11 (m, 1H), 1.55-1.74 (m, 5H), 1.15-1.46 (m, 6H).

(Compound 13)

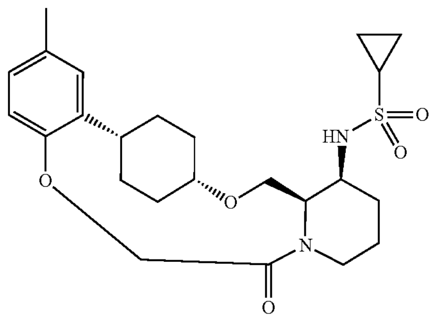

To a solution of (2$^1$S,2$^4$S,5$^2$R,5$^3$S)-5$^3$-amino-1$^5$-methyl-3,8-dioxa-5(2,1)-piperidina-1(1,2)-benzena-2(1,4)-cyclohexanacyclooctaphan-6-one (220 mg, 1.0 equiv., 0.61 mmol), DMAP (15 mg, 0.2 equiv., 0.12 mmol) and DIEA (238 mg, 3.0 equiv., 1.8 mmol) in dichloromethane (20 mL) was added cyclopropanesulfonyl chloride (173 mg, 2.0 equiv., 1.2 mmol). After stirring for 4 hr at 25 degrees C. under a nitrogen atmosphere, the resulting mixture was concentrated under reduced pressure. The residue was purified by Prep-TLC and chiral prep HPLC to afford N-((2$^1$S,2$^4$S,5$^2$R,5$^3$S)-1$^5$-methyl-6-oxo-3,8-dioxa-5(2,1)-piperidina- 1(1,2)-benzena-2(1,4)-cyclohexanacyclooctaphane-$5^3$-yl) cyclopropanesulfonamide (89.5 mg, 33%) as a solid. LCMS (ESI): m/z $[M+H]^+$=463; $^1$H NMR (400 MHz, Chloroform-d) δ 6.97 (dd, J=8.3, 2.3 Hz, 1H), 6.92 (d, J=2.3 Hz, 1H), 6.67 (d, J=8.1 Hz, 1H), 5.23-5.34 (m, 1H), 5.11 (d, J=10.6 Hz, 1H), 4.54 (d, J=8.1 Hz, 1H), 4.27 (d, J=10.6 Hz, 1H), 3.81-3.86 (m, 1H), 3.69-3.72 (m, 3H), 3.42-3.62 (m, 2H), 2.58-2.73 (m, 1H), 2.47-2.57 (m, 2H), 2.13-2.30 (m, 4H), 2.00-2.04 (m, 2H), 1.82-1.96 (m, 2H), 1.32-1.54 (m, 5H), 1.01-1.31 (m, 5H).

Example 1.4

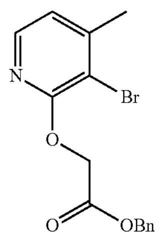 [SMILES: Cc1ccnc(OCC(=O)OCc2ccccc2)c1Br]

To a stirred mixture of benzyl 2-hydroxyacetate (21.9 g, 5.0 equiv., 131.6 mmol) in DMF (100 mL) was added NaH (60%, 5.26 g, 5.0 equiv., 131.6 mmol) in portions at 0 degrees C. The resulting mixture was stirred for 30 minutes at 0 degrees C. under nitrogen atmosphere. To the above mixture was added 3-bromo-2-fluoro-4-methylpyridine (5.00 g, 1.0 equiv., 26.314 mmol) at room temperature and the resulting mixture was stirred for an additional 2 hr at 80 degrees C. The reaction was quenched by addition of sat. $NH_4Cl$ (aq.) (500 mL) at 0 degrees C. The resulting mixture was extracted with EtOAc (3×200 mL). The combined organic layers were washed with water (3×300 mL) and dried over anhydrous $Na_2SO_4$. After filtration, the filtrate was concentrated under reduced pressure. The residue was purified by reverse flash chromatography to provide benzyl 2-((3-bromo-4-methylpyridin-2-yl)oxy)acetate (7.3 g, 83.0%) as an oil. LCMS (ESI): m/z $[M+H]^+$=337.

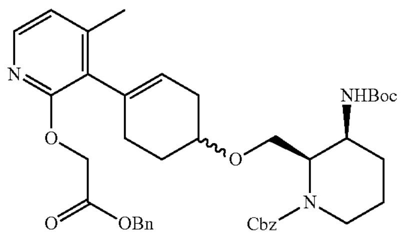 [SMILES: Cc1ccnc(OCC(=O)OCc2ccccc2)c1C1=CCC(OC[C@H]2[C@@H](NC(=O)OC(C)(C)C)CCCN2C(=O)OCc2ccccc2)CC1]

To a solution of benzyl (2R,3S)-3-((tert-butoxycarbonyl) amino)-2-(((4-(4,4,5,5-tetramethyl-1,3,2-dioxaborolan-2-yl)cyclohex-3-en-1-yl)oxy)methyl)piperidine-1-carboxylate (5.00 g, 1.0 equiv., 3.51 mmol) and benzyl 2-((3-bromo-4-methylpyridin-2-yl)oxy)acetate (1.41 g, 1.2 equiv., 4.21 mmol) in 1,4-dioxane (20 mL) and water (5.0 mL) were added $Na_2CO_3$ (1.12 g, 3.0 equiv., 10.5 mmol) and Pd(dppf)$Cl_2$ (385 mg, 0.15 equiv., 0.53 mmol). The reaction mixture was stirred for 2 hr at 80 degrees C. under nitrogen atmosphere. The crude was purified by reverse flash chromatography to afford benzyl (2R,3S)-2-(((4-(2-(2-(benzyloxy)-2-oxoethoxy)-4-methylpyridin-3-yl)cyclohex-3-en-1-yl)oxy) methyl)-3-((tert-butoxycarbonyl)amino)piperidine-1-carboxylate (2.0 g, 80.0%) as an oil.

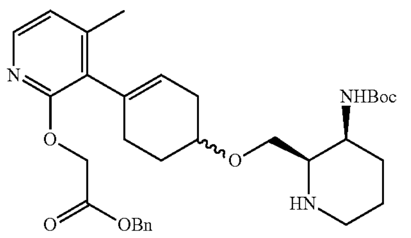 [SMILES: Cc1ccnc(OCC(=O)OCc2ccccc2)c1C1=CCC(OC[C@@H]2NCCC[C@@H]2NC(=O)OC(C)(C)C)CC1]

To a solution of benzyl (2R,3S)-2-(((4-(2-(2-(benzyloxy)-2-oxoethoxy)-4-methylpyridin-3-yl)cyclohex-3-en-1-yl) oxy)methyl)-3-((tert-butoxycarbonyl)amino)piperidine-1-carboxylate (2.00 g, 1.0 equiv., 2.86 mmol) in i-PrOH (30 mL) was added Pd/C (152 mg, 0.5 equiv., 1.43 mmol) under nitrogen atmosphere. The resulting mixture was hydrogenated at room temperature for 15 hr under hydrogen atmosphere using a hydrogen balloon. The mixture was filtered through a CELITE® (Imerys Minerals California Inc., San Jose, CA) pad and concentrated under reduced pressure to afford the crude product. The crude was purified by reverse flash chromatography to afford 2-((3-(4-(((2R,3S)-3-((tert-butoxycarbonyl)amino)piperidin-2-yl)methoxy)cyclohex-1-en-1-yl)-4-methylpyridin-2-yl)oxy)acetic acid (950 mg, 69.9%) as a solid. LCMS (ESI): m/z $[M+H]^+$=477.

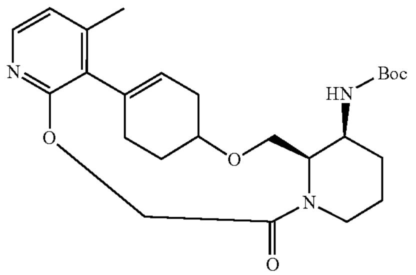 [SMILES: Cc1ccnc2c1C1=CCC(CC1)OC[C@H]1[C@@H](NC(=O)OC(C)(C)C)CCCN1C(=O)CO2]

To a stirred mixture of 2-((3-(4-(((2R,3S)-3-((tert-butoxycarbonyl)amino)piperidin-2-yl) methoxy)cyclohex-1-en-1-yl)-4-methylpyridin-2-yl)oxy)acetic acid (900 mg, 1.0 equiv., 1.89 mmol) and DIEA (734 mg, 3.0 equiv., 5.68 mmol) in MeCN (400 mL) was added HATU (1.08 g, 1.5 equiv., 2.84 mmol) at 25 degrees C. under nitrogen atmosphere. The resulting mixture was stirred for 2 hr at 25 degrees C. The mixture was concentrated under reduced pressure. The crude was purified by reverse flash chromatography to afford tert-butyl (($5^2$R,$5^3$S,E)-$1^4$-methyl-6-oxo-3,8-dioxa-1(3,2)-pyridina-5(2,1)-piperidina-2(1,4)-cyclohexanacyclooctaphan-$2^1$-en-$5^3$-yl)carbamate (650 mg, 75.1%) as a solid. LCMS (ESI): m/z $[M+H]^+$=469.

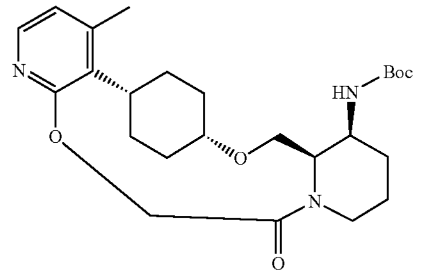 [SMILES: Cc1ccnc2c1[C@H]1CC[C@H](CC1)OC[C@H]1[C@@H](NC(=O)OC(C)(C)C)CCCN1C(=O)CO2]

To a solution of tert-butyl (($5^2$R,$5^3$S,E)-$1^4$-methyl-6-oxo-3,8-dioxa-1(3,2)-pyridina-5(2,1)-piperidina-2(1,4)-cyclohexanacyclooctaphan-$2^1$-en-$5^3$-yl)carbamate (1.2 g, 1.0 equiv., 2.6 mmol) in MeOH (200 mL) and acetic acid (20.0 mL) was added Pd/C (0.56 g, 10% weight, 0.2 equiv., 0.52 mmol). The reaction mixture was stirred for 5 days under hydrogen atmosphere. The crude was purified by reverse flash chromatography to afford tert-butyl (($2^1$S,$2^4$S,$5^2$R,$5^3$S)-$1^4$-methyl-6-oxo-3,8-dioxa-1(3,2)-pyridina-5(2,1)-piperidina-2(1,4)-cyclohexanacyclooctaphane-$5^3$-yl)carbamate (500 mg, 41.0%) as a solid. LCMS (ESI): m/z $[M+H]^+$=461.

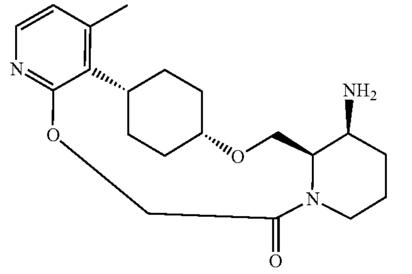 [SMILES: Cc1ccnc2c1[C@H]1CC[C@H](CC1)OC[C@H]1[C@@H](N)CCCN1C(=O)CO2]

To a solution of tert-butyl (($2^1$S,$2^4$S,$5^2$R,$5^3$S)-$1^4$-methyl-6-oxo-3,8-dioxa-1(3,2)-pyridina-5(2,1)-piperidina-2(1,4)-cyclohexanacyclooctaphane-$5^3$-yl)carbamate (400 mg, 1.0 equiv., 0.87 mmol) in DCM (15 mL) and TFA (3 mL). The reaction mixture was stirred for 1 hr at 25 degrees C. under nitrogen atmosphere. The resulting mixture was extracted with dichloromethane (3×30 mL). The combined organic layers were washed with brine, and dried over anhydrous $Na_2SO_4$. After filtration, the filtrate was concentrated under reduced pressure. The crude was purified by reverse flash chromatography to afford ($2^1$S,$2^4$S,$5^2$R,$5^3$S)-$5^3$-amino-$1^4$-methyl-3,8-dioxa-1(3,2)-pyridina-5(2,1)-piperidina-2(1,4)-cyclohexanacyclooctaphan-6-one (230 mg, 73.5%) as a solid. LCMS (ESI): m/z $[M+H]^+$=360.

(Compound 10)

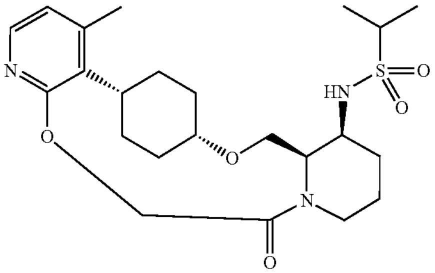

To a stirred solution of ($2^1$S,$2^4$S,$5^2$R,$5^3$S)-$5^3$-amino-$1^4$-methyl-3,8-dioxa-1(3,2)-pyridina-5(2,1)-piperidina-2(1,4)-cyclohexanacyclooctaphan-6-one (50 mg, 1.0 equiv., 0.14 mmol) and DBU (170 mg, 8.0 equiv., 1.12 mmol) in DCM (6 mL) was added a solution of propane-2-sulfonyl chloride (99 mg, 5.0 equiv., 0.70 mmol) in DCM (0.4 mL) dropwise at 25 degrees C. under nitrogen atmosphere. The resulting mixture was stirred for 4 hr at 25 degrees C. The filtrate was concentrated under reduced pressure and the residue was purified by Prep-TLC to afford N-(($2^1$S,$2^4$S,$5^2$R,$5^3$S)-$1^4$-methyl-6-oxo-3,8-dioxa-1(3,2)-pyridina-5(2,1)-piperidina-2(1,4)-cyclohexanacyclooctaphane-$5^3$-yl)propane-2-sulfonamide (55 mg, 85%) as a solid. The crude product was purified by prep-chiral-HPLC to provide pure enantiomers. LCMS (ESI): m/z $[M+H]^+$=466; $^1$H NMR (400 MHz, Methanol-$d_4$) δ 7.77-7.85 (m, 1H), 6.81 (dd, 1H), 5.18-5.37 (m, 2H), 4.53 (dd, 1H), 3.98 (t, 1H), 3.81 (d, 1H), 3.54-3.64 (m, 2H), 3.45 (d, 1H), 3.23-3.30 (m, 1H), 2.89-3.11 (m, 2H), 2.67 (dd, 1H), 2.34 (s, 4H), 2.21 (d, 1H), 1.88 (d, 3H), 1.62-1.82 (m, 2H), 1.42-1.60 (m, 2H), 1.27-1.42 (m, 8H), 1.20 (d, 1H).

Example 1.5

(Compound 16)

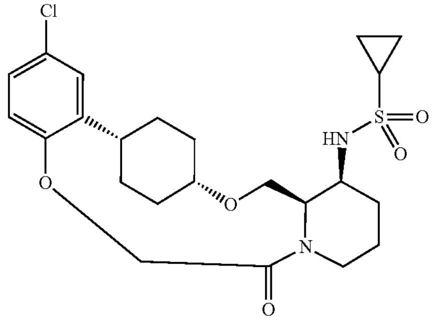

To a stirred solution of N-((2'S,$2^4$S,$5^2$R,$5^3$S)-6-oxo-3,8-dioxa-5(2,1)-piperidina-1(1,2)-benzena-2(1,4) cyclohexanacyclooctaphane-$5^3$-yl)cyclopropanesulfonamide (100 mg, 1.0 equiv., 0.2 mmol) in MeCN (5 mL) and THF (5 mL) was added NCS (59 mg, 2.0 equiv., 0.4 mmol) at room temperature under nitrogen atmosphere. The resulting mixture was stirred for 3 hr at room temperature under nitrogen atmosphere. The resulting mixture was concentrated under reduced pressure. The residue was purified by reverse flash chromatography to afford N-(($2^1$S,$2^4$S,$5^2$R,$5^3$S)-$1^5$-chloro-6-oxo-3,8-dioxa-5(2,1)-piperidina-1(1,2)-benzena-2(1,4)-cyclohexanacyclooctaphane-$5^3$-yl)cyclopropanesulfonamide (64.6 mg, 60%) as a solid. LCMS (ESI): m/z $[M+H]^+$ =483; $^1$H NMR (400 MHz, Chloroform-d) δ 7.14 (dd, J=8.5, 2.6 Hz, 1H), 7.09 (d, J=2.6 Hz, 1H), 6.69 (d, J=8.6 Hz, 1H), 5.25-5.33 (m, 1H), 5.11 (d, J=10.4 Hz, 1H), 4.40 (d, J=8.1 Hz, 1H), 4.27 (d, J=10.4 Hz, 1H), 3.83 (t, J=9.2 Hz, 1H), 3.65-3.70 (m, 3H), 3.42-3.62 (m, 2H), 2.44-2.67 (m, 3H), 2.12-2.27 (m, 1H), 2.00-2.07 (m, 2H), 1.84-1.97 (m, 2H), 1.62-1.67 (m, 2H), 1.33-1.54 (m, 4H), 1.02-1.30 (m, 5H).

Example 1.6

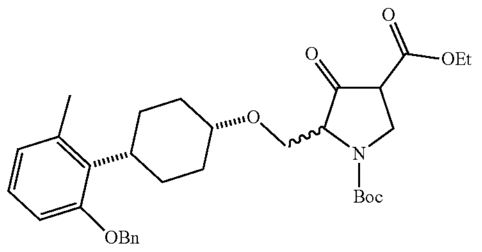 [SMILES: CCOC(=O)C1CN(C(=O)OC(C)(C)C)C(CO[C@H]2CC[C@@H](c3c(C)cccc3OCc3ccccc3)CC2)C1=O]

To a stirred solution of 1-tert-butyl 3-ethyl 4-oxopyrrolidine-1,3-dicarboxylate (1.12 g, 1.0 equiv., 4.35 mmol) and DMPU (1.92 g, 3.5 equiv., 15.0 mmol) in THF (30 mL) was added LDA (5.19 mL, 8.8 equiv., 48.4 mmol) dropwise over 5 minutes at −78 degrees C. under nitrogen atmosphere. The resulting mixture was stirred for additional 1.5 hr at −78 degrees C. To the above mixture was added the solution of 1-(benzyloxy)-2-[4-(chloromethoxy)cyclohexyl]-3-methylbenzene (1.58 g, 1.1 equiv., 4.57 mmol) in THF (5 mL) dropwise over 5 minutes at −78 degrees C. The resulting mixture was stirred for an additional 30 minutes at −78 degrees C., then the resulting mixture was stirred for an additional 3 hr at room temperature. The reaction was quenched with water and the mixture was extracted with EtOAc (3×50 mL). The organic layers dried over anhydrous $Na_2SO_4$. After filtration, the filtrate was concentrated under reduced pressure. The residue was purified by reverse flash chromatography to afford 1-(tert-butyl) 3-ethyl 5-((((1s,4s)-4-(2-(benzyloxy)-6-methylphenyl)cyclohexyl)oxy)methyl)-4-oxopyrrolidine-1,3-dicarboxylate (2.25 g, 91.4%) as an oil. LCMS (ESI): m/z $[M+H]^+$=566; $^1$H NMR (400 M Hz, Chloroform-d) δ 7.33-7.49 (m, 4H), 7.29-7.33 (m, 1H), 6.91-7.03 (m, 1H), 6.62-6.81 (m, 2H), 5.13-5.16 (m, 2H), 3.96-4.35 (m, 5H), 3.72-3.94 (m, 2H), 3.39-3.67 (m, 2H), 2.56-2.74 (m, 1H), 2.30-2.34 (m, 5H), 1.86-2.12 (m, 2H), 1.50 (d, J=3.5 Hz, 9H), 1.37-1.47 (m, 4H), 1.22-1.27 (m, 3H).

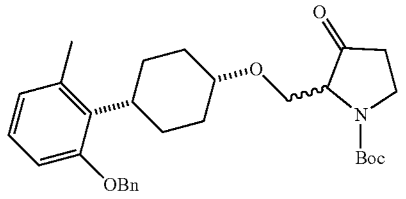

The solution of 1-(tert-butyl) 3-ethyl 5-((((1s,4s)-4-(2-(benzyloxy)-6-methylphenyl)cyclohexyl)oxy)methyl)-4-oxopyrrolidine-1,3-dicarboxylate (2.0 g, 3.54 mmol) in DMSO (10 mL) and water (1 mL) was stirred for 2 hr at 125 degrees C. The reaction was quenched with water at room temperature. The resulting mixture was extracted with EtOAc (3×20 mL) and the filtrate was concentrated under reduced pressure. The residue was purified by reverse flash chromatography to afford tert-butyl 2-((((1s,4s)-4-(2-(benzyloxy)-6-methylphenyl)cyclohexyl)oxy)methyl)-3-oxopyrrolidine-1-carboxylate (1.83 g, 100%) as an oil. LCMS (ESI): m/z $[M+H]^+$=494; $^1$H NMR (400 MHz, Chloroform-d) δ 7.34-7.44 (m, 4H), 7.29-7.34 (m, 1H), 6.96 (t, J=7.9 Hz, 1H), 6.75 (d, J=7.5 Hz, 1H), 6.69 (d, J=8.2 Hz, 1H), 5.21 (s, 2H), 3.90-3.94 (m, 2H), 3.83 (s, 2H), 3.70 (s, 1H), 3.52-3.57 (m, 1H), 2.36-2.41 (m, 7H), 1.93-2.02 (m, 2H), 1.47-1.50 (m, 10H), 1.38-1.47 (m, 4H).

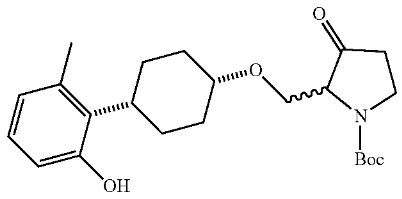

The mixture of tert-butyl 2-[([4-[2-(benzyloxy)-6-methylphenyl]cyclohexyl]oxy)methyl]-3-oxopyrrolidine-1-carboxylate (1.78 g, 1.0 equiv., 3.61 mmol) and Pd/C (1.19 g, 3.1 equiv., 0.011 mmol) in EtOH (25 mL) was stirred overnight at room temperature under hydrogen atmosphere. The resulting mixture was filtered and the filtrate was concentrated under reduced pressure. The residue was purified by reverse flash chromatography to afford tert-butyl 2-((((1s,4s)-4-(2-hydroxy-6-methylphenyl)cyclohexyl)oxy) methyl)-3-oxopyrrolidine-1-carboxylate (1.48 g, 100%) as a solid. LCMS (ESI): m/z $[M+H]^+$=404; $^1$H NMR (400 MHz, Chloroform-d) δ 6.93 (t, J=7.7 Hz, 1H), 6.71 (d, J=7.7 Hz, 1H), 6.59 (d, J=7.9 Hz, 1H), 3.92-3.96 (m, 4H), 3.67 (d, J=8.2 Hz, 1H), 3.59 (s, 1H), 2.61-2.63 (m, 2H), 2.45-2.47 (m, 1H), 2.31-2.33 (m, 3H), 2.01-2.05 (m, 1H), 1.85-1.87 (m, 1H), 1.43-1.60 (m, 11H), 1.22-1.43 (m, 3H).

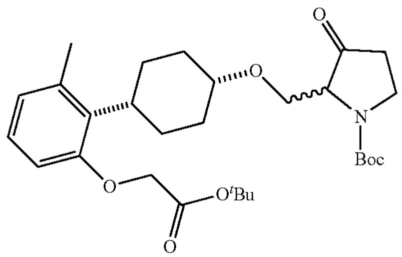

To a stirred mixture of 2-((((1s,4s)-4-(2-hydroxy-6-methylphenyl)cyclohexyl)oxy) methyl)-3-oxopyrrolidine-1-carboxylate (1.27 g, 1.0 equiv., 3.15 mmol) and $K_3PO_4$ (5.34 g, 8.0 equiv., 25.2 mmol) in MeCN (25 mL) was added tert-butyl 2-bromoacetate (3.68 g, 6.0 equiv., 18.9 mmol) dropwise over 2 minutes under nitrogen atmosphere. The resulting mixture was stirred for 5 hr at 25 degrees C. The reaction mixture was purified by reverse flash chromatography to afford tert-butyl 2-((((1s,4s)-4-(2-(2-(tert-butoxy)-2-oxoethoxy)-6-methylphenyl)cyclohexyl)oxy)methyl)-3-oxopyrrolidine-1-carboxylate (1.57 g, 84%) as an oil. LCMS (ESI): m/z $[M+H]^+$=518; $^1$H NMR (400 MHz, Chloroform-d) δ 7.00 (t, J=7.9 Hz, 1H), 6.77 (d, J=7.5 Hz, 1H), 6.54 (d, J=8.3 Hz, 1H), 4.66 (s, 2H), 4.48-4.62 (m, 1H), 4.01 (d, J=11.0 Hz, 1H), 3.92 (s, 1H), 3.80-3.86 (m, 2H), 3.78 (s, 1H), 3.55 (s, 1H), 2.48-2.67 (m, 2H), 2.32-2.35 (m, 3H), 1.93-1.96 (m, 2H), 1.52 (s, 18H), 1.40-1.43 (m, 2H), 1.33-1.36 (m, 2H).

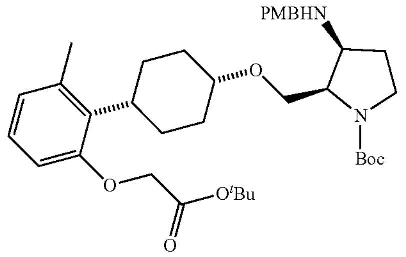

To a stirred mixture of tert-butyl 2-((((1s,4s)-4-(2-(2-(tert-butoxy)-2-oxoethoxy)-6-methylphenyl)cyclohexyl)oxy) methyl)-3-oxopyrrolidine-1-carboxylate (1.34 g, 1.0 equiv., 2.59 mmol), (4-methoxyphenyl)methanamine (2.13 g, 6.0 equiv., 15.5 mmol) and $MgSO_4$ (623 mg, 2.0 equiv., 5.18 mmol) in DCM (40 mL) was added sodium triacetoxyborohydride (4.39 g, 8.0 equiv., 20.7 mmol) under nitrogen atmosphere. The resulting mixture was stirred for 4 hr at 25 degrees C. The mixture was filtered, the filtrate was concentrated under reduced pressure, The crude was purified by reverse flash chromatography to afford tert-butyl (2R,3S)-2-((((1s,4S)-4-(2-(2-(tert-butoxy)-2-oxoethoxy)-6-methylphenyl)cyclohexyl)oxy)methyl)-3-((4-methoxybenzyl) amino)pyrrolidine-1-carboxylate (1.7 g, 99%) as an oil. LCMS (ESI): m/z $[M+H]^+$=640.45; $^1H$ NMR (400 MHz, Chloroform-d) δ 7.30 (d, J=7.9 Hz, 2H), 7.00 (t, J=8.1 Hz, 1H), 6.83-6.90 (m, 2H), 6.77 (d, J=7.7 Hz, 1H), 6.54 (d, J=8.2 Hz, 1H), 4.57 (d, J=8.6 Hz, 2H), 4.03 (s, 1H), 3.91 (s, 1H), 3.87 (s, 2H), 3.80 (s, 3H), 3.72 (d, J=10.5 Hz, 2H), 3.56 (s, 1H), 3.47-3.50 (m, 1H), 3.39 (s, 1H), 3.17-3.31 (m, 1H), 2.36 (s, 3H), 2.11-2.14 (m, 2H), 2.00-2.03 (m, 4H), 1.37-1.52 (m, 22H).

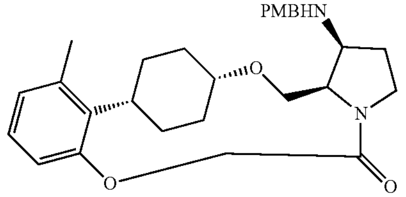

To a stirred mixture of tert-butyl (2R,3S)-2-((((1s,4S)-4-(2-(2-(tert-butoxy)-2-oxoethoxy)-6-methylphenyl)cyclohexyl)oxy)methyl)-3-((4-methoxybenzyl)amino)pyrrolidine-1-carboxylate (1.66 g, 1.0 equiv., 2.60 mmol) in DCM (10 mL) was added TFA (5 mL) under nitrogen atmosphere. The resulting mixture was stirred for 2 hr at 25 degrees C. and concentrated under reduced pressure, The crude was purified by reverse flash chromatography to afford 2-(2-((1S,4s)-4-(((2R,3S)-3-((4-methoxybenzyl)amino)pyrrolidin-2-yl)methoxy)cyclohexyl)-3-methylphenoxy)acetic acid (1.52 g, 95%) as an oil. To the above mixture and diisopropylethylamine (4.07 g, 10.0 equiv., 31.5 mmol) in DCM (30 mL) was added 2,4,6-tripropyl-1,3,5,2,4,6-trioxatriphosphinane 2,4,6-trioxide (3.01 g, 3.0 equiv., 9.45 mmol) dropwise over 2 minutes under nitrogen atmosphere. The resulting mixture was stirred for 1.5 hr at 25 degrees C. The crude was purified by reverse flash chromatography to afford ($2^1$S,$2^4$S,$5^2$R,$5^3$S)-$5^3$-((4-methoxybenzyl)amino)-16-methyl-3,8-dioxa-5(2,1)-pyrrolidina-1(1,2)-benzena-2(1,4)-cyclohexanacyclooctaphan-6-one (0.77 g, 45%) as a solid.

LCMS (ESI): m/z $[M+H]^+$=465; $^1H$ NMR (400 MHz, Chloroform-d) δ 7.30-7.37 (m, 2H), 7.05 (t, J=7.8 Hz, 1H), 6.87-6.95 (m, 2H), 6.81 (d, J=7.5 Hz, 1H), 6.63 (d, J=8.1 Hz, 1H), 4.95 (d, J=9.9 Hz, 1H), 4.48 (dd, J=7.7, 3.1 Hz, 1H), 4.22-4.32 (m, 2H), 4.14-4.18 (m, 1H), 3.81-3.87 (m, 5H), 3.79 (s, 1H), 3.40-3.56 (m, 3H), 2.87-2.90 (m, 1H), 2.52-2.56 (m, 1H), 2.31-2.35 (m, 3H), 2.13-2.28 (m, 4H), 1.81-1.85 (m, 1H), 1.43-1.54 (m, 1H), 1.32-1.42 (m, 2H), 1.25-1.28 (m, 2H).

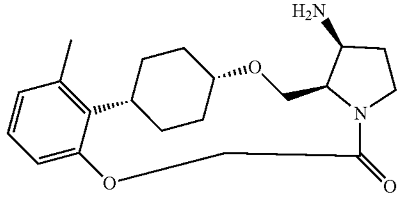 [SMILES: Cc1cccc2c1[C@H]1CC[C@H](CC1)OC[C@H]1[C@@H](N)CCN1C(=O)CO2]

To a stirred mixture of ($2^1$S,$2^4$S,$5^2$R,$5^3$S)-$5^3$-((4-methoxybenzyl)amino)-16-methyl-3,8-dioxa-5(2,1)-pyrrolidina-1(1,2)-benzena-2(1,4)-cyclohexanacyclooctaphan-6-one (236 mg, 1.0 equiv., 0.51 mmol) and Pd/C (270 mg, 5.0 equiv., 2.54 mmol) in i-PrOH (20 mL) was added ammonium formate (801 mg, 25.0 equiv., 12.7 mmol) under nitrogen atmosphere. The resulting mixture was stirred for 2 hr at 85 degrees C. The mixture was filtered, the filtrate was concentrated under reduced pressure. The crude was purified by reverse flash chromatography to afford ($2^1$S,$2^4$S,$5^2$R,$5^3$S)-$5^3$-amino-16-methyl-3,8-dioxa-5(2,1)-pyrrolidina-1(1,2)-benzena-2(1,4)-cyclohexanacyclooctaphan-6-one (169 mg, 96%) as a solid. LCMS (ESI): m/z $[M+H]^+$=345; $^1H$ NMR (400 MHz, Chloroform-d) δ 7.05 (t, J=7.8 Hz, 1H), 6.81 (d, J=7.5 Hz, 1H), 6.63 (dd, J=8.1, 1.2 Hz, 1H), 4.97 (d, J=9.9 Hz, 1H), 4.18-4.31 (m, 4H), 3.74-3.79 (m, 1H), 3.63-3.66 (m, 1H), 3.50-3.55 (m, 1H), 3.42 (d, J=9.1 Hz, 1H), 2.87-2.91 (m, 1H), 2.52-2.56 (m, 1H), 2.33 (s, 3H), 2.09-2.29 (m, 4H), 1.80-1.89 (m, 1H), 1.47-1.50 (m, 1H), 1.23-1.44 (m, 3H).

(Compound 20)

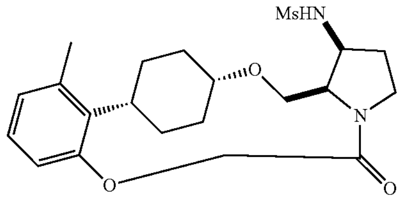

To a stirred mixture of ($2^1$S,$2^4$S,$5^2$R,$5^3$S)-$5^3$-amino-16-methyl-3,8-dioxa-5(2,1)-pyrrolidina-1(1,2)-benzena-2(1,4)-cyclohexanacyclooctaphan-6-one (155 mg, 1.0 equiv., 0.45 mmol) and DIEA (116 mg, 2.0 equiv., 0.90 mmol) in dichloromethane (15 mL) was added MsCl (77.3 mg, 1.5 equiv., 0.68 mmol) dropwise over 2 minutes under nitrogen atmosphere. The resulting mixture was stirred for 2 hr at 25 degrees C. The reaction mixture was concentrated under reduced pressure. The crude was purified by reverse flash chromatography to afford N-(($2^1$S,$2^4$S,$5^2$R,$5^3$S)-16-methyl-6-oxo-3,8-dioxa-5(2,1)-pyrrolidina-1(1,2)-benzena-2(1,4)-cyclohexanacyclooctaphane-$5^3$-yl) methanesulfonamide (126 mg, 65.9%) as a solid. LCMS (ESI): m/z $[M+H]^+$=423; $^1H$ NMR (400 MHz, Methanol-$d_4$) δ 7.03 (t, J=7.8 Hz, 1H), 6.77-6.83 (m, 1H), 6.71 (d, J=8.1 Hz, 1H), 5.11 (d, J=10.3 Hz, 1H), 4.37 (dd, J=7.9, 3.4 Hz, 1H), 4.26 (td, J=10.0, 2.1 Hz, 1H), 4.10-4.22 (m, 3H), 3.80 (s, 1H), 3.69 (td, J=10.0, 7.7 Hz, 1H), 3.51 (d, J=9.2 Hz, 1H), 3.04 (s, 3H), 2.95-2.97 (m, 1H), 2.60-2.65 (m, 1H), 2.34-2.48 (m, 1H), 2.31 (s, 3H), 2.12-2.30 (m, 3H), 1.89-1.91 (m, 1H), 1.46-1.60 (m, 2H), 1.29-1.42 (m, 2H), 1.17-1.25 (m, 1H).

Example 1.7

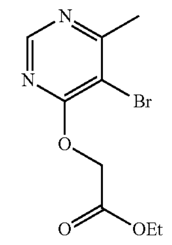

To a stirred solution of ethyl 2-hydroxyacetate (5.42 g, 1.3 equiv., 52.0 mmol) in DMF (150 mL) was added sodium hydride (3.20 g, 60% weight, 2.0 equiv., 80.0 mmol) in portions at 0 degrees C. under nitrogen atmosphere. The resulting mixture was stirred for 30 minutes at 0 degrees C. To the above mixture was added 5-bromo-4-chloro-6-methylpyrimidine (8.30 g, 1.0 equiv., 40.0 mmol) and potassium fluoride (2.32 g, 1.0 equiv., 40.0 mmol) at room temperature. The resulting mixture was stirred for an additional 30 minutes at 80 degrees C. The reaction was quenched by the addition of saturated aqueous ammonium chloride at 0 degrees C. The resulting mixture was diluted with ethyl acetate. The resulting mixture was extracted with ethyl acetate (3×100 mL). The combined organic layers were washed with brine, dried over anhydrous $Na_2SO_4$, after filtration, the filtrate was concentrated under reduced pressure. The crude product was purified by silica gel column chromatography to afford ethyl 2-((5-bromo-6-methylpyrimidin-4-yl)oxy)acetate (8.02 g, 72.9%) as a solid. $^1$H NMR (300 MHz, $CDCl_3$): δ 8.49 (s, 1H), 4.98 (s, 2H), 4.25 (q, J=7.1 Hz, 2H), 2.63 (s, 3H), 1.28 (t, J=7.2 Hz, 3H).

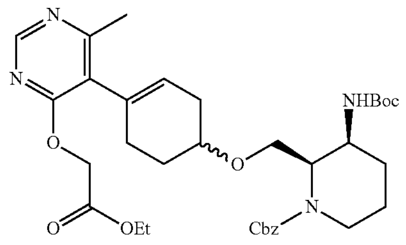 [SMILES: CCOC(=O)COc1ncnc(C)c1C1=CCC(OC[C@H]2[C@@H](NC(=O)OC(C)(C)C)CCCN2C(=O)OCc2ccccc2)CC1]

To a solution of ethyl 2-((5-bromo-6-methylpyrimidin-4-yl)oxy)acetate (3.30 g, 1.2 equiv., 12.0 mmol) and benzyl (2R,3S)-3-((tert-butoxycarbonyl)amino)-2-(((4-(4,4,5,5-tetramethyl-1,3,2-dioxaborolan-2-yl)cyclohex-3-en-1-yl)oxy)methyl)piperidine-1-carboxylate (5.70 g, 1.0 equiv., 10.0 mmol) in 1,4-dioxane (60 mL) and $H_2O$ (15 mL) were added $Pd(dppf)C_2$ (0.73 g, 0.1 equiv., 1.00 mmol) and $Na_2CO_3$ (3.20 g, 3.0 equiv., 30.0 mmol). After stirring for 2 hr at 80 degrees C. under a nitrogen atmosphere, the resulting mixture was diluted with $H_2O$ (30 mL) and extracted with ethyl acetate (3×100 mL). The combined organic layers were washed with brine (3×30 mL), dried over anhydrous $Na_2SO_4$. After filtration, the filtrate was concentrated under reduced pressure. The residue was purified by silica gel column chromatography to afford benzyl (2R,3S)-3-((tert-butoxycarbonyl)amino)-2-(((4-(4-(2-ethoxy-2-oxoethoxy)-6-methylpyrimidin-5-yl)cyclohex-3-en-1-yl)oxy)methyl)piperidine-1-carboxylate (5.40 g, 85.0%) as a solid. LCMS (ESI): m/z $[M+H]^+$=639.40; $^1$H NMR (400 MHz, Chloroform-d) δ 8.48 (s, 1H), 7.28-7.37 (m, 6H), 5.63 (s, 1H), 5.49 (s, 1H), 5.00-5.25 (m, 3H), 4.80-4.96 (m, 2H), 4.58 (s, 1H), 4.17-4.19 (m, 2H), 3.98-4.12 (m, 2H), 3.88 (s, 1H), 3.54-3.82 (m, 5H), 2.77-2.81 (m, 1H), 2.41-2.62 (m, 4H), 2.37 (s, 3H), 2.13-2.31 (m, 4H), 1.77-2.10 (m, 5H), 1.50-1.73 (m, 4H), 1.34-1.47 (m, 13H), 1.22-1.27 (m, 4H), 1.17-1.21 (m, 10H).

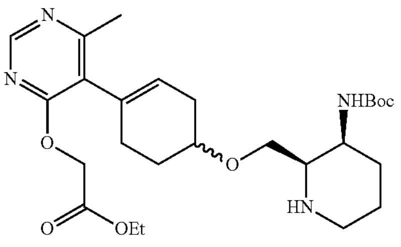

To a solution of (2R,3S)-3-((tert-butoxycarbonyl)amino)-2-(((4-(4-(2-ethoxy-2-oxoethoxy)-6-methylpyrimidin-5-yl)cyclohex-3-en-1-yl)oxy)methyl)piperidine-1-carboxylate (5.7 g, 1.0 equiv., 8.9 mmol) in 2-propanol (210 mL) was added palladium (0.95 g, 10% Wt, 0.1 equiv., 0.89 mmol) at nitrogen atmosphere. The resulting mixture was hydrogenated at room temperature for 4 hr under hydrogen atmosphere using a hydrogen balloon, filtered through a Celite pad and concentrated under reduced pressure to afford the crude product. The crude product was used in the next step directly without further purification.

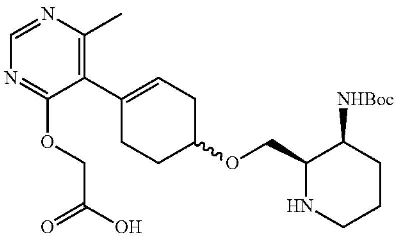 [SMILES: Cc1ncnc(OCC(=O)O)c1C1=CCC(OC[C@@H]2NCCC[C@@H]2NC(=O)OC(C)(C)C)CC1]

To a solution of ethyl 2-((5-(4-(((2R,3S)-3-((tert-butoxycarbonyl)amino)piperidin-2-yl)methoxy)cyclohex-1-en-1-yl)-6-methylpyrimidin-4-yl)oxy)acetate (4.5 g, 1.0 equiv., 8.9 mmol) in THF (24 mL) and $H_2O$ (8.0 mL) was added LiOH (0.32 g, 1.5 equiv., 13 mmol). The resulting mixture was stirred for 1 hr at 25 degrees C. and the resulting mixture was acidified to pH=5, then concentrated under reduced pressure. The crude was purified by reverse flash chromatography to afford 2-((5-(4-(((2R,3S)-3-((tert-butoxycarbonyl)amino)piperidin-2-yl)methoxy)cyclohex-1-en-1-yl)-6-methylpyrimidin-4-yl)oxy)acetic acid (3.5 g, 82%) as a solid. LCMS (ESI): m/z $[M+H]^+$=477.

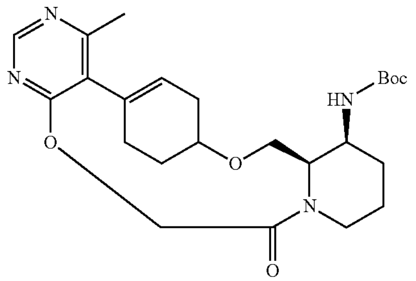 [SMILES: Cc1ncnc2c1C1=CCC(CC1)OC[C@H]1[C@@H](NC(=O)OC(C)(C)C)CCCN1C(=O)CO2]

To a stirred mixture of HATU (2.6 g, 1.5 equiv., 6.9 mmol) and DIEA (1.8 g, 3.0 equiv., 14 mmol) in acetonitrile (1.1 L) was added a solution of 2-((5-(4-(((2R,3S)-3-((tert-butoxy-carbonyl)amino)piperidin-2-yl)methoxy)cyclohex-1-en-1-yl)-6-methylpyrimidin-4-yl)oxy)acetic acid (2.2 g, 1.0 equiv., 4.6 mmol) in DMF (25 mL) dropwise over 5 minutes under nitrogen atmosphere. The resulting mixture was stirred for 1 hr at 25 degrees C. The resulting mixture was concentrated under reduced pressure to afford the crude product. The crude was purified by reverse flash chromatography to afford tert-butyl (($5^2$R,$5^3$S, E)-$1^6$-methyl-6-oxo-3,8-dioxa-1(5,4)-pyrimidina-5(2,1)-piperidina-2(1,4)-cyclohexanacyclooctaphan-$2^1$-en-$5^3$-yl) carbamate (1.8 g, 85%) as a solid. LCMS (ESI): m/z $[M+H]^+$=459; $^1$H NMR (400 MHz, Methanol-$d_4$) δ 8.50-8.58 (m, 1H), 5.20-5.42 (m, 2H), 4.53-4.72 (m, 2H), 4.40-4.43 (m, 1H), 4.05-4.08 (m, 1H), 3.79-3.97 (m, 1H), 3.71 (dd, J=11.6, 3.4 Hz, 1H), 3.50-3.53 (m, 1H), 2.80-2.89 (m, 1H), 2.50-2.55 (m, 1H), 2.37-2.41 (m, 4H), 2.13-2.38 (m, 3H), 1.70-2.12 (m, 5H), 1.52-1.70 (m, 2H), 1.35-1.53 (m, 9H), 1.32 (s, 1H).

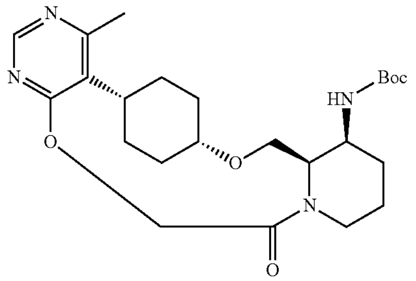 [SMILES: Cc1ncnc2c1[C@H]1CC[C@H](CC1)OC[C@H]1[C@@H](NC(=O)OC(C)(C)C)CCCN1C(=O)CO2]

To a solution of tert-butyl (($5^2$R,$5^3$S, E)-$1^6$-methyl-6-oxo-3,8-dioxa-1(5,4)-pyrimidina-5(2,1)-piperidina-2(1,4)-cyclohexanacyclooctaphan-2-en-$5^3$-yl) carbamate (500 mg, 1.0 equiv., 1.09 mmol) in MeOH (90 mL) and AcOH (10 mL) was added Pd/C (580 mg, 10% weight, 0.5 equiv., 0.55 mmol) at nitrogen atmosphere. The resulting mixture was hydrogenated at room temperature for 7 days under hydrogen atmosphere using a hydrogen balloon, filtered through a Celite pad and the filtrate then concentrated under reduced pressure. The crude was purified by reverse flash chromatography to afford tert-butyl (($2^1$S,$2^4$S,$5^2$R,$5^3$S)-$1^6$-methyl-6-oxo-3,8-dioxa-1(5,4)-pyrimidina-5(2,1)-piperidina-2(1,4)-cyclohexanacyclooctaphane-$5^3$-yl) carbamate (310 mg, 62%) as a solid. LCMS (ESI): m/z $[M+H]^+$=461; $^1$H NMR (400 MHz, Chloroform-d) δ 8.52 (d, J=9.5 Hz, 1H), 5.56 (d, J=11.8 Hz, 1H), 5.33 (s, 1H), 5.19 (d, J=11.1 Hz, 1H), 4.96 (s, 1H), 4.72-4.76 (m, 1H), 4.61 (d, J=11.2 Hz, 1H), 4.43 (s, 1H), 3.78-3.98 (m, 2H), 3.56-3.75 (m, 2H), 3.39-3.51 (m, 1H), 2.84-2.88 (m, 2H), 2.47-2.20 (m, 5H), 2.25-2.30 (m, 1H), 2.07-2.12 (m, 3H), 1.85-1.90 (m, 4H), 1.19-1.75 (m, 18H).

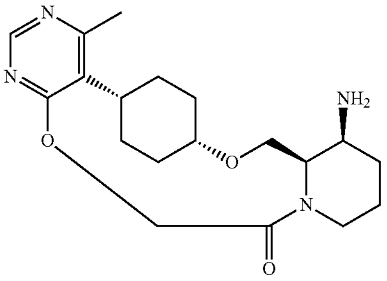 [SMILES: Cc1ncnc2c1[C@H]1CC[C@H](CC1)OC[C@H]1[C@@H](N)CCCN1C(=O)CO2]

To a solution of tert-butyl (($2^1$S,$2^4$S,$5^2$R,$5^3$S)-$1^6$-methyl-6-oxo-3,8-dioxa-1(5,4)-pyrimidina-5(2,1)-piperidina-2(1,4)-cyclohexanacyclooctaphane-$5^3$-yl) carbamate (430 mg, 1.0 equiv., 0.93 mmol) in dichloromethane (15 mL) was added TFA (0.5 mL). The resulting mixture was stirred for 1 hr at 25 degrees C. The resulting mixture was concentrated under reduced pressure. The crude was purified by reverse flash chromatography to afford ($2^1$S,$2^4$S,$5^2$R,$5^3$S)-$5^3$-amino-16-methyl-3,8-dioxa-1(5,4)-pyrimidina-5(2,1)-piperidina-2(1,4)-cyclohexanacyclooctaphan-6-one (299 mg, 89.0%) as a solid. LCMS (ESI): m/z $[M+H]^+$=361.

(Compound 27)

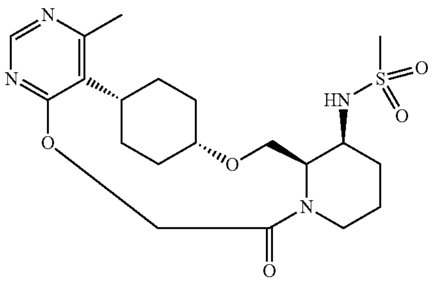

To a solution of ($2^1$S,$2^4$S,$5^2$R,$5^3$S)-$5^3$-amino-16-methyl-3,8-dioxa-1(5,4)-pyrimidina-5(2,1)-piperidina-2(1,4)-cyclohexanacyclooctaphan-6-one (45 mg, 1.0 equiv., 0.12 mmol) in DCM (2 mL) was added DIEA (81 mg, 5.0 equiv., 0.62 mmol) and methanesulfonyl chloride (43 mg, 3.0 equiv., 0.37 mmol). The resulting mixture was stirred for 1 h at 25 degrees C. The resulting mixture was concentrated under reduced pressure to afford the crude product. The crude was purified by reverse flash chromatography to afford N-(($2^1$S,$2^4$S,$5^2$R,$5^3$S)-$1^6$-methyl-6-oxo-3,8-dioxa-1(5,4)-pyrimidina-5(2,1)-piperidina-2(1,4)-cyclohexanacyclooctaphane-$5^3$-yl)methanesulfonamide (35 mg, 62.0%) as a solid. The racemic product was purified by Chiral Prep-HPLC to pure enantiomers. LCMS (ESI): m/z $[M+H]^+$=439; $^1$H NMR (400 MHz, Methanol-$d_4$) δ 8.44-8.48 (m, 1H), 5.37-5.40 (m, 1H), 5.22-5.25 (m, 1H), 4.75-4.80 (m, 1H), 4.39-4.54 (m, 1H), 3.84-4.04 (m, 2H), 3.73-3.76 (m, 1H), 3.62-3.65 (m, 1H), 3.40-3.60 (m, 1H), 2.89-3.13 (m, 5H), 2.52-2.57 (m, 1H), 2.45-2.51 (m, 3H), 2.16-2.40 (m, 2H), 1.83-1.87 (m, 3H), 1.62-1.82 (m, 2H), 1.39-1.61 (m, 3H), 1.22-1.38 (m, 2H).

Example 1.8

(Compound 2)

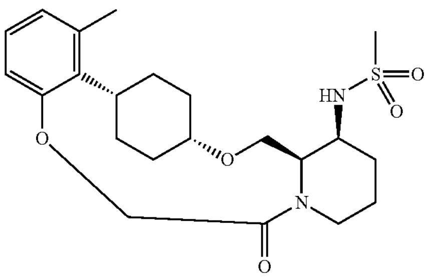

To a stirred solution of $((2^1S, 2^4S, 5^2R, 5^3S)-5^3$-amino-$1^6$-methyl-3,8-dioxa-5(2,1)-piperidina-1(1,2)-benzena-2(1,4)-cyclohexanacyclooctaphan-6-one (287.00 mg, 1.0 equiv., 0.801 mmol) and TEA (243.0 mg, 3.0 equiv., 2.40 mmol) in dichloromethane (10 mL) was added MsCl (137.6 mg, 1.5 equiv., 1.20 mmol) dropwise at 0 degrees C. under nitrogen atmosphere. The resulting mixture was stirred for 1 hour at room temperature under nitrogen atmosphere. The resulting mixture was concentrated under reduced pressure. The residue was purified by reverse flash chromatography to afford N-$((2^1S, 2^4S, 5^2R, 5^3S)-1^6$-methyl-6-oxo-3,8-dioxa-5(2,1)-piperidina-1(1,2)-benzena-2(1,4)-cyclohexanacyclooctaphane-$5^3$-yl)methanesulfonamide (260 mg, 74.4%) as a solid. LCMS (ESI): m/z $[M+H]^+$=437; $^1H$ NMR (400 MHz, Methanol-$d_4$) δ 7.02 (t, J=7.8 Hz, 1H), 6.78 (d, J=7.6 Hz, 1H), 6.74-6.67 (m, 1H), 5.31-5.20 (m, 2H), 4.09 (d, J=10.5 Hz, 1H), 3.95-3.92 (m, 1H), 3.83-3.70 (m, 2H), 3.69-3.60 (m, 1H), 3.58-3.44 (m, 2H), 3.37-3.33 (m, 6H), 3.04 (s, 3H), 2.98-2.94 (m, 1H), 2.81-2.68 (m, 1H), 2.39-2.24 (m, 4H), 2.23-2.13 (m, 1H), 1.98-1.81 (m, 3H), 1.79-1.63 (m, 2H), 1.56-1.32 (m, 3H), 1.22-1.20 (m, 1H).

Example 1.9

(Compound 11)

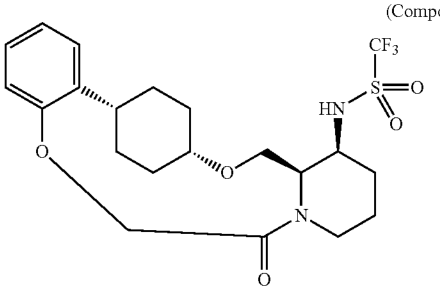

To a stirred solution of $((2^1S,2^4S,5^2R,5^3S)-5^3$-amino-3,8-dioxa-5(2,1)-piperidina-1(1,2)-benzena-2(1,4)-cyclohexanacyclooctaphan-6-one (100 mg, 1.0 equiv., 0.30 mmol) in dichloromethane (10 mL) were added $Et_3N$ (176 mg, 6.0 equiv., 1.74 mmol) and trifluoromethanesulfonyl chloride (196 mg, 4.0 equiv., 1.16 mmol) at room temperature under nitrogen atmosphere. The resulting mixture was stirred for 4 hours at 40 degrees C. under nitrogen atmosphere. The resulting mixture was concentrated under reduced pressure. The residue was purified by Prep-TLC to afford 1,1,1-trifluoro-N-$((2^1S, 2^4S, 5^2R, 5^3S)$-6-oxo-3,8-dioxa-5(2,1)-piperidina-1(1,2)-benzena-2(1,4)-cyclohexanacyclooctaphane-$5^3$-yl)methanesulfonamide (75.0 mg, 54.2%) as a solid. LCMS (ESI): m/z $[M+H]^+$=477; $^1H$ NMR (400 MHz, Methanol-$d_4$) δ 7.20-7.13 (m, 1H), 7.09 (dd, J=7.4, 1.8 Hz, 1H), 6.92-6.80 (m, 2H), 5.31 (d, J=10.6 Hz, 1H), 5.25-5.17 (m, 1H), 4.13 (d, J=10.6 Hz, 1H), 4.02-3.94 (m, 1H), 3.87-3.71 (m, 3H), 3.54-3.46 (m, 2H), 3.06-3.03 (m, 2H), 2.79-2.69 (m, 1H), 2.64-2.51 (m, 1H), 2.35-2.23 (m, 1H), 2.18-2.15 (m, 1H), 1.99-1.78 (m, 4H), 1.74-1.62 (m, 2H), 1.58-1.40 (m, 3H), 1.32-1.29 (m, 4H).

Example 1.10

(Compound 29)

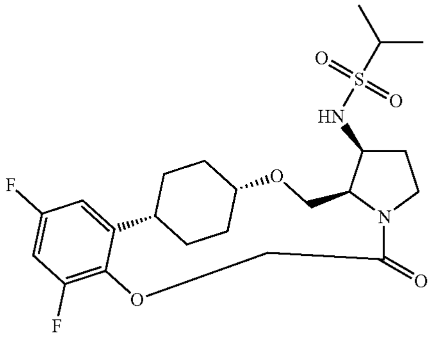

To a stirred mixture of $(2^1S, 2^4S, 5^2R, 5^3S)-5^3$-amino-$1^3$, $1^5$-difluoro-3,8-dioxa-5(2,1)-pyrrolidina-1(1,2)-benzena-2(1,4)-cyclohexanacyclooctaphan-6-one (500.0 mg, 1.0 equiv., 1.365 mmol) and DBU (1039 mg, 5.0 equiv., 6.823 mmol) in DCM (40 ml) was added propane-2-sulfonyl chloride (574 mg, 3.0 equiv., 4.026 mmol) dropwise at room temperature under nitrogen atmosphere. The resulting mixture was stirred for 1.5 hours at room temperature under nitrogen atmosphere. The reaction was quenched with water at room temperature. The resulting mixture was extracted with DCM (3×50 mL). The combined organic layers were washed with brine (1×200 mL) and dried over anhydrous $Na_2SO_4$. After filtration, the filtrate was concentrated under reduced pressure. The crude product was re-crystallized from DCM/MeOH (1:10 mL) to afford N-$((2^1S, 2^4S, 5^2R, 5^3S)-1^3$, $1^5$-difluoro-6-oxo-3,8-dioxa-5(2,1)-pyrrolidina-1(1,2)-benzena-2(1,4)-cyclohexanacyclooctaphane-$5^3$-yl) propane-2-sulfonamide (500 mg, 77.5%) as a solid. LCMS (ESI): m/z $[M+H]^+$=473; $^1H$ NMR (400 MHz, Methanol-$d_4$) δ 6.94-6.86 (m, 1H), 6.80-6.73 (m, 1H), 5.34-5.32 (m, 1H), 4.37-4.28 (m, 2H), 4.19-4.05 (m, 3H), 3.81-3.79 (s, 1H), 3.74-3.64 (m, 1H), 3.56-3.53 (m, 1H), 3.32-3.27 (m, 1H), 2.69-2.58 (m, 2H), 2.46-2.33 (m, 2H), 2.29-2.14 (m, 2H), 2.04-1.87 (m, 2H), 1.50-1.46 (m, 2H), 1.39-1.36 (m, 8H), 1.35-1.25 (m, 3H), 0.96-0.84 (m, 1H).

(Compound 37)

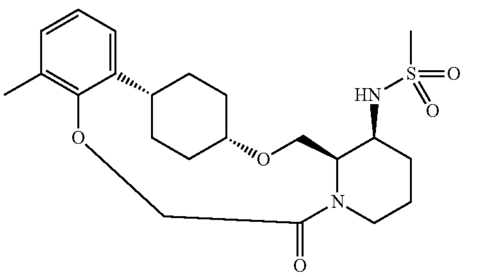

Example 1.11

To a stirred solution of ($2^1$S, $2^4$S, $5^2$R, $5^3$S)-$5^3$-amino-$1^3$-methyl-3,8-dioxa-5(2,1)-piperidina-1(1,2)-benzena-2(1,4)-cyclohexanacyclooctaphan-6-one (740.0 mg, 1.0 equiv., 2.06 mmol) and TEA (1040 mg, 5.0 equiv., 10.3 mmol) in dichloromethane (40.0 mL) was added MsCl (709.4 mg, 3.0 equiv., 6.193 mmol) dropwise at room temperature. The resulting mixture was stirred for 1.5 hours at room temperature under nitrogen atmosphere. The resulting mixture was then concentrated under reduced pressure. The residue was purified by reverse flash chromatography to provide N-(($2^1$S,24S,52R,53S)-$1^3$-methyl-6-oxo-3,8-dioxa-5(2,1)-piperidina-1(1,2)-benzena-2(1,4)-cyclohexanacyclooctaphane-$5^3$-yl)methanesulfonamide (450 mg, 49.9%) as a solid. LCMS (ESI): m/z $[M+H]^+$=437; $^1$H NMR (400 MHz, Methanol-$d_4$) δ 7.02 (dd, J=6.9, 2.1 Hz, 1H), 6.97-6.87 (m, 2H), 5.36 (d, J=12.7 Hz, 1H), 5.24 (dd, J=11.4, 5.1 Hz, 1H), 4.07 (d, J=12.7 Hz, 1H), 3.99 (d, J=13.9 Hz, 1H), 3.87 (dd, J=10.9, 8.8 Hz, 1H), 3.75 (s, 1H), 3.67-3.60 (m, 1H), 3.59-3.47 (m, 2H), 3.04-3.00 (m, 3H), 2.75-2.63 (m, 1H), 2.61-2.51 (m, 1H), 2.32-2.29 (m, 3H), 2.24-2.09 (m, 2H), 1.90-1.86 (m, 3H), 1.75-1.64 (m, 2H), 1.54-1.31 (m, 5H).

Example 1.12

(Compound 65)

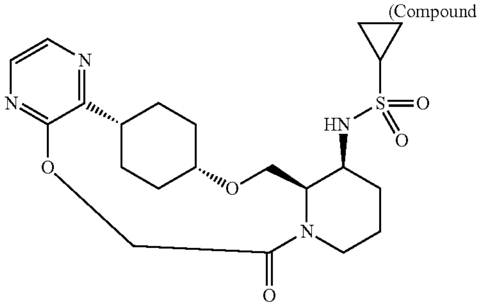

To a solution of ($2^1$S, $2^4$S, $5^2$R, $5^3$S)-$5^3$-amino-3,8-dioxa-1(2,3)-pyrazina-5(2,1)-piperidina-2(1,4)-cyclohexanacyclooctaphan-6-one (50 mg, 1.0 equiv., 144.33 μmol) and cyclopropanesulfonyl chloride (30.5 mg, 1.5 equiv., 216.5 μmol) in DCM (2 mL) was added DIPEA (37.4 mg, 2.0 equiv., 288.7 μmol) and DMAP (3.6 mg, 0.2 equiv., 28.87 μmol). The resulting mixture was stirred for 1 hour at 25 degrees C. The resulting mixture was concentrated under reduced pressure. The residue was purified by reverse flash chromatography to afford N-(($2^1$S, $2^4$S, $5^2$R, $5^3$S)-6-oxo-3,8-dioxa-1(2,3)-pyrazina-5(2,1)-piperidina-2(1,4)-cyclohexanacyclooctaphane-$5^3$-yl)cyclopropanesulfonamide (55 mg, 80%). LCMS (ESI): m/z $[M+H]^+$=451; $^1$H NMR (400 MHz, DMSO-$d_6$) δ 8.13-7.96 (m, 2H), 7.34-7.32 (m, 1H), 5.24-5.21 (m, 1H), 5.05-4.68 (m, 1H), 4.27-4.25 (m, 1H), 3.96-3.73 (m, 2H), 3.69-3.66 (m, 2H), 3.44-3.41 (m, 2H), 3.26-3.22 (m, 1H), 2.86-2.85 (m, 1H), 2.78-2.59 (m, 2H), 2.31-2.08 (m, 2H), 1.89-1.62 (m, 4H), 1.60-1.28 (m, 5H), 1.28-1.10 (m, 1H), 1.10-0.78 (m, 4H).

Example 1.13

(Compound 66)

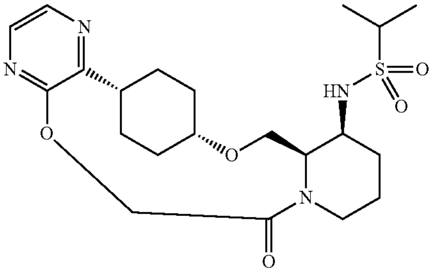

To a solution of ($2^1$S, $2^4$S, $5^2$R, $5^3$S)-$5^3$-amino-3,8-dioxa-1(2,3)-pyrazina-5(2,1)-piperidina-2(1,4)-cyclohexanacyclooctaphan-6-one (50 mg, 1.0 equiv., 144.33 μmol) and propane-2-sulfonyl chloride (30.9 mg, 1.5 equiv., 216.49 μmol) in DCM (5 mL) was added DIPEA (37.4 mg, 2.0 equiv., 288.7 μmol) and DMAP (3.6 mg, 0.2 equiv., 28.87 μmol). The resulting mixture was stirred for 1 hour at 25 degrees C. The resulting mixture was concentrated under reduced pressure. The residue was purified by reverse flash chromatography to afford N-(($2^1$S, $2^4$S, $5^2$R, $5^3$S)-6-oxo-3,8-dioxa-1(2,3)-pyrazina-5(2,1)-piperidina-2(1,4)-cyclohexanacyclooctaphane-$5^3$-yl)propane-2-sulfonamide (35 mg, 51%). LCMS (ESI): m/z $[M+H]^+$=453; $^1$H NMR (400 MHz, DMSO-$d_6$) δ 8.12-8.00 (m, 2H), 7.28-7.25 (m, 2H), 5.24-5.21 (m, 2H), 4.98-4.95 (m, 1H), 4.67-4.64 (m, 1H), 4.26-4.22 (m, 1H), 4.01-3.76 (m, 2H), 3.67-3.65 (m, 1H), 3.44-3.41 (m, 2H), 3.30-3.09 (m, 2H), 2.86-2.84 (m, 2H), 2.41-2.04 (m, 3H), 1.71-1.67 (m, 4H), 1.39-1.36 (m, 5H), 1.30-0.93 (m, 7H).

Example 1.14

(Compound 68)

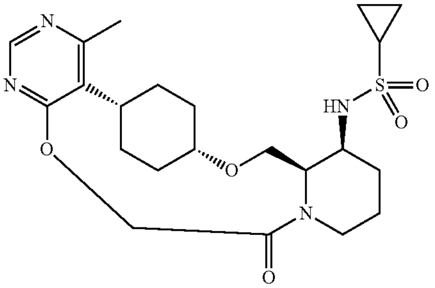

To a solution of ($2^1$S,$2^4$S,$5^2$R,$5^3$S)-$5^3$-amino-$1^6$-methyl-3,8-dioxa-1(5,4)-pyrimidina-5(2,1)-piperidina-2(1,4)-cyclohexanacyclooctaphan-6-one (760 mg, 1.0 equiv., 2.11 mmol) in DCM (30 mL) was added DMAP (25.8 mg, 0.1 equiv., 210.8 µmol), DIEA (1.47 mL, 4.0 equiv., 8.43 mmol) and cyclopropanesulfonyl chloride (889.2 mg, 3.0 equiv., 6.33 mmol) at nitrogen atmosphere. The resulting mixture was stirred for 3 hours at room temperature, and then concentrated under reduced pressure. The crude was purified by reverse flash chromatography to afford N-(($2^1$S, $2^4$S, $5^2$R, $5^3$S)-$1^6$-methyl-6-oxo-3,8-dioxa-1(5,4)-pyrimidina-5(2,1)-piperidina-2(1,4)-cyclohexanacyclooctaphane-$5^3$-yl) cyclopropanesulfonamide (990 mg, 93.8%) as a solid. LCMS (ESI): m/z $[M+H]^+$=465; $^1$H NMR (400 MHz, Methanol-$d_4$) δ 8.46 (d, J=8.1 Hz, 1H), 5.40-5.38 (m, 1H), 5.29-5.25 (m, 1H), 4.79-4.75 (m, 1H), 4.48-4.45 (m, 1H), 4.07-3.84 (m, 2H), 3.82-3.64 (m, 2H), 3.59-3.56 (m, 1H), 3.52-3.38 (m, 1H), 3.13-2.89 (m, 1H), 2.68-2.52 (m, 2H), 2.51-2.48 (m, 3H), 2.39-2.16 (m, 2H), 2.00-1.83 (m, 3H), 1.82-1.59 (m, 2H), 1.55-1.52 (m, 1H), 1.51-1.38 (m, 2H), 1.38-1.23 (m, 1H), 1.18-0.89 (m, 4H).

Example 1.15

(Compound 91)

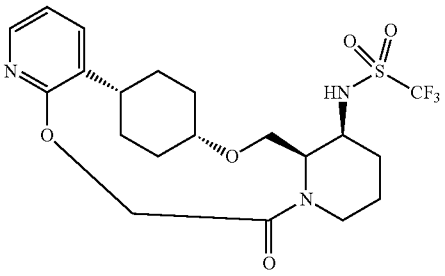

To the solution of ($2^1$S, $2^4$S, $5^2$R, $5^3$S)-$5^3$-amino-3,8-dioxa-1(3,2)-pyridina-5(2,1)-piperidina-2(1,4)-cyclohexanacyclooctaphan-6-one (1.5 g, 1.0 equiv., 4.35 mmol) in DCM (30 mL) was added TEA (1.32 g, 3.0 equiv., 13.0 mmol) at room temperature. The solution was cooled to −50 degrees C., then added $Tf_2O$ (1.84 g, 1.5 equiv., 6.51 mmol) dropwise into the solution. The resulting solution was stirred for 30 minutes at −50 degrees C. The resulting mixture was quenched with saturated $NaHCO_3$ aqueous and diluted with 20 mL water. Then the mixture was extracted with ethyl acetate (3×100 mL). The organic phases were concentrated under reduced pressure. The residue was purified by silica gel column chromatography to afford 1,1,1-trifluoro-N-(($2^1$S, $2^4$S, $5^2$R, $5^3$S)-6-oxo-3,8-dioxa-1(3,2)-pyridina-5(2,1)-piperidina-2(1,4)-cyclohexanacyclooctaphane-$5^3$-yl) methanesulfonamide (1.68 g, 81.0%) as a solid. LCMS (ESI): m/z $[M+H]^+$=478; $^1$H NMR (400 MHz, Methanol-$d_4$) δ 7.99 (ddd, J=9.6, 5.1, 1.9 Hz, 1H), 7.50 (ddd, J=7.1, 5.1, 1.9 Hz, 1H), 6.92 (dd, J=7.2, 5.2 Hz, 1H), 5.34-5.32 (m, 1H), 5.22-5.19 (m, 1H), 4.81-4.63 (m, 1H), 4.43-4.40 (m, 1H), 4.08-3.94 (m, 1H), 3.81-3.77 (m, 3H), 3.54-3.42 (m, 2H), 2.99-2.58 (m, 2H), 2.40-2.26 (m, 1H), 2.19-2.16 (m, 1H), 1.97-1.79 (m, 4H), 1.79-1.62 (m, 1H), 1.62-1.35 (m, 3H), 1.35-1.21 (m, 1H).

Example 1.16

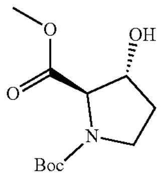 [SMILES: COC(=O)[C@H]1[C@H](O)CCN1C(=O)OC(C)(C)C]

To a stirred mixture of (2R,3R)-1-(tert-butoxycarbonyl)-3-hydroxypyrrolidine-2-carboxylic acid (20.0 g, 1.0 equiv., 86.5 mmol) and $K_2CO_3$ (19.1 g, 1.6 equiv., 138.0 mmol) in DMF (300 mL) was added MeI (14.9 g, 1.2 equiv., 104.7 mmol). The resulting mixture was stirred for 2 hours at 90 degrees C. under nitrogen atmosphere. The resulting mixture was concentrated under reduced pressure. The resulting mixture was diluted with water and extracted with EtOAc. The combined organic layers were washed with brine, dried over anhydrous $MgSO_4$. After filtration, the filtrate was concentrated under reduced pressure to give 1-tert-butyl 2-methyl (2R,3R)-3-hydroxypyrrolidine-1,2-dicarboxylate (21.0 g, 99.0%) as an oil. LCMS (ESI): m/z $[M+H]^+$=246; $^1$H NMR (400 MHz, Chloroform-d) δ 4.45 (d, J=4.6 Hz, 1H), 4.25-4.22 (m, 1H), 3.76 (s, 3H), 3.71-3.46 (m, 2H), 2.14-2.11 (m, 1H), 1.92-1.89 (m, 1H), 1.46-1.43 (m, 9H).

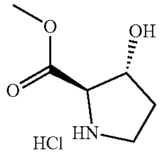

A mixture of 1-tert-butyl 2-methyl (2R,3R)-3-hydroxypyrrolidine-1,2-dicarboxylate (21.0 g, 1.0 equiv., 85.6 mmol) and 4N HCl in 1,4-dioxane (300.0 mL) was stirred for 4 hours at room temperature under nitrogen atmosphere. The precipitated solids were collected by filtration and washed with ethyl ether to provide methyl (2R,3R)-3-hydroxypyrrolidine-2-carboxylate hydrochloride (14.4 g, 92.6%) as a solid. LCMS (ESI): m/z $[M+H]^+$=146.

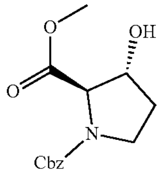 [SMILES: COC(=O)[C@H]1[C@H](O)CCN1C(=O)OCc1ccccc1]

To a stirred solution of methyl (2R,3R)-3-hydroxypyrrolidine-2-carboxylate hydrochloride (14.40 g, 1.0 equiv., 79.3 mmol) and DIEA (25.6 g, 2.5 equiv., 198.0 mmol) in DCM (300.0 mL) were added benzyl 2,5-dioxopyrrolidin-1-yl carbonate (19.8 g, 1.0 equiv., 79.3 mmol) in portions at 0 degrees C. under nitrogen atmosphere. The resulting mixture was stirred for 4 hours at room temperature under nitrogen atmosphere. The resulting mixture was diluted with dichloromethane (300 mL). The resulting mixture was washed with aq. 2N HCl (500 mL*3). The resulting organic layers were washed with brine, and dried over anhydrous $MgSO_4$. After filtration, the filtrate was concentrated under reduced pressure. The residue was purified by silica gel column chromatography to afford 1-benzyl 2-methyl (2R,3R)-3-hydroxypyrrolidine-1,2-dicarboxylate (18 g, 81.3%) as a solid. LCMS (ESI): m/z $[M+H]^+$=280; $^1$H NMR (400 MHz, Chloroform-d) δ 7.45-7.21 (m, 5H), 5.31-4.96 (m, 2H), 4.54-4.24 (m, 2H), 3.88-3.53 (m, 5H), 2.66 (s, 1H), 2.11-2.07 (m, 1H), 1.95-1.87 (m, 1H).

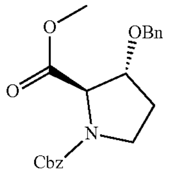 [SMILES: COC(=O)[C@H]1[C@H](OCc2ccccc2)CCN1C(=O)OCc1ccccc1]

To a stirred solution of 1-benzyl 2-methyl (2R,3R)-3-hydroxypyrrolidine-1,2-dicarboxylate (18.0 g, 1.0 equiv., 64.4 mmol) and benzyl bromide (16.5 g, 1.5 equiv., 96.7 mmol) in DCM (360.0 mL) was added $Ag_2O$ (44.8 g, 3.0 equiv., 193.3 mmol) under nitrogen atmosphere. The mixture was stirred at room temperature for 2 days with tin foil to cover the light. The resulting mixture was filtered and the filter cake was washed with DCM. The filtrate was concentrated under reduced pressure. The residue was purified by silica gel column chromatography to afford 1-benzyl 2-methyl (2R,3R)-3-(benzyloxy)pyrrolidine-1,2-dicarboxylate (17.2 g, 72.2%) as an oil. LCMS (ESI): m/z $[M+H]^+$=370; $^1$H NMR (400 MHz, Chloroform-d) δ 7.36-7.33 (m, 10H), 5.36-4.95 (m, 2H), 4.83-4.42 (m, 3H), 4.18-4.15 (m, 1H), 3.89-3.56 (m, 5H), 2.10-2.07 (m, 2H).

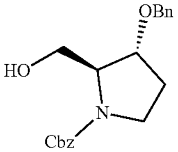 [SMILES: O=C(OCc1ccccc1)N1CC[C@@H](OCc2ccccc2)[C@@H]1CO]

To a stirred solution of 1-benzyl 2-methyl (2R,3R)-3-(benzyloxy)pyrrolidine-1,2-dicarboxylate (17.2 g, 1.0 equiv., 46.6 mmol) in THF (400 mL) were added $NaBH_4$ (17.6 g, 10 equiv., 465.6 mmol) and LiCl (19.7 g, 10 equiv., 465.6 mmol) in portions at 0 degrees C. under nitrogen atmosphere. The resulting mixture was stirred for 2 days at room temperature under nitrogen atmosphere. The mixture was allowed to cool down to 0 degrees C. The reaction was quenched by the addition of sat. $NH_4Cl$ (aq.) at 0 degrees C. The resulting mixture was extracted with EtOAc. The combined organic layers were washed with brine, and dried over anhydrous $MgSO_4$. After filtration, the filtrate was concentrated under reduced pressure. The residue was purified by silica gel column chromatography to afford benzyl (2S,3R)-3-(benzyloxy)-2-(hydroxymethyl)pyrrolidine-1-carboxylate (15 g, 94.4%) as an oil. LCMS: m/z (ES+), $[M+H]^+$=342; $^1$H NMR (400 MHz, Chloroform-d) δ 7.36-7.33 (m, 10H), 5.28-5.04 (m, 2H), 4.71-4.41 (m, 2H), 4.13 (m, 1H), 3.95-3.92 (m, 1H), 3.80-3.43 (m, 5H), 2.04-2.01 (m, 2H).

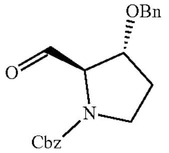 [SMILES: O=C[C@H]1[C@H](OCc2ccccc2)CCN1C(=O)OCc1ccccc1]

To a stirred solution of $(COCl)_2$ (6.69 g, 1.2 equiv., 52.7 mmol) in DCM (300 mL) was added a solution of DMSO (8.24 g, 2.4 equiv., 105.4 mmol) in DCM (50.0 mL) dropwise at −78 degrees C. under nitrogen atmosphere. The mixture was stirred at this temperature for 1.5 hours. A solution of benzyl (2S,3R)-3-(benzyloxy)-2-(hydroxymethyl)pyrrolidine-1-carboxylate (15.0 g, 1.0 equiv., 43.9 mmol) in DCM (50.0 mL) was added dropwise. The mixture was stirred at −78 degrees C. for 1 hour, then TEA (22.2 g, 5.0 equiv., 219.7 mmol) was added dropwise. The mixture was stirred at −78 degrees C. for 1 hour and the reaction mixture was allowed to warm to room temperature. The reaction was quenched by the addition of water. The resulting mixture was extracted with $CH_2Cl_2$. The combined organic layers were washed with brine and dried over anhydrous $MgSO_4$. After filtration, the filtrate was concentrated under reduced pressure. The residue was purified by silica gel column chromatography to afford benzyl (2R,3R)-3-(benzyloxy)-2-formylpyrrolidine-1-carboxylate (13.8 g, 80.7%) as an oil. LCMS: m/z (ES+), $[M+H]^+$=340; $^1$H NMR (400 MHz, Chloroform-d) δ 9.60-9.55 (m, 1H), 7.45-7.29 (m, 10H), 5.26-5.06 (m, 2H), 4.71-4.33 (m, 3H), 4.23-4.20 (m, 1H), 3.71-3.65 (m, 2H), 2.14-2.10 (m, 1H), 1.91-1.86 (m, 1H).

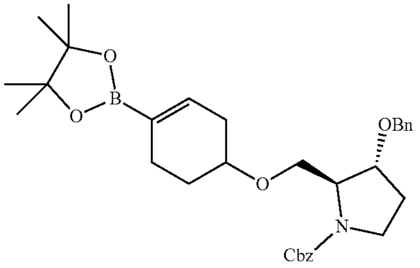 [SMILES: CC1(C)OB(C2=CCC(OC[C@H]3[C@H](OCc4ccccc4)CCN3C(=O)OCc3ccccc3)CC2)OC1(C)C]

To the benzyl (2R,3R)-3-(benzyloxy)-2-formylpyrrolidine-1-carboxylate (10.0 g, 1.0 equiv., 29.5 mmol), which was dried under high vacuum for 1 hour in a three neck round bottom flask, was added tert-butyldimethyl ((4-(4,4,5,5-tetramethyl-1,3,2-dioxaborolan-2-yl)cyclohex-3-en-1-yl)oxy)silane (9.90 g, 1.0 equiv., 29.5 mmol) in DCM (200 mL) under $N_2$ atmosphere. The mixture was cooled to −78 degrees C. TMSOTf (7.20 g, 1.1 equiv., 32.4 mmol) in DCM (20 mL) was added dropwise into the mixture solution at −78 degrees C., and subsequently the solution of triethylsilane (6.17 g, 1.8 equiv., 53.0 mmol) in DCM (20 mL) was added dropwise at −78 degrees C. The resulting reaction solution was stirred for 0.5 hours at −78 degrees C. Then, warmed to 20 degrees C. and stirred for 0.5 hours. The reaction was quenched with aq. saturated $NaHCO_3$, and extracted with DCM. The resulting organic phases was dried over anhydrous magnesium sulfate. The resulting solution was filtered, the filtrate was concentrated under reduced pressure. The residue was purified by silica gel column chromatography to afford benzyl (2S,3R)-3-(benzyloxy)-2-(((4-(4,4,5,5-tetramethyl-1,3,2-dioxaborolan-2-yl)cyclohex- 3-en-1-yl)oxy)methyl)pyrrolidine-1-carboxylate (10.0 g, 62.0%) as an oil. LCMS: m/z (ES+), [M+H]+=548, $^{1}$H NMR (400 MHz, Chloroform-d) δ 7.43-7.22 (m, 10H), 6.44 (s, 1H), 5.32-5.03 (m, 2H), 4.72-4.43 (m, 2H), 4.19-3.99 (m, 2H), 3.80-3.18 (m, 5H), 2.54-2.23 (m, 2H), 2.18-1.94 (m, 4H), 1.78 (m, 1H), 1.44 (s, 1H), 1.28-1.25 (m, 11H).

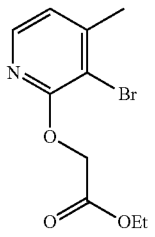

To a stirred solution of 3-bromo-2-fluoro-4-methylpyridine (10 g, 1.0 equiv., 53 mol) in DMF (150 mL) was added sodium methyl 2-hydroxyacetate (27 g, 5.0 equiv., 0.26 mol) and cesium carbonate (26 g, 1.5 equiv., 79 mol). The mixture was stirred for 4 hours at 60 degrees C. under nitrogen atmosphere. The mixture was filtered and the resulting mixture was extracted with EtOAc (3×400 mL). The combined organic layers were washed with water (3×200 mL), and dried over anhydrous $Na_2SO_4$. After filtration, the filtrate was concentrated under reduced pressure. The residue was purified by reverse flash chromatography to afford ethyl 2-((3-bromo-4-methylpyridin-2-yl)oxy)acetate (11 g, 40 mmol, 76%) as a solid. LCMS (ESI): m/z $[M+H]^+$=274.

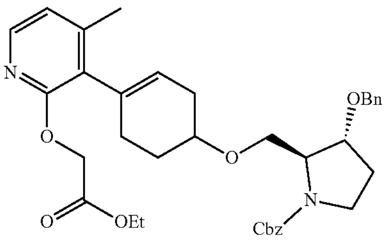 [SMILES: CCOC(=O)COc1nccc(C)c1C1=CCC(OC[C@H]2[C@H](OCc3ccccc3)CCN2C(=O)OCc2ccccc2)CC1]

To a solution of benzyl (2S,3R)-3-(benzyloxy)-2-(((4-(4,4,5,5-tetramethyl-1,3,2-dioxaborolan-2-yl)cyclohex-3-en-1-yl)oxy)methyl)pyrrolidine-1-carboxylate (20 g, 1.0 equiv., 37 mmol) and ethyl 2-((3-bromo-4-methylpyridin-2-yl)oxy) acetate (11 g, 1.1 equiv., 40 mmol) in 1,4-dioxane (400 mL) and $H_2O$ (100 mL) were added $Na_2CO_3$ (12 g, 3.0 equiv., 0.11 mol) and Pd(dppf)$Cl_2$ (2.7 g, 0.1 equiv., 3.7 mmol) under nitrogen atmosphere, the resulting mixture was stirred for 2 hours at 80 degrees C. The resulting mixture was extracted with ethyl acetate (3*300 mL). The combined organic layers were washed with brine, and dried over anhydrous $Na_2SO_4$. After filtration, the filtrate was concentrated under reduced pressure. The crude product was purified by silica gel column chromatography to afford benzyl (2S,3R)-3-(benzyloxy)-2-(((4-(2-(2-ethoxy-2-oxoethoxy)-4-methylpyridin-3-yl) cyclohex-3-en-1-yl)oxy)methyl)pyrrolidine-1-carboxylate (16 g, 26 mmol, 71%) as an oil. LCMS (ESI): m/z $[M+H]^+$=615.

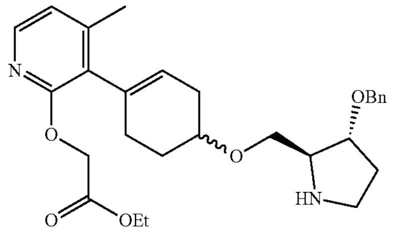

To a solution of benzyl (2S,3R)-3-(benzyloxy)-2-(((4-(2-(2-ethoxy-2-oxoethoxy)-4-methylpyridin-3-yl)cyclohex-3-en-1-yl)oxy)methyl)pyrrolidine-1-carboxylate (16 g, 1.0 equiv., 26 mmol) in i-PrOH (500 mL) was added Pd/C (0.28 g, 0.1 equiv., 2.6 mmol) at nitrogen atmosphere. The resulting mixture was hydrogenated at room temperature for 5 hours under hydrogen atmosphere using a hydrogen balloon. Then, the resultant mixture was filtered through a Celite® pad and concentrated under reduced pressure to afford the crude product. The mixture was concentrated under reduced pressure to afford ethyl 2-((3-(4-(((2S,3R)-3-(benzyloxy) pyrrolidin-2-yl)methoxy)cyclohex-1-en-1-yl)-4-methylpyridin-2-yl)oxy)acetate (11 g, 23 mmol, 88%) as a solid. The crude product was used in the next step directly without further purification. LCMS (ESI): m/z $[M+H]^+$=481.

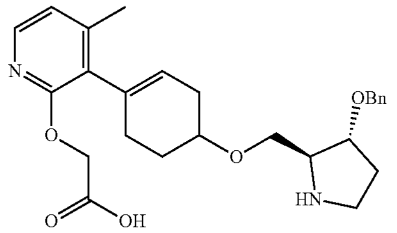 [SMILES: Cc1ccnc(OCC(=O)O)c1C1=CCC(OC[C@@H]2NCC[C@H]2OCc2ccccc2)CC1]

To a stirred mixture of ethyl 2-((3-(4-(((2S,3R)-3-(benzyloxy)pyrrolidin-2-yl)methoxy)cyclohex-1-en-1-yl)-4-methylpyridin-2-yl)oxy)acetate (11 g, 1.0 equiv., 23 mmol) in MeOH (150 mL) was added a solution of lithium hydroxide (1.6 g, 3.0 equiv., 69 mmol) in $H_2O$ (75 mL). The resulting mixture was stirred for 2 hours at 25 degrees C. The mixture was adjusted to a pH of 5-6. The crude was purified by reverse flash chromatography to afford 2-((3-(4-(((2S,3R)-3-(benzyloxy)pyrrolidin-2-yl)methoxy)cyclohex-1-en-1-yl)-4-methylpyridin-2-yl)oxy)acetic acid (9.5 g, 21 mmol, 92%) as an oil. LCMS (ESI): m/z $[M+H]^+$=453.

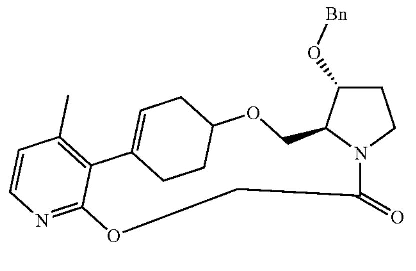 [SMILES: Cc1ccnc2c1C1=CCC(CC1)OC[C@H]1[C@H](OCc3ccccc3)CCN1C(=O)CO2]

To a stirred mixture of HATU (12 g, 1.5 equiv., 31 mmol) and diisopropylethylamine (8.1 g, 3.0 equiv., 63 mmol) in acetonitrile (200 mL) was added a solution of 2-((3-(4-(((2S,3R)-3-(benzyloxy)pyrrolidin-2-yl)methoxy)cyclohex-1-en-1-yl)-4-methylpyridin-2-yl)oxy)acetic acid (9.5 g, 1.0 equiv., 21 mmol). The resulting mixture was stirred for 2 hours at 25 degrees C. The crude was purified by reverse flash chromatography to afford (5$^2$S,5$^3$R,E)-5$^3$-(benzyloxy)-14-methyl-3,8-dioxa-1(3,2)-pyridina-5(2,1)-pyrrolidina-2(1,4)-cyclohexanacyclooctaphan-2$^1$-en-6-one (5.6 g, 13 mmol, 61%) as a solid. LCMS (ESI): m/z $[M+H]^+$=435.

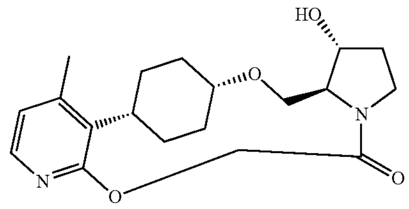

To a solution of (5$^2$S,5$^3$R,E)-5$^3$-(benzyloxy)-14-methyl-3,8-dioxa-1(3,2)-pyridina-5(2,1)-pyrrolidina-2(1,4)-cyclohexanacyclooctaphan-2$^1$-en-6-one (5.6 g, 1.0 equiv., 13 mmol) in MeOH (300 mL) was added Pd/C (1.4 g, 1.0 equiv., 13 mmol) at nitrogen atmosphere. The resulting mixture was hydrogenated at room temperature for 5 days under hydrogen atmosphere using a hydrogen balloon, filtered through a Celite® pad and concentrated under reduced pressure to afford the crude product. Then the crude product was added Pd/C (0.01 g, 5% Wt) at nitrogen atmosphere. The resulting mixture was hydrogenated at 50 degrees C. for 24 hours under 6 atm, filtered through a Celite® pad and concentrated under reduced pressure to afford the crude product. The crude was purified by reverse flash chromatography to afford (2$^1$R,2$^4$R,5$^2$S,5$^3$R)-5$^3$-hydroxy-14-methyl-3,8-dioxa-1(3,2)-pyridina-5(2,1)-pyrrolidina-2(1,4)-cyclohexanacyclooctaphan-6-one (2.9 g, 8.4 mmol, 63%) as a solid. LCMS (ESI): m/z $[M+H]^+$=347.

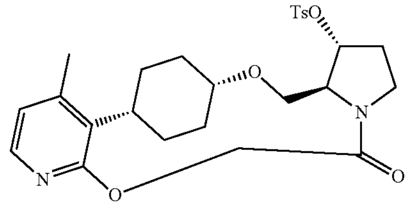 [SMILES: Cc1ccc(S(=O)(=O)O[C@@H]2CCN3C(=O)COc4nccc(C)c4[C@H]4CC[C@H](CC4)OC[C@@H]23)cc1]

To a stirred mixture of (2$^1$R,2$^4$R,5$^2$S,5$^3$R)-5$^3$-hydroxy-14-methyl-3,8-dioxa-1(3,2)-pyridina-5(2,1)-pyrrolidina-2(1,4)-cyclohexanacyclooctaphan-6-one (2.9 g, 1.0 equiv., 8.4 mmol) in dichloromethane (15 mL) was added tosyl-Cl (2.4 g, 1.5 equiv., 13 mmol), triethylamine (3.5 mL, 3.0 equiv., 25 mmol) and 4-dimethylamino pyridine (0.20 g, 0.2 equiv., 1.7 mmol). The resulting mixture was stirred for 16 hours at 40 degrees C. The reaction was monitored by LCMS. The resulting solution was concentrated under reduced pressure. The residue was purified by reverse flash chromatography to afford (2$^1$R,2$^4$R,5$^2$S,5$^3$R)-1$^4$-methyl-6-oxo-3,8-dioxa-1(3,2)-pyridina-5(2,1)-pyrrolidina-2(1,4)-cyclohexanacyclooctaphane-5$^3$-yl-4-methylbenzenesulfonate (3.4 g, 6.8 mmol, 81%) as a solid. LCMS (ESI): m/z $[M+H]^+$=501.

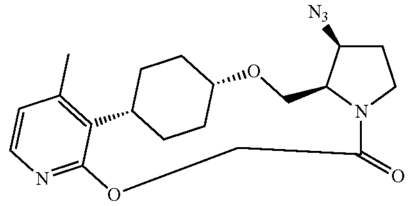 [SMILES: Cc1ccnc2c1[C@H]1CC[C@H](CC1)OC[C@H]1[C@@H](N=[N+]=[N-])CCN1C(=O)CO2]

To a stirred solution of (2$^1$R,2$^4$R,5$^2$S,5$^3$R)-1$^4$-methyl-6-oxo-3,8-dioxa-1(3,2)-pyridina-5(2,1)-pyrrolidina-2(1,4)-cyclohexanacyclooctaphane-5$^3$-yl-4-methylbenzenesulfonate (3.4 g, 1.0 equiv., 6.8 mmol) in DMF (30 mL) was added tetrabutylammonium azide (5.8 g, 3.0 equiv., 20 mmol). The resulting mixture was stirred for 16 hours at 80 degrees C. The resulting mixture was extracted with ethyl acetate (3*100 mL). The combined organic layers were washed with brine, dried over anhydrous $Na_2SO_4$. After filtration, the filtrate was concentrated under reduced pressure. The crude product was purified by silica gel column chromatography to afford (2$^1$S, 2$^4$S, 5$^2$R, 5$^3$S)-5$^3$-azido-1$^4$-methyl-3,8-dioxa-1(3,2)-pyridina-5(2,1)-pyrrolidina-2(1,4)-cyclohexanacyclooctaphan-6-one (1.6 g, 4.3 mmol, 63%) as an oil. LCMS (ESI): m/z $[M+H]^+$=372.

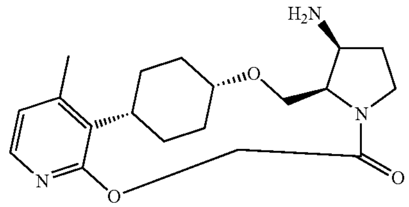 [SMILES: Cc1ccnc2c1[C@H]1CC[C@H](CC1)OC[C@H]1[C@@H](N)CCN1C(=O)CO2]

To a solution of (2$^1$S, 2$^4$S, 5$^2$R, 5$^3$S)-5$^3$-azido-14-methyl-3,8-dioxa-1(3,2)-pyridina-5(2,1)-pyrrolidina-2(1,4)-cyclohexanacyclooctaphan-6-one (1.6 g, 1.0 equiv., 4.3 mmol) in methanol (100 mL) was added Pd/C (4.6 g, 10% Wt, 4.3 mmol) at nitrogen atmosphere. The resulting mixture was hydrogenated at room temperature for 16 hours under hydrogen atmosphere using a hydrogen balloon. The crude was purified by reverse flash chromatography to afford (2$^1$S, 2$^4$S, 5$^2$R, 5$^3$S)-5$^3$-amino-1$^4$-methyl-3,8-dioxa-1(3,2)-pyridina-5(2,1)-pyrrolidina-2(1,4)-cyclohexanacyclooctaphan-6-one (905 mg, 2.62 mmol, 61%) as an oil. LCMS (ESI): m/z $[M+H]^+$=346.

(Compound 94)

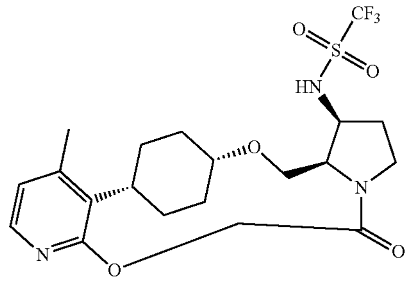

To a solution of (2$^1$S, 2$^4$S, 5$^2$R, 5$^3$S)-5$^3$-amino-1$^4$-methyl-3,8-dioxa-1(3,2)-pyridina-5(2,1)-pyrrolidina-2(1,4)-cyclohexanacyclooctaphan-6-one (10 mg, 1.0 equiv., 29 μmol) in dichloromethane (2 mL) was added trifluoromethanesulfonic anhydride (9.8 mg, 1.2 equiv., 35 μmol), and triethylamine (8.8 mg, 3.0 equiv., 87 μmol). The resulting mixture was stirred for 0.5 hours at −50 degrees C. The resulting mixture was extracted with $NH_4HCO_3$. The filtrate was concentrated under reduced pressure. The residue was purified by Prep-HPLC to afford 1,1,1-trifluoro-N-(($2^1$S, $2^4$S, $5^2$R, $5^3$S)-$1^4$-methyl-6-oxo-3,8-dioxa-1(3,2)-pyridina-5(2,1)-pyrrolidina-2(1,4)-cyclohexanacyclooctaphane-$5^3$-yl) methanesulfonamide (4.4 mg, 9.2 μmol, 32%) as a solid. LCMS (ESI): m/z $[M+H]^+$=478; H NMR (400 MHz, Methanol-$d_4$) δ 7.83 (d, J=5.1 Hz, 1H), 6.85 (d, J=5.2 Hz, 1H), 4.96 (d, J=10.7 Hz, 1H), 4.61 (d, J=10.8 Hz, 1H), 4.33 (m, 2H), 4.23-4.10 (m, 2H), 3.83 (s, 1H), 3.74 (m, 1H), 3.43 (m, 1H), 3.03 (m, 1H), 2.64-2.45 (m, 2H), 2.35 (m, 4H), 2.17 (m, 2H), 1.94 (m, 1H), 1.57 (m, 1H), 1.47-1.27 (m, 2H), 1.23-1.14 (m, 1H).

Example 1.17

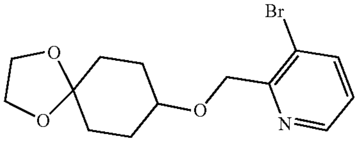 [SMILES: Brc1cccnc1COC1CCC2(CC1)OCCO2]

To a stirred solution of 1,4-dioxaspiro[4.5]decan-8-ol (753.0 g, 1.0 equiv., 4.8 mol) in THF (10 L) was added potassium t-butoxide (534.3 g, 1.3 equiv., 4.8 mol) in portions at 0 degrees C. under nitrogen atmosphere. The resulting solution was stirred for 30 minutes at 0 degrees C. To this was added a solution of 3-bromo-2-(bromomethyl) pyridine (919.0 g, 1.0 equiv., 4.8 mol) in THF (1.0 L) dropwise with stirring at 0 degrees C. The resulting solution was allowed to stir overnight at room temperature. The reaction was then quenched by the addition of 10 L of sat. $NH_4Cl$ (aq.). The resulting solution was extracted with 3×1 L of ethyl acetate, the organic layer was dried over anhydrous sodium sulfate and concentrated under vacuum. The residue was purified by silica gel column chromatography, to afford 3-bromo-2-([1,4-dioxaspiro[4.5]decan-8-yloxy] methyl)pyridine (962.0 g, 80.0%) as an oil.

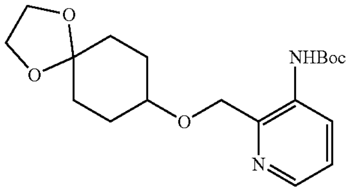 [SMILES: CC(C)(C)OC(=O)Nc1cccnc1COC1CCC2(CC1)OCCO2]

To a stirred solution of 3-bromo-2-([1,4-dioxaspiro[4.5] decan-8-yloxy]methyl)pyridine (962.0 g, 1.0 equiv., 2.9 mol) and tert-butyl carbamate (686.7 g, 2.0 equiv., 5.9 mol) in dioxane (10.0 L) was added $Pd_2(dba)_3$ (134.2 g, 0.05 equiv., 0.15 mol), Xantphos (169.6 g, 0.10 equiv., 0.29 mol) and $Cs_2CO_3$ (2395 g, 2.5 equiv., 7.3 mol) under nitrogen atmosphere. The resulting solution was stirred for 20 hours at 100 degrees C. The solids were filtered out. The resulting mixture was concentrated under vacuum. The residue was purified by a silica gel column to afford tert-butyl N-[2-([1,4-dioxaspiro[4.5]decan-8-yloxy]methyl)pyridin-3-yl]carbamate (620.0 g, 58.0%) as a solid.

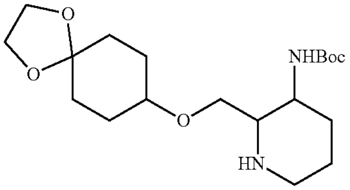 [SMILES: CC(C)(C)OC(=O)NC1CCCNC1COC1CCC2(CC1)OCCO2]

To a stirred solution of tert-butyl N-[2-([1,4-dioxaspiro [4.5]decan-8-yloxy]methyl)pyridin-3-yl]carbamate (620.0 g, 1.0 equiv., 1.7 mmol) in methanol (6.0 L) and acetic acid (600 mL) was added $Pt_2O$ (77.26 g, 0.20 equiv., 340.2 mmol). The mixture was hydrogenated under 20 atm of hydrogen at room temperature. The resulting solution was stirred overnight at room temperature. The solids were filtered out. The resulting mixture was concentrated under vacuum to afford tert-butyl N-[2-([1,4-dioxaspiro[4.5]decan-8-yloxy]methyl)piperidin-3-yl]carbamate (620.0 g, 99.9%) as an oil.

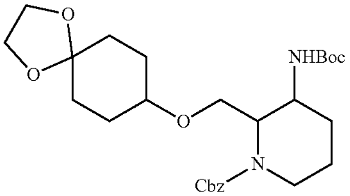 [SMILES: CC(C)(C)OC(=O)NC1CCCN(C(=O)OCc2ccccc2)C1COC1CCC2(CC1)OCCO2]

To a stirred mixture of tert-butyl N-[2-([1,4-dioxaspiro [4.5]decan-8-yloxy]methyl)piperidin-3-yl]carbamate (620.0 g, 1.0 equiv., 1.7 mmol) in DCM (6.0 L) was added N-(benzyloxycarbonyloxy)succinimide (845.9 g, 1.2 equiv., 2.0 mol) and DIEA (648.9 g, 3.0 equiv., 5.0 mol) at room temperature. The resulting solution was stirred overnight at room temperature. The reaction was then quenched by the addition of 5 L of water/ice. The resulting mixture was extracted with 2×2 L of DCM. The mixture was dried over anhydrous sodium sulfate and the organic layer was concentrated under reduced pressure. The residue was purified by silica gel column chromatography to afford benzyl 3-[(tert-butoxycarbonyl)amino]-2-([1,4-dioxaspiro[4.5]decan-8-yloxy]methyl)piperidine-1-carboxylate (422.0 g, 50.0%) as an oil.

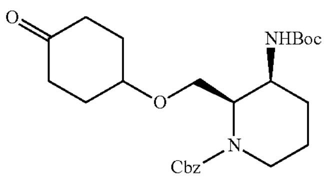 [SMILES: CC(C)(C)OC(=O)N[C@H]1CCCN(C(=O)OCc2ccccc2)[C@H]1COC1CCC(=O)CC1]

To a stirred solution of benzyl 3-[(tert-butoxycarbonyl) amino]-2-([1,4-dioxaspiro[4.5]decan-8-yloxy]methyl)piperidine-1-carboxylate (422.0 g, 1.0 equiv., 0.84 mol) in acetic acid (280 mL) was added water (140 mL) at room temperature. The resulting solution was stirred for 12 hours at 30 degrees C. The mixture was allowed to cool down to 10 degrees C. The reaction was then quenched by the addition of 6 L of ice water. The resulting solution was stirred for 1 hour at 10 degrees C. The precipitated solids were collected by filtration. The crude product was purified by re-crystallization from 5 $Et_2O$:1 EA (10 mL/g) three times to afford benzyl racemic-(cis)-3-[(tert-butoxycarbonyl)amino]-2-[[(4-oxocyclohexyl)oxy]methyl]piperidine-1-carboxylate (108.7 g, 28.2%) as a solid and the filtration was concentrated under vacuum to afford benzyl (2R,3S)-3-[(tert-butoxycarbonyl)amino]-2-[[(4-oxocyclohexyl)oxy]methyl]piperidine-1-carboxylate (64.0 g) as an oil. LCMS (ESI): m/z $[M+H]^+$=461; $^1$H-NMR (300 MHz, DMSO-$d_6$) δ 7.38-7.26 (m, 5H), 6.97-6.95 (m, 1H), 5.06 (brs, 2H), 4.60 (brs, 1H), 3.92-3.81 (m, 1H), 3.76-3.42 (m, 4H), 2.95-2.72 (m, 1H), 2.39-2.23 (s, 2H), 2.18-2.05 (m, 2H), 1.93-1.80 (m, 4H), 1.73-1.48 (m, 3H), 1.39-1.36 (m, 10H).

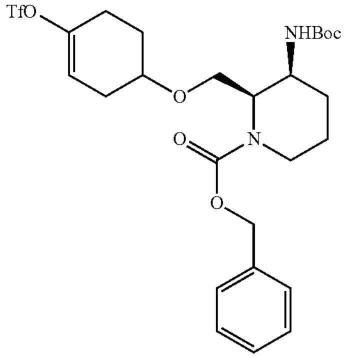 [SMILES: CC(C)(C)OC(=O)N[C@H]1CCCN(C(=O)OCc2ccccc2)[C@H]1COC1CC=C(OS(=O)(=O)C(F)(F)F)CC1]

To a stirred solution of benzyl (2R,3S)-3-[(tert-butoxycarbonyl)amino]-2-[[(4-oxocyclohexyl)oxy]methyl]piperidine-1-carboxylate (30.0 g, 1.0 equiv., 65.1 mmol) in THF (300 mL) was added KHMDS (78.2 mL, 1.2 equiv., 78.2 mmol) at −78 degrees C. under nitrogen atmosphere. The resulting mixture was stirred for 3 hours at −78 degrees C., and followed by 1,1,1-trifluoro-N-phenyl-N-trifluoromethanesulfonylmethanesulfonamide (27.9 g, 1.2 equiv., 78.2 mmol) in THF (100 mL) dropwise at −78 degrees C. The resulting mixture was stirred for 2 hours at −78 degrees C. The mixture was added dropwise to 200 mL of sat. $NH_4Cl$ (aq.) at 0 degrees C. The resulting mixture was extracted with ethyl acetate (2×50 mL). The combined organic layers were dried over anhydrous $Na_2SO_4$. After filtration, the filtrate was concentrated under reduced pressure. The residue was purified by silica gel column chromatography to afford benzyl (2R,3S)-3-[(tert-butoxycarbonyl)amino]-2-([[4-(trifluoromethanesulfonyloxy)cyclohex-3-en-1-yl]oxy]methyl)piperidine-1-carboxylate (41.0 g, crude) as an oil.

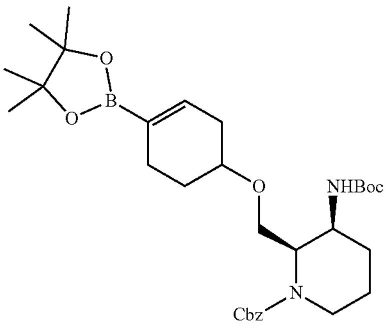 [SMILES: CC(C)(C)OC(=O)N[C@H]1CCCN(C(=O)OCc2ccccc2)[C@H]1COC1CC=C(B2OC(C)(C)C(C)(C)O2)CC1]

To a solution of benzyl (2R,3S)-3-[(tert-butoxycarbonyl)amino]-2-([[4-(trifluoromethanesulfonyloxy)cyclohex-3-en-1-yl]oxy]methyl)piperidine-1-carboxylate (350 g, 1.0 equiv., 0.59 mol) and bis(pinacolato)diboron (180 g, 1.2 equiv., 0.71 mol) in 1,4-dioxane (3.5 L) were added $Pd(dppf)Cl_2$ (24.1 g, 0.05 equiv., 29.5 mmol) and potassium acetate (116 g, 2.0 equiv., 1.18 mol) under nitrogen atmosphere. The resulting mixture was stirred for 16 hours at 100 degrees C. under nitrogen atmosphere. The resulting mixture was concentrated under reduced pressure. The residue was purified by silica gel column chromatography to afford crude product. The crude product was purified by reverse flash chromatography to afford benzyl (2R,3S)-3-[(tert-butoxycarbonyl)amino]-2-([[4-(4,4,5,5-tetramethyl-1,3,2-dioxaborolan-2-yl)cyclohex-3-en-1-yl]oxy]methyl)piperidine-1-carboxylate (90.8 g, 26.2%) as a solid. LCMS (ESI): m/z $[M+H]^+$=571; $^1$H-NMR (300 MHz, DMSO-$d_6$): δ 7.41-7.24 (m, 5H), 6.91 (brs, 1H), 6.30 (brs, 1H), 5.08 (brs, 2H), 4.54 (brs, 1H), 3.85 (d, J=13.3 Hz, 1H), 3.75-3.40 (m, 4H), 2.91-2.70 (s, 1H), 2.40-2.24 (m, 1H), 2.21-2.05 (m, 1H), 2.02-1.85 (m, 2H), 1.80-1.70 (m, 1H), 1.70-1.61 (m, 1H), 1.60-1.50 (m, 2H), 1.39 (s, 11H), 1.18 (s, 12H).

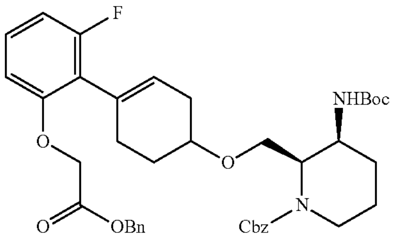 [SMILES: CC(C)(C)OC(=O)N[C@H]1CCCN(C(=O)OCc2ccccc2)[C@H]1COC1CC=C(c2c(F)cccc2OCC(=O)OCc2ccccc2)CC1]

A mixture of benzyl (2R,3S)-3-[(tert-butoxycarbonyl)amino]-2-([[4-(4,4,5,5-tetramethyl-1,3,2-dioxaborolan-2-yl)cyclohex-3-en-1-yl]oxy]methyl)piperidine-1-carboxylate (500.0 mg, 1.0 equiv., 0.876 mmol), benzyl 2-(2-bromo-3-fluorophenoxy)acetate (386.4 mg, 1.3 equiv., 1.14 mmol), $Pd(dppf)Cl_2 \cdot CH_2Cl_2$ (142.8 mg, 0.2 equiv., 0.175 mmol) and $K_2CO_3$ (302.8 mg, 2.5 equiv., 2.19 mmol) in 1,4-dioxane (8.0 mL) and $H_2O$ (2.0 mL) was stirred overnight at 80 degrees C. under nitrogen atmosphere. The reaction was quenched with water at room temperature. The resulting mixture was extracted with EtOAc (3×20 mL), dried over anhydrous $Na_2SO_4$. After filtration, the filtrate was concentrated under reduced pressure. The residue was purified by Prep-TLC to afford benzyl 2-[[(4-[2-[2-(benzyloxy)-2-oxoethoxy]-6-fluorophenyl]cyclohex-3-en-1-yl)oxy]methyl]-3-[(tert-butoxycarbonyl)amino]piperidine-1-carboxylate (470 mg, 76.3%) as an oil. LCMS (ESI): m/z $[M+H]^+$=703.

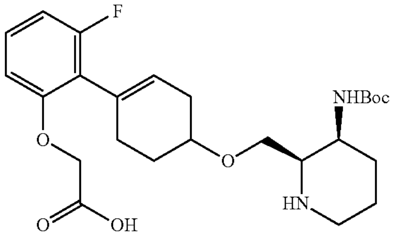 [SMILES: CC(C)(C)OC(=O)N[C@H]1CCCN[C@H]1COC1CC=C(c2c(F)cccc2OCC(=O)O)CC1]

A mixture of benzyl 2-[[(4-[2-[2-(benzyloxy)-2-oxoethoxy]-6-fluorophenyl]cyclohex-3-en-1-yl)oxy]methyl]-3-[(tert-butoxycarbonyl)amino]piperidine-1-carboxylate (100.0 mg, 1.0 equiv., 0.142 mmol) and Pd/C (30.3 mg, 2.0 equiv., 0.285 mmol) in i-PrOH (6.0 mL) was stirred for 1 hour at room temperature under hydrogen atmosphere. The resulting mixture was filtered, the filter cake was washed with i-PrOH (3×3 mL). The filtrate was concentrated under reduced pressure to afford 2-[4-([3-[(tert-butoxycarbonyl) amino]piperidin-2-yl]methoxy)cyclohex-1-en-1-yl]-3-fluorophenoxyacetic acid (58.0 mg, 85.2%) as a solid. LCMS (ESI): m/z $[M+H]^+$=479.

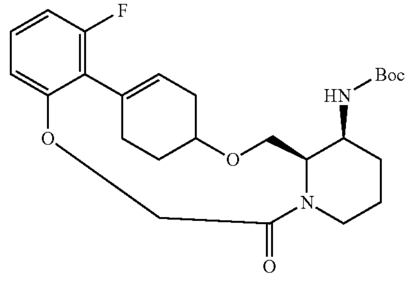 [SMILES: CC(C)(C)OC(=O)N[C@H]1CCCN2C(=O)COc3cccc(F)c3C3=CCC(CC3)OC[C@@H]12]

To a solution of 2-[4-([3-[(tert-butoxycarbonyl)amino] piperidin-2-yl]methoxy)cyclohex-1-en-1-yl]-3-fluorophenoxyacetic acid (53.0 mg, 1.0 equiv., 0.11 mmol) and diisopropylethylamine (43 mg, 3.0 equiv., 0.33 mmol) in acetonitrile (53 mL) was added HATU (63.0 mg, 1.5 equiv., 0.17 mmol). After stirring for 2 hours at room temperature under nitrogen atmosphere, the resulting mixture was concentrated under reduced pressure. The crude was purified by reverse flash chromatography to afford tert-butyl (($5^2$R,$5^3$S, E)-$1^6$-fluoro-6-oxo-3,8-dioxa-5(2,1)-piperidina-1(1,2)-benzena-2(1,4)-cyclohexanacyclooctaphan-$2^1$-en-$5^3$-yl)carbamate (36.0 mg, 71%) as a solid. LCMS (ESI): m/z $[M+H]^+$=461.

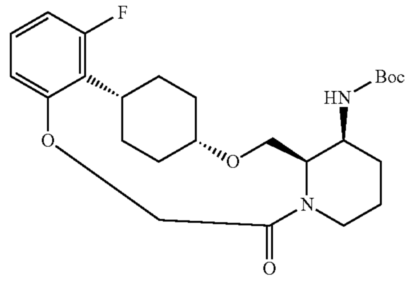 [SMILES: CC(C)(C)OC(=O)N[C@H]1CCCN2C(=O)COc3cccc(F)c3[C@H]3CC[C@H](CC3)OC[C@@H]12]

The mixture of tert-butyl (($5^2$R,$5^3$S,E)-$1^6$-fluoro-6-oxo-3,8-dioxa-5(2,1)-piperidina-1(1,2)-benzena-2(1,4)-cyclohexanacyclooctaphan-$2^1$-en-$5^3$-yl)carbamate (30.0 mg, 1.0 equiv., 65 μmol) and Pd/C (6.9 mg, 1 Eq, 65 μmol) in MeOH (6 mL) was stirred for 3 hours at room temperature under a hydrogen atmosphere. The resulting mixture was filtered, then the filter cake was washed with MeOH (3×3 mL). The filtrate was concentrated under reduced pressure to afford tert-butyl (($2^1$S,$2^4$S,$5^2$R,$5^3$S)-$1^6$-fluoro-6-oxo-3,8-dioxa-5(2,1)-piperidina-1(1,2)-benzena-2(1,4)-cyclohexanacyclooctaphane-$5^3$-yl)carbamate (28.0 mg, 93%) as a solid. LCMS (ESI): m/z $[M+H]^+$=463.

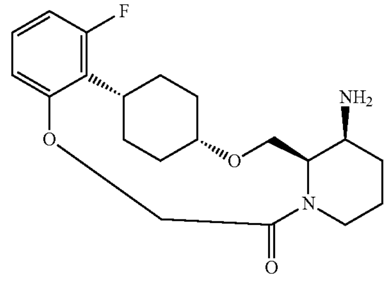 [SMILES: N[C@H]1CCCN2C(=O)COc3cccc(F)c3[C@H]3CC[C@H](CC3)OC[C@@H]12]

The mixture of tert-butyl (($2^1$S,$2^4$S,$5^2$R,$5^3$S)-$1^6$-fluoro-6-oxo-3,8-dioxa-5(2,1)-piperidina-1(1,2)-benzena-2(1,4)-cyclohexanacyclooctaphane-$5^3$-yl)carbamate (28.0 mg, 1.0 equiv., 61 μmol) in TFA (1.25 mL) and dichloromethane (5 mL) was stirred for 1 hour at room temperature. The resulting mixture was concentrated under reduced pressure to afford ($2^1$S,$2^4$S,$5^2$R,$5^3$S)-$5^3$-amino-$1^6$-fluoro-3,8-dioxa-5(2,1)-piperidina-1(1,2)-benzena-2(1,4)-cyclohexanacyclooctaphan-6-one (20.0 mg, 91%) as a solid. LCMS (ESI): m/z $[M+H]^+$=363.

(Compound 95)

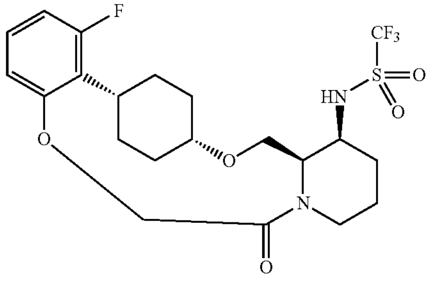

To a solution of ($2^1$S,$2^4$S,$5^2$R,$5^3$S)-$5^3$-amino-$1^6$-fluoro-3,8-dioxa-5(2,1)-piperidina-1(1,2)-benzena-2(1,4)-cyclohexanacyclooctaphan-6-one (2.00 g, 1.0 equiv., 5.52 mmol) and diisopropylethylamine (1.44 mL, 1.5 equiv., 8.28 mmol) in dichloromethane (80 mL) was added $Tf_2O$ (1.21 mL, 1.3 equiv., 7.17 mmol) in dichloromethane (0.2 mL) dropwise at −40 degrees C. The resulting mixture was stirred for 2 hours at −40 degrees C. The mixture was concentrated under reduced pressure and extracted with ethyl acetate (3×300 mL). The combined organic layers were washed with brine, dried over anhydrous $Na_2SO_4$. After filtration, the filtrate was concentrated under reduced pressure. The crude was triturated with ethyl acetate (50 ml) and finally dried under high vacuum to afford 1,1,1-trifluoro-N-(($2^1$S,$2^4$S,$5^2$R,$5^3$S)-$1^6$-fluoro-6-oxo-3,8-dioxa-5(2,1)-piperidina-1(1,2)-benzena-2(1,4)-cyclohexanacyclooctaphane-$5^3$-yl)methanesulfonamide (2.2 g, 4.2 mmol, 75%) as a solid. The isomer mixtures were purified by chiral prep-HPLC to provide pure enantiomers as a white solid. LCMS (ESI): m/z $[M+H]^+$=495; $^1$H NMR (400 MHz, DMSO-$d_6$) δ 9.72 (s, 1H), 7.17 (td, J=8.3, 6.6 Hz, 1H), 6.84-6.63 (m, 2H), 5.32 (d, J=10.4 Hz, 1H), 4.98 (dt, J=10.5, 4.5 Hz, 1H), 4.00 (d, J=10.4 Hz, 1H), 3.86 (dd, J=11.2, 9.2 Hz, 1H), 3.67 (s, 2H), 3.63-3.51 (m, 1H), 3.37 (dd, J=9.1, 3.7 Hz, 1H), 3.28 (m, 1H), 3.05 (m, 1H), 2.58 (m, 1H), 2.22 (m, 1H), 2.17-2.05 (m, 1H), 1.75 (m, 4H), 1.63-1.49 (m, 1H), 1.49-1.39 (m, 1H), 1.30 (m, 2H), 1.13 (m, 1H).

Example 1.18

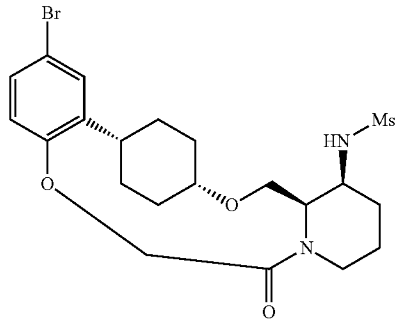 [SMILES: CS(=O)(=O)N[C@H]1CCCN2C(=O)COc3ccc(Br)cc3[C@H]3CC[C@H](CC3)OC[C@@H]12]

To a solution of N-(($2^1$S,$2^4$S,$5^2$R,$5^3$S)-6-oxo-3,8-dioxa-5(2,1)-piperidina-1(1,2)-benzena-2(1,4)-cyclohexanacyclooctaphane-$5^3$-yl)methanesulfonamide (4.00 g, 1.0 equiv., 9.0 mmol) in MeCN (40 mL) and THF (40 mL) was added N-bromosuccinimide (3.37 g, 2.0 equiv., 0.02 mol). The resulting mixture was stirred for 18 hours at 25 degrees C. The reaction was quenched by the addition of saturated aqueous ammonium chloride at 0 degrees C. The resulting mixture was extracted with ethyl acetate (3*40 mL). The combined organic layers were washed with brine, dried over anhydrous $Na_2SO_4$, after filtration, the filtrate was concentrated under reduced pressure. The crude was purified by flash chromatography to afford N-(($2^1$S,$2^4$S,$5^2$R,$5^3$S)-$1^5$-bromo-6-oxo-3,8-dioxa-5(2,1)-piperidina-1(1,2)-benzena-2(1,4)-cyclohexanacyclooctaphane-$5^3$-yl)methanesulfonamide (4.7 g, 9.4 mmol, 100%) as a solid. LCMS (ESI): m/z $[M+H]^+$=502; $^1$H NMR (400 MHz, DMSO-$d_6$) δ 7.33 (dd, J=8.5, 2.5 Hz, 1H), 7.28 (d, J=2.6 Hz, 1H), 7.23 (d, J=6.8 Hz, 1H), 6.81 (d, J=8.6 Hz, 1H), 5.31 (m, 1H), 4.98 (m, 1H), 3.95 (m, 1H), 3.84-3.75 (m, 1H), 3.65 (m, 2H), 3.41 (m, 2H), 3.26 (m, 1H), 2.96 (s, 3H), 2.57 (m, 6H), 2.19 (m, 1H), 2.09 (m, 1H), 1.75 (m, 2H), 1.68 (m, 1H), 1.64-1.49 (m, 2H), 1.34 (s, 1H), 1.27 (m, 1H), 1.17 (m, 1H).

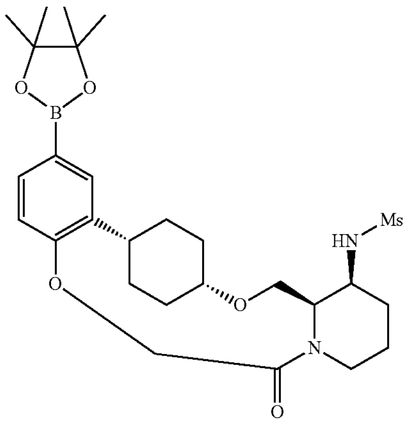 [SMILES: CC1(C)OB(c2ccc3c(c2)[C@H]2CC[C@H](CC2)OC[C@H]2[C@@H](NS(C)(=O)=O)CCCN2C(=O)CO3)OC1(C)C]

To a solution of N-(($2^1$S,$2^4$S,$5^2$R,$5^3$S)-$1^5$-bromo-6-oxo-3,8-dioxa-5(2,1)-piperidina-1(1,2)-benzena-2(1,4)-cyclohexanacyclooctaphane-$5^3$-yl)methanesulfonamide (2.50 g, 1.0 equiv., 4.99 mmol) and 4,4,4',4',5,5,5',5'-octamethyl-2,2'-bi(1,3,2-dioxaborolane) (1.90 g, 1.5 equiv., 7.48 mmol) in 1,4-dioxane (50 mL) was added KOAc (1.47 g, 3.0 equiv., 15.0 mmol), $Pd_2(dba)_3$ (457 mg, 0.1 equiv., 499 μmol) and XPhos (475 mg, 0.2 equiv., 997 μmol). The resulting mixture was stirred for 3.5 hours at 100 degrees C. under nitrogen atmosphere. The resulting mixture was concentrated under reduced pressure to afford the crude product. The crude was purified by flash chromatography to afford N-(($2^1$S,$2^4$S,$5^2$R,$5^3$S)-6-oxo-15-(4,4,5,5-tetramethyl-1,3,2-dioxaborolan-2-yl)-3,8-dioxa-5(2,1)-piperidina-1(1,2)-benzena-2(1,4)-cyclohexanacyclooctaphane-$5^3$-yl)methanesulfonamide (2.2 g, 4.0 mmol, 80%) as a solid. LCMS (ESI): m/z $[M+H]^+$=549.

(Compound 96)

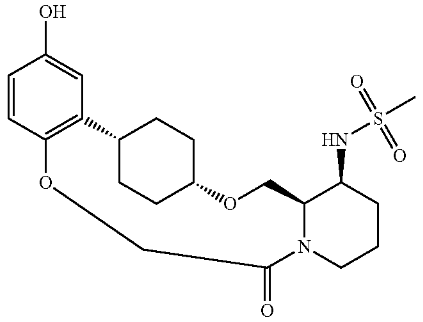

To a stirred mixture of N-((2'S,$2^4$S,$5^2$R,$5^3$S)-6-oxo-15-(4,4,5,5-tetramethyl-1,3,2-dioxaborolan-2-yl)-3,8-dioxa-5(2,1)-piperidina-1(1,2)-benzena-2(1,4)-cyclohexanacyclooctaphane-$5^3$-yl)methanesulfonamide (2.20 g, 1.0 equiv., 4.01 mmol) in 1,4-dioxane (25 mL) was added hydrogen peroxide (30% Wt, 20 equiv., 80.2 mmol) dropwise at 0 degrees C. The resulting mixture was stirred for 4 hours at 25 degrees C. The reaction was quenched by the addition of saturated $NaHSO_3$ at 0 degrees C. The resulting mixture was extracted with ethyl acetate (3*100 mL). The combined organic layers were washed with brine, dried over anhydrous $Na_2SO_4$, after filtration, the filtrate was concentrated under reduced pressure. The crude was purified by reverse flash chromatography to afford N-(($2^1$S,$2^4$S,$5^2$R,$5^3$S)-$1^5$-hydroxy-6-oxo-3,8-dioxa-5(2,1)-piperidina-1(1,2)-benzena-2(1,4)-cyclohexanacyclooctaphane-$5^3$-yl)methanesulfonamide (1.2 g, 2.7 mmol, 68%) as a solid. LCMS (ESI): m/z $[M+H]^+$=439; $^1$H NMR (400 MHz, DMSO-$d_6$) δ 8.85 (s, 1H), 7.22 (d, J=6.8 Hz, 1H), 6.65 (d, J=8.4 Hz, 1H), 6.54-6.47 (m, 2H), 5.21 (m, 1H), 4.97 (m, 1H), 3.85 (d, J=10.8 Hz, 1H), 3.77 (m, 1H), 3.46-3.37 (m, 2H), 3.26 (m, 1H), 2.96 (s, 3H), 2.68-2.56 (m, 1H), 2.38 (m, 1H), 2.19-2.02 (m, 2H), 1.75 (m, 2H), 1.69-1.51 (m, 3H), 1.42-1.10 (m, 5H).

Example 1.19

(Compound 100)

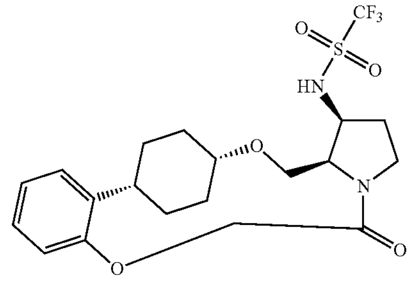

To a stirred mixture of (2'S, $2^4$S, $5^2$R, $5^3$S)-$5^3$-amino-3, 8-dioxa-5(2,1)-pyrrolidina-1(1,2)-benzena-2(1,4)-cyclohexanacyclooctaphan-6-one (1.4 g, 1.0 equiv., 4.2 mmol) and TEA (0.89 mL, 1.5 equiv., 6.4 mmol) in DCM (20 mL) was added a solution of trifluoromethanesulfonic anhydride (1.4 g, 1.2 equiv., 5.1 mmol) in DCM (5 mL) dropwise at −78 degrees C. under nitrogen atmosphere. The resulting mixture was stirred for 40 minutes at −78 degrees C. The reaction was quenched by the addition of $NaHCO_3$ (aq) at 0 degrees C. The resulting mixture was extracted with dichloromethane (3*20 mL). The combined organic layers were washed with brine, and dried over anhydrous $Na_2SO_4$. After filtration, the filtrate was concentrated under reduced pressure. The crude was purified by reverse flash chromatography to afford 1,1,1-trifluoro-N-(($2^1$S, $2^4$S, $5^2$R, $5^3$S)-6-oxo-3,8-dioxa-5(2,1)-pyrrolidina-1(1,2)-benzena-2(1,4)-cyclohexanacyclooctaphane-$5^3$-yl)methanesulfonamide (1.5 g, 3.2 mmol, 77%) as a solid. LCMS (ESI): m/z $[M+H]^+$= 463; $^1$H NMR (400 MHz, Chloroform-d) δ 7.20 (td, J=7.7, 1.7 Hz, 1H), 7.10 (dd, J=7.4, 1.8 Hz, 1H), 6.94 (dd, J=8.0, 6.8 Hz, 1H), 6.82 (d, J=8.0 Hz, 1H), 6.63 (d, J=8.9 Hz, 1H), 5.07 (d, J=10.7 Hz, 1H), 4.56 (dd, J=8.3, 2.7 Hz, 1H), 4.46-4.44 (m, 2H), 4.27 (d, J=10.6 Hz, 1H), 4.13 (dt, J=10.6, 7.6 Hz, 1H), 3.89 (d, J=4.0 Hz, 1H), 3.72 (dt, J=10.6, 6.3 Hz, 1H), 3.38 (d, J=9.8 Hz, 1H), 2.62-2.46 (m, 2H), 2.35-2.23 (m, 2H), 2.19-2.00 (m, 2H), 1.88-1.80 (m, 1H), 1.63-1.50 (m, 2H), 1.40-1.37 (m, 2H).

Example 1.20

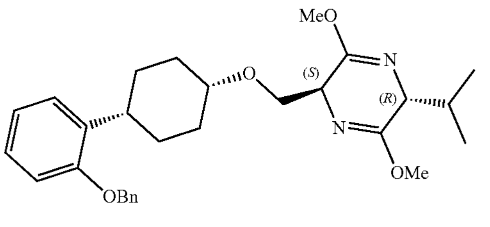

To a stirred solution of (R)-2-isopropyl-3,6-dimethoxy-2, 5-dihydropyrazine (5.0 g, 1.5 equiv., 0.03 mol) and DMPU (7.0 mL, 3.0 equiv., 0.05 mol) in THF (50 mL) was added n-butyllithium (2.0 g, 1.5 equiv., 0.03 mol) in portions at −78 degrees C. under $N_2$ atmosphere. To the above mixture was added 1-(benzyloxy)-2-((1s,4s)-4-(chloromethoxy)cyclohexyl)benzene (6.0 g, 1.0 equiv., 0.02 mol) in portions over 3 hours at −78 degrees C. The resulting mixture was stirred for an additional 4 hours at −78 degrees C. The resulting mixture was extracted with EtOAC (3*80 mL). The combined organic layers were washed with brine (3*50 mL), and dried over anhydrous $Na_2SO_4$. After filtration, the filtrate was concentrated under reduced pressure. The residue was purified by reverse flash chromatography to provide (2S, 5R)-2-((((1s,4R)-4-(2-(benzyloxy)phenyl)cyclohexyl)oxy) methyl)-5-isopropyl-3,6-dimethoxy-2,5-dihydropyrazine (5.6 g, 12 mmol, 60%) as an oil. LCMS (ESI): m/z $[M+H]^+$= 479.

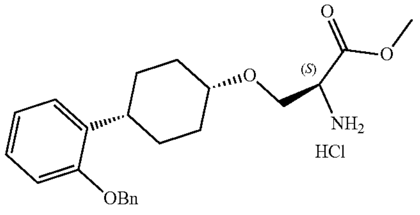

To a solution of (2S,5R)-2-((((1s,4R)-4-(2-(benzyloxy) phenyl)cyclohexyl)oxy)methyl)-5-isopropyl-3,6-dimethoxy-2,5-dihydropyrazine, 2,5-dihydropyrazine (5.2 g, 1.0 equiv., 10 mmol) in acetonitrile (72 mL) was added HCl (30%) (72 mL) and the resulting mixture was stirred for 2 hours at 40 degrees C. The crude was purified by reverse flash chromatography to afford methyl O-((1s,4R)-4-(2-(benzyloxy)phenyl)cyclohexyl)-L-serinate, HCl (3.8 g, 90%) as an oil.

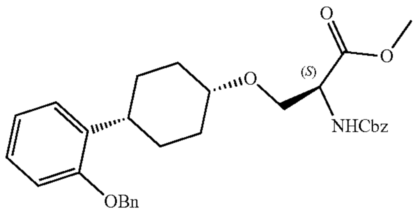

To a solution of methyl O-((1s,4R)-4-(2-(benzyloxy)phenyl)cyclohexyl)-L-serinate, HCl (3.8 g, 1.0 equiv., 9.0 mmol) and $NaHCO_3$(aq) (40 mL) in THF (40 mL) was added benzyl carbonochloridate (1.9 g, 1.2 equiv., 11 mmol). The resulting mixture was stirred for 2 hours at 25 degrees C. The resulting mixture was extracted with dichloromethane (3*50 mL). The combined organic layers were washed with brine, and dried over anhydrous $Na_2SO_4$. After filtration, the filtrate was concentrated under reduced pressure. The crude was purified by flash chromatography to afford methyl N-((benzyloxy)carbonyl)-O-((1s,4R)-4-(2-(benzyloxy)phenyl)cyclohexyl)-L-serinate (3.23 g, 69%) as an oil. LCMS (ESI): m/z $[M+H]^+$=518.

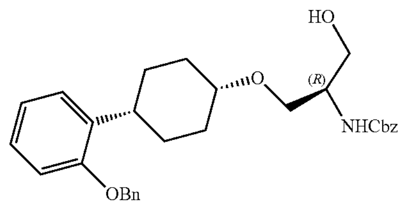

To a stirred mixture of methyl N-((benzyloxy)carbonyl)-O-((1s,4R)-4-(2-(benzyloxy)phenyl)cyclohexyl)-L-serinate (3.0 g, 1.0 equiv., 6 mmol) in diethyl ether (150 mL) was added $LiAlH_4$ (0.3 g, 1.5 equiv., 9 mmol) at −20 degrees C. under nitrogen atmosphere. The resulting mixture was stirred for 18 hours at −20 degrees C. To the above mixture was added THF at −20 degrees C. The resulting mixture was stirred for an additional 10 minutes at −20 degrees C. The reaction was quenched by the addition of $Na_2SO_4 \cdot 10H_2O$ at −20 degrees C. The resulting mixture was stirred for an additional 10 minutes. The resulting mixture was filtered and extracted with ethyl acetate. The combined organic layers were washed with brine, and dried over anhydrous $Na_2SO_4$. After filtration, the filtrate was concentrated under reduced pressure. The crude was purified by flash chromatography to afford benzyl ((R)-1-(((1s,4S)-4-(2-(benzyloxy)phenyl)cyclohexyl)oxy)-3-hydroxypropan-2-yl)carbamate (2.1 g, 70%) as an oil. LCMS (ESI): m/z $[M+H]^+$=490.

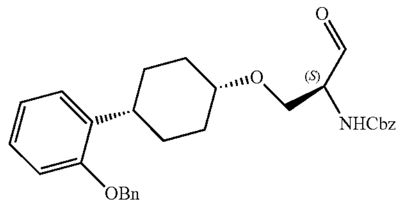

To a solution of benzyl ((R)-1-(((1s,4S)-4-(2-(benzyloxy) phenyl)cyclohexyl)oxy)-3-hydroxypropan-2-yl)carbamate (1.9 g, 1.0 equiv., 3.9 mmol) in dichloromethane (80 mL) was added Dess-Martin periodinane (2.0 g, 1.2 equiv., 4.7 mmol). The resulting mixture was stirred f or 3 hours at 25 degrees C. The resulting mixture was diluted with dichloromethane (3*20 ml). The crude was purified by flash chromatography to afford tert-butyl ((S)-1-(((1s,4R)-4-(2-(benzyloxy)phenyl)cyclohexyl)oxy)-3-oxopropan-2-yl)carbamate (1.4 g, 3.1 mmol, 80%) as a solid. LCMS (ESI): m/z $[M+H]^+$=488.

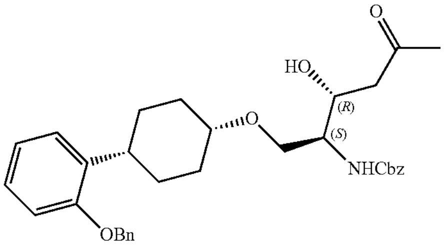

To a stirred mixture of lithium diisopropylethylamide (0.91 g, 2.5 equiv., 8.5 mmol) in THF (2 mL) was added a solution of propan-2-one (0.20 g, 1.0 equiv., 3.4 mmol) dropwise at −78 degrees C. under nitrogen atmosphere. The resulting mixture was stirred for 1 hour at −78 degrees C. To the above mixture was added a solution of benzyl ((S)-1-oxo-3-(((1s,4R)-4-phenylcyclohexyl)oxy)propan-2-yl)carbamate (1.3 g, 1.0 equiv., 3.4 mmol) in THF (2 mL) dropwise at −78 degrees C. under nitrogen atmosphere. The resulting mixture was stirred for an additional 1 hour at −78 degrees C. The reaction was warmed to room temperature and quenched with 5 ml of saturated $NH_4Cl$ at 0 degrees C. The resulting mixture was extracted with ethyl acetate (3*5 mL). The combined organic layers were washed with brine, and dried over anhydrous $Na_2SO_4$. After filtration, the filtrate was concentrated under reduced pressure. The crude was purified by flash chromatography to afford benzyl ((2S)-1-(((1s,4R)-4-(2-(benzyloxy)phenyl)cyclohexyl)oxy)-3-hydroxy-5-oxohexan-2-yl)carbamate (500 mg, 916 μmol, 27%) as an oil. LCMS (ESI): m/z $[M+H]^+$=546.

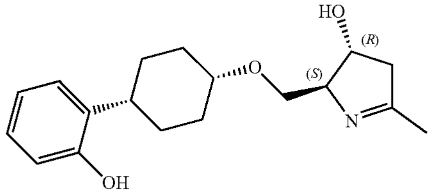

To a solution of benzyl ((2S)-1-(((1s,4R)-4-(2-(benzyloxy)phenyl)cyclohexyl)oxy)-3-hydroxy-5-oxohexan-2-yl) carbamate (0.5 g, 1.0 equiv., 0.9 mmol) in i-PrOH (50 mL) was added Pd/C (0.3 g, 10% Wt, 0.3 Eq, 0.3 mmol) at nitrogen atmosphere. The resulting mixture was hydrogenated at room temperature under hydrogen atmosphere using a hydrogen balloon, filtered through a Celite® pad and concentrated under reduced pressure to afford the crude product. The crude product was used in the next step directly without further purification. LCMS (ESI): m/z $[M+H]^+$=304.

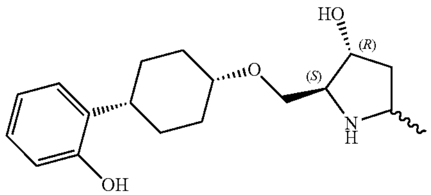

To a solution of (2S,3R)-2-((((1s,4R)-4-(2-hydroxyphenyl)cyclohexyl)oxy)methyl)-5-methyl-3,4-dihydro-2H-pyrrol-3-ol (0.5 g, 1.0 equiv., 2 mmol) in i-PrOH (30 mL) was added $NaBH(OAc)_3$ (2.0 equiv., 1.8 mmol). The resulting mixture was stirred for 3 hours at 25 degrees C. The resulting mixture was concentrated under reduced pressure to afford the crude product. The crude product was used in the next step directly without further purification. LCMS (ESI): m/z $[M+H]^+$=306.

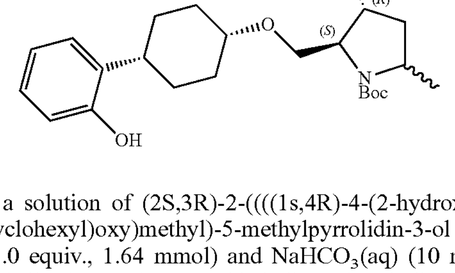

To a solution of (2S,3R)-2-((((1s,4R)-4-(2-hydroxyphenyl)cyclohexyl)oxy)methyl)-5-methylpyrrolidin-3-ol (500 mg, 1.0 equiv., 1.64 mmol) and $NaHCO_3$(aq) (10 mL) in acetonitrile (30 mL) was added di-tert-butyl dicarbonate (536 mg, 1.5 equiv., 2.46 mmol). The resulting mixture was stirred for 3 hours at 25 degrees C. The resulting mixture was extracted with ethyl acetate (3*10 mL). The combined organic layers were washed with brine, and dried over anhydrous $Na_2SO_4$. After filtration, the filtrate was concentrated under reduced pressure. The crude was purified by reverse flash chromatography to afford tert-butyl (2R,3R)-3-hydroxy-2-((((1s,4S)-4-(2-hydroxyphenyl)cyclohexyl)oxy)methyl)-5-methylpyrrolidine-1-carboxylate (210 mg, 518 μmol, 31.6%) as a solid. LCMS (ESI): m/z $[M+H]^+$=406.

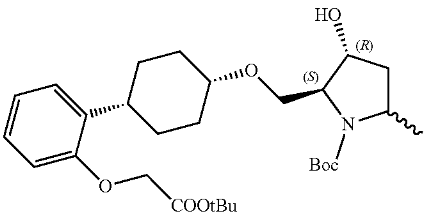

To a solution of tert-butyl (2S,3R)-3-hydroxy-2-((((1s,4R)-4-(2-hydroxyphenyl)cyclohexyl)oxy)methyl)-5-methylpyrrolidine-1-carboxylate (210 mg, 1.0 equiv., 518 μmol) and tert-butyl 2-bromoacetate (121 mg, 1.2 equiv., 621 μmol) in acetonitrile (5 mL) was added $K_2CO_3$ (143 mg, 2.0 equiv., 1.04 mmol). The resulting mixture was stirred for 3 days at 25 degrees C. The residue was purified by Prep-TLC to afford tert-butyl (2S,3R)-2-((((1s,4R)-4-(2-(2-(tert-butoxy)-2-oxoethoxy)phenyl)cyclohexyl)oxy)methyl)-3-hydroxy-5-methylpyrrolidine-1-carboxylate (195 mg, 375 μmol, 72.5%) as a semi-solid. $^1$H NMR (400 MH z, Methanol-$d_4$) δ 7.83 (d, J=5.2 Hz, 1H), 6.85 (d, J=5.2 Hz, 1H), 4.98 (d, J=10.7 Hz, 1H), 4.61 (d, J=10.8 Hz, 1H), 4.38 (dd, J=7.9, 3.4 Hz, 1H), 4.23-4.08 (m, 3H), 3.82 (s, 1H), 3.73 (m, 1H), 3.52 (d, J=9.1 Hz, 1H), 3.04-3.00 (m, 4H), 2.60-2.57 (m, 1H), 2.50-2.37 (m, 1H), 2.35 (s, 3H), 2.34-2.23 (m, 1H), 2.23-2.12 (m, 2H), 1.92 (m, 1H), 1.63-1.51 (m, 1H), 1.45-1.34 (m, 2H), 1.22-1.14 (m, 1H). LCMS (ESI): m/z $[M+H]^+$= 519.

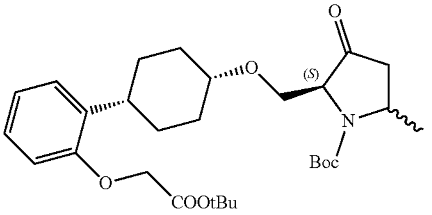

To a solution of tert-butyl (2S,3R)-2-((((1s,4R)-4-(2-(2-(tert-butoxy)-2-oxoethoxy)phenyl)cyclohexyl)oxy)methyl)-3-hydroxy-5-methylpyrrolidine-1-carboxylate (190 mg, 1.0 equiv., 366 μmol) in dichloromethane (10 mL) was added Dess-Martin periodinane (310 mg, 2.0 equiv., 731 μmol). The resulting mixture was stirred for 2 hours at 25 degrees C. The residue was purified by Prep-TLC to afford tert-butyl (2S)-2-((((1s,4R)-4-(2-(2-(tert-butoxy)-2-oxoethoxy)phenyl)cyclohexyl)oxy)methyl)-5-methyl-3-oxopyrrolidine-1-carboxylate (130 mg, 251 μmol, 68.7%) as a solid. LCMS (ESI): m/z $[M+H]^+$=518.

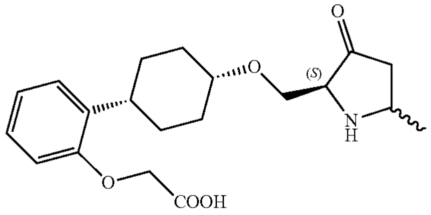

To a solution of tert-butyl (2S)-2-((((1s,4R)-4-(2-(2-(tert-butoxy)-2-oxoethoxy)phenyl)cyclohexyl)oxy)methyl)-5-methyl-3-oxopyrrolidine-1-carboxylate (120 mg, 1.0 equiv., 232 μmol) in dichloromethane (8 mL) was added triethylamine (4 mL). The resulting mixture was stirred for 3.5 hours at 25 degrees C. The crude product was used in the next step directly without further purification. LCMS (ESI): m/z $[M+H]^+$=362.

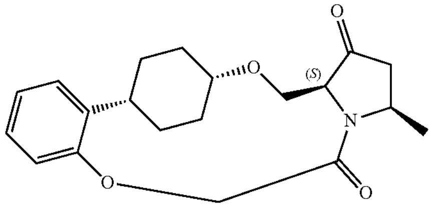

To a solution of 2-(2-((1R,4s)-4-(((2S)-5-methyl-3-oxopyrrolidin-2-yl)methoxy)cyclohexyl)phenoxy)acetic acid (100 mg, 1.0 equiv., 277 μmol) and HATU (158 mg, 1.5 equiv., 415 μmol) in acetonitrile (50 mL) was added DIEA (145 μL, 3.0 equiv., 830 μmol). The resulting mixture was stirred for 1 hour at 25 degrees C. Two peaks could be detected by LCMS. The residue was purified by Prep-TLC to afford ($2^1$R, $2^4$R, $5^2$S)-$5^5$-methyl-3,8-dioxa-5(2,1)-pyrrolidina-1(1,2)-benzena-2(1,4)-cyclohexanacyclooctaphane-$5^3$,6-dione (30 mg, 87 μmol, 32%) as a solid. LCMS (ESI): m/z $[M+H]^+$=344; $^1$H NMR (400 MHz, Chloroform-d) δ 7.21 (td, J=7.7, 1.8 Hz, 1H), 7.11 (dd, J=7.5, 1.7 Hz, 1H), 6.95 (td, J=7.4, 1.2 Hz, 1H), 6.86 (dd, J=8.0, 1.2 Hz, 1H), 5.22 (d, J=10.6 Hz, 1H), 4.96-4.93 (m, 1H), 4.40-4.37 (m, 1H), 4.33-4.29 (m, 2H), 3.71 (s, 1H), 3.38-3.34 (m, 1H), 3.12-3.07 (m, 1H), 2.59-2.56 (m, 2H), 2.30-2.27 (m, 1H), 1.78-1.75 (m, 1H), 1.47 (d, J=6.5 Hz, 4H), 1.28-1.25 (m, 4H), 0.93-0.82 (m, 2H).

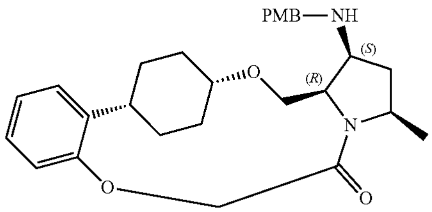

To a solution of ($2^1$R, $2^4$R, $5^2$S)-$5^5$-methyl-3,8-dioxa-5(2,1)-pyrrolidina-1(1,2)-benzena-2(1,4)-cyclohexanacyclooctaphane-$5^3$,6-dione (25 mg, 1.0 equiv., 73 μmol) and $MgSO_4$ (1.8 mg, 0.2 equiv., 15 μmol) in dichloromethane (1 mL) was added (4-methoxyphenyl)methanamine (12 mg, 1.2 equiv., 87 μmol) and sodium triacetoxyborohydride (31 mg, 2.0 equiv., 0.15 mmol). The resulting mixture was stirred for 12 hours at 25 degrees C. The residue was purified by Prep-TLC to afford ($2^1$S, $2^4$S, $5^2$R, $5^3$S)-$5^3$-((4-methoxybenzyl)amino)-$5^5$-methyl-3,8-dioxa-5(2,1)-pyrrolidina-1(1,2)-benzena-2(1,4)-cyclohexanacyclooctaphan-6-one (28 mg, 60 μmol, 83%) as a solid. LCMS (ESI): m/z $[M+H]^+$= 465.

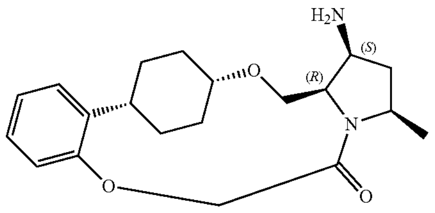

To a solution of ($2^1$S, $2^4$S, $5^2$R, $5^3$S)-$5^3$-((4-methoxybenzyl)amino)-$5^5$-methyl-3,8-dioxa-5(2,1)-pyrrolidina-1(1,2)-benzena-2(1,4)-cyclohexanacyclooctaphan-6-one (28.0 mg, 1.0 equiv., 60.3 μmol) and ammonium formate (114 mg, 90.1 μL, 30.0 equiv., 1.81 mmol) in 2-propanol (1.5 mL) was added dry-Pd/C (64.1 mg, 10% Wt, 1.0 equiv., 60.3 μmol) under $N_2$ atmosphere. The resulting mixture was stirred for 2 hours at 85 degrees C. The crude was used in the next step without further purification. LCMS (ESI): m/z $[M+H]^+$= 345.

(Compound 103)

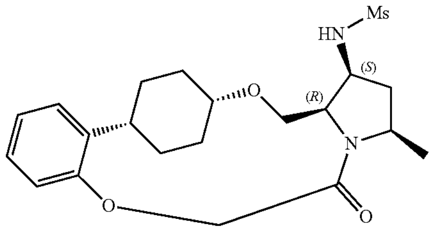

To a solution of ($2^1$S, $2^4$S, $5^2$R, $5^3$S, $5^5$R)-$5^3$-amino-$5^5$-methyl-3,8-dioxa-5(2,1)-pyrrolidina-1(1,2)-benzena-2(1,4)-cyclohexanacyclooctaphan-6-one (15 mg, 1.0 equiv., 44 μmol) in dichloromethane (1 mL) was added DIEA (17 mg, 23 μL, 3.0 equiv., 0.13 mmol) and methanesulfonic anhydride (15 mg, 2.0 equiv., 87 μmol) at room temperature. The resulting mixture was stirred for 1 hour at 20 degrees C. The residue was purified by Prep-TLC to afford N-(($2^1$S, $2^4$S, $5^2$R, $5^3$S, $5^5$R)-$5^5$-methyl-6-oxo-3,8-dioxa-5(2,1)-pyrrolidina-1(1,2)-benzena-2(1,4)-cyclohexanacyclooctaphane-$5^3$-yl)methanesulfonamide (3.0 mg, 7.0 μmol, 16%) as a solid. LCMS (ESI): m/z $[M+H]^+$=423. $^1$H NMR (400 MHz, Chloroform-d) δ 7.19 (td, J=7.7, 1.8 Hz, 1H), 7.10 (dd, J=7.4, 1.7 Hz, 1H), 6.93 (td, J=7.4, 1.1 Hz, 1H), 6.80 (dd, J=8.1, 1.2 Hz, 1H), 5.08-5.06 (m, 1H), 4.80-4.77 (m, 1H), 4.69-4.59 (m, 1H), 4.47-4.44 (m, 1H), 4.36-4.27 (m, 2H), 4.24-4.21 (m, 1H), 3.84-3.79 (m, 1H), 3.35-3.32 (m, 1H), 3.06 (s, 3H), 2.60-2.46 (m, 3H), 2.11-2.08 (m, 2H), 1.99-1.97 (m, 1H), 1.80-1.77 (m, 1H), 1.49-1.47 (m, 2H), 1.37-1.33 (m, 4H).

Example 2: Human $OX_2R$ IP1 Assay

T-Rex CHO cells stably overexpressing the human orexin-2 receptor ($OX_2R$) were induced overnight with 1 μg/mL of doxycycline in a T225 flask. 24 hours post induction, cells were lifted with accutase and plated into a 384-well proxy plate at 30,000 cells/well. Cells were then treated with different test compounds in 1× stimulation buffer containing 10 mM Hepes, 1 mM $CaCl_2$, 0.5 mM $MgCl_2$, 4.2 mM KCl, 146 mM NaCl, 5.5 mM glucose, and 50 mM LiCl, pH 7.4, for 1 hr at 37 degrees C. Following incubation, the reaction was terminated by the addition of detection mix, which is composed of IP1-d2 and anti-IP1-cryptate diluted in lysis buffer as well as 1× stimulation buffer. The plates were allowed to incubate for 1 hour at room temperature and were then read in the EnVision® multimode plate reader, measuring inositol phosphate levels.

Cisbio IP1 is a cell-based functional assay quantifying the accumulation of inositol monophosphate (IP), a metabolite released as a result of orexin 2 receptor activation through the phospholipase C-Gq signaling pathway. This is a competitive immunoassay in which the IP1 produced by the cells upon receptor activation competes with the IP1 analog coupled to the d2 fluorophore (acceptor) for binding to an anti-IP1 monoclonal antibody labeled with Eu cryptate (donor). The measured HTRF-FRET based signal is inversely proportional to the IP1 concentration produced.

The $EC_{50}$ values reported in Table 2 were obtained according to the human $OX_2R$ IP1 assay described above. Data are the mean $EC_{50}$ values ±S.E.M. Reference Compound A is methyl (2R,3S)-3-((methylsulfonyl)amino)-2-(((cis-4-phenylcyclohexyl)oxy)methyl)-piperidine-1-carboxylate (Example 5 of PCT publication No. WO2017/135306). Reference Compound B is N-((2S,3S)-1-(2-hydroxy-2-methylpropanoyl)-2-((2,3',5'-trifluorobiphenyl-3-yl)methyl)pyrrolidin-3-yl)methanesulfonamide (Example 483 of PCT publication No. WO2019/027058)

TABLE 2

| Compound | Compound No. | $EC_{50}$ (nM) |
|---|---|---|
| 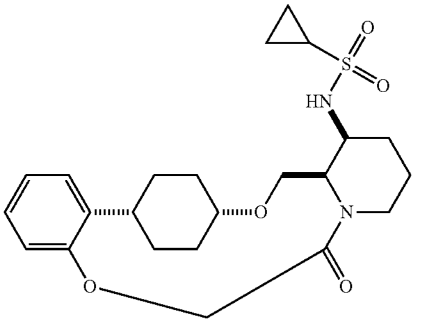 | 1 | |
| 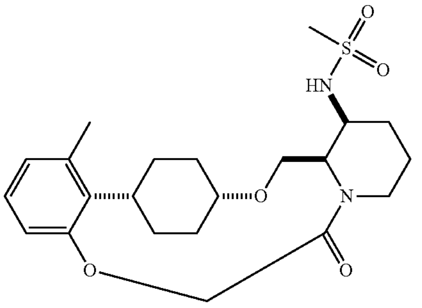 | 2 | *** |

TABLE 2-continued
| Compound | Compound No. | $EC_{50}$ (nM) |
|---|---|---|
| 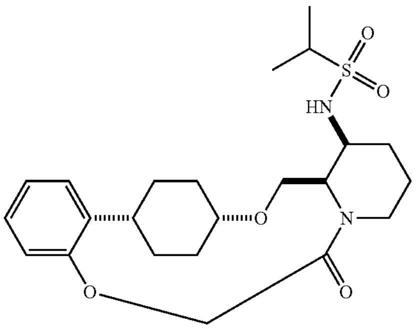 | 3 | *** |
| 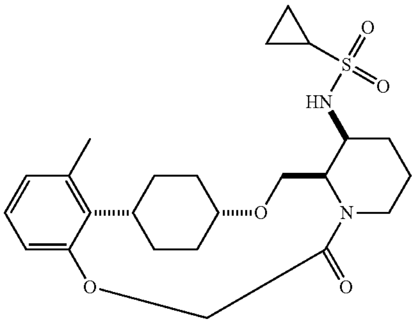 | 4 | *** |
| 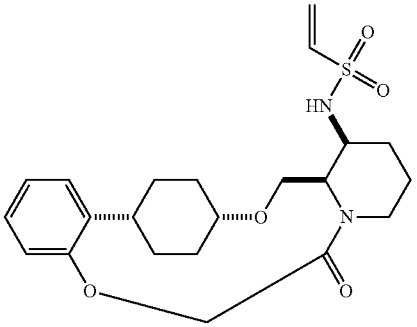 | 5 | *** |
| 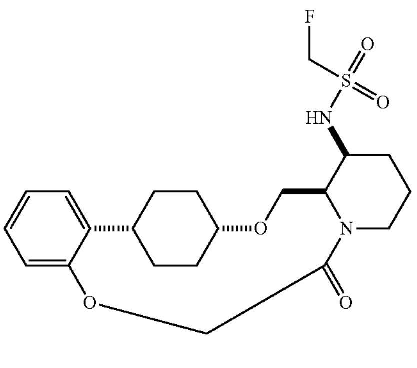 | 6 | *** |
TABLE 2-continued
| Compound | Compound No. | $EC_{50}$ (nM) |
|---|---|---|
| 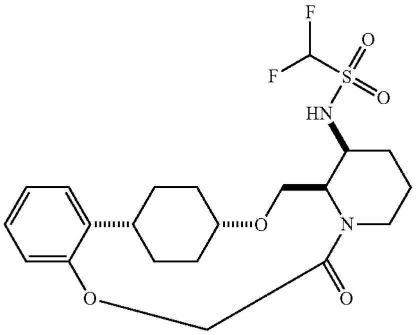 | 7 | *** |
| 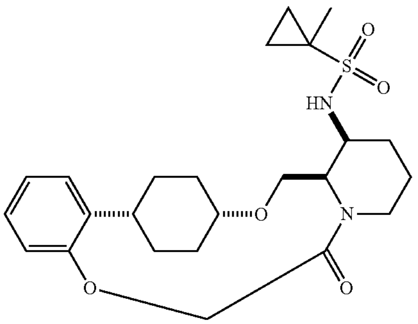 | 8 | *** |
| 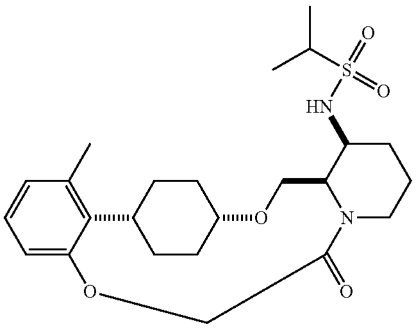 | 9 | *** |
| 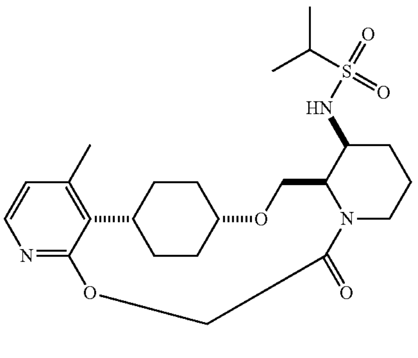 | 10 | *** |

TABLE 2-continued
| Compound | Compound No. | $EC_{50}$ (nM) |
|---|---|---|
| 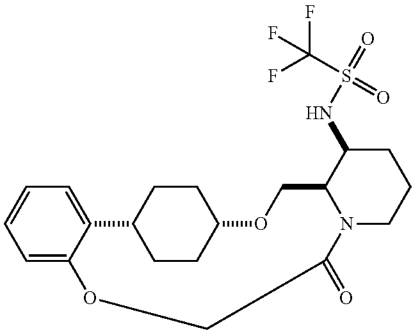 | 11 | *** |
| 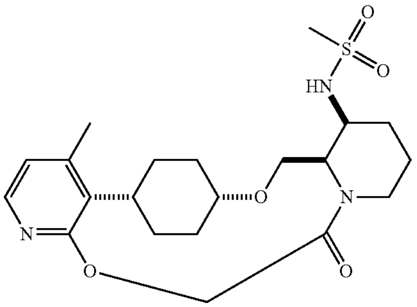 | 12 | *** |
| 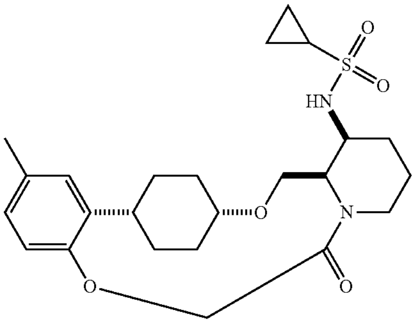 | 13 | *** |
| 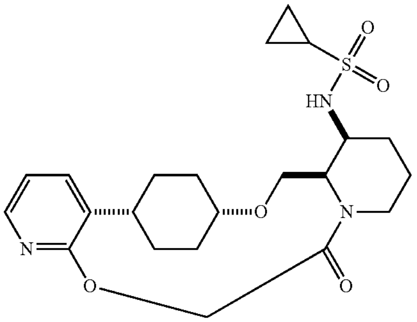 | 14 | *** |
TABLE 2-continued
| Compound | Compound No. | $EC_{50}$ (nM) |
|---|---|---|
| 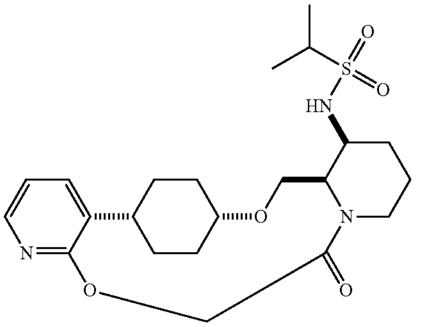 | 15 | *** |
| 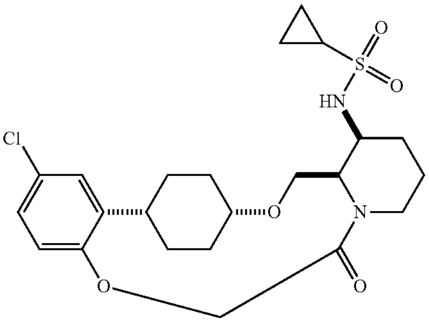 | 16 | *** |
| 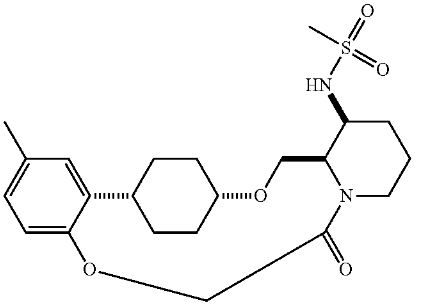 | 17 | *** |
| 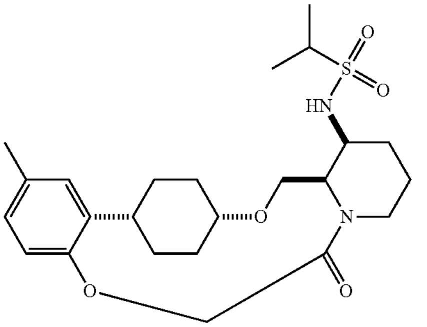 | 18 | *** |

TABLE 2-continued
| Compound | Compound No. | $EC_{50}$ (nM) |
|---|---|---|
| 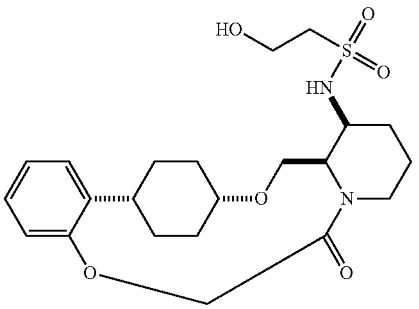 | 19 | *** |
| 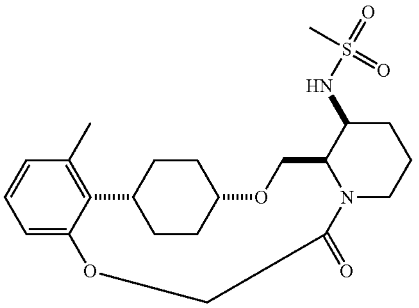 | 20 | *** |
| 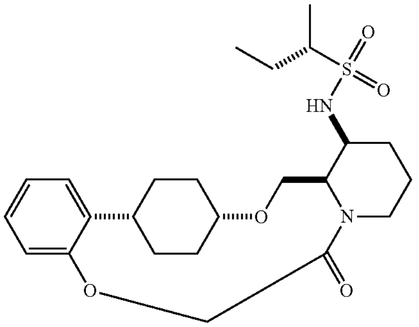 | 21 | *** |
| 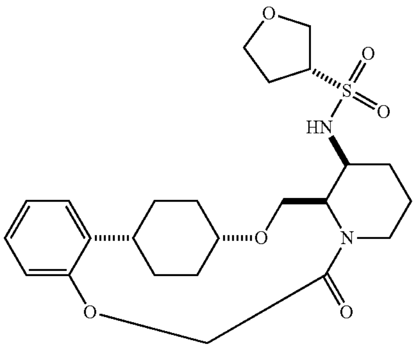 | 22 | *** |
TABLE 2-continued
| Compound | Compound No. | $EC_{50}$ (nM) |
|---|---|---|
| 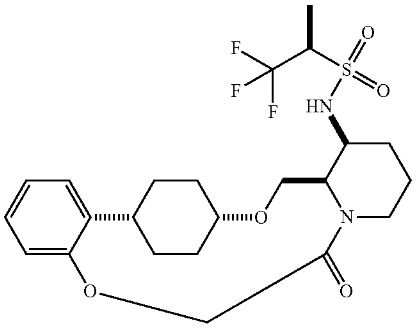 | 23 | *** |
| 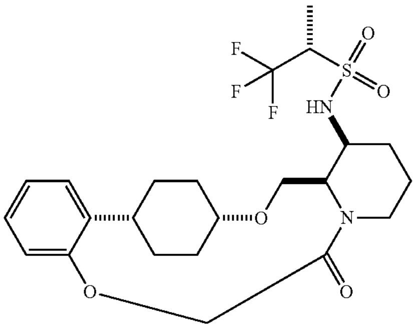 | 24 | *** |
| 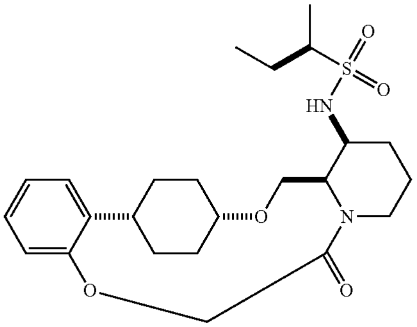 | 25 | *** |
| 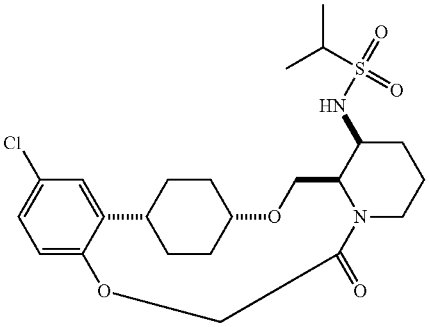 | 26 | *** |

TABLE 2-continued
| Compound | Compound No. | $EC_{50}$ (nM) |
|---|---|---|
| 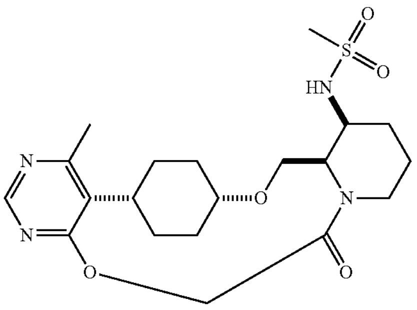 | 27 | *** |
| 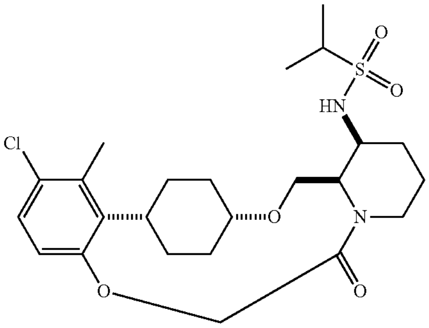 | 28 | *** |
| 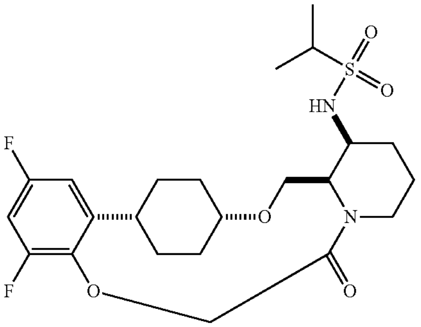 | 29 | *** |
| 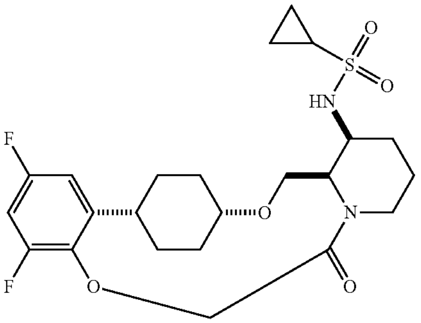 | 30 | *** |
TABLE 2-continued
| Compound | Compound No. | $EC_{50}$ (nM) |
|---|---|---|
| 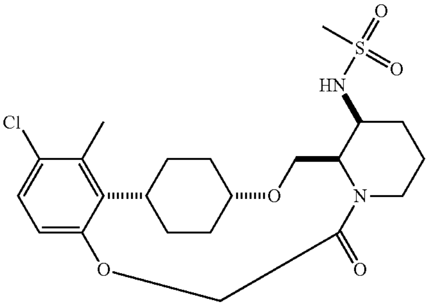 | 31 | *** |
| 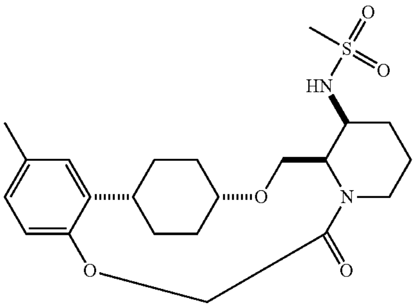 | 32 | *** |
| 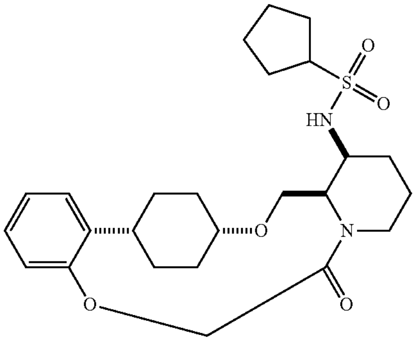 | 33 | *** |
| 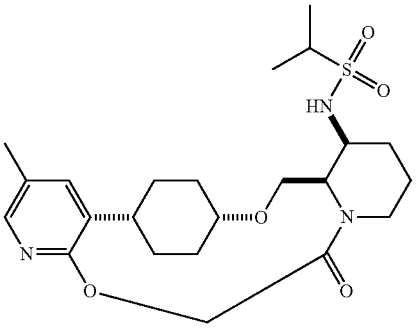 | 34 | *** |

TABLE 2-continued
| Compound | Compound No. | $EC_{50}$ (nM) |
|---|---|---|
| 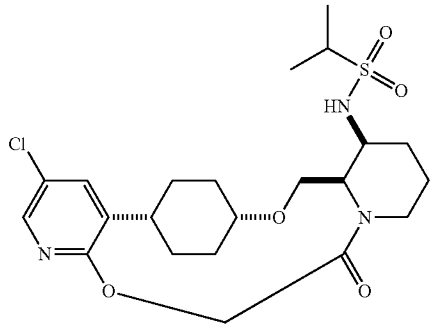 | 35 | *** |
| 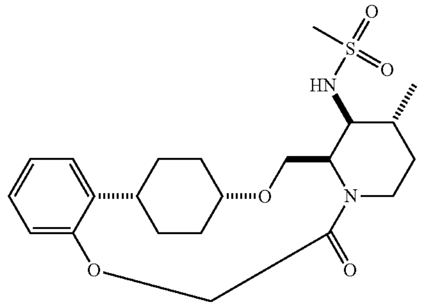 | 36 | ***^ |
| 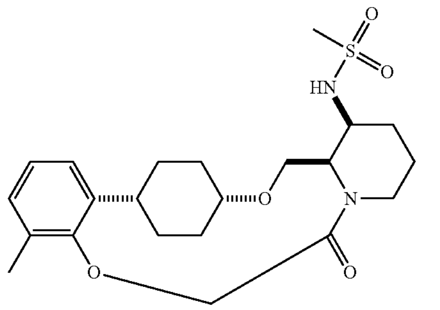 | 37 | *** |
| 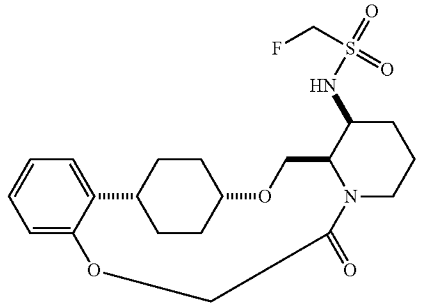 | 38 | *** |
TABLE 2-continued
| Compound | Compound No. | $EC_{50}$ (nM) |
|---|---|---|
| 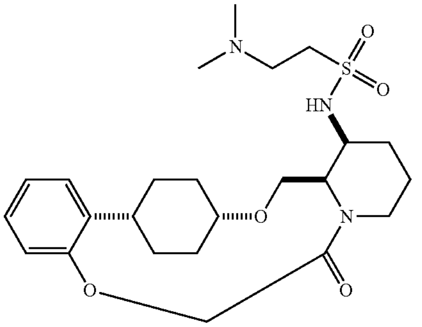 | 39 | *** |
| 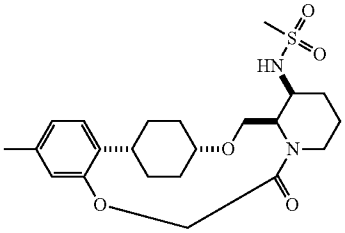 | 40 | ** |
| 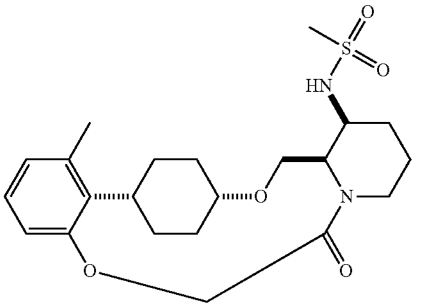 | 41 | ** |
| 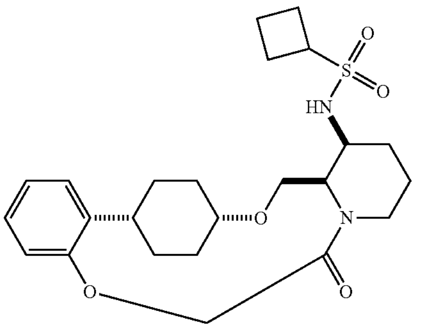 | 42 | *** |
| 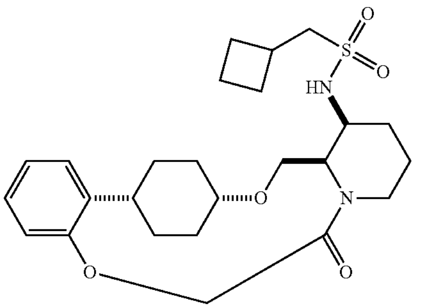 | 43 | ** |

TABLE 2-continued
| Compound | Compound No. | $EC_{50}$ (nM) |
| --- | --- | --- |
| 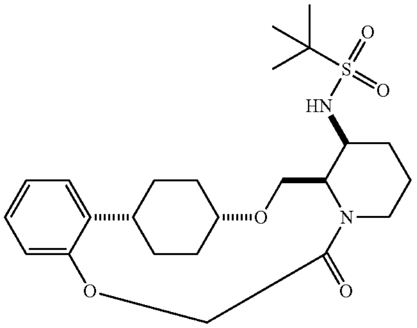 | 44 | ** |
| 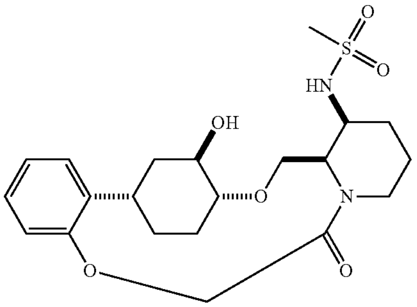 | 45 | ** |
| 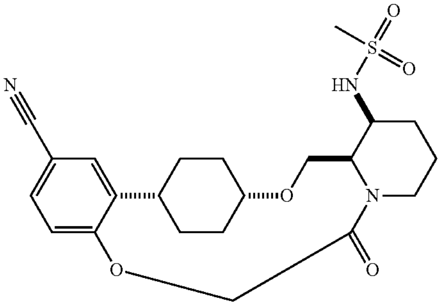 | 46 | ** |
| 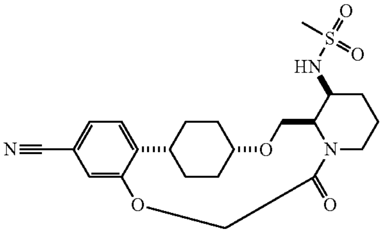 | 47 | ** |
| 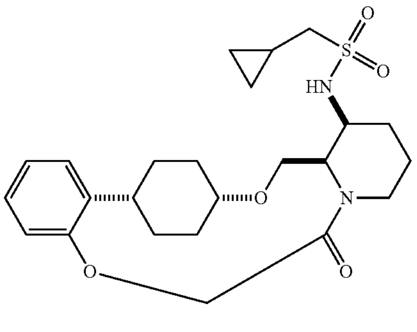 | 48 | *** |
TABLE 2-continued
| Compound | Compound No. | $EC_{50}$ (nM) |
| --- | --- | --- |
| 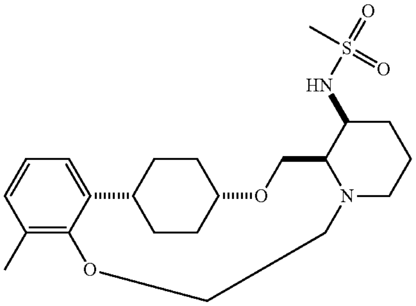 | 49 | * |
| 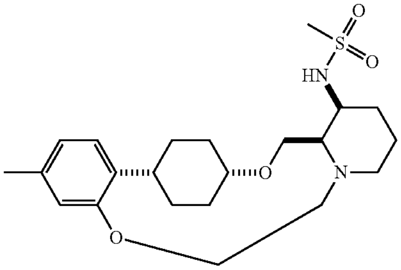 | 50 | * |
| 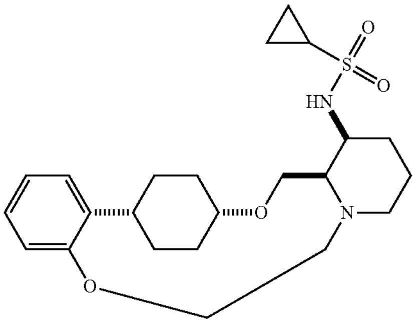 | 51 | ** |
| 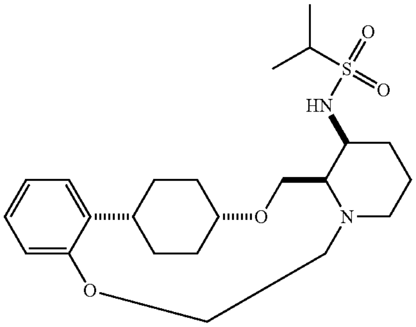 | 52 | * |
| 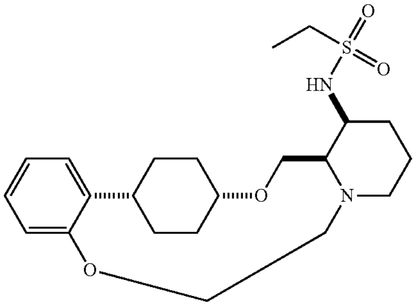 | 53 | * |

TABLE 2-continued
| Compound | Compound No. | $EC_{50}$ (nM) |
|---|---|---|
| 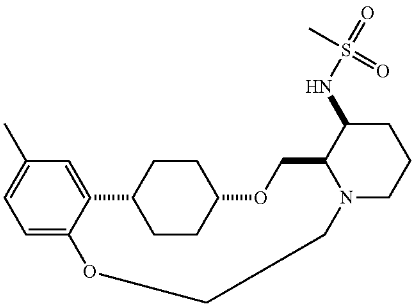 | 54 | ** |
| 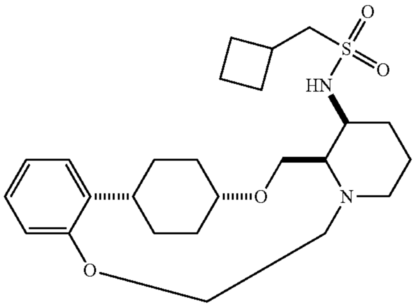 | 55 | * |
| 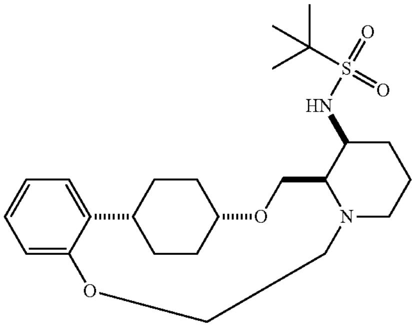 | 56 | * |
| 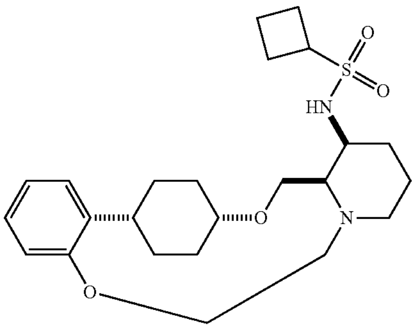 | 57 | ** |
TABLE 2-continued
| Compound | Compound No. | $EC_{50}$ (nM) |
|---|---|---|
| 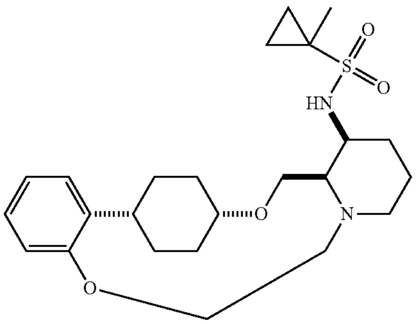 | 58 | ** |
| 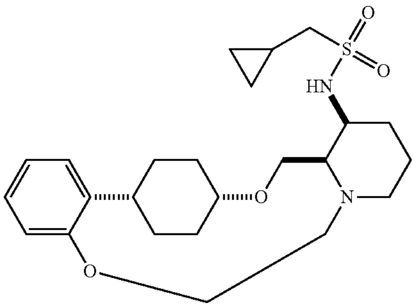 | 59 | ** |
| 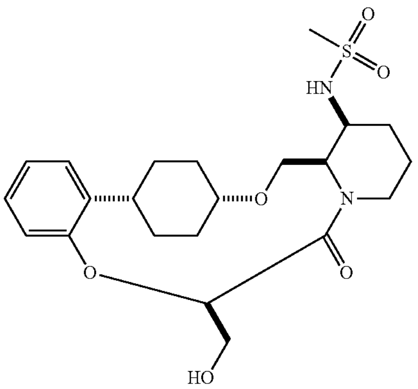 | 60 | *** |
| 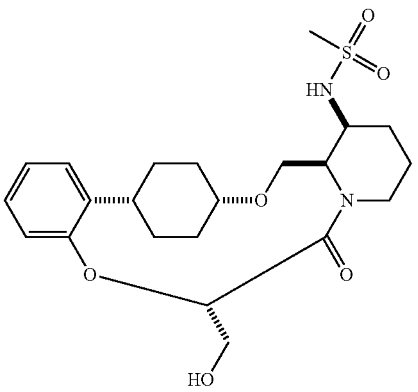 | 61 | *** |

TABLE 2-continued
| Compound | Compound No. | $EC_{50}$ (nM) |
|---|---|---|
| 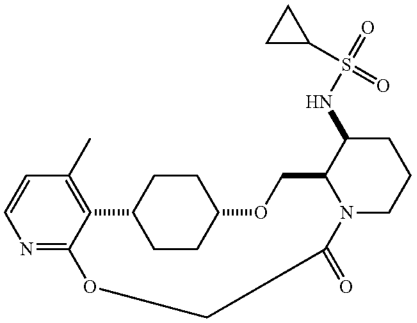 | 62 | *** |
| 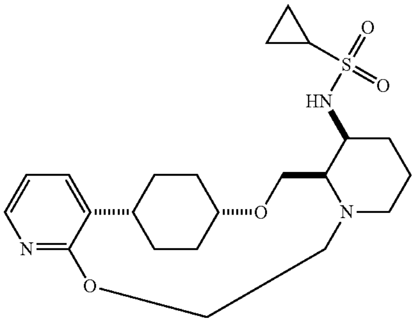 | 63 | * |
| 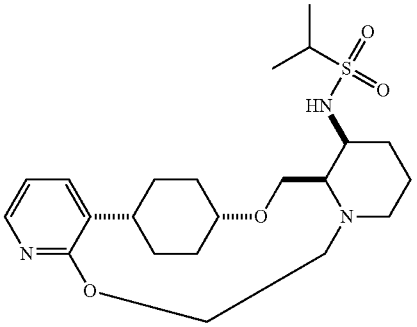 | 64 | * |
| 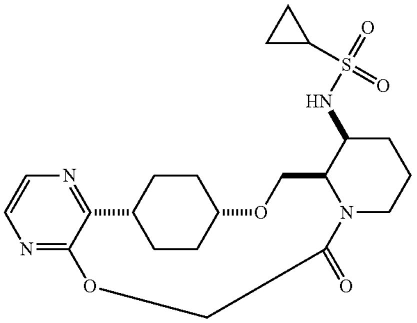 | 65 | *** |
TABLE 2-continued
| Compound | Compound No. | $EC_{50}$ (nM) |
|---|---|---|
| 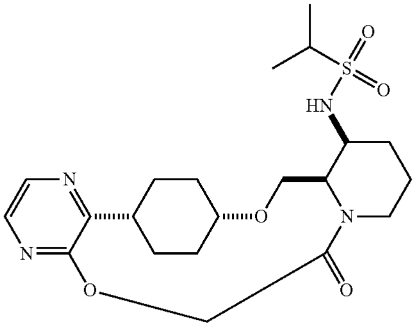 | 66 | *** |
| 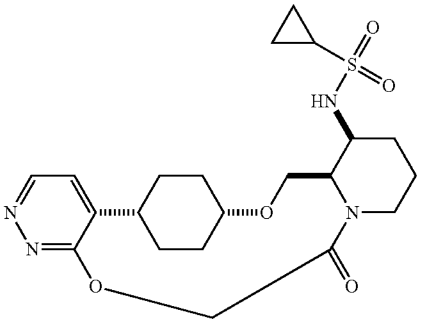 | 67 | ** |
| 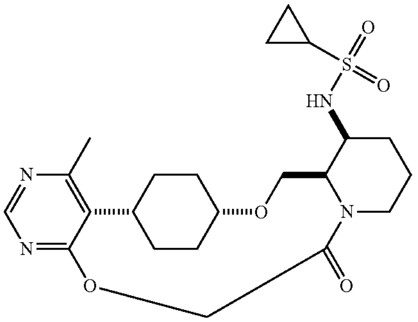 | 68 | *** |
| 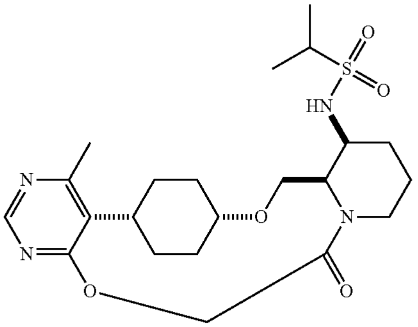 | 69 | *** |

TABLE 2-continued
| Compound | Compound No. | $EC_{50}$ (nM) |
|---|---|---|
| 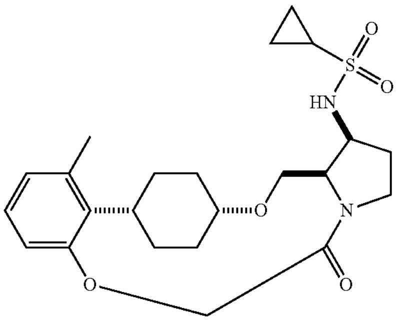 | 70 | *** |
| 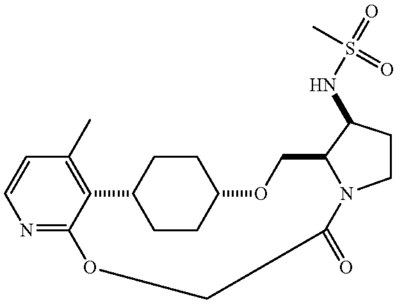 | 71 | *** |
| 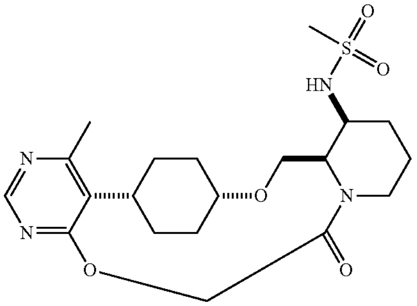 | 72 | *** |
| 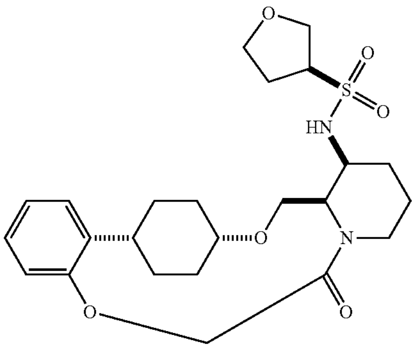 | 73 | *** |
TABLE 2-continued
| Compound | Compound No. | $EC_{50}$ (nM) |
|---|---|---|
| 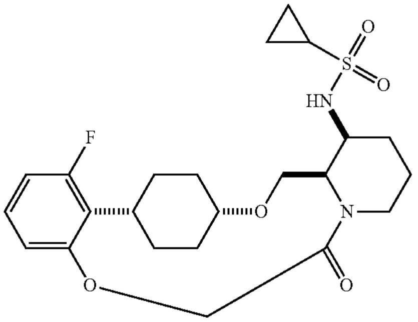 | 74 | *** |
| 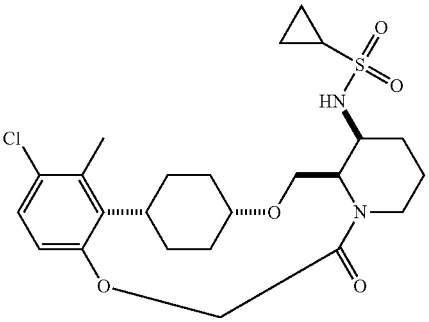 | 75 | *** |
| 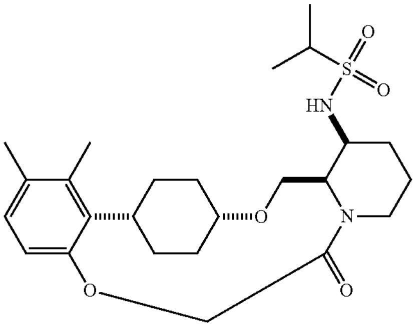 | 76 | *** |
| 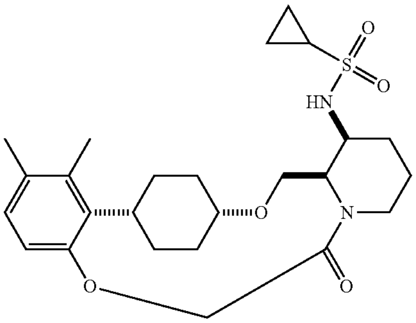 | 77 | *** |

TABLE 2-continued
| Compound | Compound No. | $EC_{50}$ (nM) |
|---|---|---|
| 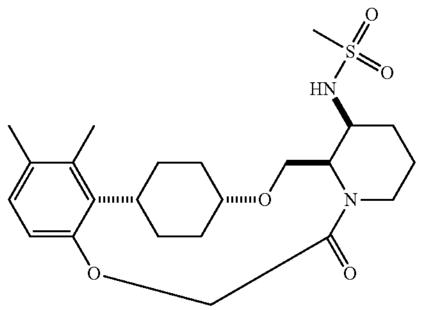 | 78 | *** |
| 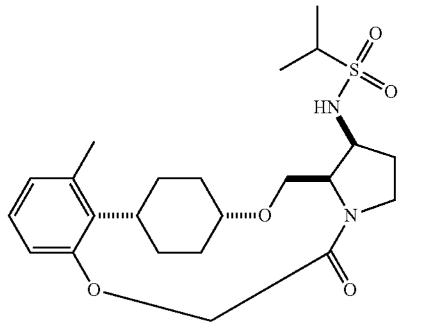 | 79 | *** |
| 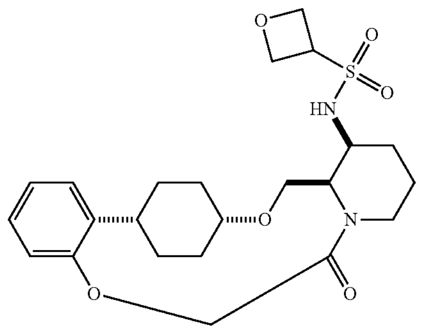 | 80 | *** |
| 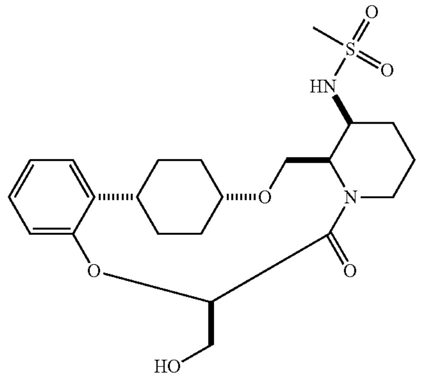 | 81 | ** |
TABLE 2-continued
| Compound | Compound No. | $EC_{50}$ (nM) |
|---|---|---|
| 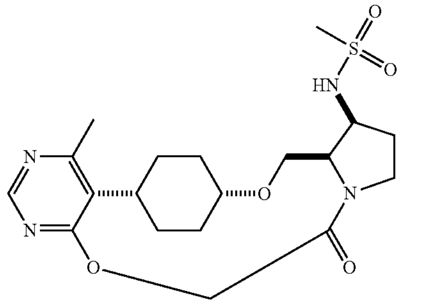 | 82 | ** |
| 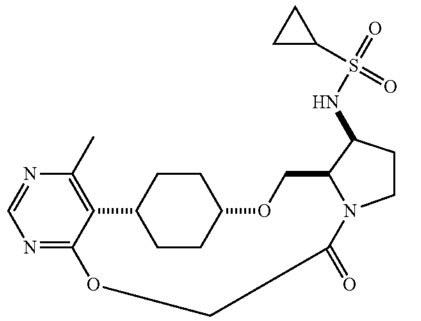 | 83 | ** |
| 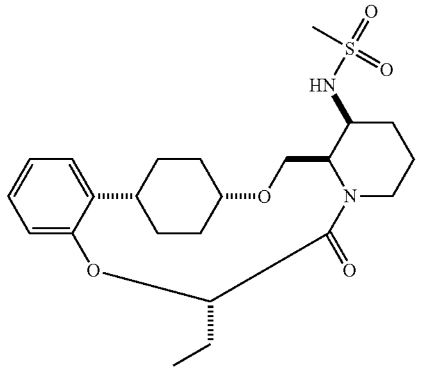 | 84 | *** |
| 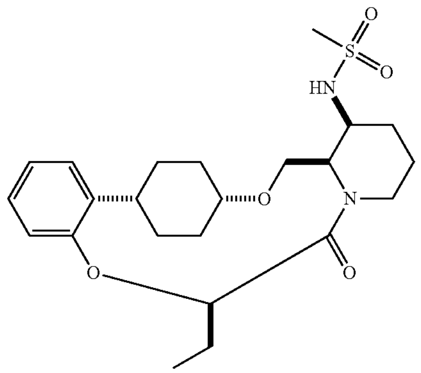 | 85 | *** |

TABLE 2-continued
| Compound | Compound No. | $EC_{50}$ (nM) |
|---|---|---|
| 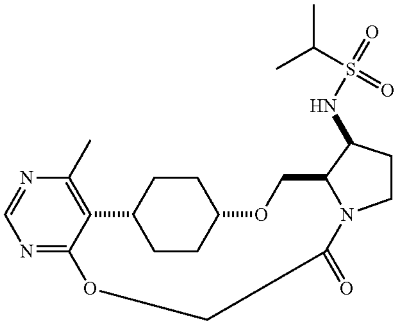 | 86 | ** |
| 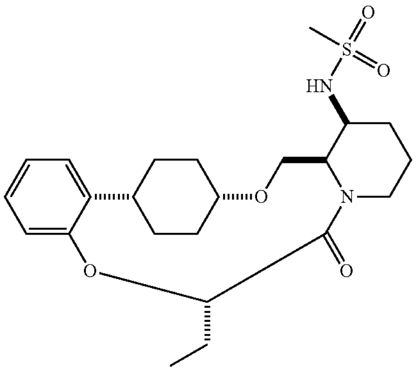 | 87 | ** |
| 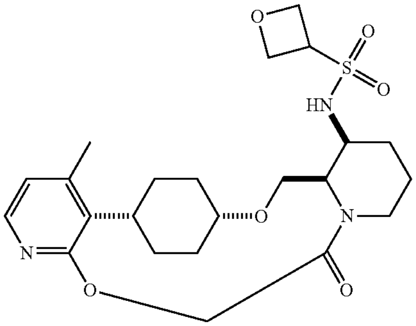 | 88 | *** |
| 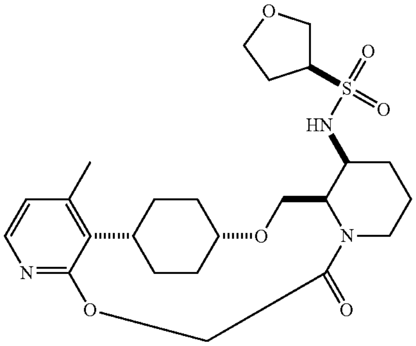 | 89 | *** |
TABLE 2-continued
| Compound | Compound No. | $EC_{50}$ (nM) |
|---|---|---|
| 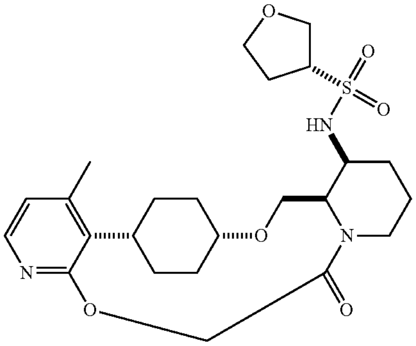 | 90 | *** |
| 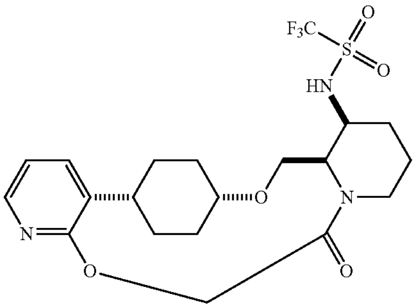 | 91 | *** |
| 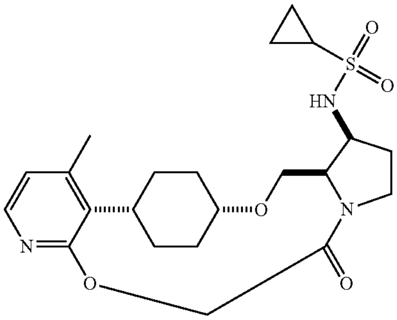 | 92 | *** |
| 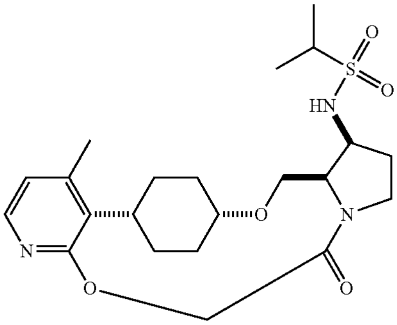 | 93 | *** |

TABLE 2-continued
| Compound | Compound No. | EC50 (nM) |
| --- | --- | --- |
| 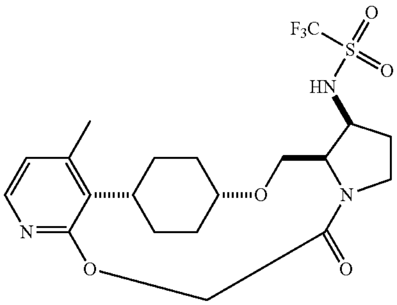 | 94 | *** |
| 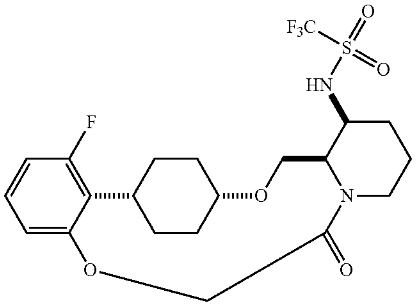 | 95 | *** |
| 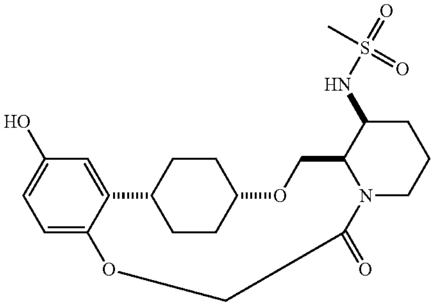 | 96 | *** |
| 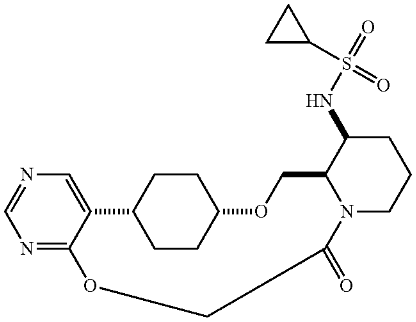 | 97 | ** |
| 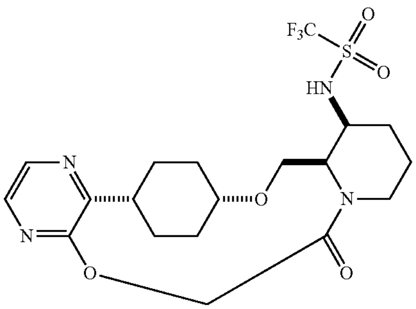 | 98 | *** |
| 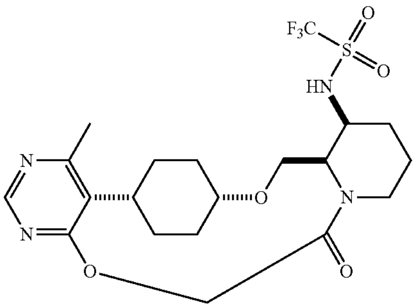 | 99 | *** |
| 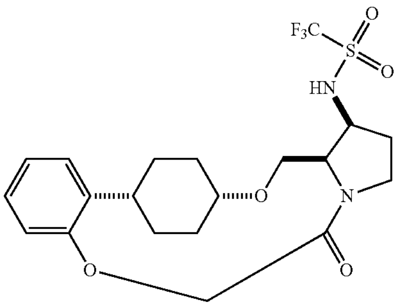 | 100 | *** |
| 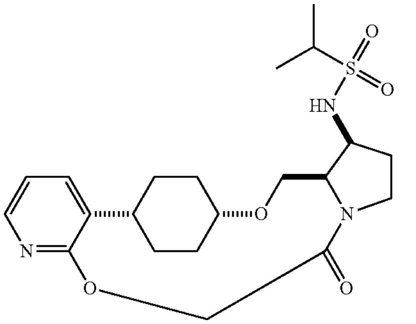 | 101 | *** |
| 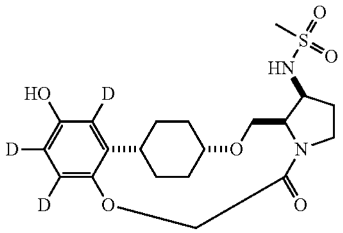 | 102 | *** |
| 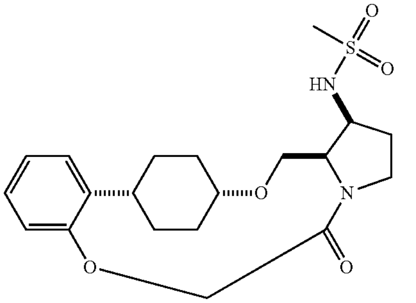 | 103 | ** |

TABLE 2-continued

| Compound | Compound No. | $EC_{50}$ (nM) |
|---|---|---|
| 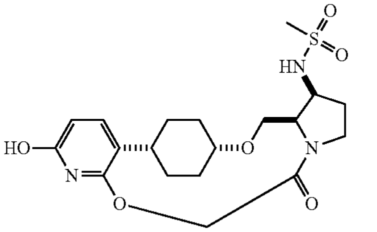 | 104 | *** |
| 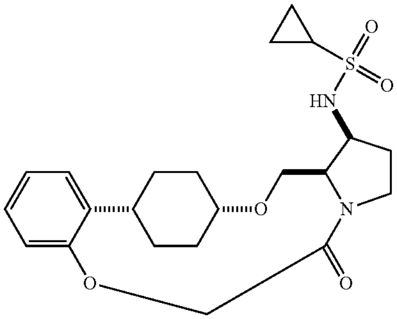 | 105 | *** |
| 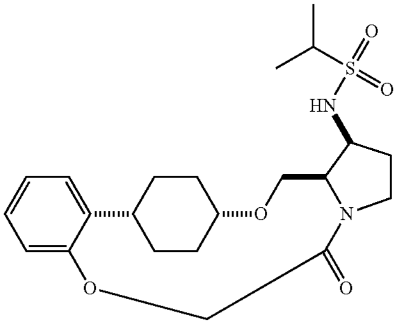 | 106 | *** |
| 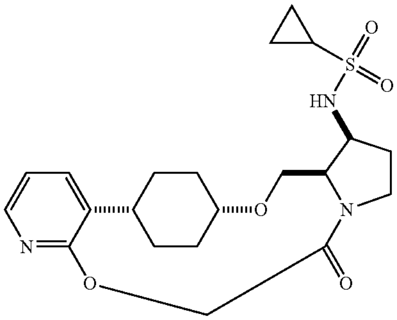 | 107 | *** |
| 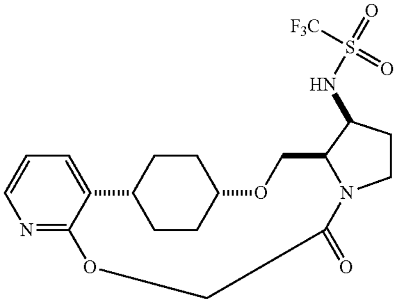 | 108 | *** |
| 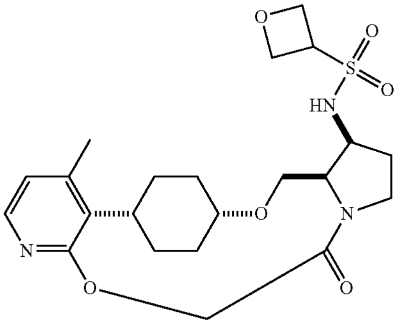 | 109 | *** |
| 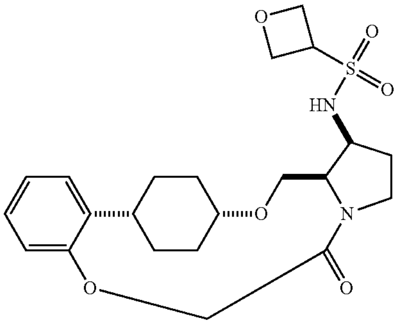 | 110 | *** |
| 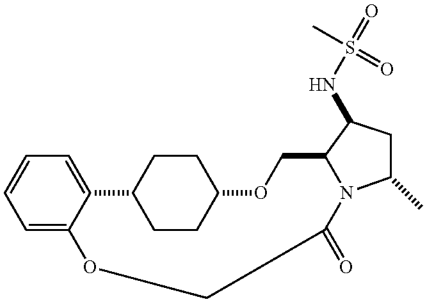 | 111 | ** |
| methyl (2R,3S)-3-((methylsulfonyl)amino)-2-(((cis-4-phenylcyclohexyl)oxy)methyl)-piperidine-1-carboxylate | Reference Compound A | *** |
| N-((2S,3S)-1-(2-hydroxy-2-methylpropanoyl)-2-((2,3',5'-trifluorobiphenyl-3-yl)methyl)pyrrolidin-3-yl)methanesulfonamide | Reference Compound B | ** |

***$EC_{50}$ <10 nM
**$EC_{50}$ 10-1,000 nM
*$EC_{50}$ >1,000 nM
^Racemic mixture Example 3. MDCK-MDR1 Permeability Assay The bidirectional permeability (Apical to Basal and Basal to Apical directions) of test compounds in MDCK-MDR1 cells were evaluated using MDCK-MDR1 cells seeded in Solvo PreadyPort™ MDCK 96-well plate. Once the plate was received from ReadyCell (Barcelona, Spain), it was treated as per PreadyPort™ user's manual.

For the Apical to Basolateral (A→B) permeability, 80 μL of test compound (3 μM) co-dosed with LY (Lucifer Yellow)

(100 μM) in HBSS (Hank's Balanced Salt Solution) assay buffer was added to the donor side (A) while 250 μL of HBSS buffer was added to the receiver side (B). For the Basolateral to Apical (B→A) permeability, 255 μL of test compound (3 μM) in HBSS assay buffer was added to the donor side (B) while 75 μL of HBSS buffer containing LY (100 μM) was added to the receiver side (A).

The plate was placed in an incubator set at 37 degrees C. After 10 minutes of pre-warming, 5 μL aliquot was taken from donor compartment and set aside as the dosing solution. The MDCK-MDR1 incubation plate was placed back into the incubator for 2 hours of incubation at 37 degrees C. After 2 hours of incubation, 25 μL and 5 μL aliquots were removed from the receiver and donor sides, respectively. To the 5 μL aliquots taken from the donor sides (before and after a 2-hour incubation) were diluted with 20 μL of the HBSS buffer. All samples were mixed with 150 μL with acetonitrile containing internal standard (IS) and 200 μL water, and analyzed by LC-MS/MS.

The apparent permeability ($P_{app}$) was calculated using the following formula:

$$P_{app} = dQ/dt \times 1/A \times C_0$$

where:

- dQ/dt: amount of translocated material over incubation time (nmol/s)
- A: area of insert (0.14 $cm^2$ for PreadyPort™ MDR1-96)
- $C_0$: initial concentration of product applied in apical (A→B) or basal (B→A) compartment (nmol/mL)

The efflux ratio (ER) was measured by dividing the $P_{app}$ (basolateral to apical direction) by $P_{app}$ (apical to basolateral direction). It is a general measure of the involvement of active processes. An ER >2 is considered positive for active transport.

Percent recovery was measured using the following equation:

$$\text{Percent Recovery} = 100 \times \frac{C_R^{final} \times V_R + C_D^{final} \times V_D}{V_D \times C_N}$$

where:

- $V_R$: Volume of the receiver compartment (mL)
- $V_D$: Volume of the donor compartment (mL)
- $C_N$: Concentration of dosing solution (μM) collected after 10 minutes of incubation
- $C_R^{final}$: Receiver concentration at the end of the incubation (μM)
- $C_D^{final}$: Donor concentration at the end of the incubation (μM)

The data reported in Table 3 were obtained according to the MDCK-MDR1 permeability assay described above.

TABLE 3

| Compound No. | $P_{app}$ A → B ($10^{-6}$ cm/s) | Efflux ratio (ER) |
|---|---|---|
| 1 | 1.6 | 6.7 |
| 2 | 0.69 | 46 |
| 3 | 1.8 | 10 |
| 4 | 0.66 | 31 |
| 5 | 1.3 | 29 |

TABLE 3-continued

| Compound No. | $P_{app}$ A → B ($10^{-6}$ cm/s) | Efflux ratio (ER) |
|---|---|---|
| 6 | 1.0 | 35 |
| 7 | 1.4 | 22 |
| 8 | 1.8 | 3.6 |
| 9 | 0.87 | 50 |
| 10 | 0.38 | >100 |
| 11 | 1.6 | 52 |
| 12 | 0.49 | 74 |
| 13 | 0.35 | 72 |
| 14 | 0.30 | >100 |
| 15 | 0.34 | 100 |
| 16 | 0.20 | >100 |
| 17 | 0.84 | 40 |
| 18 | 0.83 | 19 |
| 19 | <0.092 | >100 |
| 20 | 6.8 | 6.4 |
| 21 | 0.80 | 52 |
| 22 | 0.18 | >100 |
| 23 | 0.44 | 87 |
| 24 | 0.65 | 43 |
| 25 | 0.62 | 27 |
| 26 | <0.12 | >100 |
| 27 | 0.33 | 48 |
| 28 | 0.43 | 92 |
| 29 | 6.4 | 2.5 |
| 30 | 5.3 | 3.3 |
| 31 | 0.32 | >100 |
| 32 | 5.2 | 3.2 |
| 33 | 0.55 | 59 |
| 34 | 0.44 | 67 |
| 35 | 0.35 | 81 |
| 36 | 0.30 | >100 |
| 37 | 0.23 | >100 |
| 38 | 1.32 | 35 |
| 39 | <0.086 | >100 |
| 40 | <0.18 | >100 |
| 41 | 3.7 | 2.4 |
| 42 | 0.92 | 7.4 |
| 43 | 0.96 | 10 |
| 44 | 2.0 | 7.8 |
| 45 | <0.14 | >5.3 |
| 46 | 0.18 | 81 |
| 47 | 0.19 | >100 |
| 48 | 0.56 | 60 |
| 49 | 8.6 | 0.73 |
| 50 | 9.6 | 0.76 |
| 51 | 7.8 | 1.1 |
| 52 | 3.9 | 2.4 |
| 53 | 5.6 | 1.8 |
| 54 | 5.2 | 2.0 |
| 55 | 0.23 | 31 |
| 56 | 1.7 | 3.3 |
| 57 | 1.7 | 6.0 |
| 58 | 1.4 | 7.5 |
| 59 | 1.67 | 5.4 |
| 60 | 0.041 | >100 |
| 61 | <0.034 | >100 |
| 62 | 0.092 | >100 |
| 63 | 7.5 | 1.4 |
| 64 | 12 | 1.2 |
| 65 | 0.10 | >100 |
| 66 | 0.22 | 88 |
| 67 | <0.036 | 63 |
| 68 | 0.24 | 72 |
| 69 | <0.041 | >100 |
| 70 | 3.7 | 4.2 |
| 71 | 2.5 | 13 |
| 72 | <0.091 | 49 |
| 73 | 0.23 | >100 |
| 74 | 0.62 | 41 |
| 75 | 0.30 | 65 |
| 76 | 0.57 | 28 |
| 77 | 0.79 | 27 |
| 78 | 0.41 | 74 |
| 79 | 5.7 | 3.8 |
| 80 | 0.79 | 51 |
| 81 | 0.49 | 72 |

TABLE 3-continued

| Compound No. | $P_{app}$ A → B ($10^{-6}$ cm/s) | Efflux ratio (ER) |
|---|---|---|
| 82 | 0.58 | 59 |
| 83 | 0.85 | 46 |
| 84 | 0.43 | 100 |
| 85 | 0.45 | 97 |
| 86 | 1.9 | 24 |
| 87 | 5.0 | 4.0 |
| 88 | 0.84 | 25 |
| 89 | 0.56 | 49 |
| 90 | 0.62 | 48 |
| 91 | 0.96 | 47 |
| 92 | 3.4 | 18 |
| 93 | 4.7 | 11 |
| 94 | 8.7 | 4.7 |
| 95 | 2.0 | 15 |
| 96 | 0.53 | 9.2 |
| 97 | 0.42 | 44 |
| 98 | 0.52 | 57 |
| 99 | 0.46 | 52 |
| 100 | 12 | 1.3 |
| 101 | 3.9 | 14 |
| 102 | 0.24 | 24 |
| 103 | 1.4 | 28 |
| Reference Compound A | 5.0 | 5.9 |
| Reference Compound B | 0.21 | >100 |

Example 4: Hepatocytes Stability Assay

In vitro metabolic stability was assessed using cryopreserved hepatocytes from male Sprague Dawley rats and a pool of 50 mixed gender humans (BioIVT, Baltimore, MD). The incubation mixtures were prepared by mixing 250 μL of pre-warmed KHB (Krebs-Henseleit buffer) containing $2\times10^6$ cell/mL of hepatocytes with 250 μL of pre-warmed KHB buffer containing 2 μM of test compounds in a 48-well plate, giving a final concentration of 1 μM test compound (0.1% DMSO) and $1\times10^6$ cell/mL of hepatocytes. The reaction mixture was incubated at 37 degrees C. A 50 μL aliquot of incubation mixture was taken at time points (0, 15, 30, 60, 120 and 240 minutes) and transferred into a 96-well plate containing 300 μL ice-cold acetonitrile (containing 30 ng/mL of labetalol and 10 ng/mL of Naltrexone-d3 as internal standards) and immediately placed in ice to terminate the reaction. Samples were centrifuged, and supernatants were transferred into 96-well plates for liquid chromatography with tandem mass spectrometry (LC-MS/MS) analysis to monitor the depletion of the test compound.

Data was calculated as percent remaining by assuming zero-minute time point peak area ratio (analyte/IS) as 100% and dividing remaining time point peak area ratios by zero-minute time point peak area ratio. Data were fitted to a first-order decay model to determine half-life. From a plot of log (ln) peak area against time, the slope of the line was determined. Subsequently, half-life ($T_{1/2}$) and intrinsic clearance ($CL_{int}$) were calculated using the equations below:

$$\text{Elimination rate constant } (k) = (-\text{slope})$$

$$\text{Half-life } (T_{1/2}) \text{ min} = 0.693/k$$

$$\text{Intrinsic Clearance } (CL_{int}) \text{ (mL/min/million cells)} = (V \times 0.693)/T_{1/2}$$

$$V = \text{incubation volume mL/number of cells}$$

The in vitro $T_{1/2}$ was converted to in vitro intrinsic clearance ($CL_{int,hep}$) in units of mL/min/kg using the formula shown below:

$$CLint,\ hep = \frac{0.693}{T1/2} \times \frac{\text{mL incubation}}{\text{million cells}} \times \frac{120 \text{ million cells}}{\text{g Liver}} \times \frac{\text{g Liver}}{\text{kg body}}$$

The in vitro intrinsic clearance ($CL_{int,hep}$) was scaled to in vivo hepatic clearance ($CL_{,hep}$) using the following equation which was adapted from a well-stirred model.

$$CL,\ hep = \frac{Q \times fu \times CLint,\ hep}{Q + fu \times CLint,\ hep}$$

where Q is the liver blood flow and fu is the fraction unbound (assumed to be unity in this case). All parameters used in the calculation are shown below (Table 4).

TABLE 4

Physiological Parameters Used in the In Vitro To In Vivo Scaling

| | Mouse | Rat | Dog | Monkey | Human |
|---|---|---|---|---|---|
| Body Weight (kg) | 0.02 | 0.25 | 10 | 5 | 70 |
| Liver weight (g/kg) | 87.5 | 40 | 32 | 30 | 25.7 |
| Liver Blood Flow (mL/min/kg) | 90 | 55.2 | 30.9 | 43.6 | 20.7 |

Davies B. and Morris T. (1993) Physiological Parameters in Laboratory Animals and Humans. Pharma Res. 10 (7):1093-1095.

The extraction ratio (ER) was calculated by dividing the hepatic clearance of a compound to the liver blood flow. The data reported in Table 5 were obtained according to the human hepatocytes stability assay described above.

TABLE 5

| Compound No. | $CL_{int}$ (μL/min/ million cells) | Extraction Ratio (ER) |
|---|---|---|
| 1 | 31 | 0.82 |
| 2 | 28 | 0.80 |
| 3 | 21 | 0.76 |
| 4 | 29 | 0.81 |
| 5 | 22 | 0.77 |
| 6 | 18 | 0.73 |
| 7 | 19 | 0.74 |
| 8 | 31 | 0.82 |
| 9 | 32 | 0.83 |
| 10 | 9.4 | 0.58 |
| 11 | 4.2 | 0.38 |
| 12 | 9.7 | 0.59 |
| 13 | 6.3 | 0.48 |
| 14 | 20 | 0.75 |
| 15 | 15 | 0.69 |
| 16 | 6.1 | 0.47 |
| 17 | 7.5 | 0.53 |
| 18 | 5.8 | 0.46 |
| 19 | 6.6 | 0.50 |
| 20 | 27 | 0.80 |
| 21 | 36 | 0.84 |
| 22 | 13 | 0.66 |
| 23 | 30 | 0.82 |
| 24 | 28 | 0.81 |
| 25 | 35 | 0.84 |
| 26 | 5.1 | 0.43 |
| 27 | <1.9 | <0.22 |
| 28 | 3.8 | 0.36 |
| 29 | 15 | 0.70 |

TABLE 5-continued

| Compound No. | $CL_{int}$ (μL/min/million cells) | Extraction Ratio (ER) |
|---|---|---|
| 30 | 36 | 0.84 |
| 31 | 3.9 | 0.37 |
| 32 | 16 | 0.70 |
| 33 | 41 | 0.86 |
| 34 | 7.1 | 0.52 |
| 35 | 16 | 0.70 |
| 36 | 17 | 0.71 |
| 37 | 24 | 0.78 |
| 38 | 18 | 0.73 |
| 39 | 20 | 0.75 |
| 40 | 6.4 | 0.49 |
| 41 | 58 | 0.90 |
| 42 | 36 | 0.84 |
| 43 | 55 | 0.89 |
| 44 | 46 | 0.87 |
| 45 | <1.9 | <0.22 |
| 46 | 2.8 | 0.29 |
| 47 | 4.3 | 0.39 |
| 48 | 41 | 0.86 |
| 49 | 58 | 0.90 |
| 50 | 61 | 0.90 |
| 51 | 42 | 0.86 |
| 52 | 59 | 0.90 |
| 53 | 58 | 0.90 |
| 54 | 38 | 0.85 |
| 55 | 69 | 0.91 |
| 56 | 69 | 0.91 |
| 57 | 65 | 0.91 |
| 58 | 55 | 0.89 |
| 59 | 62 | 0.90 |
| 60 | 3.7 | 0.36 |
| 61 | 6.9 | 0.51 |
| 62 | 21 | 0.76 |
| 63 | 44 | 0.87 |
| 64 | 46 | 0.87 |
| 65 | <1.9 | <0.22 |
| 66 | <1.9 | <0.22 |
| 67 | 2.5 | 0.27 |
| 68 | 3.9 | 0.37 |
| 69 | 3.4 | 0.34 |
| 70 | 45 | 0.87 |
| 71 | 31 | 0.82 |
| 72 | <1.9 | <0.22 |
| 73 | 21 | 0.76 |
| 74 | 15 | 0.69 |
| 75 | 11 | 0.61 |
| 76 | 9.8 | 0.59 |
| 77 | 12 | 0.63 |
| 78 | 7.2 | 0.52 |
| 79 | 46 | 0.87 |
| 80 | 11 | 0.63 |
| 81 | 59 | 0.90 |
| 82 | <1.9 | <0.22 |
| 83 | 2.6 | 0.28 |
| 84 | 31 | 0.82 |
| 85 | 37 | 0.84 |
| 86 | 4.1 | 0.38 |
| 87 | 103 | 0.94 |
| 88 | 6.7 | 0.50 |
| 89 | 12 | 0.64 |
| 90 | 11 | 0.61 |
| 91 | 4.8 | 0.42 |
| 92 | 24 | 0.78 |
| 93 | 20 | 0.75 |
| 94 | <1.9 | <0.22 |
| 95 | 3.3 | 0.33 |
| 96 | 2.3 | 0.25 |
| 97 | 5.2 | 0.43 |
| 98 | <1.4 | <0.22 |
| 99 | <1.4 | <0.22 |
| 100 | 2.5 | 0.274 |
| 101 | 19 | 0.74 |
| 102 | <1.9 | <0.22 |
| 103 | 41 | 0.86 |
| Reference Compound A | 76 | 0.92 |
| Reference Compound B | 1.5 | 0.19 |

Example 5: Assessment of Wake Promotion in Sprague-Dawley Rats

Wake promotion was assessed using electroencephalography (EEG) and electromyography (EMG) in adult male Sprague-Dawley rats. All rats (Charles River Laboratories, Raleigh, NC, USA) were intraperitoneally implanted with telemetry devices (F50-EEE, Data Sciences International Inc., MN, USA) under isoflurane anesthesia. For EEG, stainless steel screws were implanted over frontal cortex and parietal cortex, and reference screws were placed over cerebellum. Additionally, an electrode was placed in neck muscle for EMG. Rats were given carprofen post-surgery and underwent a 7 to 10-day recovery period. Rats habituated to the experimental room for 7 days and were maintained on a 12-hour light-dark cycle.

EEG and EMG data were recorded using the DSI telemetry system and Ponemah software (Data Sciences International Inc., MN, USA). Sleep-wake stages were scored both manually and with Somnivore, a supervised machine learning software platform, in 10 second epochs. Records were visually inspected as needed post-processing.

All test compounds were dissolved in 5% DMSO and suspended in 95% saline with 0.5% methylcellulose and 0.5% tween. In a cross-over design, rats were dosed during the inactive light phase at zeitgeber time 5 (ZT5) at a dose volume of 3.33 ml/kg body weight. Unless otherwise indicated, all compounds were dosed orally. Recordings for each rat were initiated immediately after dosing and lasted for 6 hours post-dose.

Two key endpoints include wakefulness time and cortical activation time. Wakefulness time is derived from the sleep-wake stage analysis. Cortical activation time is based on the duration in which frontal gamma oscillatory activity (30-100 Hz), a key feature of wakefulness, was elevated relative to a pre-treatment baseline. Mean cortical activation time was computed relative to vehicle treatment for the 6-hour post-dose period. Results are shown in Table 6 below.

TABLE 6

| Compound | Route | Dose (mpk) | Mean cortical activation time (% vehicle treatment) |
|---|---|---|---|
| 1 | PO | 3 | 160.00 |
| 2 | PO | 3 | 182.50 |
| 3 | PO | 3 | 204.79 |
| 10 | PO | 3 | 82.61 |
| 11 | PO | 3 | 411.43 |
| 12 | PO | 3 | 108.70 |
| 15 | PO | 3 | 107.59 |
| 17 | PO | 3 | 212.31 |
| 20 | PO | 3 | 154.26 |
| 27 | PO | 3 | 138.57 |

TABLE 6-continued

| Compound | Route | Dose (mpk) | Mean cortical activation time (% vehicle treatment) |
|---|---|---|---|
| 29 | PO | 3 | 214.61 |
| 30 | PO | 3 | 141.24 |
| 65 | PO | 3 | 121.28 |
| 66 | PO | 3 | 141.30 |
| 68 | PO | 3 | 157.14 |
| 71 | PO | 3 | 86.52 |
| 91 | PO | 3 | 151.55 |
| 92 | PO | 3 | 97.94 |
| 93 | PO | 3 | 138.14 |
| 94 | PO | 3 | 152.81 |
| 95 | PO | 3 | 312.26 |
| 96 | PO | 3 | 74.48 |
| 97 | PO | 3 | 79.25 |
| 98 | PO | 3 | 84.91 |
| 99 | PO | 3 | 97.17 |
| 100 | PO | 3 | 265.17 |
| 101 | PO | 3 | 109.66 |
| Reference Compound A | SC | 3 | 118.75 |
| Reference Compound B | PO | 3 | 110.4 |

PO (oral);
SC (subcutaneous);
mpk (milligram per kilogram)

While this invention has been particularly shown and described with references to preferred embodiments thereof, it will be understood by those skilled in the art that various changes in form and details may be made therein without departing from the scope of the invention encompassed by the appended claims.

What is claimed is:

1. A compound of Formula I-A or a pharmaceutically acceptable salt thereof:

(I-A)

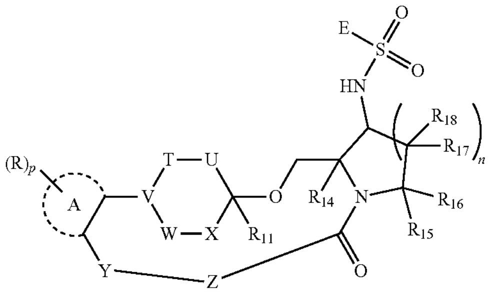

wherein:

ring A is selected from the group consisting of phenyl, pyridinyl, pyridazinyl, pyrimidinyl, pyrazinyl, and triazinyl;

n is 1, 2, or 3;

E is selected from the group consisting of $NR_aR_b$, $C_1$-$C_3$ alkylene-$NR_aR_b$, $C_1$-$C_3$ alkyl, $C_2$-$C_4$ alkenyl, $C_2$-$C_4$ alkynyl, $C_3$-$C_8$ cycloalkyl, $C_1$-$C_3$ alkylene-($C_3$-$C_8$ cycloalkyl), 4- to 10-membered heterocyclyl, $C_1$-$C_3$ alkylene-(4- to 10-membered heterocyclyl), $C_6$-$C_{10}$ aryl, $C_1$-$C_3$ alkylene-($C_6$-$C_{10}$ aryl), 5- to 10-membered heteroaryl, and $C_1$-$C_3$ alkylene-(5- to 10-membered heteroaryl), wherein the $C_1$-$C_3$ alkylene-$NR_aR_b$, $C_1$-$C_3$alkyl, $C_2$-$C_4$ alkenyl, $C_2$-$C_4$ alkynyl, $C_3$-$C_8$ cycloalkyl, $C_1$-$C_3$ alkylene-($C_3$-$C_8$ cycloalkyl), 4- to 10-membered heterocyclyl, $C_1$-$C_3$ alkylene-(4- to 10-membered heterocyclyl), $C_6$-$C_{10}$ aryl, $C_1$-$C_3$ alkylene-($C_6$-$C_{10}$ aryl), 5- to 10-membered heteroaryl, or $C_1$-$C_3$ alkylene-(5- to 10-membered heteroaryl) is unsubstituted or substituted with one or more halogen, hydroxyl, $C_1$-$C_3$ alkyl, or $C_1$-$C_3$ alkoxyl;

T is $CR_1R_2$ or O;

W is $CR_4R_5$ or O;

U is $CR_6R_7$;

X is $CR_8R_9$;

V is $CR_3$ or N;

Y is O;

Z is $(CR_{12}R_{13})_m$;

each R is, independently, selected from the group consisting of halogen, deuterium, hydroxyl, cyano, unsubstituted $C_1$-$C_3$ alkyl, and $C_1$-$C_3$ alkyl substituted with one or more halogen or deuterium;

p is 0, 1, 2, 3, or 4;

$R_a$ and $R_b$ are each, independently, H or unsubstituted $C_1$-$C_3$ alkyl;

m is 1;

and further wherein:

$R_1$, $R_2$, $R_4$, and $R_5$ are each, independently, selected from the group consisting of H, hydroxyl, halogen, and deuterium;

or, alternatively, $R_2$ and $R_5$ together with the carbon atoms to which they are attached, form a single bond;

$R_3$ is selected from the group consisting of H, deuterium, halogen, hydroxyl, and cyano;

or, alternatively, $R_3$ and $R_1$, together with the carbon atoms to which they are attached, form a $C_3$-$C_5$ cycloalkyl;

or, alternatively, $R_3$ and $R_4$, together with the carbon atoms to which they are attached, form a $C_3$-$C_5$ cycloalkyl;

$R_6$, $R_7$, $R_8$, $R_9$, and $R_{11}$ are each, independently, selected from the group consisting of H, hydroxyl, halogen, and deuterium;

each $R_{12}$ and $R_{13}$ is, independently, selected from the group consisting of H, halogen, deuterium, unsubstituted $C_1$-$C_3$ alkyl, and $C_1$-$C_3$ alkyl substituted with hydroxyl or one or more halogen; and $R_{14}$, $R_{15}$, and $R_{16}$ are each, independently, selected from the group consisting of H, unsubstituted $C_1$-$C_3$ alkyl or $C_1$-$C_3$ alkyl substituted with one or more halogen; and each $R_{17}$ and $R_{18}$ is, independently, selected from the group consisting of H, unsubstituted $C_1$-$C_3$ alkyl or $C_1$-$C_3$ alkyl substituted with one or more halogen;

with the proviso that one or more of (a)-(f) is present:

(a) at least one R is selected from the group consisting of hydroxyl, cyano, unsubstituted $C_1$-$C_3$ alkyl, and $C_1$-$C_3$ alkyl substituted with one or more halogen or deuterium;

(b) E is $NR_aR_b$, $C_1$-$C_3$ alkylene-$NR_aR_b$, $C_2$-$C_3$ alkyl, $C_2$-$C_4$ alkenyl, $C_2$-$C_4$ alkynyl, $C_3$-$C_8$ cycloalkyl, $C_1$-$C_3$ alkylene-($C_3$-$C_8$ cycloalkyl), 4- to 10-membered heterocyclyl, $C_1$-$C_3$ alkylene-(4- to 10-membered heterocyclyl), $C_6$-$C_{10}$ aryl, $C_1$-$C_3$ alkylene-($C_6$-$C_{10}$ aryl), 5- to 10-membered heteroaryl, or $C_1$-$C_3$ alkylene-(5- to 10-membered heteroaryl), wherein the $C_1$-$C_3$ alkylene-$NR_aR_b$, $C_2$-$C_3$ alkyl, $C_2$-$C_4$ alkenyl, $C_2$-$C_4$ alkynyl, $C_3$-$C_8$ cycloalkyl, $C_1$-$C_3$ alkylene-($C_3$-$C_8$ cycloalkyl), 4- to 10-membered heterocyclyl, $C_1$-$C_3$ alkylene-(4- to 10-membered heterocyclyl), $C_6$-$C_{10}$ aryl, $C_1$-$C_3$ alkylene-($C_6$-$C_{10}$ aryl), 5- to 10-membered heteroaryl, or $C_1$-$C_3$ alkylene-(5- to 10-membered heteroaryl) is unsubstituted or substituted with one or more halogen, hydroxyl, $C_1$-$C_3$ alkyl, or $C_1$-$C_3$ alkoxyl;

(c) E is $C_1$ alkyl substituted with one or more halogen, hydroxyl, $C_1$-$C_3$ alkyl, or $C_1$-$C_3$ alkoxyl;

(d) at least one of $R_{14}$, $R_{15}$, $R_{16}$, $R_{17}$, and $R_{18}$ is unsubstituted $C_1$-$C_3$ alkyl or $C_1$-$C_3$ alkyl substituted with one or more halogen;

(e) at least one of $R_1$, $R_2$, $R_4$, $R_5$, $R_6$, $R_7$, $R_8$, $R_9$, and $R_{11}$ is hydroxyl; or (f) at least one of $R_{12}$ and $R_{13}$ is $C_1$-$C_3$ alkyl substituted with hydroxyl.

2. The compound of claim 1, wherein n is 1.

3. The compound of claim 1, wherein n is 2.

4. The compound of claim 1, wherein ring A is phenyl.

5. The compound of claim 1, wherein ring A is pyridinyl.

6. The compound of claim 1, wherein T is $CR_1R_2$.

7. The compound of claim 1, wherein T is O.

8. The compound of claim 1, wherein W is $CR_4R_5$.

9. The compound of claim 1, wherein Wis O.

10. The compound of claim 1, wherein V is $CR_3$.

11. The compound of claim 1, wherein Tis $CR_1R_2$, W is $CR_4R_5$, and Vis $CR_3$.

12. The compound of claim 1, wherein ring A is phenyl, T is $CR_1R_2$, W is $CR_4R_5$, and Vis $CR_3$.

13. The compound of claim 1, wherein ring A is pyridinyl, T is $CR_1R_2$, W is $CR_4R_5$, and V is $CR_3$.

14. A compound of Formula II-A or a pharmaceutically acceptable salt thereof:

(II-A)

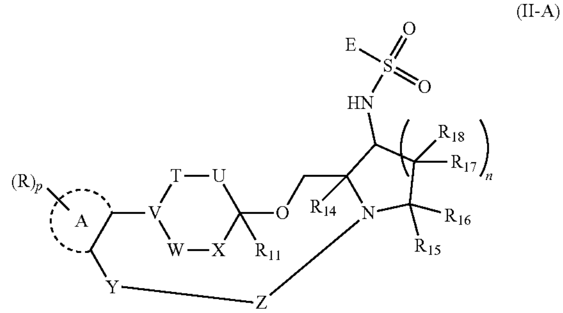

wherein:

ring A is selected from the group consisting of phenyl, pyridinyl, pyridazinyl, pyrimidinyl, pyrazinyl, and triazinyl;

n is 1, 2, or 3;

E is selected from the group consisting of $NR_aR_b$, $C_1$-$C_3$ alkylene-$NR_aR_b$, $C_1$-$C_3$ alkyl, $C_2$-$C_4$ alkenyl, $C_2$-$C_4$ alkynyl, $C_3$-$C_8$ cycloalkyl, $C_1$-$C_3$ alkylene-($C_3$-$C_8$ cycloalkyl), 4- to 10-membered heterocyclyl, $C_1$-$C_3$ alkylene-(4- to 10-membered heterocyclyl), $C_6$-$C_{10}$ aryl, $C_1$-$C_3$ alkylene-($C_6$-$C_{10}$ aryl), 5- to 10-membered heteroaryl, and $C_1$-$C_3$ alkylene-(5- to 10-membered heteroaryl), wherein the $C_1$-$C_3$ alkylene-$NR_aR_b$, $C_1$-$C_3$alkyl, $C_2$-$C_4$ alkenyl, $C_2$-$C_4$ alkynyl, $C_3$-$C_8$ cycloalkyl, $C_1$-$C_3$ alkylene-($C_3$-$C_8$ cycloalkyl), 4- to 10-membered heterocyclyl, $C_1$-$C_3$ alkylene-(4- to 10-membered heterocyclyl), $C_6$-$C_{10}$ aryl, $C_1$-$C_3$ alkylene-($C_6$-$C_{10}$ aryl), 5- to 10-membered heteroaryl, or $C_1$-$C_3$ alkylene-(5- to 10-membered heteroaryl) is unsubstituted or substituted with one or more halogen, hydroxyl, $C_1$-$C_3$ alkyl, or $C_1$-$C_3$ alkoxyl;

T is $CR_1R_2$ or O;

W is $CR_4R_5$ or O;

U is $CR_6R_7$;

X is $CR_8R_9$;

V is $CR_3$ or N;

Y is O;

Z is $(CR_{12}R_{13})_m$;

each R is, independently, selected from the group consisting of halogen, deuterium, hydroxyl, cyano, unsubstituted $C_1$-$C_3$ alkyl, and $C_1$-$C_3$ alkyl substituted with one or more halogen or deuterium;

p is 0, 1, 2, 3, or 4;

$R_a$ and $R_b$ are each, independently, H or unsubstituted $C_1$-$C_3$ alkyl;

m is 2, 3, 4, or 5 when Y is absent; or m is 1, 2, 3, or 4 when Y is $NR_{10}$ or O;

and further wherein:

$R_1$, $R_2$, $R_4$, and $R_5$ are each, independently, selected from the group consisting of H, hydroxyl, halogen, and deuterium;

or, alternatively, $R_2$ and $R_5$ together with the carbon atoms to which they are attached, form a single bond;

$R_3$ is selected from the group consisting of H, deuterium, halogen, hydroxyl, and cyano;

or, alternatively, $R_3$ and $R_1$, together with the carbon atoms to which they are attached, form a $C_3$-$C_5$ cycloalkyl;

or, alternatively, $R_3$ and $R_4$, together with the carbon atoms to which they are attached, form a $C_3$-$C_5$ cycloalkyl;

$R_6$, $R_7$, $R_8$, $R_9$, and $R_{11}$ are each, independently, selected from the group consisting of H, hydroxyl, halogen, and deuterium;

$R_{10}$ is selected from the group consisting of H, unsubstituted $C_1$-$C_3$ alkyl, and $C_1$-$C_3$ alkyl substituted with one or more halogen;

each $R_{12}$ and $R_{13}$ is, independently, selected from the group consisting of H, halogen, deuterium, unsubstituted $C_1$-$C_3$ alkyl, and $C_1$-$C_3$ alkyl substituted with hydroxyl or one or more halogen; and $R_{14}$, $R_{15}$, and $R_{16}$ are each, independently, selected from the group consisting of H, unsubstituted $C_1$-$C_3$ alkyl or $C_1$-$C_3$ alkyl substituted with one or more halogen; and each $R_{17}$ and $R_{18}$ is, independently, selected from the group consisting of H, unsubstituted $C_1$-$C_3$ alkyl or $C_1$-$C_3$ alkyl substituted with one or more halogen;

with the proviso that one or more of (a)-(f) is present:

(a) at least one R is selected from the group consisting of hydroxyl, cyano, unsubstituted $C_1$-$C_3$ alkyl, and $C_1$-$C_3$ alkyl substituted with one or more halogen or deuterium;

(b) E is $NR_aR_b$, $C_1$-$C_3$ alkylene-$NR_aR_b$, $C_2$-$C_3$ alkyl, $C_2$-$C_4$ alkenyl, $C_2$-$C_4$ alkynyl, $C_3$-$C_8$ cycloalkyl, $C_1$-$C_3$ alkylene-($C_3$-$C_8$ cycloalkyl), 4- to 10-membered heterocyclyl, $C_1$-$C_3$ alkylene-(4- to 10-membered heterocyclyl), $C_6$-$C_{10}$ aryl, $C_1$-$C_3$ alkylene-($C_6$-$C_{10}$ aryl), 5- to 10-membered heteroaryl, or $C_1$-$C_3$ alkylene-(5- to 10-membered heteroaryl), wherein the $C_1$-$C_3$ alkylene-$NR_aR_b$, $C_2$-$C_3$ alkyl, $C_2$-$C_4$ alkenyl, $C_2$-$C_4$ alkynyl, $C_3$-$C_8$ cycloalkyl, $C_1$-$C_3$ alkylene-($C_3$-$C_8$ cycloalkyl), 4- to 10-membered heterocyclyl, $C_1$-$C_3$ alkylene-(4- to 10-membered heterocyclyl), $C_6$-$C_{10}$ aryl, $C_1$-$C_3$ alkylene-($C_6$-$C_{10}$ aryl), 5- to 10-membered heteroaryl, or $C_1$-$C_3$ alkylene-(5- to 10-membered heteroaryl) is unsubstituted or substituted with one or more halogen, hydroxyl, $C_1$-$C_3$ alkyl, or $C_1$-$C_3$ alkoxyl;

(c) E is $C_1$ alkyl substituted with one or more halogen, hydroxyl, $C_1$-$C_3$ alkyl, or $C_1$-$C_3$ alkoxyl;

(d) at least one of $R_{14}$, $R_{15}$, $R_{16}$, $R_{17}$, and $R_{18}$ is unsubstituted $C_1$-$C_3$ alkyl or $C_1$-$C_3$ alkyl substituted with one or more halogen;

(e) at least one of $R_1$, $R_2$, $R_4$, $R_5$, $R_6$, $R_7$, $R_8$, $R_9$, and $R_{11}$ is hydroxyl; or (f) at least one of $R_{12}$ and $R_{13}$ is $C_1$-$C_3$ alkyl substituted with hydroxyl.

15. The compound of claim 14, wherein the compound of Formula II-A or a pharmaceutically acceptable salt thereof is a compound of Formula II or a pharmaceutically acceptable salt thereof:

(II)

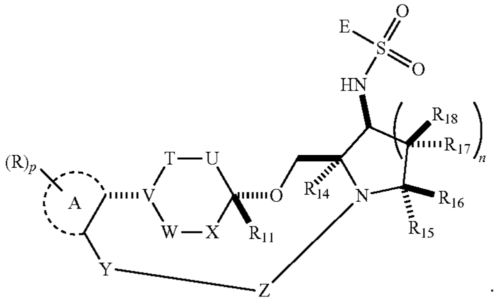

16. The compound of claim 14, wherein n is 1 or 2.

17. The compound of claim 14, wherein ring A is phenyl or pyridinyl.

18. The compound of claim 14, wherein Y is O or absent.

19. A pharmaceutical composition comprising a compound of claim 1 or a pharmaceutically acceptable salt thereof, and a pharmaceutically acceptable carrier.

20. A method of treating narcolepsy in a subject in need thereof comprising administering to the subject a compound of claim 1 or a pharmaceutically acceptable salt thereof, or a composition according to claim 19.

21. A pharmaceutical composition comprising a compound of claim 14 or a pharmaceutically acceptable salt thereof, and a pharmaceutically acceptable carrier.

22. A method of treating narcolepsy in a subject in need thereof comprising administering to the subject a compound of claim 14 or a pharmaceutically acceptable salt thereof, or a composition according to claim 21.

* * * * *